(12) United States Patent
Holmes

(10) Patent No.: US 9,619,627 B2
(45) Date of Patent: *Apr. 11, 2017

(54) SYSTEMS AND METHODS FOR COLLECTING AND TRANSMITTING ASSAY RESULTS

(71) Applicant: Theranos, Inc., Palo Alto, CA (US)

(72) Inventor: Elizabeth A. Holmes, Palo Alto, CA (US)

(73) Assignee: Theranos, Inc., Palo Alto, CA (US)

( * ) Notice: Subject to any disclaimer, the term of this patent is extended or adjusted under 35 U.S.C. 154(b) by 338 days.

This patent is subject to a terminal disclaimer.

(21) Appl. No.: 13/769,798

(22) Filed: Feb. 18, 2013

(65) Prior Publication Data

US 2014/0057255 A1    Feb. 27, 2014

Related U.S. Application Data

(63) Continuation-in-part of application No. 13/244,946, filed on Sep. 26, 2011, now Pat. No. 8,380,541, which
(Continued)

(51) Int. Cl.
G06Q 50/00 (2012.01)
G06F 19/00 (2011.01)
(Continued)

(52) U.S. Cl.
CPC ......... *G06F 19/366* (2013.01); *C12Q 1/6883* (2013.01); *G01N 21/07* (2013.01);
(Continued)

(58) Field of Classification Search
CPC ........ G06Q 50/22; G06Q 50/24; G06Q 40/08; G06Q 10/10; G06F 19/322
See application file for complete search history.

(56) References Cited

U.S. PATENT DOCUMENTS 2,398,234 A    4/1946    Long
3,640,434 A    2/1972    Walker
(Continued)

FOREIGN PATENT DOCUMENTS

CN    1526074 A    9/2004
CN    101010579 A    8/2007
(Continued)

OTHER PUBLICATIONS

Abbott. FDA Clears Abbott's i-STAT 1 Wireless Point of Care Testing System. Press release dated Mar. 29, 2011.
(Continued)

*Primary Examiner* — Tran Nguyen

(57) ABSTRACT

Systems and methods are provided for collecting, preparing, and/or analyzing a biological sample. A sample collection site may be utilized with one or more sample processing device. The sample processing device may be configured to accept a sample from a subject. The sample processing device may perform one or more sample preparation step and/or chemical reaction involving the sample. Data related to the sample may be sent from the device to a laboratory. The laboratory may be a certified laboratory that may generate a report that is transmitted to a health care professional. The health care professional may rely on the report for diagnosing, treating, and/or preventing a disease in the subject.

20 Claims, 15 Drawing Sheets

Related U.S. Application Data is a continuation-in-part of application No. PCT/US2011/053189, filed on Sep. 25, 2011, application No. 13/769,798, which is a continuation-in-part of application No. 13/244,947, filed on Sep. 26, 2011, now Pat. No. 8,435,738, which is a continuation-in-part of application No. PCT/US2011/053188, filed on Sep. 25, 2011, application No. 13/769,798, which is a continuation-in-part of application No. 13/244,949, filed on Sep. 26, 2011, and a continuation-in-part of application No. 13/244,950, filed on Sep. 26, 2011, and a continuation-in-part of application No. 13/244,951, filed on Sep. 26, 2011, now abandoned, and a continuation-in-part of application No. 13/244,952, filed on Sep. 26, 2011, now Pat. No. 8,475,739, which is a continuation-in-part of application No. PCT/US2011/053188, filed on Sep. 25, 2011, application No. 13/769,798, which is a continuation-in-part of application No. 13/244,953, filed on Sep. 26, 2011, now abandoned, and a continuation-in-part of application No. 13/244,954, filed on Sep. 26, 2011, now Pat. No. 8,840,838, and a continuation-in-part of application No. 13/244,956, filed on Sep. 26, 2011, now Pat. No. 9,268,915, and a continuation-in-part of application No. PCT/US2012/057155, filed on Sep. 25, 2012.

(51) Int. Cl.

| | |
|---|---|
| *C12Q 1/68* | (2006.01) |
| *G01N 21/07* | (2006.01) |
| *G01N 33/50* | (2006.01) |
| *G01N 35/00* | (2006.01) |
| G06Q 10/00 | (2012.01) |
| G01N 21/64 | (2006.01) |

(52) U.S. Cl.
CPC ......... *G01N 33/50* (2013.01); *G01N 35/0092* (2013.01); *G01N 21/6428* (2013.01); *G01N 2021/6441* (2013.01); *G01N 2035/00326* (2013.01); *G01N 2035/00495* (2013.01)

(56) References Cited

U.S. PATENT DOCUMENTS

| | | |
|---|---|---|
| 3,696,971 A | 10/1972 | Maclin |
| 3,766,381 A | 10/1973 | Watson |
| 3,849,654 A | 11/1974 | Malvin |
| 3,854,044 A | 12/1974 | Stay et al. |
| 3,865,495 A | 2/1975 | Sanz et al. |
| 4,010,893 A | 3/1977 | Smith et al. |
| 4,157,781 A | 6/1979 | Maruyama |
| 4,270,921 A | 6/1981 | Graas |
| 4,276,258 A | 6/1981 | Ginsberg et al. |
| 4,327,595 A | 5/1982 | Schultz |
| 4,362,698 A | 12/1982 | Boosalis et al. |
| 4,437,586 A | 3/1984 | Columbus |
| 4,488,814 A | 12/1984 | Johnson |
| 4,554,839 A | 11/1985 | Hewett et al. |
| 4,593,837 A | 6/1986 | Jakubowicz et al. |
| 4,683,195 A | 7/1987 | Mullis et al. |
| 4,744,955 A | 5/1988 | Shapiro |
| 4,756,884 A | 7/1988 | Hillman et al. |
| 4,784,834 A | 11/1988 | Hirschmann |
| 4,810,096 A | 3/1989 | Russell et al. |
| 4,816,567 A | 3/1989 | Cabilly et al. |
| 4,822,331 A | 4/1989 | Taylor |
| 4,830,832 A | 5/1989 | Arpagaus et al. |
| 4,925,629 A | 5/1990 | Schramm |
| 4,967,604 A | 11/1990 | Arpagaus et al. |
| 5,005,981 A | 4/1991 | Schulte et al. |
| 5,055,263 A | 10/1991 | Meltzer |
| 5,061,449 A | 10/1991 | Torti et al. |
| 5,072,382 A | 12/1991 | Kamentsky |
| 5,089,229 A | 2/1992 | Heidt et al. |
| 5,112,574 A | 5/1992 | Horton |
| 5,130,238 A | 7/1992 | Malek et al. |
| 5,171,534 A | 12/1992 | Smith et al. |
| 5,186,162 A | 2/1993 | Talish et al. |
| 5,230,864 A | 7/1993 | Columbus |
| 5,270,163 A | 12/1993 | Gold et al. |
| 5,270,184 A | 12/1993 | Walker et al. |
| 5,273,905 A | 12/1993 | Muller et al. |
| 5,281,395 A | 1/1994 | Markart et al. |
| 5,292,484 A | 3/1994 | Kelln et al. |
| 5,292,658 A | 3/1994 | Cormier et al. |
| 5,310,652 A | 5/1994 | Gelfand et al. |
| 5,320,808 A | 6/1994 | Holen et al. |
| 5,322,770 A | 6/1994 | Gelfand |
| 5,324,481 A | 6/1994 | Dunn et al. |
| 5,380,487 A | 1/1995 | Choperena et al. |
| 5,393,903 A | 2/1995 | Gratzel et al. |
| 5,399,491 A | 3/1995 | Kacian et al. |
| 5,414,508 A | 5/1995 | Takahashi et al. |
| 5,418,155 A | 5/1995 | Cormier et al. |
| 5,443,790 A | 8/1995 | Coeurveille et al. |
| 5,455,166 A | 10/1995 | Walker |
| 5,475,096 A | 12/1995 | Gold et al. |
| 5,480,784 A | 1/1996 | Kacian et al. |
| 5,507,410 A | 4/1996 | Clark et al. |
| 5,527,257 A | 6/1996 | Piramoon |
| 5,527,670 A | 6/1996 | Stanley |
| 5,530,101 A | 6/1996 | Queen et al. |
| 5,545,540 A | 8/1996 | Mian |
| 5,578,269 A | 11/1996 | Yaremko et al. |
| 5,578,270 A | 11/1996 | Reichler et al. |
| 5,580,529 A | 12/1996 | Devaughn et al. |
| 5,585,089 A | 12/1996 | Queen et al. |
| 5,602,647 A | 2/1997 | Xu et al. |
| 5,628,890 A | 5/1997 | Carter et al. |
| 5,670,375 A | 9/1997 | Seaton et al. |
| 5,683,888 A | 11/1997 | Campbell |
| 5,693,233 A | 12/1997 | Schembri |
| 5,693,761 A | 12/1997 | Queen et al. |
| 5,693,762 A | 12/1997 | Queen et al. |
| 5,741,411 A | 4/1998 | Yeung et al. |
| 5,741,668 A | 4/1998 | Ward et al. |
| 5,758,443 A | 6/1998 | Pedrazzini |
| 5,772,962 A | 6/1998 | Uchida et al. |
| 5,777,079 A | 7/1998 | Tsien et al. |
| 5,804,387 A | 9/1998 | Cormack et al. |
| 5,807,523 A | 9/1998 | Watts et al. |
| 5,821,337 A | 10/1998 | Carter et al. |
| 5,854,033 A | 12/1998 | Lizardi |
| 5,859,205 A | 1/1999 | Adair et al. |
| 5,874,304 A | 2/1999 | Zolotukhin et al. |
| 5,876,995 A | 3/1999 | Bryan |
| 5,902,549 A | 5/1999 | Mimura et al. |
| 5,906,795 A | 5/1999 | Nakashima et al. |
| 5,915,284 A | 6/1999 | Meltzer et al. |
| 5,925,558 A | 7/1999 | Tsien et al. |
| 5,939,291 A | 8/1999 | Loewy et al. |
| 5,961,451 A | 10/1999 | Reber et al. |
| 5,980,830 A | 11/1999 | Savage et al. |
| 5,993,417 A | 11/1999 | Yerfino et al. |
| 6,013,528 A | 1/2000 | Jacobs et al. |
| 6,033,850 A | 3/2000 | Purvis |
| 6,042,909 A | 3/2000 | Dunleavy et al. |
| 6,054,297 A | 4/2000 | Carter et al. |
| 6,056,661 A | 5/2000 | Schmidt |
| 6,063,341 A | 5/2000 | Fassbind et al. |
| 6,074,616 A | 6/2000 | Buechler et al. |
| 6,088,097 A | 7/2000 | Uhl |
| 6,115,545 A | 9/2000 | Mellquist |
| 6,121,054 A | 9/2000 | Lebl |
| 6,143,252 A | 11/2000 | Haxo, Jr. et al. |
| 6,159,368 A | 12/2000 | Moring et al. |
| 6,168,914 B1 | 1/2001 | Campbell et al. |
| 6,180,370 B1 | 1/2001 | Queen et al. |
| 6,191,852 B1 | 2/2001 | Paffhausen et al. |

(56) References Cited

U.S. PATENT DOCUMENTS

| | | |
|---|---|---|
| 6,210,891 B1 | 4/2001 | Nyren et al. |
| 6,244,119 B1 | 6/2001 | Theran |
| 6,251,639 B1 | 6/2001 | Kurn |
| 6,277,605 B1 | 8/2001 | Wijnhoven et al. |
| 6,290,907 B1 | 9/2001 | Takahashi et al. |
| 6,291,249 B1 | 9/2001 | Mahant et al. |
| 6,294,331 B1 | 9/2001 | Ried et al. |
| 6,333,157 B1 | 12/2001 | Miller-Jones et al. |
| 6,341,490 B1 | 1/2002 | Jones |
| 6,372,185 B1 | 4/2002 | Shumate et al. |
| 6,375,028 B1 | 4/2002 | Smith |
| 6,379,929 B1 | 4/2002 | Burns et al. |
| 6,396,580 B1 | 5/2002 | Tewes |
| 6,407,213 B1 | 6/2002 | Carter et al. |
| 6,410,278 B1 | 6/2002 | Notomi et al. |
| 6,420,143 B1 | 7/2002 | Kopf-Sill |
| 6,440,725 B1 | 8/2002 | Pourahmadi et al. |
| 6,468,474 B2 | 10/2002 | Bachand et al. |
| 6,477,394 B2 | 11/2002 | Rice et al. |
| 6,484,897 B1 | 11/2002 | Crawley |
| 6,491,666 B1 | 12/2002 | Santini et al. |
| 6,506,611 B2 | 1/2003 | Bienert et al. |
| 6,509,193 B1 | 1/2003 | Tajima |
| 6,517,475 B1 | 2/2003 | Brown et al. |
| 6,565,813 B1 | 5/2003 | Garyantes |
| 6,599,475 B1 | 7/2003 | Berndt et al. |
| 6,599,476 B1 | 7/2003 | Watson et al. |
| 6,605,213 B1 | 8/2003 | Smith |
| 6,627,160 B2 | 9/2003 | Wanner |
| 6,663,003 B2 | 12/2003 | Johnson et al. |
| 6,689,615 B1 | 2/2004 | Murto et al. |
| 6,732,598 B2 | 5/2004 | Schoeppe |
| 6,748,337 B2 | 6/2004 | Wardlaw et al. |
| 6,752,965 B2 | 6/2004 | Levy |
| 6,780,645 B2 | 8/2004 | Hayter et al. |
| 6,805,842 B1 | 10/2004 | Bodner et al. |
| 6,825,921 B1 | 11/2004 | Modlin et al. |
| 6,833,246 B2 | 12/2004 | Balasubramanian |
| 6,858,185 B1 | 2/2005 | Kopf-Sill et al. |
| 6,859,830 B1 | 2/2005 | Ronneburg et al. |
| 6,899,848 B1 | 5/2005 | Chen et al. |
| 6,905,816 B2 | 6/2005 | Jacobs et al. |
| 6,917,726 B2 | 7/2005 | Levene et al. |
| 6,946,251 B2 | 9/2005 | Kurn |
| 6,947,582 B1 | 9/2005 | Vilsmeier et al. |
| 6,949,377 B2 | 9/2005 | Ho |
| 7,033,764 B2 | 4/2006 | Korlach et al. |
| 7,052,847 B2 | 5/2006 | Korlach et al. |
| 7,056,676 B2 | 6/2006 | Korlach et al. |
| 7,109,293 B2 | 9/2006 | Hwang et al. |
| 7,170,050 B2 | 1/2007 | Turner et al. |
| 7,172,897 B2 | 2/2007 | Blackburn et al. |
| 7,185,551 B2 | 3/2007 | Schwartz |
| 7,272,252 B2 | 9/2007 | De La Torre-Bueno et al. |
| 7,276,158 B1 | 10/2007 | Shukla et al. |
| 7,358,098 B2 | 4/2008 | Noda et al. |
| 7,361,466 B2 | 4/2008 | Korlach et al. |
| 7,416,844 B2 | 8/2008 | Korlach et al. |
| 7,422,554 B2 | 9/2008 | Moscone et al. |
| 7,429,652 B2 | 9/2008 | Wang et al. |
| 7,438,857 B2 | 10/2008 | Massaro |
| 7,481,787 B2 | 1/2009 | Gable et al. |
| 7,494,791 B2 | 2/2009 | Goel |
| 7,548,034 B2 | 6/2009 | Takahashi et al. |
| 7,581,660 B2 | 9/2009 | Nay et al. |
| 7,587,201 B2 | 9/2009 | Ohara |
| 7,609,654 B2 | 10/2009 | Lubeck et al. |
| 7,632,462 B2 | 12/2009 | Holtlund et al. |
| 7,635,594 B2 | 12/2009 | Holmes et al. |
| 7,650,395 B2 | 1/2010 | Johnson et al. |
| 7,662,343 B2 | 2/2010 | Mathus et al. |
| 7,691,332 B2 | 4/2010 | Kacian et al. |
| 7,702,524 B1 | 4/2010 | Whibbs et al. |
| 7,711,800 B2 | 5/2010 | Gavrilescu et al. |
| 7,744,821 B2 | 6/2010 | Eberle |
| 7,771,926 B2 | 8/2010 | Petyt et al. |
| 7,824,612 B2 | 11/2010 | Fuisz et al. |
| 7,824,890 B2 | 11/2010 | Hoser et al. |
| 7,888,125 B2 | 2/2011 | Gibbons et al. |
| 7,923,256 B2 | 4/2011 | Widrig Opalsky et al. |
| 7,925,069 B2 | 4/2011 | Ortyn et al. |
| 7,955,867 B2 | 6/2011 | Park |
| 7,978,665 B1 | 7/2011 | Jaynes et al. |
| 8,008,066 B2 | 8/2011 | Lair et al. |
| 8,030,080 B2 | 10/2011 | Spence et al. |
| 8,088,593 B2 | 1/2012 | Burd et al. |
| 8,133,671 B2 | 3/2012 | Williams et al. |
| 8,158,430 B1 | 4/2012 | Roy et al. |
| 8,211,386 B2 | 7/2012 | Talmer et al. |
| 8,309,035 B2 | 11/2012 | Chen et al. |
| 8,309,317 B2 | 11/2012 | Chen et al. |
| 8,313,713 B2 | 11/2012 | Jacobs et al. |
| 8,323,564 B2 | 12/2012 | Padmanabhan et al. |
| 8,380,541 B1* | 2/2013 | Holmes .................. G06F 15/16 705/2 |
| 8,383,421 B2 | 2/2013 | Yanagida et al. |
| 8,392,585 B1 | 3/2013 | Balwani |
| 8,435,738 B2 | 5/2013 | Holmes |
| 8,475,739 B2 | 7/2013 | Holmes et al. |
| 8,588,807 B2 | 11/2013 | Kumar |
| 8,883,518 B2 | 11/2014 | Roy et al. |
| 9,121,801 B2 | 9/2015 | Clark et al. |
| 9,131,884 B2 | 9/2015 | Holmes et al. |
| 9,182,388 B2 | 11/2015 | Gibbons et al. |
| 2001/0019845 A1 | 9/2001 | Bienert et al. |
| 2001/0021726 A1 | 9/2001 | Brown |
| 2001/0028497 A1 | 10/2001 | Uhl |
| 2001/0048899 A1 | 12/2001 | Marouiss et al. |
| 2002/0001803 A1 | 1/2002 | Smith et al. |
| 2002/0039723 A1 | 4/2002 | Fox et al. |
| 2002/0052761 A1 | 5/2002 | Fey et al. |
| 2002/0059030 A1 | 5/2002 | Otworth et al. |
| 2002/0065457 A1 | 5/2002 | Kuth |
| 2002/0085952 A1 | 7/2002 | Ellingboe et al. |
| 2002/0087101 A1 | 7/2002 | Barrick et al. |
| 2002/0110496 A1 | 8/2002 | Samsoondar |
| 2002/0110809 A1 | 8/2002 | Nehls et al. |
| 2002/0114739 A1 | 8/2002 | Weigl et al. |
| 2002/0120183 A1 | 8/2002 | Abraham-Fuchs et al. |
| 2002/0120187 A1 | 8/2002 | Eiffert et al. |
| 2002/0124538 A1 | 9/2002 | Oh et al. |
| 2002/0127708 A1 | 9/2002 | Kluttz et al. |
| 2002/0130100 A1 | 9/2002 | Smith |
| 2002/0139936 A1 | 10/2002 | Dumas |
| 2002/0149772 A1 | 10/2002 | Halg |
| 2002/0155599 A1 | 10/2002 | Vellinger et al. |
| 2002/0155616 A1 | 10/2002 | Hiramatsu et al. |
| 2002/0156365 A1 | 10/2002 | Tsekos |
| 2002/0160353 A1 | 10/2002 | Sundaram et al. |
| 2002/0161606 A1 | 10/2002 | Bennett et al. |
| 2002/0168784 A1 | 11/2002 | Sundrehagen et al. |
| 2002/0176801 A1 | 11/2002 | Giebeler et al. |
| 2002/0187074 A1 | 12/2002 | O'Connor et al. |
| 2003/0012699 A1 | 1/2003 | Moore et al. |
| 2003/0049865 A1 | 3/2003 | Santini et al. |
| 2003/0052074 A1 | 3/2003 | Chang et al. |
| 2003/0064386 A1 | 4/2003 | Karaki et al. |
| 2003/0077207 A1 | 4/2003 | Tyndorf et al. |
| 2003/0100822 A1 | 5/2003 | Lew et al. |
| 2003/0104494 A1 | 6/2003 | Ravkin et al. |
| 2003/0127609 A1 | 7/2003 | El-Hage et al. |
| 2003/0138140 A1 | 7/2003 | Marcelpoil et al. |
| 2003/0170705 A1 | 9/2003 | Schulman et al. |
| 2003/0175164 A1 | 9/2003 | Micklash et al. |
| 2003/0175993 A1 | 9/2003 | Toranto et al. |
| 2003/0202905 A1 | 10/2003 | Devlin et al. |
| 2003/0205681 A1 | 11/2003 | Modlin |
| 2003/0207463 A1 | 11/2003 | Iheme et al. |
| 2003/0208113 A1 | 11/2003 | Mault et al. |
| 2003/0211618 A1 | 11/2003 | Patel |
| 2003/0233257 A1 | 12/2003 | Matian et al. |
| 2003/0236458 A1 | 12/2003 | Hochman |
| 2004/0005699 A1 | 1/2004 | Roos et al. |
| 2004/0014097 A1 | 1/2004 | McGlennen et al. |

(56) References Cited

U.S. PATENT DOCUMENTS

| | | |
|---|---|---|
| 2004/0014202 A1 | 1/2004 | King et al. |
| 2004/0020310 A1 | 2/2004 | Escal |
| 2004/0038385 A1 | 2/2004 | Langlois et al. |
| 2004/0044560 A1 | 3/2004 | Giglio et al. |
| 2004/0058378 A1 | 3/2004 | Kong et al. |
| 2004/0086872 A1 | 5/2004 | Childers et al. |
| 2004/0096959 A1 | 5/2004 | Stiene et al. |
| 2004/0099628 A1 | 5/2004 | Casterlin |
| 2004/0109793 A1 | 6/2004 | Mcneely et al. |
| 2004/0115720 A1 | 6/2004 | McWilliams et al. |
| 2004/0120848 A1 | 6/2004 | Teodorczyk |
| 2004/0126005 A1 | 7/2004 | Duvdevani et al. |
| 2004/0127252 A1 | 7/2004 | Tsunomoto et al. |
| 2004/0134750 A1 | 7/2004 | Luoma |
| 2004/0161368 A1 | 8/2004 | Holtlund et al. |
| 2004/0166027 A1 | 8/2004 | Wilmer et al. |
| 2004/0228766 A1 | 11/2004 | Witty et al. |
| 2004/0230400 A1 | 11/2004 | Tomasso et al. |
| 2004/0241043 A1 | 12/2004 | Sattler |
| 2004/0241048 A1 | 12/2004 | Shin et al. |
| 2004/0260782 A1 | 12/2004 | Affleck et al. |
| 2005/0010098 A1 | 1/2005 | Frigstad et al. |
| 2005/0030541 A1 | 2/2005 | Erlbacher et al. |
| 2005/0036907 A1 | 2/2005 | Shoji |
| 2005/0074873 A1 | 4/2005 | Shanler et al. |
| 2005/0100937 A1 | 5/2005 | Holmes |
| 2005/0106713 A1 | 5/2005 | Phan et al. |
| 2005/0125258 A1 | 6/2005 | Yellin et al. |
| 2005/0147559 A1 | 7/2005 | Von Alten |
| 2005/0159982 A1 | 7/2005 | Showalter et al. |
| 2005/0164204 A1 | 7/2005 | Reed |
| 2005/0176940 A1 | 8/2005 | King |
| 2005/0180892 A1 | 8/2005 | Davies et al. |
| 2005/0220668 A1 | 10/2005 | Coville |
| 2005/0227370 A1 | 10/2005 | Ramel et al. |
| 2005/0236317 A1 | 10/2005 | DeSilets et al. |
| 2005/0237605 A1 | 10/2005 | Vodyanoy et al. |
| 2006/0019274 A1 | 1/2006 | Goel |
| 2006/0026040 A1 | 2/2006 | Reeves et al. |
| 2006/0034732 A1 | 2/2006 | Bargh et al. |
| 2006/0043301 A1 | 3/2006 | Mantele et al. |
| 2006/0057599 A1 | 3/2006 | Dzenitis et al. |
| 2006/0062697 A1 | 3/2006 | Eberle |
| 2006/0062852 A1 | 3/2006 | Holmes |
| 2006/0074063 A1 | 4/2006 | Fernandez-Pol |
| 2006/0074294 A1 | 4/2006 | Williams et al. |
| 2006/0083660 A1 | 4/2006 | Schorno et al. |
| 2006/0095429 A1 | 5/2006 | Abhyankar et al. |
| 2006/0110725 A1 | 5/2006 | Lee et al. |
| 2006/0115384 A1 | 6/2006 | Wohleb |
| 2006/0121491 A1 | 6/2006 | Wolber et al. |
| 2006/0121502 A1 | 6/2006 | Cain et al. |
| 2006/0160170 A1 | 7/2006 | Giordano |
| 2006/0182738 A1 | 8/2006 | Holmes |
| 2006/0183217 A1 | 8/2006 | Yanagida et al. |
| 2006/0210435 A1 | 9/2006 | Alavie et al. |
| 2006/0215400 A1 | 9/2006 | Lewis et al. |
| 2006/0223178 A1 | 10/2006 | Barber et al. |
| 2006/0263263 A1 | 11/2006 | Shimizu |
| 2006/0263871 A1 | 11/2006 | Kluttz et al. |
| 2006/0264780 A1 | 11/2006 | Holmes et al. |
| 2006/0275861 A1 | 12/2006 | Angros et al. |
| 2006/0292039 A1 | 12/2006 | Iida |
| 2007/0004577 A1 | 1/2007 | Lederer |
| 2007/0035818 A1 | 2/2007 | Bahatt et al. |
| 2007/0035819 A1 | 2/2007 | Bahatt et al. |
| 2007/0048188 A1 | 3/2007 | Bigus |
| 2007/0055538 A1 | 3/2007 | Burton |
| 2007/0059196 A1 | 3/2007 | Brister et al. |
| 2007/0073113 A1 | 3/2007 | Squilla et al. |
| 2007/0077173 A1 | 4/2007 | Melet |
| 2007/0109294 A1 | 5/2007 | Gotman et al. |
| 2007/0118399 A1 | 5/2007 | Avinash et al. |
| 2007/0134128 A1 | 6/2007 | Korlach |
| 2007/0146717 A1 | 6/2007 | Prins et al. |
| 2007/0149874 A1 | 6/2007 | Say et al. |
| 2007/0154922 A1 | 7/2007 | Collier et al. |
| 2007/0172100 A1 | 7/2007 | Lefebvre |
| 2007/0192138 A1 | 8/2007 | Saito et al. |
| 2007/0202538 A1 | 8/2007 | Glezer et al. |
| 2007/0207161 A1 | 9/2007 | Ralph |
| 2007/0207450 A1 | 9/2007 | Rodgers et al. |
| 2007/0224084 A1 | 9/2007 | Holmes et al. |
| 2007/0264629 A1 | 11/2007 | Holmes et al. |
| 2007/0269345 A1 | 11/2007 | Schilffarth et al. |
| 2007/0295113 A1 | 12/2007 | Londo et al. |
| 2008/0001735 A1 | 1/2008 | Tran |
| 2008/0003649 A1 | 1/2008 | Maltezos et al. |
| 2008/0038771 A1 | 2/2008 | Taylor et al. |
| 2008/0065420 A1 | 3/2008 | Tirinato et al. |
| 2008/0118988 A1 | 5/2008 | Johnson et al. |
| 2008/0144005 A1 | 6/2008 | Guiney et al. |
| 2008/0153096 A1 | 6/2008 | Witty et al. |
| 2008/0166753 A1 | 7/2008 | Storey et al. |
| 2008/0179301 A1 | 7/2008 | Garty et al. |
| 2008/0198379 A1 | 8/2008 | Coker et al. |
| 2008/0206751 A1 | 8/2008 | Squirrell et al. |
| 2008/0228107 A1 | 9/2008 | Reddy |
| 2008/0235055 A1 | 9/2008 | Mattingly et al. |
| 2008/0253933 A1 | 10/2008 | Redfern |
| 2008/0261210 A1 | 10/2008 | Frantzen et al. |
| 2008/0262321 A1 | 10/2008 | Erad et al. |
| 2008/0262873 A1 | 10/2008 | Bayne et al. |
| 2008/0299652 A1 | 12/2008 | Owen et al. |
| 2009/0004754 A1 | 1/2009 | Oldenburg |
| 2009/0043607 A1 | 2/2009 | Nemoto et al. |
| 2009/0057259 A1 | 3/2009 | Johnson et al. |
| 2009/0081648 A1 | 3/2009 | Wangh |
| 2009/0088336 A1 | 4/2009 | Burd et al. |
| 2009/0093970 A1* | 4/2009 | Lewy ............... A61B 5/417 702/21 |
| 2009/0094361 A1 | 4/2009 | Srinivasan |
| 2009/0098594 A1 | 4/2009 | Fantl et al. |
| 2009/0104079 A1 | 4/2009 | O'Connell et al. |
| 2009/0117009 A1 | 5/2009 | Cote |
| 2009/0124284 A1 | 5/2009 | Scherzer et al. |
| 2009/0143235 A1 | 6/2009 | Drmanac et al. |
| 2009/0148941 A1 | 6/2009 | Florez et al. |
| 2009/0181463 A1 | 7/2009 | Chen |
| 2009/0187348 A1 | 7/2009 | Ariyoshi |
| 2009/0190822 A1 | 7/2009 | Ortyn et al. |
| 2009/0203085 A1 | 8/2009 | Kurn et al. |
| 2009/0204435 A1 | 8/2009 | Gale |
| 2009/0208966 A1 | 8/2009 | Kacian et al. |
| 2009/0215157 A1 | 8/2009 | Jung et al. |
| 2009/0246782 A1 | 10/2009 | Kelso et al. |
| 2009/0274587 A1 | 11/2009 | Butz et al. |
| 2009/0298075 A1 | 12/2009 | Travers et al. |
| 2009/0298129 A1 | 12/2009 | Spence et al. |
| 2009/0305392 A1 | 12/2009 | Alfredsson et al. |
| 2009/0318775 A1 | 12/2009 | Michelson et al. |
| 2010/0009364 A1 | 1/2010 | Fantl et al. |
| 2010/0009456 A1 | 1/2010 | Prins et al. |
| 2010/0009460 A1 | 1/2010 | Clark et al. |
| 2010/0015634 A1 | 1/2010 | VanDine et al. |
| 2010/0034706 A1 | 2/2010 | Mathus et al. |
| 2010/0047128 A1 | 2/2010 | Mototsu et al. |
| 2010/0047790 A1 | 2/2010 | Southern et al. |
| 2010/0056895 A1 | 3/2010 | Temple et al. |
| 2010/0080440 A1 | 4/2010 | Yamada |
| 2010/0081144 A1 | 4/2010 | Holmes et al. |
| 2010/0081894 A1 | 4/2010 | Zdeblick et al. |
| 2010/0082781 A1 | 4/2010 | Lubeck et al. |
| 2010/0111773 A1 | 5/2010 | Pantelidis |
| 2010/0121156 A1 | 5/2010 | Yoo |
| 2010/0124746 A1 | 5/2010 | Liew |
| 2010/0128256 A1 | 5/2010 | Thomson |
| 2010/0151472 A1 | 6/2010 | Nolan et al. |
| 2010/0152885 A1 | 6/2010 | Regan et al. |
| 2010/0174181 A1 | 7/2010 | Nemoto |
| 2010/0184093 A1 | 7/2010 | Donovan et al. |
| 2010/0215644 A1 | 8/2010 | Fantl et al. |
| 2010/0240544 A1 | 9/2010 | Liu et al. |
| 2010/0246416 A1 | 9/2010 | Sinha et al. |

(56) References Cited

U.S. PATENT DOCUMENTS

| | | |
|---|---|---|
| 2010/0249652 A1 | 9/2010 | Rush et al. |
| 2010/0256470 A1 | 10/2010 | Miller |
| 2010/0262432 A1 | 10/2010 | Benja-Athon |
| 2010/0291588 A1 | 11/2010 | McDevitt et al. |
| 2011/0003392 A1 | 1/2011 | Stayton et al. |
| 2011/0003699 A1 | 1/2011 | Yoder et al. |
| 2011/0008825 A1 | 1/2011 | Ingber et al. |
| 2011/0093249 A1 | 4/2011 | Holmes et al. |
| 2011/0116385 A1 | 5/2011 | Turlington et al. |
| 2011/0129931 A1 | 6/2011 | Reboud et al. |
| 2011/0130740 A1 | 6/2011 | Levy |
| 2011/0143947 A1 | 6/2011 | Chamberlin et al. |
| 2011/0183433 A1 | 7/2011 | Motadel et al. |
| 2011/0201121 A1 | 8/2011 | Kaartinen |
| 2011/0207617 A1 | 8/2011 | Faham et al. |
| 2011/0213564 A1 | 9/2011 | Henke |
| 2011/0213579 A1 | 9/2011 | Henke |
| 2011/0213619 A1 | 9/2011 | Henke |
| 2011/0218428 A1 | 9/2011 | Westmoreland et al. |
| 2011/0233148 A1 | 9/2011 | Antonchuk et al. |
| 2011/0242535 A1 | 10/2011 | Frose |
| 2011/0256025 A1 | 10/2011 | Mabuchi et al. |
| 2011/0287447 A1 | 11/2011 | Norderhaug et al. |
| 2012/0053068 A1 | 3/2012 | Remacle et al. |
| 2012/0059664 A1 | 3/2012 | Georgiev et al. |
| 2012/0141339 A1 | 6/2012 | Sattler et al. |
| 2012/0142043 A1 | 6/2012 | Koyata et al. |
| 2012/0149035 A1 | 6/2012 | Burd et al. |
| 2012/0171759 A1 | 7/2012 | Williams et al. |
| 2012/0206587 A1 | 8/2012 | Oz et al. |
| 2012/0309636 A1 | 12/2012 | Gibbons et al. |
| 2013/0074614 A1 | 3/2013 | Holmes et al. |
| 2013/0078149 A1 | 3/2013 | Holmes et al. |
| 2013/0078624 A1 | 3/2013 | Holmes et al. |
| 2013/0078625 A1 | 3/2013 | Holmes et al. |
| 2013/0079599 A1 | 3/2013 | Holmes et al. |
| 2013/0080071 A1 | 3/2013 | Holmes |
| 2013/0088221 A1 | 4/2013 | Van Zon et al. |
| 2013/0156286 A1 | 6/2013 | Holmes |
| 2013/0243794 A1 | 9/2013 | Hauser |
| 2013/0244898 A1 | 9/2013 | Burd et al. |
| 2013/0252320 A1 | 9/2013 | Burd et al. |
| 2013/0274139 A1 | 10/2013 | Burd et al. |
| 2014/0030737 A1 | 1/2014 | Holmes et al. |
| 2014/0038206 A1 | 2/2014 | Holmes et al. |
| 2014/0045170 A1 | 2/2014 | Patel et al. |
| 2014/0057770 A1 | 2/2014 | Holmes et al. |
| 2014/0073043 A1 | 3/2014 | Holmes |
| 2014/0081665 A1 | 3/2014 | Holmes |
| 2014/0170688 A1 | 6/2014 | Matje et al. |
| 2014/0170691 A1 | 6/2014 | Ingber et al. |
| 2014/0170735 A1 | 6/2014 | Holmes |
| 2014/0186238 A1 | 7/2014 | Holmes et al. |
| 2014/0193892 A1 | 7/2014 | Mohan et al. |
| 2014/0229955 A1 | 8/2014 | Holmes et al. |
| 2014/0234949 A1 | 8/2014 | Wasson et al. |
| 2014/0272938 A1 | 9/2014 | Loo et al. |
| 2014/0273188 A1 | 9/2014 | Mohan et al. |
| 2014/0287955 A1 | 9/2014 | Wende et al. |
| 2014/0295439 A1 | 10/2014 | Patel |
| 2014/0295440 A1 | 10/2014 | Belhocine et al. |
| 2014/0295447 A1 | 10/2014 | Hayashizaki et al. |
| 2014/0296089 A1 | 10/2014 | Holmes et al. |
| 2014/0308661 A1 | 10/2014 | Holmes et al. |
| 2014/0335505 A1 | 11/2014 | Holmes |
| 2014/0335506 A1 | 11/2014 | Burd et al. |
| 2014/0342371 A1 | 11/2014 | Holmes |
| 2015/0031051 A1 | 1/2015 | Mohan et al. |
| 2015/0072338 A1 | 3/2015 | Holmes |
| 2015/0072362 A1 | 3/2015 | Lui et al. |
| 2015/0072889 A1 | 3/2015 | Lui et al. |
| 2015/0198588 A1 | 7/2015 | Burd et al. |
| 2015/0204788 A1 | 7/2015 | Pangarkar et al. |
| 2015/0299777 A1 | 10/2015 | Patel et al. |
| 2016/0266108 A1 | 9/2016 | Burd |
| 2016/0266158 A1 | 9/2016 | Burd |
| 2016/0266163 A1 | 9/2016 | Burd |

FOREIGN PATENT DOCUMENTS

| | | |
|---|---|---|
| CN | 101031362 A | 9/2007 |
| CN | 101128738 A | 2/2008 |
| CN | 201156031 | 11/2008 |
| EA | 007146 B1 | 8/2006 |
| EP | 0410645 A2 | 1/1991 |
| EP | 0684315 A1 | 11/1995 |
| EP | 684315 A1 | 11/1995 |
| EP | 0781987 A2 | 7/1997 |
| EP | 0488761 B1 | 1/1998 |
| EP | 0871034 A2 | 10/1998 |
| EP | 1054250 A1 | 11/2000 |
| EP | 1498067 A | 1/2005 |
| EP | 1722235 A | 11/2006 |
| EP | 0828222 B1 | 3/2010 |
| EP | 2259070 A2 | 12/2010 |
| FR | 2498331 A | 7/1982 |
| JP | 61202142 A | 9/1986 |
| JP | S61254833 A | 11/1986 |
| JP | H03181853 A | 8/1991 |
| JP | 07027700 | 1/1995 |
| JP | H07304799 A | 11/1995 |
| JP | 8122336 | 5/1996 |
| JP | H08211071 | 8/1996 |
| JP | 2000258341 A | 9/2000 |
| JP | 2001255272 A | 9/2001 |
| JP | 2002538440 A | 11/2002 |
| JP | 2004101381 A | 4/2004 |
| JP | 2005010179 A | 1/2005 |
| JP | 2005130855 A | 5/2005 |
| JP | 2005291954 A | 10/2005 |
| JP | 2007127449 A | 5/2007 |
| JP | 2007178328 A | 7/2007 |
| JP | 2007187677 A | 7/2007 |
| JP | 2010175342 A | 8/2010 |
| RU | 2147123 C1 | 3/2000 |
| RU | 2179887 C1 | 2/2002 |
| RU | 2237426 C2 | 10/2004 |
| WO | 9013668 A1 | 11/1990 |
| WO | 9215673 A1 | 9/1992 |
| WO | 9507463 A | 3/1995 |
| WO | 9508774 A2 | 3/1995 |
| WO | 9603637 A1 | 2/1996 |
| WO | 9735171 A1 | 9/1997 |
| WO | 9814605 A1 | 4/1998 |
| WO | 9826277 A2 | 6/1998 |
| WO | 9904043 A1 | 1/1999 |
| WO | 9949019 A2 | 9/1999 |
| WO | 0049176 A1 | 8/2000 |
| WO | 0244703 A2 | 6/2002 |
| WO | 02064038 A | 8/2002 |
| WO | 02093141 A1 | 11/2002 |
| WO | 2004055198 A2 | 7/2004 |
| WO | 2004059312 A1 | 7/2004 |
| WO | 2004112602 A1 | 12/2004 |
| WO | 2005025413 A2 | 3/2005 |
| WO | 2005065538 A2 | 7/2005 |
| WO | 2005072145 A2 | 8/2005 |
| WO | 2006090154 A | 8/2006 |
| WO | 2006121510 A2 | 11/2006 |
| WO | 2007002579 A | 1/2007 |
| WO | 2008050254 A1 | 5/2008 |
| WO | 2009046227 A1 | 4/2009 |
| WO | 2011106512 A | 9/2011 |
| WO | 2012040641 A | 3/2012 |
| WO | 2010090857 | 6/2012 |
| WO | 2012100235 A | 7/2012 |
| WO | 2012178069 A | 12/2012 |
| WO | 2013043203 A | 3/2013 |
| WO | 2013043204 A1 | 3/2013 |
| WO | 2013052318 A1 | 4/2013 |
| WO | 2014018805 A2 | 1/2014 |

(56) References Cited

FOREIGN PATENT DOCUMENTS

| | | |
|---|---|---|
| WO | 2014127372 A2 | 8/2014 |
| WO | 2014127379 A1 | 8/2014 |
| WO | 2015035256 A2 | 3/2015 |

OTHER PUBLICATIONS

Abbott. Procedure Manual for the i-STAT System. Rev. dated Jul. 12, 2004.
Abbott. Testing Cartridges for the i-STAT System. Rev. B. Jun. 2009. Available at http://www.abbottpointofcare.com/PDFs/17845_CrtrdgeBrochure_M1.pdf. Accessed Sep. 13, 2011.
Botstein, et al. Construction of a genetic linkage map in man using restriction fragment length polymorphisms. Am J Hum Genet. May 1980;32(3):314-31.
Di Serio, et al. Integration between the tele-cardiology unit and the central laboratory: methodological and clinical evaluation of point-of-care testing cardiac marker in the ambulance. Clin Chem Lab Med. 2006;44(6):768-73.
Guatelli, et al. Isothermal, in vitro amplification of nucleic acids by a multienzyme reaction modeled after retroviral replication. Proc. Natl. Acad. Sci. USA. 1990;87:1874-1878.
Health Buddy device. Available at http://www.3hc.org/images/2009%20images/health-buddy-appliance.gif. Accessed Aug. 26, 2011.
Health Buddy Health Management Programs. Available at http://www.bosch-telehealth.com/content/language1/img_zoom/health_buddy_system.gif. Accessed Aug. 26, 2011.
International search report and written opinion dated Jan. 18, 2012 for PCT/US2011/053189.
International Search Report and Written Opinion dated Jul. 16, 2014 for PCT/US2014/016593.
Janet Rehnquist. Enrollment and Certification Processes in the Clinical Laboratory Improvement Amendments Program.
Kwok, et al. Increasing the information content of STS-based genome maps: identifying polymorphisms in mapped STSs. Genomics. Jan. 1, 1996;31(1):123-6.
Landgren. Molecular mechanics of nucleic acid sequence amplification. Trends Genet. Jun. 1993;9(6):199-204.
Lizardi, et al. Exponential amplification of recombinant-RNA hybridization probes. BioTechnol. 1988; 6:1197-1202.
Office Action dated Jan. 11, 2012 for U.S. Appl. No. 13/244,951.
Office Action dated Jan. 27, 2012 for U.S. Appl. No. 13/244,946.
Office Action dated Jun. 18, 2012 for U.S. Appl. No. 13/244,951.
Office Action dated Jun. 20, 2012 for U.S. Appl. No. 13/244,946.
PCT Application No. PCT/US2014/016593 filed Jul. 16, 2014.
Tautz. Hypervariability of simple sequences as a general source for polymorphic DNA markers. Nucleic Acids Res. Aug. 25, 1989;17(16):6463-71.
U.S. Appl. No. 14/335,780, filed Jul. 18, 2014.
Weber, et al. Abundant class of human DNA polymorphisms which can be typed using the polymerase chain reaction. Am J Hum Genet. Mar. 1989;44(3):388-96.
Williams, et al. DNA polymorphisms amplified by arbitrary primers are useful as genetic markers. Nucleic Acids Res. Nov. 25, 1990;18(22):6531-5.
Zhao, et al. Phylogenetic distribution and genetic mapping of a (GGC)n. microsatellite from rice (Oryza sativa L). Plant Mol Biol. Feb. 1993;21(4):607-14.
Zietkiewicz, et al. Genome fingerprinting by simple sequence repeat (SSR)-anchored polymerase chain reaction amplification. Genomics. Mar. 15, 1994;20(2):176-83.
Office Action dated Nov. 17, 2014 for U.S. Appl. No. 14/335,780.
Third-Party Preissuance Submission under 37 C.F.R. 1.290 dated Nov. 13, 2013 for U.S. Appl. No. 13/768,748.
Vos, et al. AFLP: a new technique for DNA fingerprinting. Nucleic Acids Res. Nov. 11, 1995;23(21):4407-14.
Office Action dated Aug. 27, 2014 for U.S. Appl. No. 14/335,780.
Office Action dated Mar. 4, 2015 for U.S. Appl. No. 13/768,748.
Office Action dated Jul. 2, 2015 for U.S. Appl. No. 14/335,780.
Notice of Allowance dated Dec. 2, 2016 for U.S. Appl. No. 15/007,585.
Notice of Allowance dated Sep. 28, 2016 for U.S. Appl. No. 14/831,734.
Office Action dated Oct. 20, 2016 for U.S. Appl. No. 13/768,748.
Office Action dated Oct. 20, 2016 for U.S. Appl. No. 14/848,032.
Office Action dated Jan. 4, 2016 for U.S. Appl. No. 14/161,639.
Office Action dated Jan. 5, 2016 for U.S. Appl. No. 14/831,734.
Office Action dated Dec. 4, 2015 for U.S. Appl. No. 14/670,200.
Office Action dated Jan. 20, 2016 for U.S. Appl. No. 14/335,780.
Diamandis. Theranos phenomenon: promises and fallacies. Clin Chem Lab Med. Jun. 2015;53(7):989-93.
Papautsky, et al. Micromachined pipette arrays. IEEE Trans Biomed Eng. Jun. 2000;47(6):812-9.
Plebani. Evaluating and using innovative technologies: a lesson from Theranos? Clin Chem Lab Med. Jun. 2015;53 (7):961-2.
Von Lode, P. Point-of-care immunotesting: approaching the analytical performance of central laboratory methods. Clin Biochem. Jul. 2005;38(7):591-606.
U.S. Appl. No. 61/766,113, filed Feb. 18, 2013.
U.S. Appl. No. 61/766,119, filed Feb. 18, 2013.
U.S. Appl. No. 61/805,923, filed Mar. 27, 2013.
U.S. Appl. No. 61/435,250, filed Jan. 21, 2011.
U.S. Appl. No. 60/997,460, filed Oct. 2, 2007.
U.S. Appl. No. 13/896,171, filed May 16, 2013.
Voudoukis et al., 2011, Med Sci Monit, 17(4), pp. 185-188.
U.S. Appl. No. 14/050,235, filed Oct. 9, 2013.
510(k) Substantial Equivalence Determination Decision Summary dated Jul. 16, 2015 for "Theranos Herpes Simplex Virus-1 (HSV-1) IgG Assay".
510(k) Substantial Equivalence Determination issued for "Theranos Herpes Simplex Virus-1 IgG Assay" by the FDA on Jul. 7, 2015.
Fuller K. Centers for Medicare and Medicaid Services (CMS). Condition Level Deficiencies Notice—Immediate Jeopardy. Notice to Theranos, Inc. director Dr. Sunil Dhawan. Jan. 25, 2016. https://cdn2.vox-cdn.com/uploads/chorus_asset/file/59699231Theranos_Inc_Cover_Letter_01-25-2016.0.pdf.
Loria K. More skeptical than ever: Experts respond to the government's warning letter to Theranos. Jan. 28, 2016. Tech Insider http://www.techinsider/io/how-bad-the-cms-letter-to-theranos-really-is-2016-1.
Ramsey L. Theranos has a week to respond to the searing report about its business. Business Insider. Feb. 5, 2016. http://www.businessinsider.com/theranos-response-to-cms-2016-2.
Rappleye E. Theranos gets extension to fix issues following CMS investigation. Becker's Hospital Review. Feb. 8, 2016. http://www.beckershospitalreview.com/hospital-management-adminstration/theranos-gets-extension-to-fix-issues-following-cms-investigation.html.
Advisory Action dated Apr. 4, 2016 for U.S. Appl. No. 14/335,780.
Dhawan et al. Multispectral Optical Imaging of Skin-Lesions for Detection of Malignant Melanomas. Proceeding of the 31st Annual International Conference of the IEEE Engineering in Medicine and Biology Society: Engineering the Future of Biomedicine, EMBC 2009, IEEE, Sep. 3, 2009, pp. 5352-5355.
Lee et al. Integrated optical molecular imaging system for four-dimensional real-time detection in living single cells, Biosensors and Bioelectronics, Elsevier BV, NL, vol. 31 No. 1, Oct. 27, 2011, pp. 393-398.
Notice of Allowance dated Mar. 25, 2016 for U.S. Appl. No. 13/951,449.
Notice of Allowance dated Apr. 14, 2016 for U.S. Appl. No. 14/161,639.
Office Action dated Apr. 7, 2016 for U.S. Appl. No. 15/007,585.
Thompson, Fluorescence Correlation Spectroscopy, Topics in Fluorescence Spectroscopy, Jan. 1, 2002, Kluwer Academic Publishers, Boston.
Advisory Action dated Apr. 28, 2016 for U.S. Appl. No. 13/951,063.
Dzenitis, Presentation of Autonomous Pathogen Detection System, Lawrence Livermore National Laboratory, Aug. 21, 2006, Washington, DC, UCRL-PRES-22311.
Notice of Allowance dated Jul. 19, 2016 for U.S. Appl. No. 15/007,585.

(56) References Cited

OTHER PUBLICATIONS

Office Action dated Apr. 21, 2016 for U.S. Appl. No. 13/768,748.
Office Action dated May 12, 2016 for U.S. Appl. No. 14/508,137.
Office Action dated May 19, 2016 for U.S. Appl. No. 14/831,734.
Office Action dated Jun. 30, 2016 for U.S. Appl. No. 14/872,718.
Office Action dated Jul. 14, 2016 for U.S. Appl. No. 14/848,032.
Office Action based Jul. 27, 2016 for U.S. Appl. No. 14/335,780.
Office Action dated Sep. 13, 2016 for U.S. Appl. No. 14/831,734.
Office Action dated Sep. 9, 2016 for U.S. Appl. No. 14/508,137.
Office Action dated Sep. 9, 2016 for U.S. Appl. No. 15/160,491.
Office Action dated Aug. 22, 2014 for U.S. Appl. No. 13/244,950.
Office Action dated Sep. 18, 2014 for U.S. Appl. No. 14/339,946.
Office Action dated Sep. 21, 2015 for U.S. Appl. No. 14/508,137.
Office Action dated Sep. 24, 2015 for U.S. Appl. No. 14/479,245.
Office Action dated Sep. 26, 2013 for U.S. Appl. No. 13/889,674.
Office Action dated Sep. 8, 2014 for U.S. Appl. No. 13/244,956.
Okamatsu, et al. Epitope mapping of H9N2 influenza virus hemagglutinin and neuraminidase molecule. The Japanese Society of Veterinary Science, Journal of Veterinary Medical Science, Presentation Abstracts, 2004, vol. 137, p. 91, DV-05.
Queen, et al. A humanized antibody that binds to the interleukin 2 receptor. Proc. Natl. Acad. Sci. USA. 1989; 86 (24):10029-33.
Ray, et al. Distinct hemagglutinin and neuraminidase epitopes involved in antigenic variation of recent human parainfluenza virus type 2 isolates. Virus Res. Jun. 24, 1992;24(1):107-13.
Resch-Genger, Ute, et al., "Quantum dots versus organic dyes as fluorescent labels," Sep. 2008, Nature Methods, 5, pp. 763-775.
Restriction Requirement dated Aug. 1, 2013 for U.S. Appl. No. 13/916,553.
Restriction Requirement dated Aug. 26, 2013 for U.S. Appl. No. 13/916,533.
Riechmann, et al. Reshaping human antibodies for therapy. Nature. Mar. 24, 1988;332(6162):323-7.
Roskos et al. Simple System for Isothermal DNA Amplification Coupled to Lateral Flow Detection. PLOS One. Jul. 26, 2013;8(7):e69335. Print 2013.
Rouzic. Contamination-pipetting: relative efficiency of filter tips compared to Microman(R) postitive displacement pipette. Nature Methods (2006) 3 iii-iv.
Sahni et al. Reverse transcription loop-mediated isothermal amplification (RT-LAMP) for diagnosis of dengue. Med J Armed Forces India. Jul. 2013; 69(3):246-53. doi: 10.1016/j.mjafi.2012.07.017. Dec. 1, 2012.
Sakas. Trends in Medical Imaging from 2D to 3D. Computers and Graphics. 2002;26:577-587.
Singapore combined search report/examination dated Jan. 3, 2012 for Application No. 201002319.
The International Search Report and the Written Opinion dated Mar. 24, 2014 for Application No. PCT/US2013/052141.
Thermo Scientific: Thermo Scientific Heraeus Labofuge 400 and 400 R Centrifuges Great value and performance for everyday use in the lab, Jan. 1, 2008.
Tholouli, Eleni, et al., "Imaging of multiple mRNA targets using quantum dot based in situ hybridization and spectral deconvolution in clinical biopsies," Jul. 31, 2006, Biochemical and Biophysical Research Communications, 348, pp. 628-636.
U.S. Appl. No. 13/896,171, filed May 16, 2013. Inventors: Holmes, et al.
U.S. Appl. No. 14/050,235, filed Oct. 9, 2013. Inventors: Holmes, et al.
U.S. Appl. No. 14/600,630, filed Jan. 20, 2015.
U.S. Appl. No. 60/997,460, filed Oct. 2, 2007. Inventors: Burd et al.
U.S. Appl. No. 61/435,250, filed Jan. 21, 2011. Inventors: Gibbons et al.
Verhoeyen, et al. Reshaping human antibodies: grafting an antilysozyme activity. Science. 1988;239:1534-1536.
Von Lode, P. P Point-of-care immunotesting: approaching the analytical performance of central laboratory methods. Clin Biochem. Jul. 2005;38(7):591-606.
Wang Y. et al. "Methicillin resistant *Staphyloccus aureus* infection: a case report and literature review". Zhonghua Jie He Hu Xi Za Zhi, Sep. 2009; 32(9):pp. 665-659, abstract.
Wikipedia. Electric motor. Available at http://en.wikipedia.org/wiki/Electric_motor. Accessed May 22, 2012.
Wikipedia. Outrunner. Available at http://en.wikipedia.org/wiki/Outrunner. Accessed May 22, 2012.
World Health Organization (WHO) Guide to Field Operations, Oct. 2006, pp. 1-80.
Written Opinion and International Search Report dated Dec. 18, 2014 for PCT/US2014/054424.
Zimmerman O et al. C-reactive protein serum levels as an early predictor of outcome in patients with pandemic H1N1 influenza a virus infection. BMC Infect Dis. Oct. 4, 2010;10:288.
Office Action dated Jan. 3, 2012 for Application No. SG201002319-0.
Office Action dated Oct. 17, 2011 for Application No. MX/a/2010/003578.
Office Action dated Oct. 25, 2012 for Application No. SG201002319-0.
Office Action dated Nov. 12, 2014 for U.S. Appl. No. 14/479,245.
Office Action dated Nov. 12, 2015 for U.S. Appl. No. 14/562,066.
Office Action dated Nov. 15, 2012 for Application No. JP2010-528139.
Office Action dated Nov. 19, 2015 for U.S. Appl. No. 14/604,194.
Office Action dated Nov. 24, 2015 for U.S. Appl. No. 14/831,838.
Office Action dated Nov. 14, 2015 for U.S. Appl. No. 13/933,035.
Office Action dated Nov. 5, 2015 for U.S. Appl. No. 13/951,449.
Office Action dated Nov. 6, 2012 for U.S. Appl. No. 13/244,954.
Office Action dated Nov. 6, 2013 for U.S. Appl. No. 13/916,553.
Office Action dated Dec. 3, 2015 for U.S. Appl. No. 14/848,032.
Office Action dated Feb. 12, 2015 for U.S. Appl. No. 14/479,190.
Office Action dated Feb. 15, 2012 for U.S. Appl. No. 13/244,952.
Office Action dated Feb. 20, 2014 for U.S. Appl. No. 13/764,642.
Office Action dated Feb. 24, 2012 for U.S. Appl. No. 13/244,954.
Office Action dated Mar. 1, 2012 for U.S. Appl. No. 13/244,953.
Office Action dated Mar. 12, 2012 for Application No. IL204877.
Office Action dated Mar. 12, 2012 for U.S. Appl. No. 13/244,947.
Office Action dated Mar. 21, 2012 for U.S. Appl. No. 13/244,950.
Office Action dated Mar. 22, 2012 for U.S. Appl. No. 13/244,949.
Office Action dated Mar. 25, 2014 for U.S. Appl. No. 13/889,674.
Office Action dated Mar. 26, 2012 for U.S. Appl. No. 13/244,836.
Office Action dated Mar. 17, 2012 for U.S. Appl. No. 13/244,952.
Office Action dated Apr. 22, 2015 for U.S. Appl. No. 13/244,956.
Office Action dated Apr. 3, 2015 for U.S. Appl. No. 14/479,245.
Office Action dated Apr. 6, 2015 for U.S. Appl. No. 13/244,950.
Office Action dated May 6, 2015 for U.S. Appl. No. 13/951,449.
Office Action dated Jun. 12, 2015 for U.S. Appl. No. 13/326,023.
Office Action dated Jun. 12, 2015 for U.S. Appl. No. 14/161,639.
Office Action dated Jun. 19, 2015 for U.S. Appl. No. 13/647,325.
Office Action dated Jun. 21, 2011 for Application No. NZ584963.
Office Action dated Jun. 22, 2012 for Application No. EP 8836072.2.
Office Action dated Jun. 29, 2012 for Application No. CN 200880118646.2.
Office Action dated Jun. 5, 2015 for U.S. Appl. No. 14/508,137.
Office Action dated Jun. 9, 2010 for U.S. Appl. No. 12/244,723.
Office Action dated Jul. 13, 2012 for U.S. Appl. No. 13/244,836.
Office Action dated Jul. 13, 2012 for U.S. Appl. No. 13/244,956.
Office Action dated Jul. 18, 2013 for U.S. Appl. No. 13/893,258.
Office Action dated Jul. 24, 2012 for U.S. Appl. No. 13/244,947.
Office Action dated Jul. 28, 2014 for U.S. Appl. No. 13/244,949.
Office Action dated Jul. 7, 2014 for U.S. Appl. No. 13/769,779.
Office Action dated Jul. 8, 2014 for U.S. Appl. No. 13/355,458.
Office Action dated Jul. 8, 2014 for U.S. Appl. No. 14/157,343.
Office Action dated Jul. 8, 2015 for U.S. Appl. No. 13/951,063.
Office Action dated Jul. 8, 2015 for U.S. Appl. No. 14/479,241.
Office Action dated Aug. 1, 2012 for U.S. Appl. No. 13/244,949.
Office Action dated Aug. 16, 2012 for U.S. Appl. No. 13/244,950.
Office Action dated Aug. 16, 2012 for U.S. Appl. No. 13/244,953.
Advisory Action dated Sep. 25, 2015 for U.S. Appl. No. 14/479,241.
Anders et al., Am Journal Med Hyg 87(1), 2012, pp. 165-170.

(56) References Cited

OTHER PUBLICATIONS

AppliedBiosystems StepOne Real-Time PCR System Manual, Rev. 2010.
B. Rodriguez-Sanchez et al. Improved Diagnosis for Nine Viral Diseases Considered as Notifiable by the World Organization for Animal Health. Transbound Emerg Dis. Aug. 2008; 55(5-6): 215-25.
Bruggemann, et al. Production of human antibody repertoires in transgenic mice. Curr Opin Biotechnol. 1997; 8 (4):455-458.
Carter, et al. Humanization of an anti-p185HER2 antibody for human cancer therapy. Proc. Natl. Acad. Sci. USA. 1992;89(10):4285-9.
Chantreuil J. et al. "Artial chaotic tachycardia during a respiratory tract infection due to NL63 coronavirus". Arch Pediatr, Mar. 2013; 20(3):pp. 278-281, abstract.
Dapat I.C. et al. Genetic characterization of human influenza viruses in the pandemic (2009-2010) and post-pandemic (2010-2011) periods in Japan. PLoS One, 2012; 7(6):e36455.
ebm Industries, Inc. Motor Design, Quality and Performance are Critical to Reliable Operation of Fans and Blowers. pp. 15-17. emb Industries, Inc. 1995, 1996, 1997, 1999.
European search report and opinion dated Sep. 18, 2013 for Application No. 13178059.5.
European search report dated Aug. 31, 2010 for Application No. 8836072.2.
Gibbons, et al. Patient-side immunoassay system with a single-use cartridge for measuring analytes in blood. Clin Chem. Sep. 1989;35(9):1869-73.
Gill, et al. Nucleic acid isothermal amplification technologies: a review. Nucleosides, Nucleotides and Nucleic Acids. Mar. 2008; 27(3):224-43.
Griffiths, et al. Strategies for selection of antibodies by phage display. Curr Opin Biotechnol. Feb. 1998;9(1):102-8.
Hung et al. Effect of clinical and virological parameters on the level of neutralizing antibody against pandemic influenza A virus H1N1 2009. Clin Infect Dis. Aug. 1, 2010;51(3):274-9.
International Search Report and Written Opinion dated Jan. 16, 2014 for Application No. PCT/US2013/061485.
International search report and written opinion dated Jan. 20, 2012 for PCT/US2011/053188.
International search report and written opinion dated Nov. 5, 2012 for PCT/US2012/057093.
International search report and written opinion dated Feb. 6, 2013 for PCT/US2012/057155.
International Search Report and Written Opinion dated Jun. 19, 2014 for PCT/US2014/016997.
International search report and written opinion dated Aug. 3, 2012 for PCT/US2012/022130.
International Search Report and Written Opinion dated Sep. 11, 2014 for Application No. PCT/US2014/016962.
International search report and written opinion dated Sep. 16, 2008 for PCT/US2007/009878.
International search report dated Dec. 5, 2008 for PCT Application No. US2008/78636.
Jones, et al. Replacing the complementarity-determining regions in a human antibody with those from a mouse. Nature. 1986;321:522-525.
Kautner et al., Journal of Pediatrics, 1997, 131, pp. 516-524.
Khan, et al. Detection of influenza virus neuraminidase-specific antibodies by an enzyme-linked immunosorbent assay. J Clin Microbiol. Jul. 1982;16(1): 115-22.
Kimura Y et al. Tail variation of the folding primer effects the SmartAmp2 process differently. Biochem Biophys Res Commun. Jun. 12, 2009;383(4):455-9.
Lee, et al. Nucleic Acid Amplification Technologies. 1997. (Textbook).
Li, Peng. (2012) Microfluidics for IVD: in Pursuit of the Holy Grail. J Bioengineer & Biomedical Sci S8:e001.
Little, et al. Of mice and men: hybridoma and recombinant antibodies. Immunol Today. Aug. 2000;21(8):364-70.
Lounsbury et al., Lab Chip, 2013, 13, pp. 1384-1393.
Luk F.O. et al. A case of dengue maculopathy with spontaneous recovery. Case Rep Ophthalmol, Jun. 8, 2013;4(2):pp. 28-33.
Notice of Allowance dated Nov. 20, 2015 for U.S. Appl. No. 13/244,956.
Notice of Allowance dated Dec. 15, 2014 for U.S. Appl. No. 14/339,946.
Notice of Allowance dated May 29, 2015 for U.S. Appl. No. 14/480,960.
Notice of Allowance dated May 6, 2015 for U.S. Appl. No. 13/893,258.
Notice of Allowance dated Aug. 11, 2014 for U.S. Appl. No. 13/244,954.
Notice of Allowance issued for U.S. Appl. No. 13/916,553 on Dec. 20, 2013.
Obryadina A.P. et al, "Avidnost antitel v diagnostike infektsionnykh zabolevaniy" Laboratornaya diagnostika infektsionnykh zabolevaniy, 2007, No. 4, p. 3-7.
O'Connor, et al. Humanization of an antibody against human protein C and calcium-dependence involving framework residues. Protein Eng. 1998; 11(4):321-8.
Office Action dated Jan. 13, 2015 for U.S. Appl. No. 13/647,325.
Office Action dated Jan. 14, 2014 for U.S. Appl. No. 13/893,258.
Office Action dated Jan. 19, 2011 for U.S. Appl. No. 12/244,723.
Office Action dated Jan. 19, 2012 for U.S. Appl. No. 13/244,956.
Office Action dated Jan. 23, 2013 for U.S. Appl. No. 13/355,458.
Office Action dated Jan. 24, 2012 for Application No. MX/a/2010/003578.
Office Action dated Jan. 29, 2015 for U.S. Appl. No. 13/893,258.
Office Action dated Jan. 29, 2015 for U.S. Appl. No. 14/479,241.
Office Action dated Jan. 3, 2017 for U.S. Appl. No. 15/160,578.
Office Action dated Dec. 28, 2016 for U.S. Appl. No. 14/872,718.
Office Action dated Dec. 30, 2016 for U.S. Appl. No. 14/848,084.
Office Action dated Dec. 15, 2016 for U.S. Appl. No. 14/335,780.

\* cited by examiner

SYSTEMS AND METHODS FOR COLLECTING AND TRANSMITTING ASSAY RESULTS

CROSS-REFERENCE

This application is: a continuation-in-part of, and claims priority to, U.S. patent application Ser. No. 13/244,946, filed Sep. 26, 2011, now U.S. Pat. No. 8,380,541, which is a continuation-in-part of, and claims priority to, Patent Cooperation Treaty Application No. PCT/US11/53189, filed Sep. 25, 2011; a continuation-in-part of, and claims priority to, U.S. patent application Ser. No. 13/244,947, filed Sep. 26, 2011, now U.S. Pat. No. 8,435,738, which is a continuation-in-part of, and claims priority to, Patent Cooperation Treaty Application No. PCT/US2011/53188, filed Sep. 25, 2011; a continuation-in-part of, and claims priority to, Patent Cooperation Treaty Application No. PCT/US2012/57155; a continuation-in-part of, and claims priority to, U.S. patent application Ser. No. 13/244,949, filed Sep. 26, 2011; a continuation-in-part of, and claims priority to, U.S. patent application Ser. No. 13/244,950, filed Sep. 26, 2011; a continuation-in-part of, and claims priority to, U.S. patent application Ser. No. 13/244,951, filed Sep. 26, 2011, now abandoned; a continuation-in-part of, and claims priority to, U.S. patent application Ser. No. 13/244,952, filed Sep. 26, 2011, now U.S. Pat. No. 8,475,739, which is a continuation-in-part of, and claims priority to, Patent Cooperation Treaty Application No. PCT/US2011/53188, filed Sep. 25, 2011; a continuation-in-part of, and claims priority to, U.S. patent application Ser. No. 13/244,953, filed Sep. 26, 2011; a continuation-in-part of, and claims priority to, U.S. patent application Ser. No. 13/244,954, filed Sep. 26, 2011; and a continuation-in-part of, and claims priority to, U.S. patent application Ser. No. 13/244,956, filed Sep. 26, 2011, all of which applications and patents are hereby incorporated by reference herein in their entireties.

BACKGROUND OF THE INVENTION

Existing systems and methods for clinical testing suffer many drawbacks from the perspectives of patients, health care professionals, and taxpayers or insurance companies. Today, consumers can purchase certain specialized tests from various locations for consumer use. For example, a consumer can purchase a pregnancy test at a pharmacy and review the results. However, such results are to be viewed by the consumer, and are not to be relied on by the consumer's physician in forming a screening, diagnosis or treatment plan.

Additionally, if a test result is to be conducted and to be relied on by a doctor, physical samples are transported to a laboratory where the tests on the samples are performed. For example, blood from a fingerstick or venous draw is typically collected from a subject at a hospital or physician's office. The blood sample is shipped to a Clinical Laboratory Improvement Amendments (CLIA) certified laboratory which performs the tests and analysis that is provided to the patient's doctor. Such techniques are cumbersome and cause significant delay in providing the result of a test ordered by a physician, especially because the physical specimens must be transported to a different site for analysis. Moreover, the sample collection sites often have limited hours which further causes inconvenience to patients.

Conventional techniques are also problematic for certain diagnoses. Some tests are time sensitive, and the results of which may take days or weeks to complete. In such a time, a disease can progress past the point of treatment. This impairs a medical professional's ability to provide quality care.

Traditional systems and methods also affect the integrity and quality of a clinical test due to degradation of a sample that often occurs while transporting such sample from the site of collection to the place where actual analysis of the sample is performed. For examples, analytes decay at a certain rate, and the time delay for analysis can result in loss of the sample integrity. Different laboratories also work with different qualities which can result in varying degrees of error. Each laboratory can have its own set of references that further introduce a wide range of variability in coefficients of variation. Additionally, preparation of samples by hand permit upfront human error to occur from various sample collection sites. These and other drawbacks inherent in the conventional setup make it difficult to perform longitudinal analysis with high quality.

Furthermore, the conventional techniques are typically not very cost effective. For example, delays in test results lead to delays in diagnoses and treatments that can have a deleterious effect on a patient's health. For example, a disease may progress further, resulting in the patient needing additional treatment. Payers, such as health insurance companies and taxpayers contributing to governmental health programs, end up paying more to treat problems that could have been averted with more accessible and faster clinical test results.

SUMMARY

A need exists for improved systems and methods that allow higher quality of care, more rapid and accurate screening, diagnosis and/or treatment. Specifically, there is a considerable need for sample collection, preparation and analysis. A further need exists for easily accessible sample collection sites, while permitting the analysis of data that can be relied on by a health care professional.

Systems and methods are further needed for earlier intervention and providing high quality of care with little variability and reduced human error to enable the performance of longitudinal analysis of data. Systems and methods disclosed herein meet this need and provide related advantages as well.

An aspect of the invention is directed a method of evaluating a biological sample collected from a subject, said method comprising: (a) receiving data transmitted from a device placed in or on the subject or at a retailer site, wherein the device is configured to process the biological sample by: (i) receiving the biological sample; (ii) preparing the biological sample for a subsequent qualitative and/or quantitative evaluation, to yield data necessary for the subsequent qualitative and/or quantitative evaluation of said biological sample; and (iii) transmitting electronically the data to an authorized analytical facility and/or an affiliate thereof for performance of said subsequent qualitative and/or quantitative evaluation; and (b) analyzing the data transmitted from the device, at the authorized analytical facility and/or the affiliate thereof, to provide said qualitative and/or quantitative evaluation of said biological sample.

In accordance with another aspect of the invention, a method of evaluating a biological sample collected from a subject may comprise: (a) receiving electronic data representative of an image of said biological sample and/or an image of a physical process or chemical reaction performed with said biological sample or a portion thereof, said data being transmitted from a device placed in or on the subject or at a designated sample collection site, wherein the device is configured to process the biological sample by: (i) receiving the biological sample; (ii) preparing the biological sample for a subsequent qualitative and/or quantitative evaluation, wherein said preparation yields the electronic data representative of the image of said biological sample and/or the image of the physical process or the chemical reaction; and (iii) transmitting the electronic data representative of the image to an authorized analytical facility and/or an affiliate thereof for performance of said subsequent qualitative and/or quantitative evaluation; wherein the processing generates the electronic data representative of the image necessary for the subsequent qualitative and/or quantitative evaluation of said biological sample, and (b) analyzing the electronic data representative of the image transmitted from the device, at the authorized analytical facility and/or the affiliate thereof, to provide said qualitative and/or quantitative evaluation of said biological sample.

A method of evaluating a plurality of types of biological samples collected from a subject may be provided in accordance with another aspect of the invention. The method may comprise: (a) receiving data transmitted from a device placed in or on the subject or at a designated sample collection site, wherein the device is configured to process the plurality of types of biological samples by: (i) receiving the plurality of types of biological samples; (ii) preparing the biological samples for a subsequent qualitative and/or quantitative evaluation, to yield data necessary for the subsequent qualitative and/or quantitative evaluation of said plurality of types of biological samples; and (iii) transmitting electronically the data to an authorized analytical facility and/or an affiliate thereof for performance of said subsequent qualitative and/or quantitative evaluation; and (b) analyzing the data transmitted from the device, at the authorized analytical facility and/or the affiliate thereof, to provide said qualitative and/or quantitative evaluation of said plurality of types of biological samples.

An additional aspect of the invention may be directed to a method of evaluating a biological sample collected from a subject at a designated site, said method comprising: (a) collecting and processing the biological sample at said designated site wherein the sample is collected by a device that is configured to (i) receive the biological sample; (ii) prepare the biological sample for a subsequent qualitative and/or quantitative evaluation, to yield data necessary for the subsequent qualitative and/or quantitative evaluation of said biological sample; and (iii) transmit the data to a health care provider of an authorized analytical facility and/or an affiliate thereof for performance of said subsequent qualitative and/or quantitative evaluation; and (b) transmitting the data to the authorized analytical facility and/or an affiliate thereof; and (c) analyzing the data transmitted from the device, at the authorized analytical facility and/or the affiliate thereof, to provide said qualitative and/or quantitative evaluation of said biological sample.

Also, aspects of the invention may be directed to a method of evaluating a biological sample collected from a subject, said method comprising: (a) receiving data transmitted from a device placed in or on the subject or at a designated sample collection site, wherein the device is configured to process the biological sample by (i) receiving the biological sample; (ii) preparing the biological sample for a subsequent qualitative and/or quantitative evaluation, to yield data necessary for the subsequent qualitative and/or quantitative evaluation of said biological sample; and (iii) transmitting the data to a health care provider of an authorized analytical facility and/or an affiliate thereof for performance of said subsequent qualitative and/or quantitative; and (b) analyzing the data transmitted from the device, at the authorized analytical facility and/or the affiliate thereof, to provide said qualitative and/or quantitative evaluation of said biological sample; and (c) verifying (x) whether the subject received an order from a health care professional to undertake said subsequent qualitative and/or quantitative evaluation of said biological sample, or (y) whether the order for the subsequent qualitative and/or quantitative evaluation of said biological sample is within the policy restrictions of a payer or a prescribing physician for said subsequent qualitative and/or quantitative evaluation, and/or (z) whether the subject is covered by health insurance for said qualitative and/or quantitative evaluation of the biological sample; wherein said verifying step is performed prior to, concurrently with, or after steps (a) and/or (b).

A method of performing a pathological study of a biological sample collected from a subject may be provided in accordance with another aspect of the invention. The method may comprise: (a) receiving electronic data representative of an image of said biological sample, a physical process and/or chemical reaction performed with said biological sample or a portion thereof, wherein the data is received from a device placed in or on the subject or at a designated sample collection site, wherein the device is configured to: (i) receive said biological sample; (ii) prepare the collected biological sample for a subsequent qualitative and/or quantitative evaluation, wherein said preparation yields the electronic data representative of the image of said biological sample and/or the chemical reaction; and (iii) transmit the electronic data representative of the image to a pathologist of an authorized analytical facility and/or its affiliate thereof; (b) analyzing the electronic data by the pathologist of the authorized analytical facility and/or the affiliate thereof, to provide said qualitative and/or quantitative evaluation.

Additional aspects of the invention may be directed to a method of performing a pathological study of a biological sample collected from a subject, said method comprising: (a) receiving electronic data representative of an image of said biological sample and/or a chemical reaction performed with at least one component from said biological sample from a device placed in or on the subject or at a designated sample collection site, wherein the device is configured to: (i) receive said biological sample; (ii) prepare the collected biological sample for a subsequent qualitative and/or quantitative evaluation, wherein said preparation yields the electronic data representative of the image of said biological sample and/or the chemical reaction; and (iii) transmit the electronic data representative of the image to a pathologist of an authorized analytical facility; (b) analyzing the electronic data by the pathologist of the authorized analytical facility to provide said subsequent qualitative and/or quantitative evaluation.

Furthermore, aspects of the invention may be directed to a method of evaluating a biological sample collected from a subject, said method comprising: (a) receiving data transmitted from a device placed in or on the subject or at a designated sample collection site, wherein the device is configured to process the biological sample by: (i) receiving the biological sample; (ii) preparing the biological sample for a subsequent qualitative and/or quantitative evaluation, to yield data necessary for the subsequent qualitative and/or quantitative evaluation of said biological sample; and (iii) transmitting electronically the data to an authorized analytical facility and/or an affiliate thereof; (b) analyzing the data transmitted from the device, at the authorized analytical facility and/or the affiliate thereof, to provide said subsequent qualitative and/or quantitative evaluation of said biological sample.

Additional aspects of the invention may be directed to a method of evaluating a biological sample collected from a subject, said method comprising: (a) receiving data transmitted from a device placed in or on the subject or at a retailer site, wherein the device is configured to process the biological sample by: (i) receiving the biological sample; (ii) preparing the biological sample for a subsequent qualitative and/or quantitative evaluation, to yield data necessary for the subsequent qualitative and/or quantitative evaluation of said biological sample; and (iii) transmitting electronically the data to an authorized analytical facility and/or an affiliate thereof; and (b) analyzing the data transmitted from the device, at the authorized analytical facility and/or the affiliate thereof, to provide said subsequent qualitative and/or quantitative evaluation of said biological sample.

In accordance with additional aspects of the invention, a method of evaluating a biological sample may comprise: (a) processing, with the aid of a device, a biological sample collected from a subject, wherein the device is placed in or on the subject or at a designated sample collection site, wherein the processing generates data necessary for a subsequent qualitative and/or quantitative evaluation of said biological sample, and wherein the device is configured to (i) receive the biological sample; (ii) prepare the biological sample for the subsequent qualitative and/or quantitative evaluation; and (iii) transmit the data to an authorized analytical facility and/or an affiliate thereof; (b) transmitting the data from the device, at the authorized analytical facility and/or the affiliate thereof, to provide said subsequent qualitative and/or quantitative evaluation of said biological sample; and (c) verifying whether the subject has healthcare coverage, wherein said verifying step is performed prior to, concurrently with, or after steps (a) and/or (b).

A method of evaluating a biological sample collected from a subject may provided in accordance with another aspect of the invention. The method may comprise: (a) receiving electronic data representative of an image of said biological sample and/or chemical reaction performed with at least one component from said biological sample transmitted from a device placed in or on the subject or at a designated sample collection site, wherein the device is configured to process the biological sample by: (i) receiving the biological sample; (ii) preparing the biological sample for a subsequent qualitative and/or quantitative evaluation, wherein said preparation yields the electronic data representative of the image of said biological sample and/or the chemical reaction; and (iii) transmitting the electronic data representative of the image to an authorized analytical facility and/or an affiliate thereof; wherein the processing generates the electronic data representative of the image necessary for the subsequent qualitative and/or quantitative evaluation of said biological sample, and (b) analyzing the electronic data representative of the image transmitted from the device, at the authorized analytical facility and/or the affiliate thereof, to provide said subsequent qualitative and/or quantitative evaluation of said biological sample.

Additional aspects may be directed to a method of evaluating a biological sample collected from a subject, said method comprising: (a) receiving data transmitted from a device placed in or on the subject or at a designated sample collection site, wherein the device is configured to process the biological sample by (i) receiving the biological sample; (ii) preparing the biological sample for a subsequent qualitative and/or quantitative evaluation, to yield data necessary for the subsequent qualitative and/or quantitative evaluation of said biological sample; and (iii) transmitting the data to a health care provider of an authorized analytical facility and/or an affiliate thereof; and (b) analyzing the data transmitted from the device, at the authorized analytical facility and/or the affiliate thereof, to provide said subsequent qualitative and/or quantitative evaluation of said biological sample (c) verifying whether the subject received an order from a health care professional to undertake said subsequent qualitative and/or quantitative evaluation of said biological sample, wherein said verifying step is performed prior to, concurrently with, or after steps (a) and/or (b).

Also, aspects of the invention may be directed to a method of evaluating a biological sample, said method comprising: (a) processing, with aid of a device, a biological sample collected from a subject having received an order for undertaking a subsequent qualitative and/or quantitative evaluation of the biological sample, wherein the device is placed in or on the subject or at a designated sample collection site, wherein the processing generates data necessary for the subsequent qualitative and/or quantitative evaluation of said biological sample, and wherein the device is configured to (i) receive the biological sample; (ii) prepare the biological sample for a subsequent qualitative and/or quantitative evaluation; and (iii) transmit the data to an authorized analytical facility and/or an affiliate thereof; (b) transmitting the data from the device, for analysis at the authorized analytical facility and/or the affiliate thereof, to provide said subsequent qualitative and/or quantitative evaluation of said biological sample; and (c) verifying whether the order for the subsequent qualitative and/or quantitative evaluation of said biological sample is within the policy restrictions of a payer or a prescribing physician for said subsequent qualitative and/or quantitative evaluation, wherein said verifying step is performed prior to, concurrently with, or after steps (a) and/or (b).

Another aspect of the invention provides a method of evaluating a biological sample collected from a subject, said method comprising: (a) receiving data transmitted from a device placed in or on the subject or at a designated sample collection site, wherein the device is configured to process the biological sample by: (i) receiving the biological sample; (ii) preparing the biological sample for a subsequent qualitative and/or quantitative evaluation, to yield information necessary for the subsequent qualitative and/or quantitative evaluation of said biological sample; and (iii) transmitting electronically the data to an authorized analytical facility and/or an affiliate thereof; and (b) analyzing the data transmitted from the device, at the authorized analytical facility and/or the affiliate thereof, to provide said subsequent qualitative and/or quantitative evaluation of said biological sample, wherein the subsequent qualitative and/or quantitative evaluation of said biological sample yields a determination of the presence or concentration of an analyte selected from one or more of the following: sodium, potassium, chloride, $TCO_2$, anion Gap, ionized calcium, glucose, urea nitrogen, creatinine, lactate, hematocrit, hemoglobin, pH, $PCO_2$, $PO_2$, $HCO_3$, base excess, $sO_2$, ACT Kaolin, ACT Celite, PT/INR, cTnI, CK-MB, or BNP.

Moreover, aspects of the invention may be directed to a method of evaluating a plurality of types of biological samples collected from a subject, said method comprising: (a) receiving data transmitted from a device placed in or on the subject or at a designated sample collection site, wherein the device is configured to process the plurality of types of biological samples by: (i) receiving the plurality of types of biological samples; (ii) preparing the biological samples for a subsequent qualitative and/or quantitative evaluation, to yield data necessary for the subsequent qualitative and/or quantitative evaluation of said plurality of types of biological samples; and (iii) transmitting electronically the data to an authorized analytical facility and/or an affiliate thereof; and (b) analyzing the data transmitted from the device, at the authorized analytical facility and/or the affiliate thereof, to provide said subsequent qualitative and/or quantitative evaluation of said plurality of types of biological samples.

In practicing any of the methods above or elsewhere herein, alone or in combination, the qualitative and/or quantitative evaluation of said biological sample may be effected without physically transporting said sample from the site where the sample is collected to an authorized analytical facility and/or an affiliate thereof.

The methods above or elsewhere herein, alone or in combination, may include methods wherein the biological sample is selected from the group consisting of blood, serum, plasma, nasal swab or nasopharyngeal wash, saliva, urine, tears, gastric fluid, spinal fluid, stool, mucus, sweat, earwax, oil, glandular secretion, cerebral spinal fluid, tissue, semen, and vaginal fluid, throat swab, breath, hair, finger nails, skin, biopsy, placental fluid, amniotic fluid, cord blood, emphatic fluids, cavity fluids, sputum, mucus, puss, micropiota, meconium, breast milk and/or other excretions.

Any of the methods above or elsewhere herein, alone or in combination, may be practiced wherein the biological sample has a volume of 250 microliters (uL) or less.

In practicing the methods described above or elsewhere herein, alone or in combination, the methods may further comprise the step of providing oversight by a health care professional of the authorized analytical facility and/or by a software program.

In some embodiments, the methods above or elsewhere herein, alone or in combination may further comprising the step of verifying insurance eligibility of said subject prior to, concurrent with or subsequent to said analysis.

The methods above or elsewhere herein, alone or in combination, may further comprise generating a report that comprises the analysis for said subject based on said qualitative and/or quantitative evaluation.

In practicing the methods above or elsewhere herein, alone or in combination, the analysis may determine presence or concentration of analyte present in the biological sample.

The methods provided above or elsewhere herein, alone or in combination, may include an analyte selected from the group consisting of protein, nucleic acid, drug, drug metabolite, gas, ions, particles, small molecules and metabolites thereof, elements, toxins, lipids, carbohydrates, prions, formed elements, and combination thereof.

A designated sample collection site may be a retailer location or a physician's office, in accordance with the practice of any of the methods described above or elsewhere herein, alone or in combination. In some embodiments when practicing any of the methods described above or elsewhere herein, alone or in combination, the designated sample collection site may be the subject's home. A designated sample collection site may be an employer site, provider office, or hospital in methods above or elsewhere herein, alone or in combination.

In practicing the methods above or elsewhere herein, alone or in combination, a further step may be provided of aggregating the data to a yield a longitudinal analysis over time.

The methods described above or elsewhere herein, alone or in combination may utilize a biological sample that is collected from a fingerstick.

In practicing the methods above or elsewhere herein, alone or in combination, in some instances, the processing of the biological sample does not involve a display of the presence or concentration level of one or more analyte selected for determination of cardiac markers, chemistries, blood gases, electrolytes, lactate, hemoglobin, coagulation or hematology.

Methods described above or elsewhere herein, alone or in combination, may include a device that is configured to verify whether the subject is covered by health insurance for said qualitative and/or quantitative evaluation of the biological sample.

The device may be configured to verify whether the subject received an order from a health care professional to undertake said qualitative and/or quantitative evaluation of the biological sample, in the practice of any of the methods above or elsewhere herein, alone or in combination.

In some embodiments, the methods above or elsewhere herein, alone or in combination, may include the device that is configured to verify the subject's identity prior to receiving the biological sample, transmitting electronically the data, or analyzing the transmitted data. In some embodiments, the verification of the subject's identity may comprise receiving a genetic signature of the subject. In some of the methods described above or elsewhere herein, alone or in combination, the genetic signature may be obtained by nucleic acid amplification of a biological sample from the subject. The verification of the subject's identity may comprise one or more biometric measurement of the subject, in the practice of the methods described above or elsewhere herein, alone or in combination. The verification of the subject's identity may be performed by an authorized technician, in some embodiments of the methods described above or elsewhere herein, alone or in combination.

In practicing the methods above or elsewhere herein, alone or in combination, the identity of the authorized technician may be verified prior to receiving the biological sample, transmitting electronically the data, or analyzing the transmitted data.

The device may be configured to receive one or more cartridge configured for the qualitative and/or quantitative evaluation ordered by a health care professional, in the practice of one or more of the methods above or elsewhere herein, alone or in combination.

In some embodiments, one or more of the methods above or elsewhere herein, alone or in combination, may provide cartridge that has one or more identifier that is readable by the device.

The methods above or elsewhere herein, alone or in combination, may further comprise receiving the identifier information from the device.

The performance of methods above or elsewhere herein, alone or in combination may further comprise the step of providing one or more protocol to said device based on the identifier information received, wherein said protocol effects the preparation of the biological sample.

In practicing methods above or elsewhere herein, alone or in combination, the device may be contained within a housing.

Methods above or elsewhere herein, alone or in combination, may comprise a qualitative and/or quantitative evaluation that involves a determination of clinical relevance of the biological sample or lack thereof.

The designated sample collection site may be a retailer location in the practice of methods above or elsewhere herein, alone or in combination. In some embodiments of the invention, including methods above or elsewhere herein, alone or in combination, the designated sample collection site is a chain store, pharmacy, supermarket, or department store. The designated sample collection site may be the subject's home in methods above or elsewhere herein, alone or in combination.

The performance of methods above or elsewhere herein, alone or in combination may comprise data that includes electronic bits representative of the sample. The data may be aggregated and may be useful for longitudinal analysis over time to facilitate screening, diagnosis, treatment, and/or disease prevention in the methods above or elsewhere herein, alone or in combination.

The biological sample in the methods above or elsewhere herein, alone or in combination, may have a volume of 250 microliters ("uL") or less. In some embodiments, the biological sample may be blood, serum, saliva, urine, tears, gastric and/or digestive fluid, stool, mucus, sweat, earwax, oil, glandular secretion, semen, or vaginal fluid in the methods above or elsewhere herein, alone or in combination. In the practice of methods above or elsewhere herein, alone or in combination, the biological sample may be a tissue sample. The methods above or elsewhere herein, alone or in combination, may include a biological sample that is collected from a fingerstick.

Methods above or elsewhere herein, alone or in combination, may further comprise generating a report based on said qualitative and/or quantitative evaluation of said biological sample. In some embodiments, the performance of one or more methods above or elsewhere herein, alone or in combination, may further comprise transmitting said report to an additional health care professional. The additional health care professional may have provided the order to the subject to undertake said qualitative and/or quantitative evaluation of said biological sample in methods above or elsewhere herein, alone or in combination. In some instances, the additional health care professional is at a different location from the authorized analytical facility in the performance of methods above or elsewhere herein, alone or in combination.

In the practice of methods above or elsewhere herein, alone or in combination, processing may include adding one or more reagent or fixatives.

In some embodiments, the data is transmitted to a cloud computing based infrastructure in methods above or elsewhere herein, alone or in combination.

Methods above or elsewhere herein, alone or in combination, may comprise an image wherein the image is a video image. The data may comprise electronic data representative of an image and/or audio signal in the practice of methods above or elsewhere herein, alone or in combination.

In the practice of methods above or elsewhere herein, alone or in combination, a payer may receive an electronic bill from the designated sample collection site.

A health care professional of the authorized analytical facility may receive an electronic payment from the designated sample collection site in the practice of one methods above or elsewhere herein, alone or in combination.

The device utilized in methods above or elsewhere herein, alone or in combination, may be configured to additionally prepare the biological sample based on at least one of: prior preparation of the biological sample, analysis of the data at the authorized analytical facility and/or the affiliate thereof.

In the performance of methods above or elsewhere herein, alone or in combination the authorized analytical facility may be separate from the sample collection site.

A preparation of a biological sample may be automated when practicing one or more of the methods above or elsewhere herein, alone or in combination.

Methods above or elsewhere herein, alone or in combination may further comprise overseeing said subsequent qualitative and/or quantitative evaluation. The overseeing step may be performed by a health care professional of the authorized analytical facility and/or by a software program in methods above or elsewhere herein, alone or in combination. In some embodiments, transmitting the data from the device may also be for oversight of said subsequent qualitative and/or quantitative evaluation in some methods above or elsewhere herein, alone or in combination. Methods above or elsewhere herein, alone or in combination, may be provided wherein the oversight is provided by the health care professional of the authorized analytical facility and/or by a software program.

The data utilized in methods above or elsewhere herein, alone or in combination, may be representative of the biological sample and/or any portion thereof. In some embodiments, the data may be representative of a preparation of the collected biological sample. The data may comprise information of one or more conditions under which a preparation of the collected biological sample occurs. The one or more conditions may comprise one or more characteristics listed from the group: amount of the biological sample, concentration of the biological sample, quality of the biological sample, temperature, or humidity.

In some of the methods above or elsewhere herein, alone or in combination, the data is representative of a reaction run by the device. The data may comprise information of the rate of the reaction. In some instances, the data may comprise information about a control reaction and a chemical reaction involving the biological sample.

In practicing methods above or elsewhere herein, alone or in combination, such methods may further comprise (c) overseeing one or more steps of (i)-(iii) to improve quality of said evaluation, wherein said overseeing is performed prior to, concurrently with, or subsequent to any of steps (i)-(iii).

Methods above or elsewhere herein, alone or in combination may further comprise (iv) overseeing one or more steps of (i)-(iii) to improve quality of said evaluation, wherein said overseeing is performed prior to, concurrently with, or subsequent to any of steps (i)-(iii).

In some embodiments, methods above or elsewhere herein, alone or in combination may be provided wherein the overseeing is of data representative of the biological sample and/or any portion thereof. The overseeing may be of data representative of the biological sample and/or any portion thereof. The overseeing may be of data representative of a preparation of the collected biological sample. In some instances, the overseeing is of data representative of a preparation of the collected biological sample. The overseeing may be of information of one or more conditions under which a preparation of the collected biological sample occurs. In methods above or elsewhere herein, alone or in combination, overseeing may be of information of one or more conditions under which a preparation of the collected biological sample occurs. The overseeing may be of data that is representative of a chemical reaction run by the device. In some embodiments, overseeing may be of data is representative of a chemical reaction run by the device.

In the performance of methods above or elsewhere herein, alone or in combination, the healthcare coverage may be provided by a health insurance company Methods above or elsewhere herein, alone or in combination may comprise the preparing step that involves one or more of the types of chemical reactions selected from immunoassay, nucleic acid assay, receptor-based assay, cytometric assay, colorimetric assay, enzymatic assay, electrophoretic assay, electrochemical assay, spectroscopic assay, chromatographic assay, microscopic assay, topographic assay, calorimetric assay, turbidmetric assay, agglutination assay, radioisotope assay, viscometric assay, coagulation assay, clotting time assay, protein synthesis assay, histological assay, culture assay, or osmolarity assay.

The device may be further configured to process the biological sample by transmitting electronically data representative of one or more biometric measurement of the subject, in accordance with methods above or elsewhere herein, alone or in combination.

In some methods above or elsewhere herein, alone or in combination, the processing of the biological sample does not encompass an analysis of the presence or concentration level of three or more analytes belonging to categories of cardiac marker, blood gas, electrolyte, lactate, hemoglobin, and coagulation factors.

In some embodiments, the processing of the biological sample does not encompass an analysis of the presence or concentration level of three or more analytes belonging to the following: sodium, potassium, chloride, $TCO_2$, anion Gap, ionized calcium, glucose, urea nitrogen, creatinine, lactate, hematocrit, hemoglobin, pH, $PCO_2$, $PO_2$, $HCO_3$, base excess, $sO_2$, ACT Kaolin, ACT Celite, PT/INR, cTnI, CK-MB, and BNP, in the practice of methods above or elsewhere herein, alone or in combination.

In the practice of some methods above or elsewhere herein, alone or in combination, the sample collection site may be one or more of the following: a hospital, clinic, military site, or subject's home.

In some embodiments, data may be displayed on the touch screen after analysis, for methods above or elsewhere herein, alone or in combination.

Methods above or elsewhere herein may include imaging data of body parts that may be done for analysis simultaneously with biochemical analyses.

An aspect of the invention may be directed to a system of evaluating a biological sample collected from a subject, said system comprising: (a) a communication unit configured to receive data from a device placed in or on the subject or at a designated sample collection site, wherein the device is configured to process the biological sample, thereby generating data necessary for a subsequent qualitative and/or quantitative evaluation of said biological sample, and wherein the device comprises (i) a sample collection unit configured to receive the biological sample; (ii) a sample preparation unit configured to prepare the biological sample for the subsequent qualitative and/or quantitative evaluation; and (iii) transmission unit configured to transmit the data to an authorized analytical facility and/or an affiliate thereof; and (b) a processor that processes said data for the qualitative and/or quantitative evaluation of said biological sample at the authorized analytical facility and/or the affiliate thereof, and wherein said processor communicates with a record database comprising one or more medical records and/or insurance information of the subject.

Additional aspects of the invention may be directed to a system of evaluating a biological sample collected from a subject, said system comprising: (a) a communication unit configured to receive data from a device placed in or on the subject or at a designated sample collection site, wherein the device is configured to process the biological sample, thereby generating data necessary for a subsequent qualitative and/or quantitative evaluation of said biological sample, and wherein the device comprises (i) a sample collection unit configured to receive the biological sample; (ii) a sample preparation unit configured to prepare the biological sample for the subsequent qualitative and/or quantitative evaluation; and (iii) transmission unit configured to transmit the data to an authorized analytical facility and/or an affiliate thereof; (b) a processor that processes said data for the subsequent qualitative and/or quantitative evaluation of said biological sample at the authorized analytical facility and/or the affiliate thereof, and wherein said processor communicates with a record database comprising one or more medical records for the subject, and/or wherein the processor communicates with a payer database comprising insurance information for the subject.

In accordance with another aspect of the invention, a system of evaluating a blood sample collected from a subject may be provided. The system may comprise: (a) a communication unit configured to receive data from a device placed in or on the subject or at a designated sample collection site, wherein the device is configured to process the blood sample, thereby generating data necessary for a subsequent qualitative and/or quantitative evaluation of said blood sample, and wherein the device comprises (i) a sample collection unit configured to receive the blood sample; (ii) a sample preparation unit configured to prepare the biological sample for the subsequent qualitative and/or quantitative evaluation, wherein the sample preparation unit permits at least one reagent to be added to the blood sample; and (iii) transmission unit configured to transmit the data to an authorized analytical facility and/or an affiliate thereof; and (b) a processor that processes said data for the subsequent qualitative and/or quantitative evaluation of said blood sample at the authorized analytical facility and/or the affiliate thereof, and wherein said processor accesses a record database comprising one or more medical records for the subject, and/or wherein the processor accesses a payer database comprising insurance information for the subject.

A system for rapid evaluation of a biological sample collected from a subject to aid in screening, diagnosis, treatment, or prevention of a disease may be provided in accordance with an additional aspect of the invention. The system may comprise: a communication unit for receiving from a device electronic data representative of an image of said biological sample and/or a chemical reaction performed with at least one component from said biological sample; said device being placed in or on the subject or at a designated sample collection site, wherein said device is for processing the biological sample thereby generating the electronic data representative of the image of said biological sample necessary for a subsequent qualitative and/or quantitative evaluation of said biological sample, and wherein the device comprises, within a housing, (i) a sample collection unit for receiving the biological sample; (ii) a sample preparation unit for preparing the biological sample for the subsequent qualitative and/or quantitative evaluation, wherein the preparation of the biological sample is automated; (iii) an imaging unit for recording an image of the biological sample and/or a chemical reaction performed with at least one component from said biological sample; and (iv) a transmission unit for transmitting the electronic data representative of the image and/or the chemical reaction; and a processor that processes said electronic data representative of the image for subsequent qualitative and/or quantitative evaluation of said biological sample.

In practicing the systems above or elsewhere herein, alone or in combination, the process may be configured to communicate with a payer database comprising the insurance information for the subject.

The systems described above or elsewhere herein, alone or in combination may include a device that is configured to receive information relating to said qualitative and/or quantitative evaluation and optionally display said information on said device.

The device may comprises a processing unit configured to verify whether the subject is covered by health insurance for said qualitative and/or quantitative evaluation of the biological sample in the practice of systems above or elsewhere herein, alone or in combination.

In some embodiments, systems above or elsewhere herein, alone or in combination may comprise a device that is configured to verify whether the subject received an order from a health care professional to undertake said qualitative and/or quantitative evaluation of the biological sample.

The processor provided in systems above or elsewhere herein, alone or in combination, may access the records database prior to providing said qualitative and/or quantitative evaluation. Optionally, the processor accesses the payer database prior to providing said qualitative and/or quantitative evaluation in systems above or elsewhere herein, alone or in combination.

Prior to providing said qualitative and/or quantitative evaluation, said systems above or elsewhere herein, alone or in combination, may determine which records database to access.

The device may be configured to receive one or more cartridge configured for the qualitative and/or quantitative evaluation ordered by a health care professional, in the practice of systems above or elsewhere herein, alone or in combination.

In some embodiments, the device is contained within a housing in systems above or elsewhere herein, alone or in combination.

In systems above or elsewhere herein, alone or in combination, the qualitative and/or quantitative evaluation may involve a determination of clinical relevance of the biological sample or lack thereof.

The designated sample collection site may be a chain store, pharmacy, supermarket, or department store in systems above or elsewhere herein, alone or in combination. In some embodiments, the designated sample collection site is the subject's home.

The systems above or elsewhere herein, alone or in combination, may comprise a biological sample that has a volume of 250 uL or less. The biological sample may be blood, serum, saliva, urine, tears, gastric and/or digestive fluid, stool, mucus, sweat, earwax, oil, glandular secretion, semen, or vaginal fluid. In some instances, the biological sample may be a tissue sample.

In some systems above or elsewhere herein, alone or in combination, the biological sample may be collected from a fingerstick.

In some embodiments, systems above or elsewhere herein may utilize a designated sample collection site that may be a retailer. A designated sample collection site may be an employer site, provider office, or hospital in systems above or elsewhere herein, alone or in combination.

An authorized analytical facility, in some systems above or elsewhere herein, alone or in combination, may be separate from the sample collection site.

A user interface may be accessible by a health care professional for said subsequent qualitative and/or quantitative evaluation and/or oversight of said subsequent qualitative and/or quantitative evaluation in systems above or elsewhere herein, alone or in combination.

In systems above or elsewhere herein, alone or in combination, a processor may further provide oversight of said subsequent qualitative and/or quantitative evaluation.

A sample preparation unit may comprise (i) a pipette, and optionally (ii) one or more of the following: centrifuge, magnetic separator, filter, vessels, containers, assay units, reagent units, heater, thermal controller, cytometer, electromagnetic source, temperature sensor, motion sensor, or sensor for electrical properties, in systems above or elsewhere herein, alone or in combination.

In some embodiments, systems above or elsewhere herein, alone or in combination may comprise an image. The image may be static. In some embodiments, the image may be a video image. Systems above or elsewhere herein, alone or in combination may include the transmission unit that is configured to transmit the electronic data representative of the image wirelessly.

In systems above or elsewhere herein, alone or in combination, data may comprise electronic data representative of the image and an audio signal.

A device in systems above or elsewhere herein, alone or in combination, may be configured to receive one or more cartridge configured for the qualitative and/or quantitative evaluation. In some embodiments, the cartridge may have one or more identifier that is readable by the device.

In some systems above or elsewhere herein, alone or in combination, at least one component may be a biological analyte made of carbohydrate, lipid, protein or a combination thereof.

In utilizing the systems above or elsewhere herein, alone or in combination, a chemical reaction may be performed without the biological sample.

In some embodiments, data may be displayed on the touch screen after analysis, for systems above or elsewhere herein, alone or in combination.

Systems above or elsewhere herein may include imaging data of body parts that may be done for analysis simultaneously with biochemical analyses.

Some aspects of the invention are directed to a method of performing a pathological study of a biological sample collected from a subject, said method comprising (a) receiving electronic data representative of an image of said biological sample and/or a chemical reaction performed with at least one component of the biological sample from a device placed in or on the subject or at a designated sample collection site, wherein the device is configured to: (i) receive said biological sample; (ii) prepare the collected biological sample for a subsequent qualitative and/or quantitative evaluation, wherein said preparation yields the electronic data representative of the image of said biological sample and/or the chemical reaction; and (iii) transmit the electronic data representative of the image to a pathologist of an authorized analytical facility; and (b) analyzing the electronic data by the pathologist of the authorized analytical facility to provide said subsequent qualitative and/or quantitative evaluation.

An aspect of the invention is directed to a method of evaluating a biological sample collected from a subject. The method comprises (a) receiving data transmitted from a device placed in or on the subject or at a designated sample collection site, wherein the device is configured to process the biological sample by: (i) receiving the biological sample;

(ii) preparing the biological sample for a subsequent qualitative and/or quantitative evaluation, to yield data necessary for the subsequent qualitative and/or quantitative evaluation of said biological sample; and (iii) transmitting electronically the data to an authorized analytical facility and/or an affiliate thereof; and (b) analyzing the data transmitted from the device, at the authorized analytical facility and/or the affiliate thereof, to provide said subsequent qualitative and/or quantitative evaluation of said biological sample. This may be in contrast to conventional devices which may only transmit results of an analysis, not data for subsequent qualitative and/or quantitative evaluation of a sample. Such conventional devices that only transmit results may not be relied upon by one or more health care professional in diagnosing, treating and/or preventing a disease for subject.

In some embodiments, the processing of the biological sample does not encompass an analysis of the presence or concentration level of three or more analytes belonging to categories of cardiac marker, blood gas, electrolyte, lactate, hemoglobin, and coagulation factors. In some instances, the processing of the biological sample does not encompass an analysis of the presence or concentration level of three or more analytes belonging to the following: sodium, potassium, chloride, $TCO_2$, anion Gap, ionized calcium, glucose, urea nitrogen, creatinine, lactate, hematocrit, hemoglobin, pH, $PCO_2$, $PO_2$, $HCO_3$, base excess, $sO_2$, ACT Kaolin, ACT Celite, PT/INR, cTnI, CK-MB, and BNP.

A method of evaluating a biological sample collected from a subject is provided in accordance with another aspect of the invention. The method comprises (a) receiving data transmitted from a device placed in or on the subject or at a retailer site, wherein the device is configured to process the biological sample by: (i) receiving the biological sample; (ii) preparing the biological sample for a subsequent qualitative and/or quantitative evaluation, to yield data necessary for the subsequent qualitative and/or quantitative evaluation of said biological sample; and (iii) transmitting electronically the data to an authorized analytical facility and/or an affiliate thereof; and (b) analyzing the data transmitted from the device, at the authorized analytical facility and/or the affiliate thereof, to provide said subsequent qualitative and/or quantitative evaluation of said biological sample.

An additional aspect of the invention is a method of evaluating a biological sample, said method comprising: (a) processing, with the aid of a device, a biological sample collected from a subject, wherein the device is placed in or on the subject or at a designated sample collection site, wherein the processing generates data necessary for a subsequent qualitative and/or quantitative evaluation of said biological sample, and wherein the device is configured to (i) receive the biological sample; (ii) prepare the biological sample for the subsequent qualitative and/or quantitative evaluation; and (iii) transmit the data to an authorized analytical facility and/or an affiliate thereof; (b) transmitting the data from the device, at the authorized analytical facility and/or the affiliate thereof, to provide said subsequent qualitative and/or quantitative evaluation of said biological sample; and (c) verifying whether the subject has healthcare coverage, wherein said verifying step is performed prior to, concurrently with, or after steps (a) and/or (b).

Another aspect of the invention is a method of evaluating a biological sample collected from a subject, said method comprising (a) receiving electronic data representative of an image of said biological sample and/or chemical reaction performed on a device, wherein the electronic data is transmitted from a device placed in or on the subject or at a designated sample collection site, wherein the device is configured to process the biological sample by: (i) receiving the biological sample; (ii) preparing the biological sample for a subsequent qualitative and/or quantitative evaluation, wherein said preparation yields the electronic data representative of the image of said biological sample and/or the chemical reaction; and (iii) transmitting the electronic data representative of the image to an authorized analytical facility and/or an affiliate thereof; wherein the processing generates the electronic data representative of the image necessary for the subsequent qualitative and/or quantitative evaluation of said biological sample; and (b) analyzing the electronic data representative of the image transmitted from the device, at the authorized analytical facility and/or the affiliate thereof, to provide said subsequent qualitative and/or quantitative evaluation of said biological sample.

A system of evaluating a biological sample collected from a subject is provided in accordance with yet another aspect of the invention. The system comprises (a) a communication unit configured to receive data from a device placed in or on the subject or at a designated sample collection site, wherein the device is configured to process the biological sample, thereby generating data necessary for a subsequent qualitative and/or quantitative evaluation of said biological sample, and wherein the device comprises (i) a sample collection unit configured to receive the biological sample; (ii) a sample preparation unit configured to prepare the biological sample for the subsequent qualitative and/or quantitative evaluation; and (iii) transmission unit configured to transmit the data to an authorized analytical facility and/or an affiliate thereof; (b) a processor that processes said data for the subsequent qualitative and/or quantitative evaluation of said biological sample at the authorized analytical facility and/or the affiliate thereof, and wherein said processor communicates with a record database comprising one or more medical records for the subject, and/or wherein the processor communicates with a payer database comprising insurance information for the subject.

Furthermore, a method of evaluating a biological sample collected from a subject is provided. The method comprises (a) receiving data transmitted from a device placed in or on the subject or at a designated sample collection site, wherein the device is configured to process the biological sample by (i) receiving the biological sample; (ii) preparing the biological sample for a subsequent qualitative and/or quantitative evaluation, to yield data necessary for the subsequent qualitative and/or quantitative evaluation of said biological sample; and (iii) transmitting the data to a health care provider of an authorized analytical facility and/or an affiliate thereof; and (b) analyzing the data transmitted from the device, at the authorized analytical facility and/or the affiliate thereof, to provide said subsequent qualitative and/or quantitative evaluation of said biological sample; and (c) verifying whether the subject received an order from a health care professional to undertake said subsequent qualitative and/or quantitative evaluation of said biological sample, wherein said verifying step is performed prior to, concurrently with, or after steps (a) and/or (b).

An additional aspect of the invention is directed to a method of evaluating a biological sample, said method comprising (a) processing, with aid of a device, a biological sample collected from a subject having received an order for undertaking a subsequent qualitative and/or quantitative evaluation of the biological sample, wherein the device is placed in or on the subject or at a designated sample collection site, wherein the processing generates data necessary for the subsequent qualitative and/or quantitative evaluation of said biological sample, and wherein the device is configured to (i) receive the biological sample; (ii) prepare the biological sample for a subsequent qualitative and/or quantitative evaluation; and (iii) transmit the data to an authorized analytical facility and/or an affiliate thereof; (b) transmitting the data from the device, for analysis at the authorized analytical facility and/or the affiliate thereof, to provide said subsequent qualitative and/or quantitative evaluation of said biological sample; and (c) verifying whether the order for the subsequent qualitative and/or quantitative evaluation of said biological sample is within the policy restrictions of a payer or a prescribing physician for said subsequent qualitative and/or quantitative evaluation, wherein said verifying step is performed prior to, concurrently with, or after steps (a) and/or (b).

A method of evaluating a biological sample collected from a subject is illustrated in accordance with an aspect of the invention. The method comprises (a) receiving data transmitted from a device placed in or on the subject or at a designated sample collection site, wherein the device is configured to process the biological sample by (i) receiving the biological sample; (ii) preparing the biological sample for a subsequent qualitative and/or quantitative evaluation, to yield information necessary for the subsequent qualitative and/or quantitative evaluation of said biological sample; and (iii) transmitting electronically the data to an authorized analytical facility and/or an affiliate thereof; and (b) analyzing the data transmitted from the device, at the authorized analytical facility and/or the affiliate thereof, to provide said subsequent qualitative and/or quantitative evaluation of said biological sample, wherein the subsequent qualitative and/or quantitative evaluation of said biological sample yields a determination of the presence or concentration of an analyte belonging selected from one or more of the following: sodium, potassium, chloride, $TCO_2$, anion Gap, ionized calcium, glucose, urea nitrogen, creatinine, lactate, hematocrit, hemoglobin, pH, $PCO_2$, $PO_2$, $HCO_3$, base excess, $sO_2$, ACT Kaolin, ACT Celite, PT/INR, cTnl, CK-MB, or BNP.

In another aspect, the invention provides a system of evaluating a blood sample collected from a subject, said system comprising (a) a communication unit configured to receive data from a device placed in or on the subject or at a designated sample collection site, wherein the device is configured to process the blood sample, thereby generating data necessary for a subsequent qualitative and/or quantitative evaluation of said blood sample, and wherein the device comprises (i) a sample collection unit configured to receive the blood sample; (ii) a sample preparation unit configured to prepare the biological sample for the subsequent qualitative and/or quantitative evaluation, wherein the sample preparation unit permits at least one reagent to be added to the blood sample; and (iii) transmission unit configured to transmit the data to an authorized analytical facility and/or an affiliate thereof; and (b) a processor that processes said data for the subsequent qualitative and/or quantitative evaluation of said blood sample at the authorized analytical facility and/or the affiliate thereof, and wherein said processor accesses a record database comprising one or more medical records for the subject, and/or wherein the processor accesses a payer database comprising insurance information for the subject.

Another method of evaluating a plurality of types of biological samples collected from a subject is provided. The method comprises (a) receiving data transmitted from a device placed in or on the subject or at a designated sample collection site, wherein the device is configured to process the plurality of types of biological samples by (i) receiving the plurality of types of biological samples; (ii) preparing the biological samples for a subsequent qualitative and/or quantitative evaluation, to yield data necessary for the subsequent qualitative and/or quantitative evaluation of said plurality of types of biological samples; and (iii) transmitting electronically the data to an authorized analytical facility and/or an affiliate thereof; and (b) analyzing the data transmitted from the device, at the authorized analytical facility and/or the affiliate thereof, to provide said subsequent qualitative and/or quantitative evaluation of said plurality of types of biological samples.

In some embodiments, the processing of the biological sample does not involve a display of the presence or concentration level of one or more analyte selected for determination of cardiac markers, chemistries, blood gases, electrolytes, lactate, hemoglobin, coagulation or hematology. In some embodiments, the processing of the biological sample does not involve a display of the presence or concentration level of three or more analytes belonging to the following: sodium, potassium, chloride, $TCO_2$, anion Gap, ionized calcium, glucose, urea nitrogen, creatinine, lactate, hematocrit, hemoglobin, pH, $PCO_2$, $PO_2$, $HCO_3$, base excess, $sO_2$, ACT Kaolin, ACT Celite, PT/INR, cTnl, CK-MB, and BNP. After the subsequent analysis, such information can be transmitted back to the device, such as for display, storage, or analysis.

Furthermore, in some embodiments, the device is configured to verify whether the subject is covered by health insurance for said qualitative and/or quantitative evaluation of the biological sample. The device can comprise a processing unit configured to verify whether the subject is covered by health insurance for said qualitative and/or quantitative evaluation of the biological sample. The device can be configured to verify whether the subject received an order from a health care professional to undertake said qualitative and/or quantitative evaluation of the biological sample.

In some instances, the processor accesses the records database prior to providing said qualitative and/or quantitative evaluation. The processor may access the payer database prior to providing said qualitative and/or quantitative evaluation. In some embodiments, prior to providing said qualitative and/or quantitative evaluation, said system determines which records database to access.

In some embodiments, the device is configured to verify the subject's identity prior to receiving the biological sample, transmitting electronically the data, or analyzing the transmitted data. The verification of the subject's identity can comprise receiving a genetic signature of the subject. The genetic signature can be obtained by nucleic acid amplification of a biological sample from the subject. The verification of the subject's identity can comprise one or more biometric measurement of the subject. The verification of the subject's identity can be performed by an authorized technician. The identity of the authorized technician can be verified prior to receiving the biological sample, transmitting electronically the data, or analyzing the transmitted data.

In accordance with some embodiments of the invention, the device can be configured to receive one or more cartridge configured for the qualitative and/or quantitative evaluation ordered by a health care professional. The device can be configured to receive one or more cartridge configured for the qualitative and/or quantitative evaluation ordered by a health care professional. The cartridge can have one or more identifier that is readable by the device. In some instances, methods are provided further comprising receiving the identifier information from the device. Such methods can also further comprise providing one or more protocol to said device based on the identifier information received, wherein said protocol effects the preparation of the biological sample. A protocol may be provided from a server wirelessly to facilitate preparation and/or processing of the biological sample. The protocol may be provided from the cloud or from any external device.

In some embodiments, the device is contained within a housing.

The qualitative and/or quantitative evaluation can involve a determination of clinical relevance of the biological sample or lack thereof.

The designated sample collection site is a retailer location in some embodiments of the invention. The designated sample collection site can be a chain store, pharmacy, supermarket, or department store. The designated sample collection site can be the subject's home.

In some embodiments, the data includes electronic bits representative of the sample. The data can be aggregated and is useful for longitudinal analysis over time to facilitate screening, diagnosis, progress treatment, and/or disease prevention. The data can also be useful and viewable for longitudinal analysis over time to facilitate screening, diagnosis, progress treatment, and/or disease prevention, as well as a better understanding of disease progression or regression, or efficacy of an intervention, including a treatment or lifestyle change.

The biological sample can have a volume of 250 uL or less. The biological sample is blood, serum, saliva, urine, tears, gastric and/or digestive fluid, stool, mucus, sweat, earwax, oil, glandular secretion, semen, or vaginal fluid. The biological sample can be a tissue sample. The biological sample can be collected from a fingerstick.

In some embodiments, a method can further comprise generating a report based on said qualitative and/or quantitative evaluation of said biological sample. The method can further comprise transmitting said report to an additional health care professional. In some instances, the additional health care professional provided the order to the subject to undertake said qualitative and/or quantitative evaluation of said biological sample. The additional health care professional can be at a different location from the authorized analytical facility.

In some embodiments, processing includes adding one or more reagent or fixatives.

The data can be transmitted to a cloud computing based infrastructure in accordance with an embodiment of the invention. The image can be a video image. The data can comprise electronic data representative of an image and/or audio signal. The cloud computing based infrastructure may be self learning. Data may be provided to a model that may refit and retune based on the data that is collected. The cloud computing based infrastructure can perform the analysis.

In some embodiments, the processor accesses the payer database. A payer can receive an electronic bill from the designated sample collection site. A health care professional of the authorized analytical facility can receive an electronic payment from the designated sample collection site.

The device can be configured to additionally prepare the biological sample based on at least one of: prior preparation of the biological sample, analysis of the data at the authorized analytical facility and/or the affiliate thereof.

In some embodiments, the authorized analytical facility is separate from the sample collection site.

The preparation of the biological sample can be automated.

Methods may be provided further comprising overseeing said subsequent qualitative and/or quantitative evaluation. The overseeing step can be performed by a health care professional of the authorized analytical facility and/or by a software program. Transmitting the data from the device can also be for oversight of said subsequent qualitative and/or quantitative evaluation. The oversight can be provided by the health care professional of the authorized analytical facility and/or by a software program. A user interface can be provided accessible by a health care professional for said subsequent qualitative and/or quantitative evaluation and/or oversight of said subsequent qualitative and/or quantitative evaluation. The processor can further provide oversight of said subsequent qualitative and/or quantitative evaluation.

In some embodiments, the data is representative of the biological sample and/or any portion thereof. The data can be representative of a preparation of the collected biological sample. The data can comprise information of one or more conditions under which a preparation of the collected biological sample occurs. One or more conditions can comprise one or more characteristics listed from the group: amount of the biological sample, concentration of the biological sample, quality of the biological sample, temperature, or humidity. The data can be representative of a reaction run by the device. The data can comprise information of the rate, quality, and/or performance of the reaction. The data can comprise information about a control reaction and a chemical reaction involving the biological sample. Collected data can be a photon as a result of a chemical reaction. Other examples of data may include electrons, photons, intensities, frequencies, colors, sounds, or temperatures.

In some embodiments, methods are provided further comprising (c) overseeing one or more steps of (i)-(iii) to improve quality of said evaluation, wherein said overseeing is performed prior to, concurrently with, or subsequent to any of steps (i)-(iii). Additionally methods are provided further comprising (iv) overseeing one or more steps of (i)-(iii) to improve quality of said evaluation, wherein said overseeing is performed prior to, concurrently with, or subsequent to any of steps (i)-(iii). The overseeing can be of data that is representative of the biological sample and/or any portion thereof. The overseeing can be of data that is representative of a preparation of the collected biological sample. The overseeing can be of information of one or more conditions under which a preparation of the collected biological sample occurs. The overseeing can be of that is data representative of a reaction run by the device. The overseeing can be of data that is representative of a reaction run that occurs within the system.

In some embodiments, healthcare coverage is provided by a health insurance company and/or employer.

In some embodiments, a preparing step involves one or more of the types of reactions selected from immunoassay, nucleic acid assay, receptor-based assay, cytometry, colorimetric assay, enzymatic assay, spectroscopic assay (e.g., mass spectrometry, infrared spectroscopy, x-ray photoelectron spectroscopy), electrophoresis, nucleic acid sequencing, agglutination, chromatography, coagulation, electrochemical assay, histology, or cell analysis, including dead and/or live cell analysis, molecular biology, chemistry, turbidmetric assay, agglutination assay, radioisotope assay, viscometric assay, coagulation assay, clotting time assay, protein synthesis assay, histological assay, culture assay, osmolarity assay, microscopic assay, topographic assay, calorimetric assay, and/or other types of assays or combinations thereof.

The device can be further configured to process the biological sample by transmitting electronically data representative of one or more biometric measurements of the subject.

In some embodiments, a sample collection site is one or more of the following: a hospital, clinic, emergency room, military site, or subject's home.

An aspect of the invention may be directed to a system for rapid evaluation of a biological sample collected from a subject to aid in screening, diagnosis, treatment, or prevention of a disease, said system comprising: a communication unit for receiving from a device electronic data representative of an image of said biological sample and/or a chemical reaction performed with at least one component from said biological sample; said device being placed in or on the subject or at a designated sample collection site, wherein said device is for processing the biological sample thereby generating the electronic data representative of the image of said biological sample necessary for a subsequent qualitative and/or quantitative evaluation of said biological sample, and wherein the device comprises, within a housing, (i) a sample collection unit for receiving the biological sample; (ii) a sample preparation unit for preparing the biological sample for the subsequent qualitative and/or quantitative evaluation, wherein the preparation of the biological sample is automated; (iii) an imaging unit for recording an image of the biological sample and/or a chemical reaction performed with at least one component from said biological sample; and (iv) a transmission unit for transmitting the electronic data representative of the image and/or the chemical reaction; and a processor that processes said electronic data representative of the image for subsequent qualitative and/or quantitative evaluation of said biological sample.

In some embodiments, the sample preparation unit may comprise (i) a pipette, and optionally (ii) one or more of the following: centrifuge, magnetic separator, filter, vessels, containers, assay units, reagent units, heater, thermal controller, cytometer, electromagnetic source, temperature sensor, motion sensor, or sensor for electrical properties.

The image may be static and/or a video image. The data may comprise electronic data representative of the image and an audio signal.

The biological sample may be selected from one or more of the following: blood, serum, saliva, urine, tears, gastric and/or digestive fluid, stool, mucus, sweat, earwax, oil, glandular secretion, semen, or vaginal fluid. In some embodiments, the biological sample has a volume of 250 uL or less. A component of a biological sample may be a biological analyte made of carbohydrate, lipid, protein or a combination thereof. A chemical reaction may be performed without the biological sample.

The transmission unit may be configured to transmit the electronic data representative of the image wirelessly.

The device may be configured to receive one or more cartridge configured for the qualitative and/or quantitative evaluation. In some embodiments, the cartridge may have one or more identifier that is readable by the device.

In accordance with another aspect of the methods, systems, and devices disclosed herein, Applicants disclose a method of evaluating a biological sample collected from a subject, said method comprising:

(a) receiving at a laboratory location data transmitted from a device having a housing, said device placed in or on the subject or at a designated sample collection site, said data comprising raw data from said biological sample, said biological sample comprising a cell, wherein the device is configured to process the biological sample within said housing by: (i) receiving the biological sample; (ii) preparing the biological sample and yielding raw data within said housing for a subsequent qualitative and/or quantitative evaluation of said biological sample, said raw data comprising (1) numerical values representative of a physical process or chemical reaction performed by the device and (2) electronic data representative of an image of a cell in said biological sample; and (iii) transmitting electronically the raw data from said sample collection site to an authorized analytical facility and/or an affiliate thereof for performance of said subsequent evaluation at said laboratory location;

(b) analyzing the raw data transmitted from the device at the authorized analytical facility and/or the affiliate thereof, to provide said evaluation of said biological sample, wherein said analysis is performed using a processor alone or in conjunction with an individual affiliated with the authorized analytical facility; and (c) providing oversight of integrity of said analysis and operation of said device such that results generated from said analysis can be utilized by a health care professional for screening, diagnosis or treatment of said subject, wherein the oversight is performed at said laboratory location using a processor alone or in conjunction with an individual affiliated with the authorized analytical facility. In embodiments, the evaluation of a biological sample is effected without physically transporting said sample from the site where the sample is collected to the authorized analytical facility or affiliate thereof. The authorized analytical facility and/or affiliate thereof may be a Clinical Laboratory Improvement Amendments (CLIA)-compliant laboratory. In embodiments, a designated sample collection site may be a retailer site, a military site, the subject's home, a health assessment location, or a health treatment location.

In embodiments of such methods, preparing the biological sample and yielding raw data within said housing may comprise transporting a reagent, the biological sample, or a portion of the biological sample, with a pipette within the housing; and may comprise centrifuging the biological sample, or a portion thereof, within the housing. In embodiments of such methods, electronic data representative of an image of a cell may include electronic data derived from an optical assessment of histology of said cell, morphology of said cell, hematology, or cell count. In embodiments of such methods, receiving data comprises may include receiving data from an image of a physical process or chemical reaction performed by the device with some or all of a biological sample. In embodiments of such methods, raw data may be yielded by more than one assay, including at least two assays selected from an immunoassay, a nucleic acid assay, a receptor-based assay, and an enzymatic assay. In embodiments, raw data may be yielded by at least three assays selected from an immunoassay, a nucleic acid assay, a receptor-based assay, and an enzymatic assay.

A biological sample may be selected from the group consisting of blood, serum, plasma, nasal swab, nasopharyngeal wash, saliva, urine, tears, gastric fluid, spinal fluid, stool, mucus, sweat, earwax, oil, glandular secretion, cerebral spinal fluid, tissue, semen, and vaginal fluid, throat swab, breath, hair, finger nails, skin, biopsy, placental fluid, amniotic fluid, cord blood, lymphatic fluids, cavity fluids, sputum, mucus, pus, microbiota, meconium, breast milk and other excretions. A biological sample may be a fluid sample having a volume of 250 μL or less.

In embodiments, the methods include evaluating a plurality of types of biological samples collected from a subject, wherein said data transmitted from said device comprises raw data from said plurality of types of biological samples, wherein at least one of said biological samples comprises a cell. In embodiments including evaluating a plurality of types of samples, yielding raw data may include yielding raw data from at least two types of biological samples and at least two assays selected from an immunoassay, a nucleic acid assay, a receptor-based assay, and an enzymatic assay. Such evaluation of a plurality of types of biological samples may be effected without physically transporting any of the samples from the site where the sample is collected to the authorized analytical facility and/or an affiliate thereof. Fluid samples of such a plurality of types of biological samples may each have a volume of 250 μL or less. In embodiments evaluating a plurality of types of samples, oversight may include the selection of analysis methodology and procedures for each of the plurality of types of biological samples.

In embodiments of these methods, oversight includes the selection of analysis methodology and procedures. In embodiments, these methods include a step of verifying insurance eligibility of said subject prior to, concurrent with or subsequent to said analysis. In embodiments, these methods include generating a report for a subject based on the evaluation.

In accordance with aspects of the methods disclosed herein, the device may be a Clinical Laboratory Improvement Amendments (CLIA)-waived device. In accordance with other aspects of the methods disclosed herein, the device may be a CLIA-compliant device, may be operated in compliance with CLIA, may be operated by a CLIA-compliant laboratory, or may be operated in a CLIA-compliant location; or may be a CLIA-certified device, may be operated by a CLIA-certified laboratory, or may be operated in a CLIA-certified location; or may be a device that has been cleared for use by the U.S. Food and Drug Administration; or may be a device that has been classified exempt by the U.S. Food and Drug Administration; or may be a device that has not been cleared or approved by any regulatory body. The device may comprise a sample processing device, or may comprise a sample processing unit. The device may comprise a device that has been classified by a regulatory body as a sample processing device, or as a sample processing unit. The device may be a sample processing device, or may comprise a sample processing unit. The device may be a device that has been classified by a regulatory body as a sample processing device, or as a sample processing unit.

In accordance with aspects of the methods disclosed herein, the authorized analytical facility and/or affiliate thereof may be a Clinical Laboratory Improvement Amendments (CLIA)-compliant laboratory, and may be a CLIA-certified laboratory. In accordance with aspects of the methods disclosed herein, the device may be operated under the control or oversight of a CLIA-compliant laboratory, and may be operated under the control or oversight of a CLIA-certified laboratory. For example, in accordance with aspects of the methods disclosed herein, the device may be a CLIA-waived device operated under the control of a CLIA-compliant or CLIA-certified laboratory. In accordance with aspects of the methods disclosed herein, the device may be a CLIA-waived device operated under the oversight of a CLIA-compliant laboratory or CLIA-certified laboratory. In accordance with other aspects of the methods disclosed herein, the device may be operated under the oversight or control of a CLIA-compliant laboratory, or a CLIA-certified laboratory, where the device may be a CLIA-compliant device or a CLIA-certified device; or may be a device that has been cleared for use by the U.S. Food and Drug Administration; or may be a device classified as exempt by the U.S. Food and Drug Administration; or may be a device that has not been cleared or approved by any regulatory body.

In accordance with another aspect of the systems, methods, and devices disclosed herein, Applicants disclose a system of evaluating a biological sample collected from a subject, the system comprising:

(a) a communication unit placed at a laboratory location configured to receive data from a device placed in or on the subject or at a designated sample collection site, wherein the device comprises a housing and is configured to process a biological sample within said housing, said biological sample comprising a cell, said processing by said device generating raw data for a subsequent qualitative and/or quantitative evaluation of said biological sample, and wherein the device comprises: (i) a sample collection unit within said housing configured to receive the biological sample; (ii) a sample preparation unit within said housing configured to prepare the biological sample and to yield raw data for the evaluation within said housing, wherein said raw data (1) comprises numerical values representative of a physical process or chemical reaction performed by the device and (2) and electronic data representative of an image of a cell in said biological sample; and a (iii) transmission unit configured to transmit the raw data from said sample collection site to an authorized analytical facility and/or an affiliate thereof at said laboratory location;

(b) a processor at said laboratory location that processes said data alone or in conjunction with an individual affiliated with the authorized analytical facility for (a) the evaluation of said biological sample at the authorized analytical facility and/or the affiliate thereof, and (b) the oversight of said integrity of evaluation and operation of said device, such that results generated from said evaluation can be utilized by a health care professional for screening, diagnosis or treatment of said subject. An authorized analytical facility may be a Clinical Laboratory Improvement Amendments (CLIA)-compliant laboratory. A designated sample collection site may be a retailer site, a military site, the subject's home, a health assessment location, or a health treatment location. Evaluation of a biological sample may be effected without physically transporting said sample from the site where the sample is collected to the authorized analytical facility or an affiliate thereof.

In embodiments, sample preparation units of such systems may include a fluid handling system comprising a pipette within the housing; and may include a centrifuge within the housing. Electronic data representative of an image of a cell in said biological sample may include electronic data derived from an optical assessment of histology or morphology of said cells, and raw data may include raw data from an image of a physical process or chemical reaction performed by the device with said biological sample or a portion thereof. Raw data may include raw data from at least two assays, or from at least three assays, selected from an immunoassay, a nucleic acid assay, a receptor-based assay, and an enzymatic assay.

In accordance with aspects of the systems disclosed herein, the device may be a Clinical Laboratory Improvement Amendments (CLIA)-waived device. In accordance with other aspects of the systems disclosed herein, the device may be a CLIA-compliant device, may be operated in compliance with CLIA, may be operated by a CLIA-compliant laboratory, or may be operated in a CLIA-compliant location; or may be a CLIA-certified device, may be operated by a CLIA-certified laboratory, or may be operated in a CLIA-certified location; or may be a device that has been cleared for use by the U.S. Food and Drug Administration; or may be a device that has been classified exempt by the U.S. Food and Drug Administration; or may be a device that has not been cleared or approved by any regulatory body.

In accordance with aspects of the systems disclosed herein, the authorized analytical facility and/or affiliate thereof may be a Clinical Laboratory Improvement Amendments (CLIA)-compliant laboratory. In accordance with aspects of the systems disclosed herein, the device may be operated under the control or oversight of a CLIA-compliant laboratory, or CLIA-certified laboratory. For example, in accordance with aspects of the systems disclosed herein, the device may be a CLIA-waived device operated under the control of a CLIA-compliant or CLIA-certified laboratory. In accordance with aspects of the systems disclosed herein, the device may be a CLIA-waived device operated under the oversight of a CLIA-compliant of CLIA-certified laboratory. In accordance with other aspects of the systems disclosed herein, the device may be operated under the oversight or control of a CLIA-compliant or CLIA-certified laboratory, where the device may be a CLIA-compliant device or CLIA-certified device; or may be a device that has been cleared for use by the U.S. Food and Drug Administration; or may be a device classified as exempt by the U.S. Food and Drug Administration; or may be a device that has not been cleared or approved by any regulatory body.

In embodiments of systems disclosed herein, a processor at a laboratory location may be configured to generate a report; may be configured to communicate with a record database comprising one or more medical records of, or insurance information for, the subject; and may be configured to communicate with a payer database comprising the insurance information for the subject.

In accordance with another aspect of the methods, systems, and devices disclosed herein, Applicants disclose a method of evaluating a biological sample collected from a subject, said method comprising: (a) transmitting protocol information from a laboratory to a device placed at a sample collection site, said device comprising a housing, wherein said protocol information identifies, updates, or comprises a protocol that governs actions performed and data collected by the device; (b) contacting a biological sample collected from a subject at said sample collection site with a first plurality of reagents selected from a second plurality of reagents according to said protocol, wherein said the number of reagents in said second plurality is greater than the number of reagents in said first plurality of reagents; (c) transmitting data from the device to the laboratory, wherein said data comprises data obtained from said biological sample within said housing of said device according to said protocol; (d) analyzing said transmitted data at said laboratory effective to provide an evaluation of said biological sample, wherein said analysis is performed using a processor at said laboratory or by an individual associated with said laboratory; and (e) providing oversight, wherein said oversight comprises oversight of integrity of said analyzing transmitted data or oversight of the operation of said device at said sample collection site, effective that results generated from analyzing transmitted data are suitable for use by a health care professional for screening, diagnosis or treatment of the subject, wherein the oversight is performed using a processor at said laboratory or by an individual associated with said laboratory. Contacting a biological sample with a first plurality of reagents may include transporting a reagent or at least a portion of a biological sample with a pipette. In embodiments, transmitted data may be obtained following centrifugation of at least a portion of a biological sample within the housing.

In embodiments, the evaluation of a biological sample is effected without physically transporting the sample from the sample collection site to the laboratory location. In embodiments, a sample collection site may be selected from the group consisting of a site in said subject, a site on said subject, a retail site, a military site, the subject's home, a health assessment location, and a health treatment location.

In embodiments, transmitting data to a laboratory may include transmitting raw data to a laboratory. In embodiments, analyzing transmitted data may be effective to determine the presence or concentration of analyte present in the biological sample, or a disease condition associated with the biological sample. In embodiments, such methods include transmitting identification information from the sample collection site to the laboratory; and include selecting or generating said protocol information transmitted from the laboratory to the device based on said identification information. A laboratory may be an authorized analytical facility, an affiliate of an authorized analytical facility, or a CLIA-compliant laboratory.

In embodiments, a device may be configured to accept a cartridge, the cartridge may include a second plurality of reagents, and may be configured to allow delivery of said first plurality of reagents to said device. A cartridge may be configured to deliver a biological sample to the device. Identification information may include subject identifying information, information based on signals generated related to the sample, information based on signals generated related to reactions performed with the sample, information based on signals detected related to the sample, information based on signals detected related to reactions performed with the sample, device identification information, cartridge identification information, component identifying information, and other information transmitted from the device.

In embodiments, a protocol may include instructions regarding one or more of: preparation of a sample; preparation of a plurality of samples; performing a chemical reaction; performing a plurality of chemical reactions; sequence of performing a plurality of chemical reactions; performing a clinical test; performing a plurality of clinical tests; sequence of performing a plurality of clinical tests; detecting the presence of an analyte; detecting the presences of a plurality of analytes; sequence of detecting the presences of a plurality of analytes; detecting the concentration of an analyte; detecting the concentrations of a plurality of analytes; sequence of detecting the concentrations of a plurality of analytes; pre-processing data; and sequence of steps in processing data. In embodiments, protocol information may be changed according to transmitted data obtained from said biological sample within said housing of said device according to said protocol.

In embodiments, a biological sample may have a volume of 250 µL or less. In embodiments, a biological sample may include cells, wherein the device is configured to process the biological sample within said housing effective to obtain raw data from the sample, raw data may include: electronic data representative of an image derived from an optical assessment of histology, morphology, kinematics, or dynamics of cells in at least a portion of said biological sample; and (2) data derived from an assay performed on at least a portion of said biological sample, wherein said assay is selected from an immunoassay, a nucleic acid assay, a receptor-based assay, an enzymatic assay, and a spectroscopic assay. In embodiments, raw data may be obtained from two or more, or from three or more, assays selected from immunoassays, nucleic acid assays, receptor-based assays, enzymatic assays, and spectroscopic assays. In embodiments, obtaining raw data may include obtaining electronic data representative of an image or images derived from two or more optical assessments selected from optical assessments of histology, morphology, kinematics, and dynamics of cells in at least a portion of said biological sample.

In embodiments, transmitting data may include transmitting data derived from a plurality of types of biological samples collected from the subject, at least one of the biological samples comprising cells.

Embodiments of the methods disclosed herein include embodiments where obtaining a sample comprises obtaining a first sample at a first time, and obtaining a subsequent sample at a subsequent time.

In embodiments, providing oversight may include providing oversight of the operation of the device by a processor at said laboratory location; and may include selection of analysis methodology and procedures used in analyzing the transmitted data. In embodiments, these methods may include verifying insurance eligibility of said subject; such verification may be performed at a time prior to, at a time concurrent with, or at a time subsequent to, said analysis.

In embodiments, methods disclosed herein may further comprise generating a report regarding said subject based on said evaluation of said biological sample.

In embodiments of methods, systems, and devices disclosed herein, a device may comprise a temperature sensor, wherein the sensor may be configured to detect and measure temperature within the device or external to the device. A temperature within the device may include a temperature of a sample, a reagent, a component of the device, a region, a surface, or a compartment within the device. In embodiments of methods, systems, and devices disclosed herein, a device may comprise a temperature control component effective to maintain a temperature in the device at a desired temperature, or within a desired temperature range. A temperature may be measured, or may be maintained, on a surface or within a region, compartment, or component of the device. In embodiments of the methods, systems, and devices disclosed herein, a device may be configured to report a temperature to a laboratory, wherein the temperature may be a temperature of a surface of the device, a temperature within the device, a temperature within a region of the device, a temperature within a compartment of the device, a temperature within a component of the device, or a temperature external to the device.

Other goals and advantages of the invention will be further appreciated and understood when considered in conjunction with the following description and accompanying drawings. While the following description may contain specific details describing particular embodiments of the invention, this should not be construed as limitations to the scope of the invention but rather as an exemplification of preferable embodiments. For each aspect of the invention, many variations are possible as suggested herein that are known to those of ordinary skill in the art. A variety of changes and modifications can be made within the scope of the invention without departing from the spirit thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1A:
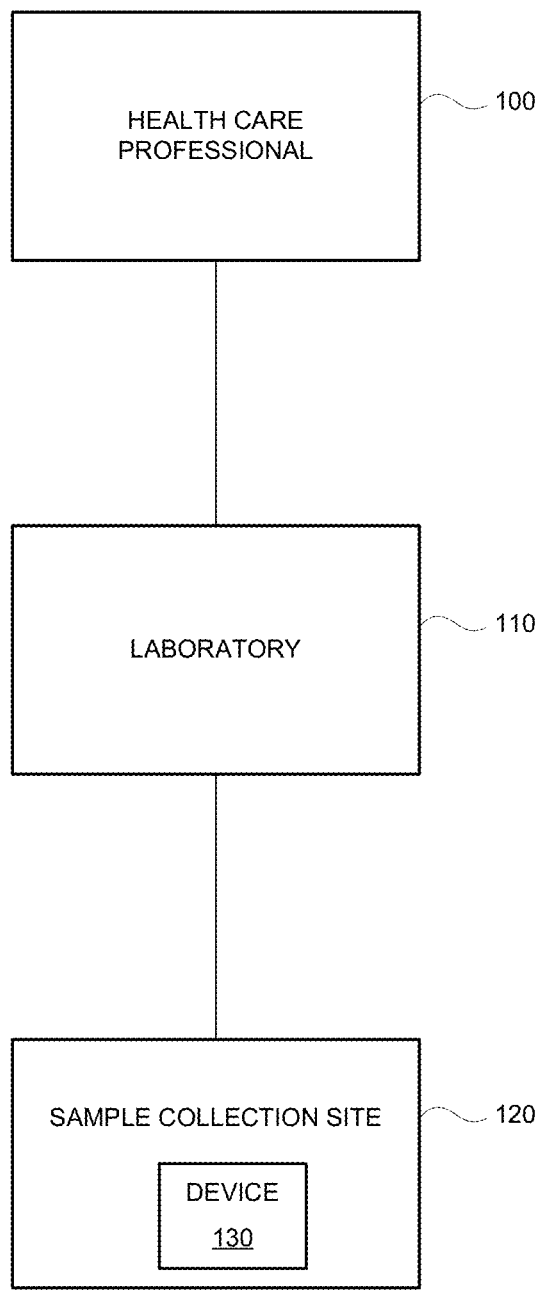
FIG. 1A shows an operation scheme involving a laboratory, a sample collection site, and a health care professional.

While preferable embodiments of the invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

The invention provides systems and methods for collecting and transmitting data relating to a sample, and often representative of the sample so that further analysis of the sample does not require physical transportation of the sample. Various aspects of the invention described herein may be applied to any of the particular applications set forth below or for any other types of diagnostic or assay systems. The invention may be applied as a standalone system or method, or as part of an integrated system, such as in a system between laboratories, health care professionals, and sample collection sites. It shall be understood that different aspects of the invention can be appreciated individually, collectively, or in combination with each other.

It must be noted that, as used in the specification and the appended claims, the singular forms "a", "an", and "the" include plural referents unless the context clearly dictates otherwise. Thus, for example, reference to "a reagent" refers to a single reagent and to multiple reagents, and reference to "an assay" refers to a single assay and to multiple assays.

As used in the description herein and throughout the claims that follow, the meaning of "in" includes "in" and "on" unless the context clearly dictates otherwise.

As used in the description herein and throughout the claims that follow, the meaning of "or" includes both the conjunctive and disjunctive unless the context expressly dictates otherwise. Thus, the term "or" includes "and/or" unless the context expressly dictates otherwise.

As used in the description herein, the term "embodiments" and the phrase "in embodiments" and linguistic variants thereof refer to exemplary features, elements, capabilities, and combinations thereof, of devices, systems, and methods as disclosed herein. Disclosure of a particular feature, or element, or capability, or particular combination of features, elements, or capabilities, is not limiting, but are illustrative of such, and may include other combinations and other aspects of such features, elements, and capabilities.

In this specification and in the claims that follow, reference will be made to a number of terms, which shall be defined to have the following meanings:

The term "analyte" and its plural and other forms, as used herein, includes without limitation drugs, prodrugs, pharmaceutical agents, drug metabolites, biomarkers such as expressed proteins and cell markers, antibodies, antigens, proteins, hormones, polypeptides, glycoproteins, polysaccharides, lipids, viruses, cholesterol, polysaccharides, nucleic acids, genes, nucleic acids, and combinations thereof.

As used herein, the term "cell count" refers to a qualitative or quantitative assessment of the number of cells in a sample, or in a volume, or in a field of view, or on a surface. An estimate of the number of cells in a sample, e.g., by absorbance of light passing through, or scattered or otherwise altered by cells in a sample; by light or other radiation emitted by cells expressing fluorescent or otherwise detectable proteins, or labeled by dyes, radionuclides, or other markers; an enumeration of the number of cells in an image (e.g., an image of a blood or urine sample, a tissue slice, or other biological sample, acquired by a camera, a microscope, or other optical imaging device), and a quantitative measurement of the number of cells adherent to a surface are all examples of a cell count.

As used herein, the term "cytometry" refers to observations, analysis, methods, and results regarding cells of a biological sample, where the cells are substantially at rest in a fluid or on a substrate. Cells detected and analysed by cytometry may be detected and measured by any optical, electrical or acoustic detector. Cytometry may include preparing and analyzing images of cells in or from a biological sample (e.g., two-dimensional images). The cells may be labeled (e.g., with fluorescent, chemiluminescent, enzymatic, or other labels) and plated (e.g., allowed to settle on a substrate) and detected. Cells may be, for example, imaged by a camera. A microscope may be used for cell imaging in cytometry; for example, cells may be imaged by a camera and a microscope, e.g., by a camera forming an image using a microscope. An image formed by, and used for, cytometry typically includes more than one cell. As used herein, the term "cytometry" refers to measurements made without substantial cell motion with respect to the device (e.g., the cells are observed and imaged while at rest with respect to a surface of the device). In this regard, the term "cytometry" as used herein is different from, and refers to different observations, analysis, methods, and results than are referred to by the more limited term "flow cytometry."

As used herein, the term "flow cytometry" refers to observations and analysis of cells, where the cells are in motion within a device, or with respect to a surface of a device. Flow cytometry typically uses a mobile liquid medium that sequentially carries individual cells to an optical, electrical or acoustic detector; e.g., in a typical flow cytometer, cells are carried by a moving fluid past a stationary detector.

As used herein, the term "microscopy" refers to the use of magnifying lenses and other optical methods to provide an image of a target, such as a cell or a plurality of cells. Microscopy typically uses optical or acoustic means to detect stationary cells, generally by recording at least one magnified image. An image formed by microscopy typically provides greater resolution than is possible when viewing the target by eye alone; for example, the image may be enlarged. Optical methods and techniques used in microscopy, in addition to the use of lenses for refraction, include the use of mirrors, prisms, filters, polarizers, gratings, grids, light sources, scanning methods and techniques (e.g., as used in confocal microscopy), special apertures (e.g., a pin-hole), and other methods.

As used herein, "spectroscopy" refers to assays and measurements using light intensity, including light intensity as a function of light wavelength to detect and assess a sample. Spectoscopy includes measurements of the reflection or transmission of electromagnetic waves, including visible, UV, and infrared light. Spectroscopy includes any and all assays that produce luminescence or change light (e.g., color chemistry). These may include one or more of the following: spectrophotometry, fluorimetry, luminometry, turbidimetry, nephelometry, refractometry, polarimetry, and measurement of agglutination.

The term "fluorimetry" as used herein refers to measuring the light emitted by a fluorescent molecule coupled to a subject upon exciting the fluorescent molecule with incident light.

As used herein, "luminometry" refers to measurements and observations that use no external illumination method, but instead detects electromagnetic radiation emitted by or from the object, chemical reaction, or area of interest. The emitted light may be weak, and thus luminometry may require the detection of low light or other radiation levels; such signals can be detected using an extremely sensitive sensor such as a photomultiplier tube (PMT). Luminometry includes assays that produce chemiluminescence, such as those using luciferases or some assays using peroxidases.

As used herein, "turbidimetry" refers to detection, measurement, or observation of a sample or reaction in a sample by backlighting the sample and components within the sample with white light, with the result being sensed by an imaging sensor. The reduction of the intensity of the transmitted light is measured (the intensity of the incident light being known). Turbidimetry may be used, for example, to determine a concentration of cells in solution. In some embodiments, turbimetry is measured by nephelometry.

As used herein, the term "nephelometry" refers to measurements of light that is transmitted or scattered after passing through a suspension, e.g., a suspension of target analytes in a solution. For example, the amount of a substrate bound to an immunoglobin such as IgM, IgG, and IgA may be measured by nephelometry.

As used herein, the term "polarimetry" refers to measurements of the polarization of light or other electromagnetic radiation following reflection, refraction, or other contact with subject object or field. Polarimetry assays include circular dichroism, which may provide structural information and light scattering assays, which may provide information about the size and/or shape of the subject. One nonlimiting example of light scattering assays uses dynamic light scattering (DLS).

As used herein, the terms "colorant" and "chromogen" refer to a compound which produces or provides a detectable change in color, absorbance, turbidity, or other optical property of a medium. Chromagens may be used to signal the occurrence, progress, or results of a chemical reaction, which may be detected and measured by colorimetric or other means (e.g., by luminometer, spectrophotometer, or other light detector).

As used herein, the terms "product formation," "colored product," "colored product formation," and the like are used to refer to the act of, and the products that result from, addition of a colorant to a solution. For example, addition of a colorant to a solution may result in a reaction effective to alter an optical property of the solution. Such a reaction may result in the formation of molecules originally not present in the solution, or may result in the aggregation of molecules or compounds previously in the solution, or may result in the degradation or other alteration of molecules or compounds previously in the solution, effective to alter the color, absorbance, and/or other optical properties of a solution to which a colorant is added.

As used herein, the terms "reflex" and "reflex testing" refer to the initiation, modification or repetition of a protocol, measurement, assay method, or analysis based on information or results obtained following an initial measurement, assay, or analysis. A reflex test may be performed where information is obtained by an initial measurement that can be supplemented by further testing, suggests that a more precise or specific test should be performed, or that an additional test should be performed for an analyte or condition related to or suggested by the initial measurement. Typically, a reflex test is performed based on the results of an initial test; the initial test is typically less sensitive, cheaper or faster than the reflex test. For example, reflex testing may occur when, after detecting a possible abnormality with an initial PAP smear, a more specific or precise test, such as one using nucleic acid analysis, may be performed to more accurately assess the subject's condition. Another example of reflex testing might include measurement of the folate level in the blood of a subject based on finding a low hematocrit level in an initial blood test.

As used herein, the terms "sample" and "biological sample" include the entire sample and include a portion, or portions, of the entire sample, unless the context clearly dictates otherwise. A "sample" may include, but is not limited to, a sample selected from the group consisting of blood, serum, plasma, a nasal swab, a nasopharyngeal wash, saliva, urine, tears, a gastric fluid, spinal fluid, stool, mucus, sweat, earwax, oil, a glandular secretion, cerebral spinal fluid, tissue, semen, vaginal fluid, a throat swab, breath, hair, finger nails, skin, biopsy tissue or fluid, placental fluid, amniotic fluid, cord blood, lymphatic fluids, cavity fluids (e.g., a fluid collected or drained from a body cavity of a subject), sputum, mucus, pus, microbiota, meconium, breast milk and other secretions and excretions.

As used herein, "processing" a sample refers to actions taken to receive, modify, test, represent, and characterize a sample, and may include diluting a sample, subjecting a sample to treatment (e.g., centrifugation, filtration, or other treatment), fractionating or separating sample constituents, contacting a sample with a reagent, staining or dying a sample, observing a sample, testing a sample, or other action, e.g., for determination of characteristics or properties of the sample, Processing a sample may include obtaining an image or representation of a sample or sample constituents, As used herein, the term "sample collection site" refers to a location at which a sample may be obtained from a subject. A sample collection site may be, for example, a retailer location (e.g., a chain store, pharmacy, supermarket, or department store), a provider office, a physician's office, a hospital, the subject's home, a military site, an employer site, or other site or combination of sites. As used herein, the term "sample collection site" may also refer to a proprietor or representative of a business, service, or institution located at, or affiliated with, the site. Thus, for example, the phrases "an electronic bill from the designated sample collection site" and "an electronic payment from the designated sample collection site" refer to a bill or payment from the proprietor, or the representative of the proprietor, located at, or affiliated with, the sample collection site.

As used herein, the terms "retailer", "retailer site, "retail site", and the like, refer to a location at which a retail operations (sales and other commercial transactions) occur. As used herein, these terms may also refer to a proprietor or representative of a business, service, or institution located at, or affiliated with, the retail site.

As used herein, the phrase "no processing of the sample by the subject or by an operator" and linguistic equivalents means that a sample, such as a blood sample, urine sample, stool sample, or other sample, may be placed directly in a container for further processing, and that no action other than those required to effect the placement of the sample in the container is required.

As used herein, "numerical values", such as, e.g., numerical values representative of a physical process or chemical reaction performed by the device, refer to output of a sensor, detector, or other component or device for measuring a physical parameter such as light intensity, absorbance of light, temperature, pH, or other parameter useful for the measurement of a physical process or chemical reaction. Such numerical values may be analog values (i.e., continuous variables) or digital values (i.e., discrete variables), and may be summed, averaged, normalized, binned, or otherwise manipulated as needed or convenient for the measurement.

As used herein, "electronic data representative of an image" refers to electronic output of a camera, microscope, charge-coupled device, or other sensor capable of providing data that can be used to form an image or a representation of an image. Where configured to form or provide an image (e.g., in arrays), sensors and components including photodiodes, photomultiplier tubes, photoelectric cells, and other light-sensitive electronic components may be used to provide, in whole or in part, electronic data representative of an image.

As used herein, the term "data" includes all information, in any form, obtained from or related to a test, measurement, or observation of a sample (including a portion of a sample)

or a reaction in which a sample participates. Data includes raw data, pre-processed data, and processed data.

As used herein, "raw data" includes signals and direct read-outs from sensors, cameras, and other components and instruments which detect or measure properties or characteristics of a sample. For example, raw data includes voltage or current output from a sensor, detector, counter, camera, or other component or device; raw data includes digital or analog numerical output from a sensor, detector, counter, camera, or other component or device; and raw data may include digitized or filtered output from a sensor, detector, counter, camera, or other component or device. For example, raw data includes the output of a luminometer, which may include output in "relative light units" which are related to the number of photons detected by the luminometer. Raw data may include a JPEG, bitmap, or other image file produced by a camera. Raw data may include cell counts; light intensity (at a particular wavelength, or at or within a range of wavelengths); a rate of change of the output of a detector; a difference between similar measurements made at two times; a number of events detected; the number of events detected within a pre-set range or that meet a pre-set criterion; the minimum value measured within a time period, or within a field of view; the maximum value measured within a time period, or within a field of view; and other data. Where sufficient, raw data may be used without further processing or analysis; typically, raw data is further processed or used for further analysis related to the sample, the subject, or for other purposes.

As used herein, "pre-processed" data includes data derived from raw data that has been baseline corrected, filtered, summed, averaged, normalized, scaled, or otherwise manipulated. Pre-processed data may include binned data, or transformed data (e.g., time domain data transformed by Fourier Transform to frequency domain), or may be combined with other data. The pre-processing may put the data into a desired form, and may involve modifying the format of data; however, data pre-processing does not perform actual data analysis or comparison with any threshold values, and does not alter the content of the data.

As used herein, "processed data" includes data and analyses resulting from combination, manipulation or analysis of raw data, pre-processed data, or other processed data. Processing may include comparison (e.g., with a baseline, threshold, standard curve, historical data, or data from other sensors), combination, mathematical manipulation or correction, curve-fitting, use of data as the basis of mathematical or other analytical reasoning (including deductive, inductive, Bayesian, or other reasoning), and other forms of processing known to those of skill in the art.

As used herein, the term "immunoassay" refers to tests which utilize antibodies (including antibody fragments) and their binding to target molecules to label, identify, quantify, or otherwise provide information regarding the presence, amounts, and properties of target molecules and samples containing them. One useful immunoassay that can be run on a device disclosed herein is an ELISA (Enzyme-Linked ImmunoSorbent Assay) Immunoassays also include, for example, competitive binding assays, sandwich assays, Western blots, and other assays utilizing antibodies and antibody fragments.

As used herein, the term "nucleic acid" refers to molecules formed of chains of nucleotides, such as deoxyribonucleic acid molecules (DNA), ribonucleic acid molecules (RNA), and including locked nucleic acids, "peptide nucleic acids" (PNA) and other nucleic acid analogs similar to, or which mimic, DNA or RNA.

As used herein, the term "nucleic acid assay" refers to any and all assays which utilize nucleic acids or which detect nucleic acids in a sample. Nucleic acids hybridize to complementary nucleic acids, a property which is useful for identifying target nucleic acids, and for identifying samples, whether fluid, tissue, or other samples, containing target nucleic acids. Nucleic acid assays use, and include, techniques for amplifying target nucleic acids (e.g., by producing copies of target nucleic acids, or copies of nucleic acids that are complementary to target nucleic acids). Nucleic acid assays include, for example, assays using polymerase chain reaction (PCR), Southern blots, Northern blots, and other assays which may identify and allow detection of nucleic acids in a sample.

As used herein, the term "receptor-based assay" refers to an assay which utilizes, or detects, the binding of a receptor to its ligand, or the dissociation of a ligand from its receptor. Such assays may use the binding directly to detect or quantify the presence or amount of a receptor or ligand, may use competitive binding techniques to detect or quantify the presence or amount of a target molecule in a sample, or may detect or quantify the presence or amount of a target by use of other methods based on binding between a receptor and ligand or ligands.

As used herein, the term "enzymatic assay" refers to an assay which utilizes, or detects, the presence or action of an enzyme. For example, an assay which provides a substrate for a target enzyme, and detects the presence of that enzyme, or quantifies the activity of that enzyme in a sample following addition of the substrate is an enzymatic assay. An assay which utilizes the enzymatic production of a detectable substance is another example of an enzymatic assay; for example, colorimetric assays (e.g., in which a detectable product is produced by an enzyme, which may be an endogenous enzyme or which may be supplied with the assay reagents) such as assays in which horseradish peroxidase or alkaline phosphatase is used to produce a colored product as an indicator of the progress of the reaction or presence of a target, are enzymatic assays.

As used herein, "Clinical Laboratory Improvement Amendments" and "CLIA" refer to sections of 42 U.S.C. Part F, e.g., subpart 2, sections 263a through 263a7, Federal Regulations 42 CFR Chapter IV (sections 493.1 to 493.2001), and related laws, regulations, and as amended. Regulations pursuant to CLIA are administered by the Centers for Medicare and Medicaid Services (CMS) of the United States Department of Health and Human Services.

As used herein, the term "CLIA-compliant" means that a device, a procedure, an operation, a laboratory, or other facility, complies with CLIA, as amended.

As used herein, the term "CLIA-certified" means a device, a procedure, an operation, a laboratory, or other facility, that has been certified, by an appropriate regulatory body empowered to do so, as compliant with CLIA, as amended.

As used herein, the term "CLIA-compliant laboratory" means a laboratory, or other facility, that complies with CLIA, as amended.

As used herein, the term "CLIA-certified laboratory" means a laboratory, or other facility, that has been certified, by an appropriate regulatory body empowered to do so, as being compliant with CLIA, as amended. A CLIA-certified laboratory is a CLIA-compliant laboratory.

As used herein, a device that is a "CLIA-compliant device" is a device that complies with CLIA, as amended, or whose use complies with CLIA, as amended.

As used herein, a "CLIA-waived device" is a device for which a certificate of waiver, under CLIA, has been issued by an appropriate regulatory body empowered to do so, as compliant with CLIA, as amended, or whose use complies with a certificate of waiver, under CLIA, issued by an appropriate regulatory body empowered to do so. A CLIA-waived device is a CLIA-compliant device.

As used herein, a "CLIA-certified device" is a device that has been certified, by an appropriate regulatory body empowered to do so, as compliant with CLIA, as amended, or whose use complies with a certification issued under CLIA by an appropriate regulatory body empowered to do so. A CLIA-certified device is a CLIA-compliant device.

As used herein, a device that has been "cleared under section 510(k) of the U.S. Food, Drug and Cosmetic Act" means a device that has been cleared by the U.S. Food and Drug Administration, or its successor, for sale or use in the United States under section 510(k) of the U.S. Food, Drug and Cosmetic Act.

As used herein, a device for which there is "no substantial equivalent under section 510(k) of the U.S. Food, Drug and Cosmetic Act" means a device for which no substantial equivalent device has been approved for sale in the United States under section 510(k) of the U.S. Food, Drug and Cosmetic Act.

As used herein, a device that has "not been cleared or approved by any regulatory body" means a device that has not received certification under CLIA, and has not been cleared by the U.S. Food and Drug Administration, or its successor, for sale or use in the United States under section 510(k) of the U.S. Food, Drug and Cosmetic Act.

As used herein, the phrase "operated under the control of a CLIA-compliant laboratory" means that the operation of a device, method, or system is being controlled by a CLIA-compliant laboratory.

As used herein, the phrase "operated under the oversight of a CLIA-compliant laboratory" means that the operation of a device, method, or system is under the oversight of a CLIA-compliant laboratory.

As used herein, the phrase "operated under the control or oversight of a CLIA-compliant laboratory" means: that the operation of a device, method, or system is being controlled by a CLIA-compliant laboratory; that the operation of a device, method, or system is under the oversight of a CLIA-compliant laboratory; or that the operation of a device, method, or system is being controlled by, and is under the oversight of, a CLIA-compliant laboratory.

FIG. 1A shows a system comprising a laboratory 110, a designated sample collection site 120, and a health care professional 100. A device 130 may be provided at the designated sample collection site. A sample collection site may be a first location, and a laboratory may be provided at a second location. The first location and the second location may be different locations. The first and second locations may be located so that they are not proximate to one another. A health care professional may be provided at a third location, although he/she may be affiliated with, employed by, or contracted by the laboratory. The third location may be a different location from the first and second locations. The third location may be located so that it is not proximate to the first or second locations. A laboratory, health care professional, and sample collection site may all be at different locations from one another. In one example, a laboratory, health care professional, and/or sample collection site may be at separate facilities. Alternatively, one or more of them may be at the same location.

A laboratory can be an entity or facility or system or device capable of performing a clinical test or analyzing collected data. A laboratory can provide controlled conditions in which scientific research, experiments, and measurement can be performed. The laboratory can be a medical laboratory or clinical laboratory where tests can be done on clinical specimens, or analysis can occur on data collected from clinical specimens, in order to get information about the health of a patient as pertaining to the screening, diagnosis, prognosis, treatment, and/or prevention of disease. A clinical specimen may be a sample collected from a subject. Preferably, a clinical specimen may be collected from the subject at a sample collection site that is at a separate facility from the laboratory, as described in further detail elsewhere herein. The clinical specimen may be collected from the subject using a device, which is placed at a designated sample collection site or in or on the subject.

In some embodiments, a laboratory may be a certified laboratory. The certified laboratory may be an authorized analytical facility. In some embodiments, authorized analytical facilities may include contracted analytical facilities. For example, a certified laboratory or other laboratory may send images to experts at another laboratory (which may be a certified laboratory) for analysis.

Any description herein of a laboratory may apply to an authorized analytical facility and vice versa. In some instances, the laboratory may be certified by a governmental agency or professional association. A laboratory may receive certification or oversight by a regulatory body. In one example, the laboratory may be certified by an entity, such as Centers for Medicare & Medicaid Services (CMS), College of American Pathologists, ISO standards 15189 or 17025 or equivalents thereof. For instance, an authorized analytical facility may be a Clinical Laboratory Improvement Amendments (CLIA) certified laboratory in the United States or its equivalent in a foreign jurisdiction.

An authorized analytical facility is typically subject to oversight or regulation. For example, a laboratory may have oversight by a board-certified entity (which may include one or more board-certified personnel). In some embodiments, oversight can include validating one or more clinical test. Oversight may also include assessing the performance of, correcting, calibrating, running controls, replicates, adjusting, or analyzing one or more clinical test. Oversight can include evaluation of one or more sets of data to provide a quality control for a clinical test. The authorized analytical facility can have one or more qualified person providing the oversight. For example, one or more pathologist or other health care professional may review data and/or analysis that is processed by the facility. At an authorized analytical facility, a trained pathologist or other certified health care professional may provide oversight. In some instances, the certified health care professional providing oversight may be one or more of the following: a doctor certified in pathology, a doctor with laboratory training or experience in the specialty areas of service for which the health care professional is responsible, or an individual with experience or laboratory training in the specialty.

The oversight may further include the certified health care professional who may establish the procedures and rules in the laboratory, deal with problems that arise, and/or train/evaluate the lab personnel. Oversight may also include selecting test methodology, verifying test procedures and establishment of laboratory's test performance characteristics, enrollment in participation in an HHS approved proficiency testing program, establishing a quality control program appropriate for the testing performed, establishing the parameters for acceptable levels of analytic performance, ensuring that those levels are maintained throughout the entire testing process, resolving technical problems and ensuring that remedial actions are taken when test systems deviate from the established performance specifications, ensuring patient test results are not reported until all corrective actions have been taken, identifying training needs and assuring that each individual performing tests receives regular in-service training and education, evaluating the competency of all testing personnel and assuring that the staff maintain their competency to perform test procedures (e.g., also procedures for evaluation of the staff: direct observation of routine test performance, monitoring the recording/reporting of results, review of intermediate test results, records, etc, observation of performance of instrument maintenance, assessment of test performance, assessment of problem solving skills), and/or evaluating and documenting the performance of individuals responsible for moderate complexity testing (e.g., semiannually during the first year; thereafter, at least annually unless test methodology or instrumentation changes). Oversight may include reviewing and/or verifying functionality of laboratory procedures or devices, and/or validity of data collected and/or generated. The oversight may assure the quality of the rest and/or put the data into a condition upon which a health care professional can rely upon it to provide a screening, diagnosis, treatment, including but not limited to prophylactic treatment. Oversight may include reviewing a test empirically. Oversight may include one or more, two or more, or any of the number of items described elsewhere herein.

In some instances, the oversight may be provided by an oversight software program rather than the certified health care professional. In some instances, one, two or more of the types of oversight provided may be implemented by an oversight software program. A combination of an oversight software program and health care professional may be employed to provide oversight. In some instances, one, two or more of the types of oversight may be implemented by a health care professional over a software program. For example, the health care professional may determine the procedures and rules associated with the software program. In some instances, the software program may be self-learning. The software program may access an increasing pool of data and/or evolving rules or procedures.

In some embodiments, the oversight software program may be provided on a device. The oversight software program may be provided at a sample collection site, on or off the device. The software program may be provided a laboratory, such as an authorized analytical facility. In some instances, the device may receive updates to the oversight software program. The updates may or may not be provided by the laboratory. The oversight software may be stored in a memory, and may include computer readable media comprising code, instructions, or logics that may be capable of executing a step.

In some instances, the oversight software may include one or more algorithm that may review a qualitative and/or quantitative evaluation of the sample that may be performed. The oversight software program may look for outliers, may determine whether the qualitative and/or quantitative evaluation was properly performed, may perform one or more comparison with records or data points, may perform statistical analysis of the evaluation, or any other oversight action as described elsewhere herein. The oversight software may be able to perform one or more calibrations and/or diagnostics.

A health care professional of an authorized analytical facility may receive and/or view data. A health care professional of an authorized analytical facility may be affiliated with or associated with the authorized analytical facility. In some instances, the health care professional may be employed by or under contract with the authorized analytical facility. The health care professional may be located at the authorized analytical facility, may be located remotely from the authorized analytical facility, or in another analytical facility (e.g., hospital, center of excellence, specialized leading path/group). In some instances, the health care professional is not required to be on-site at all times while testing is performed, or when data is received at an authorized analytical facility, but may be available on an as needed basis to provide consultation. The health care professional may be accessible to provide on-site, telephone and/or electronic consultation.

The health care professional providing oversight may be a different individual from or the same individual as the health care professional that may receive a report from the authorized analytical facility for diagnosing, treating, monitoring, or preventing a disease for the subject. For example, a pathologist of an authorized analytical facility may be a different individual from a prescribing physician of the subject. A health care professional of authorized analytical facility may be a reviewing health care professional or an overseeing health care professional. The health care professional who may receive the report may be the health care professional who has ordered the test that the subject has undertaken. A different health care professional may provide analysis, and a different health care professional may provide oversight. Alternatively, the same health care professional may provide both analysis and oversight.

A designated sample collection site may be a point of service (POS) location. Any disclosure herein of a sample collection site may also apply to a point of service location and vice versa. A point of service location where a sample may be collected from a subject or provided by a subject may be a location remote to the laboratory. The sample collection site may have a separate facility from a laboratory. The sample may or may not be collected fresh from the subject at the sample collection site. Alternatively, the sample may be collected from the subject elsewhere and brought to the sample collection site. A sample collection site at a point of service location may be a blood collection center, or any other bodily fluid collection center. The sample collection site may be a biological sample collection center. In some embodiments, a sample collection site may be a retailer. Examples of retailers are provided in further detail elsewhere herein. Other examples of sample collection sites may include hospitals, clinics, health care professionals' offices, schools, day-care centers, health centers, assisted living residences, government offices, traveling medical care units, mobile units, emergency vehicles (e.g., air, boat, ambulance), or the home. For example, a sample collection site may be a subject's home. A sample collection site may be at a sample acquisition site and/or health assessment and/or treatment locations (which may include any of the sample collection sites described elsewhere herein including but not limited to emergency rooms, doctors' offices, urgent care, tents for screening (which may be in remote locations), a health care professional walking into someone's house to provide home care). A sample collection site may be any location where a sample from the subject is received by the device. Any location may be designated as a sample collection site. The designation may be made by any party, including but not limited to the laboratory, entity associated with the laboratory, governmental agency, or regulatory body. Any description herein relating to sample collection site or point of service may relate to or be applied to retailers, hospitals, clinics, or any other examples provided herein and vice versa.

A device may be provided at the sample collection site. The device may be configured to accept a sample. The device may be referred to as a sample collection device. The device may also be referred to as a sample processing device. The device may also be referred to as a reader device. Any description of a reader device may apply to any device that may be capable of receiving a sample and/or processing the sample. The device may accept a sample collected from a subject at the sample collection site, or that the subject or subject's proxy brings to the service location. The device may directly collect the sample from the subject, or an intermediate device or technique may be used to collect the sample from the subject. Examples of collection techniques and mechanisms are described in greater detail elsewhere herein.

In some instances, the device may be placed in or on a subject. For example, a device may be ingested by a subject (see e.g. U.S. Patent Publication No. 2006/0182738, U.S. Patent Publication No. 2006/0062852, U.S. Patent Publication No. 2005/0147559, U.S. Patent Publication No. 2010/0081894, which are hereby incorporated by reference in their entirety). The device may be a pill or have another format that may pass through the digestive tract of a subject. The device may be implanted within the subject. For example, the device may be subcutaneously implanted within the subject. In another example, the device may be worn by the subject. The device may be attached to the subject via strap, adhesive, integrated into clothing, or any other technique. The device may comprise one or more needle or microneedle that may penetrate the skin of the subject. The device may be a patch that may be worn by the patient. The device may include an automated lancing cartridge. The cartridge may be disposable. One or more disposable component may be used to collect a sample from a subject. The disposable component may provide the sample to a non-disposable device. Alternatively, the disposable component may be the sample processing device.

The device may receive a sample from the subject at one time. Alternatively, the device may periodically receive a sample from the subject. This may be at regularly scheduled intervals or in response to one or more detected conditions. The device may optionally administer therapy to the subject. The device may administer one or more therapeutic agent to the subject. The therapeutic agent may be administered at scheduled intervals or in response to one or more detected conditions. The therapeutic agent may be administered in response to one or more detected conditions from the sample.

In some instances, the device may be provided to a subject at a designated sample collection site. Alternatively, the subject may obtain or come into contact with the device at any other location.

Examples of samples may include various fluid or solid samples. In some instances, the sample can be a bodily fluid sample from the subject. The sample can be an aqueous or gaseous sample. In some instances, solid or semi-solid samples can be provided. The sample can include tissues and/or cells collected from the subject. The sample can be a biological sample. Examples of biological samples can include but are not limited to, blood, serum, plasma, a nasal swab, a nasopharyngeal wash, saliva, urine, gastric fluid, spinal fluid, tears, stool, mucus, sweat, earwax, oil, a glandular secretion, cerebral spinal fluid, tissue, semen, vaginal fluid, interstitial fluids derived from tumorous tissue, ocular fluids, spinal fluid, a throat swab, breath, hair, finger nails, skin, biopsy, placental fluid, amniotic fluid, cord blood, lymphatic fluids, cavity fluids, sputum, pus, microbiota, meconium, breast milk and/or other excretions. The samples may include nasopharyngeal wash. Nasal swabs, throat swabs, stool samples, hair, finger nail, ear wax, breath, and other solid, semi-solid, or gaseous samples may be processed in an extraction buffer, e.g., for a fixed or variable amount of time, prior to their analysis. The extraction buffer or an aliquot thereof may then be processed similarly to other fluid samples if desired. Examples of tissue samples of the subject may include but are not limited to, connective tissue, muscle tissue, nervous tissue, epithelial tissue, cartilage, cancerous sample, or bone. The sample may be provided from a human or animal. The sample may be provided from a mammal, vertebrate, such as murines, simians, humans, farm animals, sport animals, or pets. The sample may be collected from a living or dead subject. The sample may be collected fresh from a subject or may have undergone some form of pre-processing, storage, or transport.

One or more, two or more, three or more, four or more, five or more, six or more, seven or more, eight or more, ten or more, twelve or more, fifteen or more, or twenty or more different types of samples may be collected from a subject. A single type of sample or a plurality of types of samples may be collected from the subject simultaneously or at different times. A single type of sample or a plurality of types of samples may be received or capable of being received by the device simultaneously or at different times. A plurality of types of samples may be processed by the device in parallel and/or in sequence. For example, a device may be capable of receiving both a bodily fluid and a tissue, or a stool sample and a bodily fluid. In another example, a device may be capable of receiving a plurality of types of bodily fluids, such as blood and urine. For example, the device may be capable of receiving one or more type, two or more type, three or more types, four or more types, five or more types, six or more types, seven or more types, eight or more types, ten or more types, or twenty or more types of bodily fluid.

Different collection mechanisms or the same collection mechanism of a device may be used to collect a plurality of types of samples.

A subject may provide a sample, and/or the sample may be collected from a subject. A subject may be a human or animal. The subject may be a mammal, vertebrate, such as murines, simians, humans, farm animals, sport animals, or pets. The subject may be living or dead. The subject may be a patient, clinical subject, or pre-clinical subject. A subject may be undergoing screening, diagnosis, treatment, monitoring and/or disease prevention. The subject may or may not be under the care of a health care professional. The subject may be a person of any age, an infant, a toddler, an adult or an elderly.

Any volume of sample may be provided from the subject. Examples of volumes may include, but are not limited to, about 10 mL or less, 5 mL or less, 3 mL or less, 1 microliter (µL, also "uL" herein) or less, 500 µL, or less, 300 µL, or less, 250 µL, or less, 200 µL, or less, 170 µL, or less, 150 µL, or less, 125 µL, or less, 100 µL, or less, 75 µL, or less, 50 µL, or less, 25 µL, or less, 20 µL, or less, 15 µL, or less, 10 µL, or less, 5 µL, or less, 3 µL, or less, 1 µL, or less, 500 nL or less, 250 nL or less, 100 nL or less, 50 nL or less, 20 nL or less, 10 nL or less, 5 nL or less, 1 nL or less, 500 pL or less, 100 pL or less, 50 pL or less, or 1 pL or less. The amount of sample may be about a drop of a sample. The amount of sample may be the amount collected from a pricked finger or fingerstick. The amount of sample may be the amount collected from a microneedle or a venous draw. Any volume, including those described herein, may be provided to the device.

A health care professional may include a person or entity that is associated with the health care system. A health care professional may be a medical health care provider. A health care professional may be a doctor. A health care professional may be an individual or an institution that provides preventive, curative, promotional or rehabilitative health care services in a systematic way to individuals, families and/or communities. Examples of health care professionals may include physicians (including general practitioners and specialists), dentists, audiologists, speech pathologists, physician assistants, nurses, midwives, pharmaconomists/pharmacists, dietitians, therapists, psychologists, chiropractors, clinical officers, physical therapists, phlebotomists, occupational therapists, optometrists, emergency medical technicians, paramedics, medical laboratory technicians, medical prosthetic technicians, radiographers, social workers, and a wide variety of other human resources trained to provide some type of health care service. A health care professional may or may not be certified to write prescriptions. A health care professional may work in or be affiliated with hospitals, health care centers and other service delivery points, or also in academic training, research and administration. Some health care professionals may provide care and treatment services for patients in private homes. Community health workers may work outside of formal health care institutions. Managers of health care services, medical records and health information technicians and other support workers may also be health care professionals or affiliated with a health care provider.

In some embodiments, the health care professional may already be familiar with the subject or have communicated with the subject. The subject may be a patient of the health care professional. In some instances, the health care professional may have prescribed the subject to undergo a clinical test. The health care professional may have instructed or suggested to the subject to undergo a clinical test conducted at the sample collection site or by the laboratory. In one example, the health care professional may be the subject's primary care physician. The health care professional may be any type of physician for the subject (including general practitioners, and specialists).

A health care professional may receive a report from an authorized analytical facility. The health care professional that receives a report may be an ordering health care professional or health care professional in the analytical facility and/or sample collection site.

A laboratory 110 may be in communication with a sample collection site 120 and a health care professional 100. The laboratory may be in communication with any number of sample collection sites and health care professionals. For example, the laboratory may be in communication with one or more, two or more, three or more, five or more, ten or more, fifteen or more, twenty or more, 30 or more, 50 or more, 100 or more, 200 or more, 500 or more, 1000 or more, 5000 or more, 10,000 or more, 100,000 or more, or 1,000,000 or more sample collection sites and/or health care professionals. In some systems, one, two, three, four, or more laboratories may be provided that may communicate with any number of sample collection sites and/or health care professionals. The laboratories may or may not communicate with one another. The sample collection sites, laboratories, and/or health care professionals may be scattered geographically at any location. In some embodiments, the sample collection sites and/or health care professionals in communication with a laboratory may be in the same geographic region (e.g., town, city, state, region, country). Alternatively, the sample collection sites and/or health care professionals in communication with a laboratory may be scattered anywhere globally.

The laboratory may communicate with the health care professional and the sample collection site in any manner known in the art. In some embodiments, the laboratory may communicate directly with a device located at the sample collection site or in or on a subject. Such communications may be via electronic signals, radiofrequency signals, optical signals, cellular signals, or any other type of signals that may be transmitted via a wired or wireless connection. Any transmission of data or description of electronic data or transmission described elsewhere herein may occur via electronic signals, radiofrequency signals, optical signals, cellular signals, or any other type of signals that may be transmitted via a wired or wireless connection. For example, data may be transmitted electronically from a sample collection site to a laboratory and vice versa. Data may be transmitted from a device which may be at the sample collection site or in or on a subject to the laboratory and vice versa. Similarly, data may be transmitted electronically from a laboratory to a health care professional and vice versa. The communications may be over a network such as a local area network (LAN), wide area network (WAN) such as the Internet, personal area network, a telecommunications network such as a telephone network, cell phone network, mobile network, a wireless network, a data-providing network, or any other type of network. The communications may utilize wireless technology, such as Bluetooth or RTM technology. Alternatively, various communication methods may be utilized, such as a dial-up wired connection with a modem, a direct link such as TI, ISDN, or cable line. In some embodiments, a wireless connection may be using exemplary wireless networks such as cellular, satellite, or pager networks, GPRS, or a local data transport system such as Ethernet or token ring over a LAN. In some embodiments, the device may communicate wirelessly using infrared communication components. A device 130, personal computer, server, laptop computer, tablet, mobile phone, cell phone, satellite phone, smartphone (e.g., iPhone, Android, Blackberry, Palm, Symbian, Windows), personal digital assistant, Bluetooth device, pager, land-line phone, or other network device may be used in order to provide communications. Such devices may be communication-enabled devices.

The laboratory may communicate with a device at a sample collection site, or in or on a subject. The device from the sample collection site may communicate with any communication-enabled device of the laboratory. The device may provide data to a cloud computing infrastructure that may be accessed by any communication-enabled device of the laboratory. The device may transmit data to the laboratory.

The data provided by the device may include data relating to a sample from a subject. The data may be information necessary and/or sufficient for a qualitative and/or quantitative evaluation of the sample. The data may include information for oversight. The data may include information for analysis. The data may be an electronic representation of a sample. An electronic representation of a sample may include an electronic representation of the entire sample and/or any portion thereof. The data may be electronic data. In some instances, the data may be electronic bits representative of the sample or reaction or reagents. The data may be digital and/or analog. The data may be representative of one or more measurable parameter relating to, based on, or of the sample.

The data may be representative of a sample and/or any portion thereof. In some embodiments, the data is representative of a preparation of the collected biological sample. The data may be collected prior to, during, and/or after the preparation of the sample. The data may be collected over time. The data may comprise information of one or more conditions under which a preparation of the collected biological sample occurs. Examples of such conditions may comprise one or more characteristics listed from the group: amount of the biological sample, concentration of the biological sample, quality of the biological sample, temperature, or humidity. Such conditions may include environmental conditions. Environmental conditions may refer to conditions of the sample, and/or the surroundings of the sample. The environmental conditions may be provided prior to, during, and/or after the sample is received by the device, prepared by the device, and/or data is transmitted by the device.

The data may include amounts, concentrations, proportions, purity, or other information of sample, reagents, diluents, wash, dyes or any other material that may be involved in the preparation of a sample, reactions, and/or controls/calibrations on the device. Physical and/or chemical properties of a sample and/or other materials, and/or a chemical reaction may be measured at one or more points in time, and may be aggregated as data. In some embodiments, the data may determine whether a sample, reagent, diluents, wash, dye, or any other material is suitable for use in the device for said sample preparation and/or to permit subsequent qualitative and/or quantitative evaluation. For example, the data may be indicative of any error conditions that may indicate a sample and/or any of the other materials have gone bad, or are otherwise unsuitable. In some instances, data is collected during any processes the device is performing.

In some embodiments, the data may be representative of a chemical reaction which may be run by the device. The chemical reaction may include a chemical reaction with the sample, or without the sample. The chemical reaction may include one or more reagents that may react with the sample. The chemical reaction may include a control or calibration reaction. The data representative of the reaction may include one or more measurement of the chemical reaction. The data may also include the rate or speed of the chemical reaction, and/or the acceleration of the chemical reaction. The data may include how complete a chemical reaction is (e.g., whether the chemical reaction has started, whether the chemical reaction is taking place, whether the chemical reaction is complete, how far along the chemical reaction is—e.g., 10%, 50%, etc.). The data may comprise information about a control reaction and a chemical reaction involving the biological sample. These reactions may occur simultaneously and/or sequentially. The data may pertain to one or more chemical reactions that may or may not occur simultaneously. The data may pertain to one or more sample preparation step that may or may not occur simultaneously. The data may also include physical processing, such as centrifugation, pulveration, or any other actions described herein, which may be represented through bits of data. The data can be utilized for oversight functionally performed on-board, remotely by a health care professional, and/or an external device configured to render such oversight.

The occurrence, progress, or results of a chemical reaction may be detected and measure by colorimetric or other means. For example, chromogens (also termed herein, e.g., colorants, colored products, and other terms) that may be used with systems, devices, and methods provided herein may include, for example, i) substrates which may be oxidized (e.g. molecules that change color upon oxidization, such as by peroxidase and hydrogen peroxide), for example: aniline derivatives [e.g. 2-amino-4-hydroxybenzenesulfonic acid (AHBS) (forms a yellow dye upon oxidation which may be monitored at 415 nm); N-(2-hydroxy-3-sulfopropyl)-3,5-dimethyoxyaniline (forms a dye upon oxidation that may be monitored at 610 nm)], o-dianisidine (forms a yellow-orange dye upon oxidation that may be monitored at 405 nm), 10-acetyl-3,7-dihydroxyphenoxazine (ADHP) (forms a dye upon oxidation that may be monitored, for example, colorimetrically at 570 nm or fluorescently at EX/EM=535/587 nm), ii) substrates of kinases (e.g. molecules that change color upon phosphorylation), for example: iii) substrates of phosphatases (e.g. molecules that change color upon dephosphorylation), for example: p-nitrophenyl phosphate (pNPP) (forms p-nitrophenol upon dephosphorylation, which may be measured by absorbance at 405 nm); iv) substrates of hydrolases (e.g. molecules that change color upon hydrolysis), for example: ortho-nitrophenyl-beta-galactoside (ONPG) (may be hydrolyzed by beta-galactosidase to galactose and ortho-nitrophenol; ortho-nitrophenol may be measured by absorbance at 420 nm); v) substrates which may change color upon complex formation, for example: o-cresolphthalein (forms a complex with calcium, which may be measured by absorbance at 575 nm).

Hydrogen peroxide, in the presence of horseradish peroxidase and colorants such as an aminoantipyrene (e.g., 4-aminoantipyrene) and an aniline-containing compound (e.g., N-Ethyl-N-(2-hydroxy-3-sulfopropyl)-3,5-dimethoxyaniline) may react to form a colored product (e.g., a Trinder (e.g., quinoneimine) dye as indicated in the figure).

For example, HRP may react with an aniline-containing compound such as N-Ethyl-N-(2-hydroxy-3-sulfopropyl)-3, 5-dimethoxyaniline (ALPS), or with an aminoantipyrene compound such as 4-aminoantipyrene or with phenolic compounds. Thus, for example, a peroxidase (e.g., HRP, myeloperoxidase, or other peroxidase), an aniline-containing compound, and an aminoantipyrene may all be termed "colorants" or "chromagens." In further examples, HRP may react with a benzidine-containing compound (e.g., with diaminobenzidine (DAB); tetramethylbenzidine (TMB); 2,2'-azino-bis(3-ethylbenzothiazoline-6-sulphonic acid) (DABS); 3-dimethylaminobenzoic acid (DMAB); hydroquinone; o-tolidine; o-phenylenediamine; o-chlorophenol; p-hydroxy-benzenesulfonate; p-anisidine; a Trinder reagent (such as 4-aminoantipyrene, methylbenzothiazolinonehydrazone (MBTH), or other compound for producing a Trinder dye); and derivatives and related compounds) to form a colored product. HRP or other peroxidase may also react with other compounds to form a chemiluminescent product; for example, HRP or other peroxidase may react with luminol to form a chemiluminescent product (other molecules may be present, and may enhance such reactions; for example, HRP-mediated production of luminescent products from luminol is enhanced in the presence of 4-iodophenol).

Further chromagens include, for example, alkaline phosphatase; resazurin (7-Hydroxy-3H-phenoxazin-3-one 10-oxide); 10-acetyl-3,7-dihydroxyphenoxazine (Amplex Red) and similar compounds (e.g., Amplex UltraRed (A36006 from Life Technologies, Carlsbad, Calif. 92008); resorufin compounds (e.g., 7-ethoxyresorufin); dyes such as e.g., fluorescein, calcein, rhodamine, and ethidium dyes; N-methyl-4-hydrazino-7-nitrobenzofurazan; acridinium (acridine-9-carboxylic acid) esters and compounds which react with these compounds to alter an optical property of a solution; phenols and phenol derivatives (e.g., p-iodophenol and p-phenylphenol); luminescent amines, including amine adducts (e.g., as may be derived from copper cyanide), and other molecules. It will be understood that other enzymes and reactants may be used to form colored products, or to detect an analyte in a biological sample, such as a blood sample.

In some examples, the data may be one or more image, and/or audio data representative of the sample. An image may be a digital image or an analog image. The audio data may be digital and/or analog. The data may include a video representative of the sample. An image may include a video image. The data may include electronic data representative of a digital image and/or audio data of the sample. In one example, the data may include video imaging that may capture changes over time. For example, a video may be provided to provide evaluation on dynamic actions, such as lysing, agglutination, mixing, movement of cells or other molecules in a sample or matrix, or assays.

The data may be collected at one time, or at a plurality of times. The data may be collected at discrete points in time, or may be continuously collected over time. Data collected over time may be aggregated and/or analyzed. In some instances, data may be aggregated and may be useful for longitudinal analysis over time to facilitate screening, diagnosis, treatment, and/or disease prevention.

Data may be collected from a device over time. The aggregated data from a single device for a given sample may be useful to facilitate the qualitative and/or quantitative evaluation of the sample. For example, it may be useful to determine how a sample reacts and/or changes over time in order to provide a screening, diagnosis, treatment, and/or disease prevention.

In some embodiments, data may be displayed in a lab report, medical record, or any other type of display. The display may show patient health, provider's level of care, disease regression, progression, and/or onset through longitudinal analysis of high integrity data that is may be obtainable more frequently or obtained frequently through the described infrastructure over time.

Data may be collected from multiple devices. The aggregated data from multiple devices may be useful to facilitate the qualitative and/or quantitative evaluation of the sample. The aggregated data may include data relating to samples collected from a single subject, received at the multiple devices. Alternatively, the aggregated data may include data relating to samples collected from other subjects, received at the multiple devices. The aggregated data may be collected and/or stored in a database. The database may be accessed to provide data to perform a longitudinal analysis that takes past collected data into account. Trends, and changes over time may be monitored. The multiple devices may be standardized and/or may provide data that is of sufficient quality, precision, and/or accuracy in order to aggregate the data and perform a longitudinal analysis therefrom. Very little or no variation may be provided between devices. The devices may also create standardized environments in which the sample preparation may occur. The standardized environments may also be provided during a chemical reaction. The devices may also provide standardized pre-analytic steps. The multiple devices may be distributed globally. This may provide a global evaluation infrastructure, which may better permit the monitoring of disease progression and/or regression. By standardizing a device, data may be longitudinally analyzed looking at velocity of markers in one or more subject over time. The data may be analyzed and/or displayed in a form of lab report or electronic medical record or decision support system for consumers, providers, and/or payers (e.g., health plans, employers, governmental payers, etc.). Such display may include displays of data over time, which may include trending analysis or other analysis relating to changes in values, rates of changes, or rates of rates of change.

The data may be of a quality suitable for a longitudinal analysis over time. The suitable quality of data may be useful for lab reports and/or electronic medical records that may incorporate data collected over time. This may include data collected over long periods of time (e.g., multiple visits, or based off multiple samples), or shorter periods of time (within a single visit, or based on single received sample). The data may have a sufficient quality, precision, and/or accuracy for longitudinal analysis. For example, the sample may be collected from a subject a plurality of times. The sample may be collected from the subject at different times. The samples may be collected at predetermined intervals or according to a predetermined schedule. Alternatively, samples may be collected from the subject when one or more condition or event triggers the collection. Multiple collections of samples may permit the sample to be analyzed over a period of time, thereby permitting longitudinal analysis. In some embodiments, in order to permit longitudinal analysis, the data may have a high degree of precision and/or accuracy. In one example, the data may have a coefficient of variation of 20% or less, 15% or less, 10% or less, 9% or less, 8% or less, 7% or less, 6% or less, 5% or less, 4% or less, 3% or less, 2% or less, 1% or less, 0.5% or less, or 0.1% or less over time. In some instances, the multiple devices may provide data having a coefficient of variation of 20% or less, 15% or less, 10% or less, 9% or less, 8% or less, 7% or less, 6% or less, 5% or less, 4% or less, 3% or less, 2% or less, 1% or less, 0.5% or less, or 0.1% or less over time.

The data over time may be analyzed longitudinally. This may include the change in data over time, the rate of change of data over time, the rate of change of the rate of change of data over time, or any derivative thereof. For example, velocity and/or acceleration of data change may be collected and/or analyzed. The increase and/or decrease in the data values and/or the various rates of change may be beneficial in determining a screening, diagnosis, treatment, and/or disease prevention.

The device is capable of processing a sample collected from a subject to yield data for subsequent analysis. The device may be configured to facilitate collection of the sample from the subject. The device may be configured to receive the sample from the subject. The device may be configured to prepare the sample for a clinical test to detect and/or quantitate an analyte of interest. The device may comprise one or more reagents useful for the clinical test. The preparation or the clinical test may include a chemical reaction with the reagents. The device may include one or more detector that may be capable of detecting signals generated from processing the sample. The device may transmit data relating to the sample. The data relating to the sample may include the raw data from the detected signals, such signals relating to unreacted sample, a sample that has undergone a reaction, and/or device configurations. In some instances, the device may pre-process some of the raw data to get it into a desired format, and transmit the pre-processed data. In some instances, the device may perform one or more analysis step, and transmit analyzed data. Alternatively, the device does not perform any pre-processing and/or analysis. The pre-processing and/or analysis may occur at the laboratory. In some instances, pre-processing and/or analysis may occur at both the device and the laboratory. The laboratory may also include a hospital who may be leveraging its pathologists so data can be transmitted to centers of excellence for the analysis of different types of specific conditions.

In embodiments, a device may monitor its environment, including its internal and external environment. In embodiments, a device may provide device environmental information to a laboratory. Device environmental information includes, e.g., internal temperature, external temperature, internal humidity, external humidity, time, status of components, error codes, images from an internal camera, images from an external camera, air pressure (barometric pressure), and other information. In embodiments, an internal camera may be fixed at an internal location. In embodiments, an internal camera may be fixed at an internal location and may be configured to rotate, scan, or otherwise provide views of multiple areas or regions within the device. In embodiments, an internal camera may be movable within the device; for example, an internal camera may be mounted on a movable element, such as a pipette, within the device. In embodiments, an internal camera may be movable within the device and may be configured to rotate, scan, or otherwise provide multiple views of areas within the device from multiple locations within the device. In embodiments, an external camera may be fixed at an external location. In embodiments, an external camera may be fixed at an external location and may be configured to rotate, scan, or otherwise provide multiple views of areas outside the device. In embodiments, an external camera may be movable on or around the outside of the device. In embodiments, an external camera may be movable and may be configured to rotate, scan, or otherwise provide multiple views of areas outside the device from multiple locations on or around the outside of the device.

Thus, in embodiments, monitoring, and reporting the results of such monitoring, of the device environment may be part of the oversight of the operation of the device and of the integrity of results and analysis. Such monitoring provides information, oversight, and control of quality regarding the device and its output (of the condition, operation, results generated, and data transmitted). Such monitoring may include: measurement and control of air temperature; measurement and control of liquid (volume, temperature, mixing, etc.); monitoring of sample collection; imaging of a cartridge to determine the position of a cartridge in the device; imaging of a cartridge to correct its position, if necessary, per such imaging of the cartridge in the device; imaging of tips to confirm proper engagement with pipette nozzles; imaging of liquid volumes in tips; imaging of bubbles in liquids, if any; imaging of samples to assess sample volume, sample quality and presence or absence of conditions which may interfere with proper processing or analysis (such as hemolysis, lipemic, icteric conditions of a sample); feedback control and error detection of status and condition of motors on a pipette for control and oversight concerning accurate aspiration and dispensing of liquids; feedback control and error detection of a centrifuge for precise centrifugal force control, determination of position, and other information regarding status and condition of a centrifuge; feedback control and error detection for gantry, robots and shuttle positions, including or oversight and control of the positioning of pipettes, cartridges, and tips/cuvettes for processing and analysis of a sample; control of reactions (between a sample and a reagent) to confirm proper device operation (e.g., using sensors, pipette, gantry, thermal sensors and control, etc.); monitoring and control of the proper state of reagents; the running of control reactions at the same time as the sample analysis, or beforehand or subsequently; performance of replicate analysis of the sample to enhance precision; performing blank reads to control for possible changes in background signals in samples and for possible small fluctuations in sensor performance and in output of light sources.

In embodiments, monitoring, and reporting the results of such monitoring, may include calibration. Calibration of the device, reagents, disposables, and of their manufacture and assembly may be part of the oversight of the operation of the device and of the integrity of results and analysis. During manufacturing, each device is calibrated to a set of controlled standards. During manufacturing, reagents and disposables (e.g., tips, cuvettes, and other elements) is calibrated to a set of controlled standards, and identification information related to each cartridge containing these reagents and disposables includes information about these calibrations. Such calibration may include: each pipette nozzle of each pipette is calibrated—for example, for each pipette nozzle, information regarding how a given displacement of the motor translates to a given amount of liquid volume is measured and provided in the information recorded for each motor for use in protocols used with the device in which that motor is a component; each sensor and illumination source in a device is calibrated against a set of controlled standards, and provided in the information for each device, so that the resulting signals from all sensors across all devices results in the same measurement; each motor control algorithm is calibrated during manufacturing such that speeds and position of the motors can be controlled similarly across each device; each camera and each illumination source is characterized, including a flat field correction; during manufacturing, each of lot reagents is calibrated such that any change in potency of the reagents still results in the same analytic result. Thus, since each sample is analyzed by processing on the device (for which such component and device specific calibration information is known) the raw data resulting from sample processing can be calibrated and corrected according to the information and calibrations for each reagent, and each device and its components. Such oversight and calibration insures the integrity of the results obtained, and thus also provides for the integrity of analysis of such results. The raw data from a device is analyzed by utilizing the device-specific calibration and the reagent lot-specific calibration to arrive at the result. Each result arrived at in this way is thus accurate, precise, and reliable, and may be compared with analogous results obtained from other samples in the same instrument, and with other instruments and samples, reducing variance and errors and allowing for better analysis and better confidence in diagnoses and inferences drawn from the analysis of samples.

Quality control runs may be performed on a device and reagents on a periodic basis, e.g., as overseen by CLIA, to ensure that the reagents and devices are still performing within specifications. If discrepancies are found, reagents and/or devices may be determined to need recalibration. Devices can be recalibrated in the field by running defined protocols, which may or may not require inserting a calibration cartridge into the device. Reagents may be recalibrated by generating a standard curve using the same lot of reagents and deriving a calibration function. Such reagent recalibration can performed on any one of the devices and can be applied to all devices.

Transmission of device environmental information to a laboratory is useful for the oversight and control of the device, including being useful for the oversight and control of the operation of the device. Transmission of device environmental information to a laboratory is useful for maintaining the integrity of the operation and control of the device, quality control of the operation and control of the device, and for reducing variation or error in the data collection and sample processing performed by the device. Device environmental information may be used, for example, by a laboratory to modify, correct, or update a protocol or other instruction or command to a device. Device environmental information may be used, for example, by a laboratory to modify, correct, or update an analysis of data received from a device. For example, transmission of temperature information to a laboratory is useful for the oversight and control of the device, and is useful in the analysis by the laboratory of data provided by the device to the laboratory.

In embodiments, a device may be configured to control the temperature within the device, or within a portion of the device. Such control improves the reproducibility of measurements made within the device, may unify or provide regularity of conditions for all samples, and reduce the variability of measurements and data, e.g., as measured by the coefficient of variance of multiple measurements or replicate measurements. Temperature information may be useful for quality control. In embodiments, a device may monitor temperature and control its internal temperature. Temperature control may be useful for quality control. A device that monitors and controls its temperature may transmit temperature information to a laboratory; a laboratory may use such temperature information in the control of the operation of the instrument, in the oversight of the instrument, and in the analysis of data transmitted from the instrument.

In embodiments, a device may be configured to acquire images from within the device, or within a portion of the device. Such images may provide information about the position, condition, availability, or other information regarding components, reagents, supplies, or samples within the device, and may provide information used in control of the operation of the device. Such images may be useful for quality control. A device that acquires images from within the device may transmit image information to a laboratory; a laboratory may use such image information in the control of the operation of the instrument, in the oversight of the instrument, and in the analysis of data transmitted from the instrument.

In one scenario, a device may perform a sample preparation step without performing any analysis or receiving any oversight. The data from the sample preparation step may be sent to the laboratory, which may perform the analysis, and which may be an authorized analytical facility that includes oversight. In another scenario, the device may perform one or more sample preparation step and may perform analysis on board. Data from the analysis may be sent to an authorized analytical facility, which may provide oversight. Alternatively, oversight may occur on board the device.

In some embodiments, oversight may include a review of the data in raw form, pre-processed form, or after analysis. Oversight may occur of a qualitative and/or quantitative evaluation of the sample. Examples of a qualitative evaluation of the sample may include but are not limited to review of an image, video, or audio file. Examples of a quantitative evaluation of the sample may include a numerical value indicating a presence or concentration level of a signal, series of signals, or an analyte. Oversight may include one or more, or two or more of the examples provided elsewhere herein. Oversight may be provided by a health care professional of an authorized analytical facility. In some other instances, oversight may be provided by a software program or automated review system. The software program and/or automated review system may or may not be under the review or care of a qualified person, such as a health care professional (such as a laboratory director).

The device may duplicate manual analytical procedures. In some instances, the device may perform automatically various steps, such as pipetting, preparing filtrates, heating, and/or measuring color intensity. The device may be used in conjunction with materials to measure one or more analytes. The device may measure the presence or concentration of one or more analytes. The device may include reagent-containing components that may serve as reaction units. Examples of device components and steps that may be taken by the device can be described in greater detail elsewhere herein.

The laboratory may communicate with a health care professional. The laboratory may generate a report based on analyzed data. In some instances, the laboratory may analyze raw data or pre-processed data provided from the device. Alternatively, the laboratory may receive analyzed data from the device. The laboratory may or may not perform further analysis and/or oversight from analyzed data received from the device.

The laboratory and/or device may generate a report that may present the analyzed data in a meaningful or desired manner. The report may have a format that may enable a viewer of the report to rely on the report to make a medical determination. The laboratory and/or device may transmit the report to a health care professional (or laboratory director). In some embodiments, a pathologist, other health care professional, or other qualified person may review the report prior to transmitting the report to the health care professional. A reviewing health care professional may review the report or qualitative and/or quantitative evaluation useful for generating the report prior to transmission to an ordering health care professional. Review or oversight may occur of the analyzed data and/or report at the laboratory. Alternatively, review or oversight may occur on-board the device. The health care professional who receives the report may or may not rely on the report for screening, diagnosis, treatment and/or disease prevention of the subject.

The laboratory and/or device may also provide a report to the subject. The report provided to the subject may be the same as or different from the report provided to the health care professional. The report provided to the health care professional may have more detail or vice versa. The formats between the reports provided to the subject and the health care professional may or may not vary. Alternatively, the laboratory and/or device does not provide a report to the subject. The subject may receive information based on the report from the health care professional. A device or laboratory can directly provide a lab report automatically to a consumer upon a test being performed and/or analysis being done, or being sent to a physician for review and/or after the physician's review.

Any transmission of data and/or reports may incorporate the use of a cloud computing infrastructure. The sending party may provide the data to or have the data on a cloud computing infrastructure. The receiving party and/or parties (e.g., health care professional or patient) may access the cloud computing infrastructure. The cloud computing infrastructure may be provided on the sending party side and/or the receiving party side. Alternatively, traditional fixed data storage techniques may be employed.

Figure 1B:
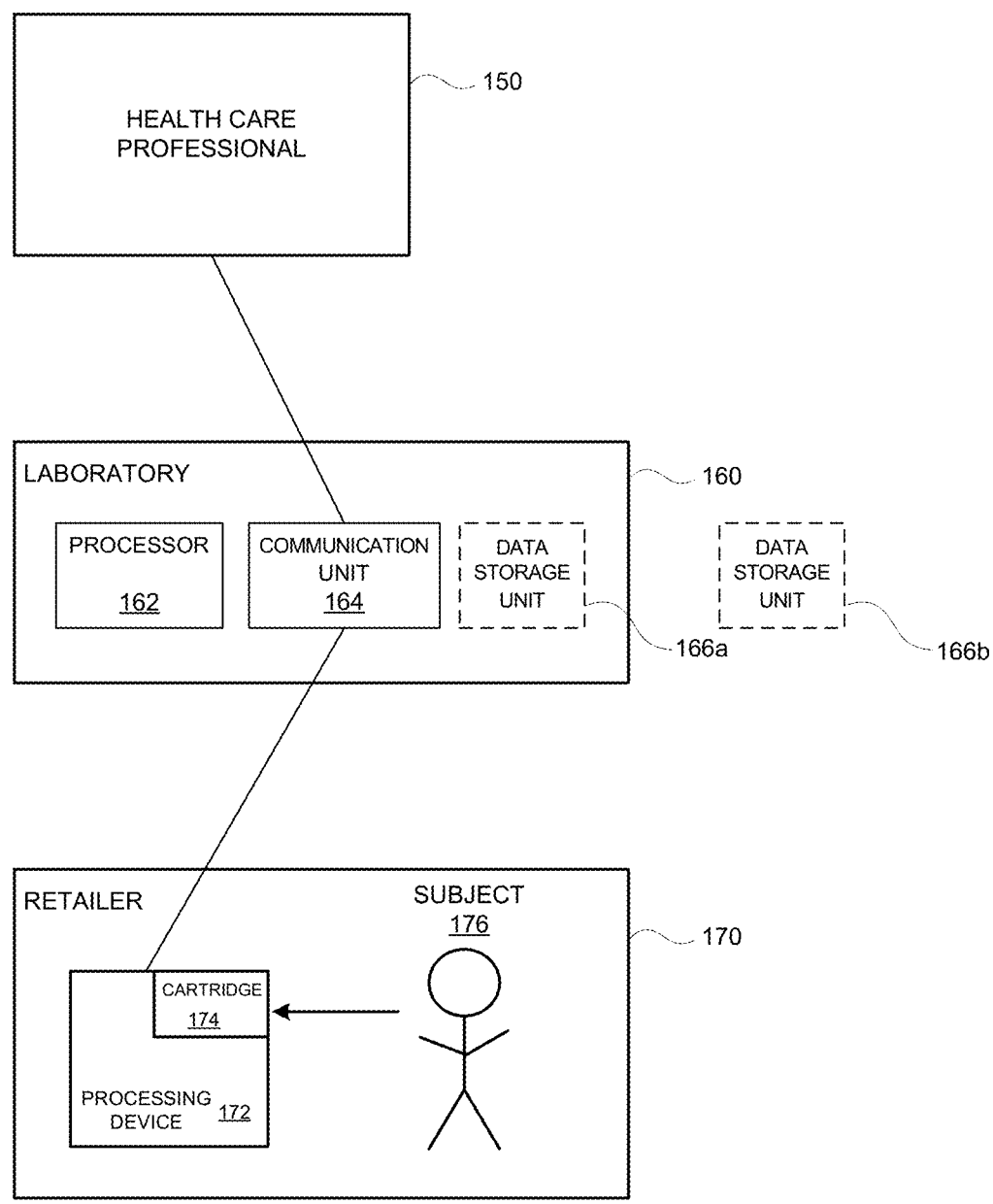
FIG. 1B shows a retailer having a processing device in communication with a laboratory (e.g. a CLIA certified laboratory).

FIG. 1B shows a retailer 170 having a processing device 172 in communication with a laboratory 160. The laboratory or reader device may be in communication with a health care professional 150. As previously described, any discussion herein of retailers or other examples of sample collection sites may apply to any type of sample collection site, and vice versa. A retailer may be provided at a first location and a health care professional may be provided at a second location. The first location and the second location may be different locations. In some embodiments, the first and second locations are not proximate to one another. A laboratory may be provided at a third location. The third location may be a different location from the first and/or second location. For example, the first, second, and third locations need not be proximate to one another. The first, second, and/or third locations may be located in different facilities. Alternatively, the first, second, and/or third could all be the same location (point of service).

A retailer may be an entity that sells a product or service. In some embodiments, the product or service may relate to health or medical care. For example, the retailer may sell medicine or health care supplies and/or insurance. In some embodiments, a retailer may be a pharmacy (e.g., retail pharmacy, clinical pharmacy, hospital pharmacy), drugstore, chain store, supermarket, or grocer. Examples of retailers may include but are not limited to Walgreens, CVS Pharmacy, Duane Reade, Walmart, Target, Rite Aid, Kroger, Costco, Kaiser Permanente, or Sears.

A retailer may be provided at a retailer location. In some embodiments, the retailer may be at a different geographic location than a health care professional and/or laboratory location. Alternatively, the health care professional may be provided at the retailer location.

A retailer 170 may have a sample processing device 172 at the retailer's location. In some embodiments, the retailer may have one or more, two or more, three or more, four or more, five or more, six or more, or ten or more sample processing devices at the retailer's location. The sample processing device may be a point of service device. The sample processing devices may be capable of communication with communication-enabled devices. For example, the sample processing devices at a retailer location may communicate with one another. Alternatively, sample processing devices may communicate with other reader devices at different locations, such as other sample collection sites, or in or on a subject. Sample processing devices may communicate with other types of communication-enabled devices, such as a computer at a laboratory and/or biometric devices. Such communications may be wired or wireless.

The sample processing device 172 may be configured to accept a sample. The sample processing device may be configured to collect the sample directly from a subject. The sample processing device may be configured to perform one or more sample preparation step on the subject. The sample processing device may be configured to run an assay. In some embodiments, the sample processing device may be configured to run one or more assay. The sample processing device may be capable of performing multiplexed assays on a single sample. Where desired, the device is configured to perform at least 2, 3, 4, 5, 6, 7, 8, 9, 10, 20, 30, 40, 50, 100, 200, 500, 1000 or more assays. The plurality of assays may be run simultaneously in parallel. One or more control assays and/or calibrators (e.g., including a configuration with a control of a calibrator for the assay/tests) can also be incorporated into the device to be performed in parallel if desired. In some instances, assays may be run in sequence, or any combination of in sequence and in parallel, based on the sample. The reader device may be effecting one, two, or more chemical reactions or other processing tests (e.g., pulverizing). The sample processing device may be configured to detect one or more signal relating to the sample. The sample may be a sample of bodily fluid, a biological sample, or any other example as provided elsewhere herein.

In some embodiments, the sample processing device 172 may comprise a cartridge 174. The cartridge may be removable from the sample processing device. In some embodiments, a sample may be provided to the cartridge of the sample processing device. Alternatively, the sample may be provided to another portion of the sample processing device. The cartridge and/or device may comprise a sample collection unit that may be configured to accept a sample. The sample processing device is described in further detail elsewhere herein. The cartridge and device may be integrated into a single device or may be separable devices. A device may include a pill or patch that may link to a mobile device or other network device for processing.

A subject 176 may be provided at the retailer 170. The subject may provide a sample of bodily fluid to the sample processing device 172 and/or cartridge 174 of the device. A bodily fluid may be drawn from a subject and provided to a device in a variety of ways, including but not limited to, fingerstick, lancing, injection, and/or pipetting. The bodily fluid may be collected using venous, or non-venous methods. The bodily fluid may be provided using a bodily fluid collector. A bodily fluid collector may include a lancet, microneedle, porous membrane (e.g., for a pill), capillary, tube, pipette, syringe, venous draw, or any other collector described elsewhere herein. In one embodiment, a lancet punctures the skin and withdraws a sample using, for example, gravity, capillary action, aspiration, or vacuum force. The lancet may be part of the sample processing device, part of the cartridge of the device, part of a system, or a standalone component. Where needed, the lancet may be activated by a variety of mechanical, electrical, electromechanical, or any other known activation mechanism or any combination of such methods. In one example, a subject's finger (or other portion of the subject's body) may be punctured to yield a bodily fluid. The bodily fluid may be collected using a capillary tube, pipette, or any other mechanism known in the art. The capillary tube or pipette may be separate from the device and/or cartridge, or may be a part of a device and/or cartridge. A transfer device may require no additional processing steps, and may be pre-coated with anti-coagulants or other pre-treatments in a single step. In another embodiment where no active mechanism is required, a subject can simply provide a bodily fluid to the device and/or cartridge, as for example, could occur with a saliva sample, or touching a pierced body part to a surface directly. The collected fluid can be placed within the device. A bodily fluid collector may be attached to the device, removably attachable to the device, or may be provided separately from the device.

A cartridge 174 may be inserted into the sample processing device 172 or otherwise interfaced with the sample processing device. The cartridge may be removed from the sample processing device. In one example, a sample may be provided to a sample collection unit of the cartridge. The sample may be provided directly to the cartridge. The sample may or may not be provided to the sample collection unit via a bodily fluid collector. A bodily fluid collector may be attached to the cartridge, removably attachable to the cartridge, or may be provided separately from the cartridge. The bodily fluid collector may or may not be integral to the sample collection unit. The cartridge may then be inserted into the sample processing device. Alternatively, the sample may be provided directly to the sample processing device, which may or may not utilize the cartridge. The cartridge may comprise one or more reagents, which may be used in the operation of the sample processing device. Alternatively, one or more reagents may already be provided onboard the sample processing device.

The cartridge may or may not be disposable. Cartridges may be specially configured for one or more types of clinical tests. For example, a first cartridge may have a first configuration to enable a first set of tests, and a second cartridge may have a second configuration to enable a second set of tests. Alternatively, universal cartridges that may be configured for the same selection of tests may be provided. In some instances, universal cartridges may be dynamically programmed for certain tests through remote or on-board protocols.

When a cartridge is inserted into the sample processing device, one or more components of the cartridge may be brought into fluid communication with other components of the sample processing device. For example, if a sample is collected at a cartridge, the sample may be transferred to other portions of the sample processing device. Similarly, if one or more reagents are provided on a cartridge, the reagents may be transferred to other portions of the sample processing device, or other components of the sample processing device may be brought to the reagents. One or more components of the cartridge may be transferred in an automated fashion to other portions of the sample processing device, and vice versa. In some embodiments, the reagents or components of a cartridge may remain on-board the cartridge. In some embodiments, no fluidics are included that require tubing or maintenance (e.g., manual or automated maintenance).

The sample processing device may be configured to be placed in or on a subject. The sample processing device may receive a sample from the subject through a housing of the device. For example, if the sample processing device is ingestible or implanted within a subject, it may include a housing or a biocompatible coating. The biocompatible coating may be permeable to the desired sample. The sample may penetrate the coating or housing of the sample processing device, thereby being received by the sample processing device. If the sample processing device is on the subject, the sample may be received through the housing and/or coating of the device. Alternatively, the sample may be received using one or more needle or microneedle that may be provided on the device (which may or may not be provided on the cartridge portion of the device).

The sample processing device may be configured to facilitate sample collection, prepare the sample for a clinical test, and/or may comprise one or more reagents useful for a clinical test. In some embodiments, the sample processing device may be configured to run one or more test from the sample. A chemical reaction or other processing step may be performed, with or without the sample. In some embodiments, assays, such as immunoassays or nucleic acid assays may be run. Examples of steps and/or tests that may be prepared or run by the device may include, but are not limited to immunoassay, nucleic acid assay, receptor-based assay, cytometric assay, colorimetric assay, enzymatic assay, electrophoretic assay, electrochemical assay, spectroscopic assay, chromatographic assay, microscopic assay, topographic assay, calorimetric assay, turbidmetric assay, agglutination assay, radioisotope assay, viscometric assay, coagulation assay, clotting time assay, protein synthesis assay, histological assay, culture assay, osmolarity assay, and/or other types of assays, centrifugation, separation, filtration, dilution, enriching, purification, precipitation, pulverization, incubation, pipetting, transport, cell lysis, or other sample preparation steps, or combinations thereof. Sample processing may include chemical reactions and/or physical processing. Sample processing may include the assessment of histology, morphology, kinematics, dynamics, and/or state of a sample, which may include such assessment for cells. The device may perform one or more, two or more, three or more, or four or more of these steps/tests.

Processing of a biological sample may include preprocessing (e.g., preparation of a sample for a subsequent processing or measurement), processing (e.g., alteration of a sample so that it differs from its original, or previous, state), and post-processing (e.g., fixing a sample, or disposing of all or a portion of a sample following its measurement or use). A biological sample may be divided into portions, such as aliquots of a blood or urine sample, or such as slicing, mincing, or dividing a tissue sample into two or more pieces. Processing of a biological sample, such as blood sample, may include mixing, stirring, sonication, homogenization, or other processing of a sample or of a portion of the sample. Processing of a biological sample, such as blood sample, may include centrifugation of a sample or a portion thereof. Processing of a biological sample, such as blood sample, may include providing time for components of the sample to separate or settle, and may include filtration (e.g., passing the sample or a portion thereof through a filter). Processing of a biological sample, such as blood sample, may include allowing or causing a blood sample to coagulate. Processing of a biological sample, such as blood sample, may include concentration of the sample, or of a portion of the sample (e.g., by sedimentation or centrifugation of a blood sample, or of a solution containing a homogenate of tissue from a tissue sample) to provide a pellet and a supernatant. Processing of a biological sample, such as blood sample, may include dilution of a portion of the sample. Dilution may be of an entire sample, or of a portion of a sample, including dilution of a pellet or of a supernatant from sample. A biological sample may be diluted with water, or with a saline solution, such as a buffered saline solution. A biological sample may be diluted with a solution which may or may not include a fixative (e.g., formaldehyde, paraformaldehyde, or other agent which cross-links proteins). A biological sample may be diluted with a solution effective that an osmotic gradient is produced between the surrounding solution and the interior, or an interior compartment, of such cells, effective that the cell volume is altered. For example, where the resulting solution concentration following dilution is less than the effective concentration of the interior of a cell, or of an interior cell compartment, the volume of such a cell will increase (i.e., the cell will swell). A biological sample may be diluted with a solution which may or may not include an osmoticant (such as, for example, glucose, sucrose, or other sugar; salts such as sodium, potassium, ammonium, or other salt; or other osmotically active compound or ingredient). In embodiments, an osmoticant may be effective to maintain the integrity of cells in the sample, by, for example, stabilizing or reducing possible osmotic gradients between the surrounding solution and the interior, or an interior compartment, of such cells. In embodiments, an osmoticant may be effective to provide or to increase osmotic gradients between the surrounding solution and the interior, or an interior compartment, of such cells, effective that the cells at least partially collapse (where the cellular interior or an interior compartment is less concentrated than the surrounding solution), or effective that the cells swell (where the cellular interior or an interior compartment is more concentrated than the surrounding solution).

A biological sample may be dyed, or markers may be added to the sample, or the sample may be otherwise prepared for detection, visualization, or quantification of the sample, a portion of a sample, a component part of a sample, or a portion of a cell or structure within a sample. For example, a biological sample may be contacted with a solution containing a dye. A dye may stain or otherwise make visible a cell, or a portion of a cell, or a material or molecule associated with a cell in a sample. A dye may bind to or be altered by an element, compound, or other component of a sample; for example a dye may change color, or otherwise alter one of more of its properties, including its optical properties, in response to a change or differential in the pH of a solution in which it is present; a dye may change color, or otherwise alter one of more of its properties, including its optical properties, in response to a change or differential in the concentration of an element or compound (e.g., sodium, calcium, $CO_2$, glucose, or other ion, element, or compound) present in a solution in which the dye is present. For example, a biological sample may be contacted with a solution containing an antibody or an antibody fragment. For example, a biological sample may be contacted with a solution that includes particles. Particles added to a biological sample may serve as standards (e.g., may serve as size standards, where the size or size distribution of the particles is known, or as concentration standards, where the number, amount, or concentration of the particles is known), or may serve as markers (e.g., where the particles bind or adhere to particular cells or types of cells, to particular cell markers or cellular compartments, or where the particles bind to all cells in a sample).

The sample processing device may be configured to perform one, two or more assays on a small sample of bodily fluid. One or more chemical reaction may take place on a sample having a volume, as described elsewhere herein. For example one or more chemical reaction may take place in a pill having less than femtoliter volumes. In an instance, the sample collection unit is configured to receive a volume of the bodily fluid sample equivalent to a single drop or less of blood or interstitial fluid. The sample collection unit may be able to collect a volume of bodily fluid sample without piercing a subject's skin. In one example, light may be shined to optically measure a sample. In additional examples, ultrasound, MRI, or a scan may be used to perform analysis non-invasively.

The device may be capable of performing all on-board steps in a short amount of time. For example, from sample collection from a subject to transmitting data and/or to analysis may take about 3 hours or less, 2 hours or less, 1 hour or less, 50 minutes or less, 45 minutes or less, 40 minutes or less, 30 minutes or less, 20 minutes or less, 15 minutes or less, 10 minutes or less, 5 minutes or less, 4 minutes or less, 3 minutes or less, 2 minutes or less, 1 minute or less, 50 seconds or less, 40 seconds or less, 30 seconds or less, 20 seconds or less, 10 seconds or less, 5 seconds or less, 3 seconds or less, 1 second or less, 500 ms or less, 200 ms or less, or 100 ms or less. The amount of time from accepting a sample within the device to transmitting data and/or to analysis from the device may take about 3 hours or less, 2 hours or less, 1 hour or less, 50 minutes or less, 45 minutes or less, 40 minutes or less, 30 minutes or less, 20 minutes or less, 15 minutes or less, 10 minutes or less, 5 minutes or less, 4 minutes or less, 3 minutes or less, 2 minutes or less, 1 minute or less, 50 seconds or less, 40 seconds or less, 30 seconds or less, 20 seconds or less, 10 seconds or less, 5 seconds or less, 3 seconds or less, 1 second or less, 500 ms or less, 200 ms or less, or 100 ms or less.

A laboratory, device, or other entity or software may perform analysis on the data in real-time. Analysis may include qualitative and/or quantitative evaluation of a sample. A laboratory, device, or other entity may analyze the data within 48 hours or less, 36 hours or less, 24 hours or less, 12 hours or less, 8 hours or less, 6 hours or less, 4 hours or less, 3 hours or less, 2 hours or less, 1 hour or less, 45 minutes or less, 30 minutes or less, 20 minutes or less, 15 minutes or less, 10 minutes or less, 5 minutes or less, 3 minutes or less, 1 minute or less, 30 seconds or less, 15 seconds or less, 10 seconds or less, 5 seconds or less, or 1 second or less. The analysis may include the comparison of the data with one or more threshold value. The analysis may or may not include review by a pathologist or other qualified person. The time included for analysis may or may not include time to generate a report based on the data. The time included for analysis may or may not include the time it takes to transmit a report to a health care professional.

A device 172 may be provided to a sample collection site 170 by a laboratory 160. The device may be sold to the sample collection site, leased/rented by the sample collection site, or the sample collection site may be used as a location at which the laboratory may conduct sample collection and/or other steps.

Similarly, one or more cartridge 174 may be provided to the sample collection site 170 by the laboratory 160. Alternatively, the cartridge may be provided by another source. The cartridge may be sold to the sample collection site, leased/rented by the sample collection site, or may be utilized as part of the location where the laboratory may collect samples and/or perform other steps. The cartridge may be from a same or different source as the device.

A laboratory 160 may have a processor 162 and a communication unit 164. A laboratory may be provided within a facility. The processor and communication unit may be provided within the facility. The laboratory may have one or a plurality of processors and one or a plurality of communication units.

A processor 162 may be configured to generate a report for a health care professional 150. The processor may be on a server side with a software performing the processing. The processor may generate the report based on data received from the sample processing device 172 or may provide oversight or analysis. The processor may perform qualitative and/or quantitative evaluation of the sample. In some embodiments, the processor may compare data received from the sample processing device with a threshold value. The threshold value may be for one or more analyte. Said comparison may include a comparison of whether a data value is greater than, equal to, or less than a threshold value. The comparison may include whether the data value is qualitatively and/or quantitatively the same as the threshold value. The comparison may include one or more forms of statistical or physiological analysis of the data in relation to one or more stored values. Examples may include best-fit analysis, and/or analysis such as curve fitting, extrapolation, interpolation, regression analysis, least squares, mean calculations, multivariate, simulation analysis, or variation calculations. The processor may analyze the data received from the sample processing device. The processor may be configured to perform one or more steps for statistical analysis of the data.

In some embodiments, a threshold value may refer to a single value. The threshold value may be a numerical value or an alphanumeric value. The threshold value may be a string or any other form of data. The threshold value may refer to a range of values and/or set of values. A threshold value may refer to a single value or a plurality of values. A plurality of values may fall within one or more continuous spectrum. Alternatively, the plurality of values may be discrete. Examples of threshold ranges may include 1-100 units, or 5-10 units, and examples of threshold sets may include values falling within a list selected from 1 unit, 3 units, 5 units, 8 units, 13 units, 20 units, or 50 units. A unit may refer to any dimension or measureable quantity. Such values are provided by way of example only. In some instances, the processor may compare one or more image, video, or audio file or other data. The processor may make such comparisons against one or more reference image, video, or audio file or other data. An algorithm may be capable of evaluating one or more feature of the files or other data. In some instances, the processor may automatically sort the files for viewing by a health care professional.

The processor may be able to access one or more data storage unit 166a, 166b which may contain stored information. The stored information may include the threshold value for one or more analyte. The threshold value may be useful for determining the presence or concentration of the one or more analyte. The threshold value may be useful for detecting situations where an alert may be useful. The data storage unit may include any other information relating to sample preparation or clinical tests that may be run on a sample. The data storage unit may include records or other information that may be useful for generating a report for a health care professional. The data storage units may also be capable of storing computer readable media which may include code, logic, or instructions for the processor to perform one or more step.

In some embodiments, a data storage unit 166a may be provided at the laboratory 160. The processor may be able to access the local data storage unit. In another embodiment, the data storage unit 166b may be provided remote to the laboratory. For example, the data storage unit may be provided at a sample collection site 170 or with a health care professional 150. The data storage unit may be provided on the device. Alternatively, the data storage unit may be provided at any other location. Any combination of data storage unit locations may be utilized by the processor. For example, the processor may access data storage units that may be provided at the laboratory and external to the laboratory.

In some embodiments, the data storage units may be electronic medical records (EMR) or EMR databases. The data storage units may contain information associated with a subject. The information associated with the subject may include medical records of the subject, health history of the subject, identifying information associated with the subject, payment information associated with the subject, or any other information associated with the subject. The data storage units may be payer databases. The data storage units may include information associated with a payer, such as a health insurance company or governmental payer. Such information may include treatment records, insurance records, or financial information associated with the subject.

One or more communication unit 164 may be provided at the laboratory 160. The laboratory may be at the same location as or different location from, or may actually be the same as the sample collection or processing center or provider or hospital office/location. Any description herein of the laboratory may apply to any other locations provided herein and vice versa. The communication unit may be configured to receive data from a device 172. The communication unit may receive data relating to a sample of a subject from the device at a sample collection site 170. The communication unit may receive information about the subject from the device and/or the sample collection site. The communication unit may receive identifying information about the subject. The communication unit may receive information from the device and/or any other machine (e.g., biometric devices, mobile devices) or entity associated with the sample collection site.

The communication unit 164 may be configured to transmit data to a device 172 and/or any other machine or entity associated with the sample collection site 170. In some embodiments, the communication unit may provide one or more protocol to the device. The communication may provide the protocol in addition to receiving data. The protocol may effect the collection of a sample, prepare the sample for a clinical test, or permit a chemical reaction with one or more reagents on the device. The protocol may effect the running of the clinical test on the device. The protocol may effect the detection of the presence and/or concentration of an analyte at the device. Any description of detection and/or analysis relating to the presence and/or concentration of an analyte may include and/or be applied to assessing a disease condition. The protocol may effect the pre-processing of raw data and/or analysis of data at the device.

The communication unit may permit two-way communication unit between the sample collection site and the laboratory. The communication unit may permit two-way communication between a sample processing device at a sample collection site or in or on a subject, and a processor at the laboratory. In some embodiments, one or more protocol may be sent to a device based on data sent by the device. The data sent by the device may include subject identifying information, information based on signals generated and/or detected relating to the sample or reactions, device identification information, cartridge identification information, or any other information sent from the device. Data may be collected from the device depending on protocols provided to the device. The protocols may govern the type of data that is collected and the actions performed by the device. In some embodiments, one, two, or more subsequent sets of protocols may be sent to a device based on data collected from the device. The data from the device may provide feedback which may govern further actions to be taken by the device, dictated by the protocols.

In alternate embodiments of the invention, the laboratory need not send protocols to the device. The protocols may be stored locally on the device. Alternatively, the system may provide protocols to the device. The protocols may be provided from an entity external to the device. The protocols may be on a cartridge.

The laboratory may have an output unit which may display or transmit the report to the health care professional. The output unit may be a video display. Alternatively, the output unit may be a communication unit. In one example, the output unit may be a touchscreen. The touchscreen may have an intrinsic imaging capability through built-in sensors, which may include LEDs or other light sources.

The device may have one or more identifier. The device may be capable of transmitting the device identifier to the laboratory. One or more components of the device may have an identifier. For example, a cartridge may have one or more identifier. The cartridge identifier may be readable by the device. For example, when a cartridge is provided to the device, the device may automatically read the cartridge identifier. The device may transmit the cartridge identifier or other component identifiers to the laboratory. The device, cartridge, or other component identifiers may provide information about the configuration and/or capabilities of the device, cartridge, or other components respectively. For example, an identifier may indicate which reagents or device components are available. A protocol may be transmitted to the device from the laboratory based on the identification information received or from a device to a laboratory for review. A protocol may be run on the device based on the identification information.

An identifier may be a physical object formed on the device, cartridge, or other component. For example, the identifier may be read by an optical scanner. In some embodiments, a camera may capture an image of the identifier and the image may be analyzed to identify the device, cartridge, or other component. In one example, the identifier may be a barcode. A barcode may be a 1D or 2D barcode. In some embodiments, the identifier may emit one or more signal that may identify the device, cartridge, or component. For example, the identifier may provide an infrared, ultrasonic, optical, audio, electrical, or other signal that may indicate the identity of the device, cartridge, or component. The identifier may utilize a radiofrequency identification (RFID) tag. The identifier may be stored on a memory of the device, cartridge, or other component. In one example, the identifier may be a computer readable medium.

The communication unit 164 may be configured to transmit data to a health care professional 150. In some embodiments, the communication unit may transmit a report or analysis generated based on data relating to the sample. The communication unit may be in communication with a network device used by the health care professional. For example, the communication unit may be capable of communicating with a computer, tablet, or mobile device of the health care professional.

Alternatively, another entity or source may generate a report, and/or transmit a report to the health care professional. For example, a laboratory may analyze data provided by the device at a sample collection site or in or on a subject or by a laboratory, hospital, sample collection center, or any other location described herein. The laboratory, device or another entity may generate a report or analysis based on the analyzed data. The report may include longitudinal data over time, which may include concentration or presence of one or more analytes or changes in disease states over time. The report and/or analysis may make use of clinical outcome assessments, such as those described in U.S. Patent Publication No. 2009/0318775, which is hereby incorporated by reference in its entirety. The laboratory, device, the other entity, or an additional entity may transmit the report to the health care professional. Various rounds of analysis or data processing may occur by one or more entity. The various entities may be provided at different facilities. Alternatively, some of the various entities may be provided at the same facility.

In some embodiments, the processor, communication unit, and data storage unit may be provided on the same machine. Alternatively, two or more of the processor, communication unit, and data storage unit may be provided on the same machine. The machine may be a computer, or any other network device as described elsewhere herein. Two or more of the processor, communication unit, and data storage may be located on a laboratory-located computer. Alternatively, the processor, communication unit, and data storage may all be located on different machines. In some instances, multiple processors, communication units, and data storage units may be provided that may be distributed over one or a plurality of machines.

Figure 2:
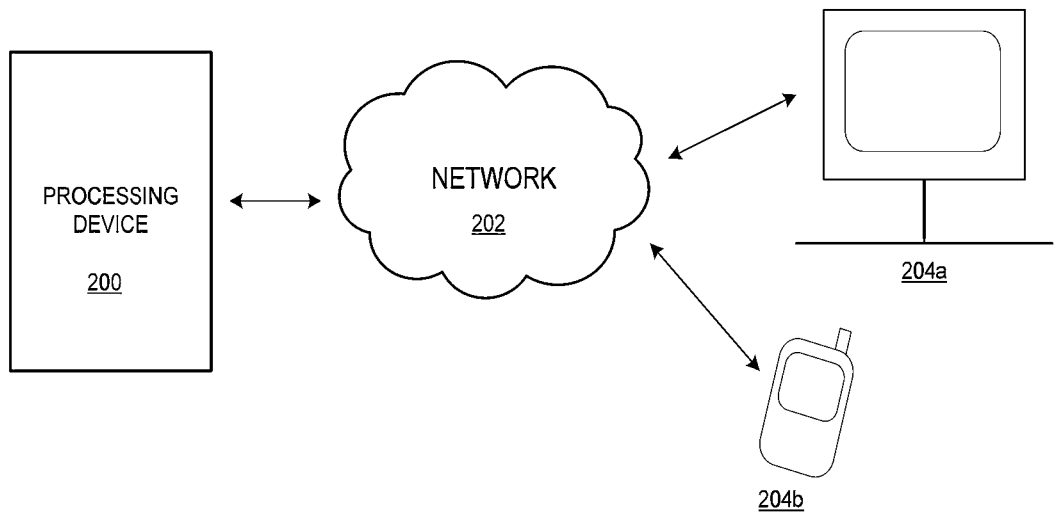
FIG. 2 shows a processing device that can be placed in a designated sample collection site and is configured to be in communication over a network with one or more other devices.

FIG. 2 shows a sample processing device 200 in communication over a network 202 with one or more other devices 204a, 204b.

A sample processing device may be described further elsewhere herein. The sample processing device may be configured to accept one or more cartridge. The sample processing device may be configured to accept a sample from a subject. The sample processing device may be configured to facilitate collection of the sample, prepare the sample for a clinical test, and/or effect a chemical reaction with one or more reagents or other chemical or physical processing. The sample processing device may be configured to detect one or more signals relating to the sample. The sample processing device may be configured to run a test. The test may include running one or more chemical reactions. The sample processing device may be configured to identify one or more properties of the sample. In some embodiments, the device may not be configured to perform a qualitative and/or quantitative evaluation of the sample on board the device. Alternatively, the device may perform such a qualitative and/or quantitative evaluation. For instance, the sample processing device may be configured to detect the presence or concentration of one analyte or a plurality of analytes or a disease condition in the sample (e.g., in or through a bodily fluid, secretion, tissue, or other sample). Alternatively, the sample processing device may be configured to detect signals that may be analyzed to detect the presence or concentration of one or more analytes (which may be indicative of a disease condition) or a disease condition in the sample. The signals may be analyzed on board the device, or at another location. Running a clinical test may or may not include any analysis or comparison of data collected.

A sample processing device 200 may be configured to communicate over a network 202. The sample processing device may include a communication module that may interface with the network. The sample processing device may be connected to the network via a wired connection or wirelessly. The network may be a local area network (LAN) or a wide area network (WAN) such as the Internet. In some embodiments, the network may be a personal area network. The network may include the cloud. The sample processing device may be connected to the network without requiring an intermediary device. Any other description of networks provided herein may be applied.

In some embodiments, the sample processing device 200 may communicate over the network 202 with another device 204a, 204b. The other device may be a communication-enabled device. For example, the other device may be a client computer or a mobile device comprising a video display with at least one display page comprising data. The other device may be any type of networked device, including but not limited to a personal computer, server computer, or laptop computer; personal digital assistants (PDAs) such as a Palm-based device or Windows CE device; phones such as cellular phones, smartphones (e.g., iPhone, Android, Blackberry, etc.), or location-aware portable phones (such as GPS); a roaming device, such as a network-connected roaming device; a wireless device such as a wireless email device or other device capable of communicating wireless with a computer network; or any other type of network device that may communicate possibly over a network and handle electronic transactions. Any discussion of any device mentioned may also apply to other devices, including those described elsewhere herein. The sample processing device may communicate with one or more, two or more, three or more, or any number of other devices. Such communication may or may not be simultaneous. Such communication may include providing data to a cloud computing infrastructure or any other type of data storage infrastructure which may be accessed by other devices.

The other device 204a, 204b that may communicate with the sample processing device 200 may have a video display. Video displays may include components upon which information may be displayed in a manner perceptible to a user, such as, for example, a computer monitor, cathode ray tube, liquid crystal display, light emitting diode display, touchpad or touchscreen display, and/or other means known in the art for emitting a visually perceptible output. Video displays may be electronically connected to a client computer according to hardware and software known in the art.

In one implementation of the invention, a display page may include a computer file residing in memory which may be transmitted from a server over a network to a client computer or other device, which can store it in memory. A client computer may receive tangible computer readable media, which may contain instructions, logic, data, or code that may be stored in persistent or temporary memory of the client computer, or may somehow affect or initiate action by a client computer. Similarly, one or more devices may communicate with one or more client computers across a network, and may transmit computer files residing in memory. One or more devices may communicate computer files or links that may provide access to other computer files.

At a client computer 204a, mobile device 204b, or any other network device as described elsewhere herein, the display page may be interpreted by software residing in memory of the client computer, mobile device, or network device, causing the computer file to be displayed on a video display in a manner perceivable by a user. The display pages described herein may be created using a software language known in the art such as, for example, the hypertext mark up language ("HTML"), the dynamic hypertext mark up language ("DHTML"), the extensible hypertext mark up language ("XHTML"), the extensible mark up language ("XML"), or another software language that may be used to create a computer file displayable on a video or other display in a manner perceivable by a user. Any computer readable media with logic, code, data, instructions, may be used to implement any software or steps or methodology. Where a network comprises the Internet, a display page may comprise a webpage of a type known in the art.

A display page according to the invention may include embedded functions comprising software programs stored on a memory device, such as, for example, VBScript routines, JScript routines, JavaScript routines, Java applets, ActiveX components, ASP.NET, AJAX, Flash applets, Silverlight applets, or AIR routines.

A display page may comprise well known features of graphical user interface technology, such as, for example, frames, windows, scroll bars, buttons, icons, and hyperlinks, and well known features such as a "point and click" interface or a touchscreen interface. Pointing to and clicking on a graphical user interface button, icon, menu option, or hyperlink also is known as "selecting" the button, option, or hyperlink. A display page according to the invention also may incorporate multimedia features, multi-touch, pixel sense, IR LED based surfaces, vision-based interactions with or without cameras.

A user interface may be displayed on a video display and/or display page. The user interface may display a report generated based on analyzed data relating to the sample. The report may include information about the presence or concentration of one or more analyte. The user interface may display raw or analyzed data relating to the sample. The data may include information about the presence or concentration of one or more analyte. The user interface may display an alert. One example of an alert may be if an error is detected on the device, or if an analyte concentration exceeds a predetermined threshold.

In some embodiments, one or more network devices 204a, 204b may be provided at a laboratory facility. The network devices at the laboratory may receive or access data provided by the sample processing device 200. In some other embodiments, one or more network devices may be provided at a health care professional location. In some embodiments, both laboratory devices and health care professional devices may be able to receive or access data provided by the sample processing device. In an additional example, the one or more network devices may belong to the subject. One or more of the laboratory, health care professional, or subject may have a network device able to receive or access data provided by the sample processing device. The one or more laboratory health care professional and/or subject, or the network device of the laboratory, health care professional, and/or subject may be authenticated prior to being granted access to the data. For example, the laboratory personnel, health care professional, and/or subject may have a login ID and/or password in order to access the data. In some embodiments, the data can be sent to the email of the laboratory personnel, health care professional, and/or subject.

In some embodiments, the sample processing device may provide data to a cloud computing infrastructure. The network device (e.g., of a laboratory, health care professional, or other entity) may access the cloud computing infrastructure. In some embodiments, on-demand provision of computational resources (data, software) may occur via a computer network, rather than from a local computer. The network device may contain very little software or data (perhaps a minimal operating system and web browser only), serving as a basic display terminal connected to the Internet. Since the cloud may be the underlying delivery mechanism, cloud-based applications and services may support any type of software application or service. Information provided by the sample processing device and/or accessed by the network devices may be distributed over various computational resources. Alternatively, they may be stored in one or more fixed data storage unit or database.

Figure 3A:
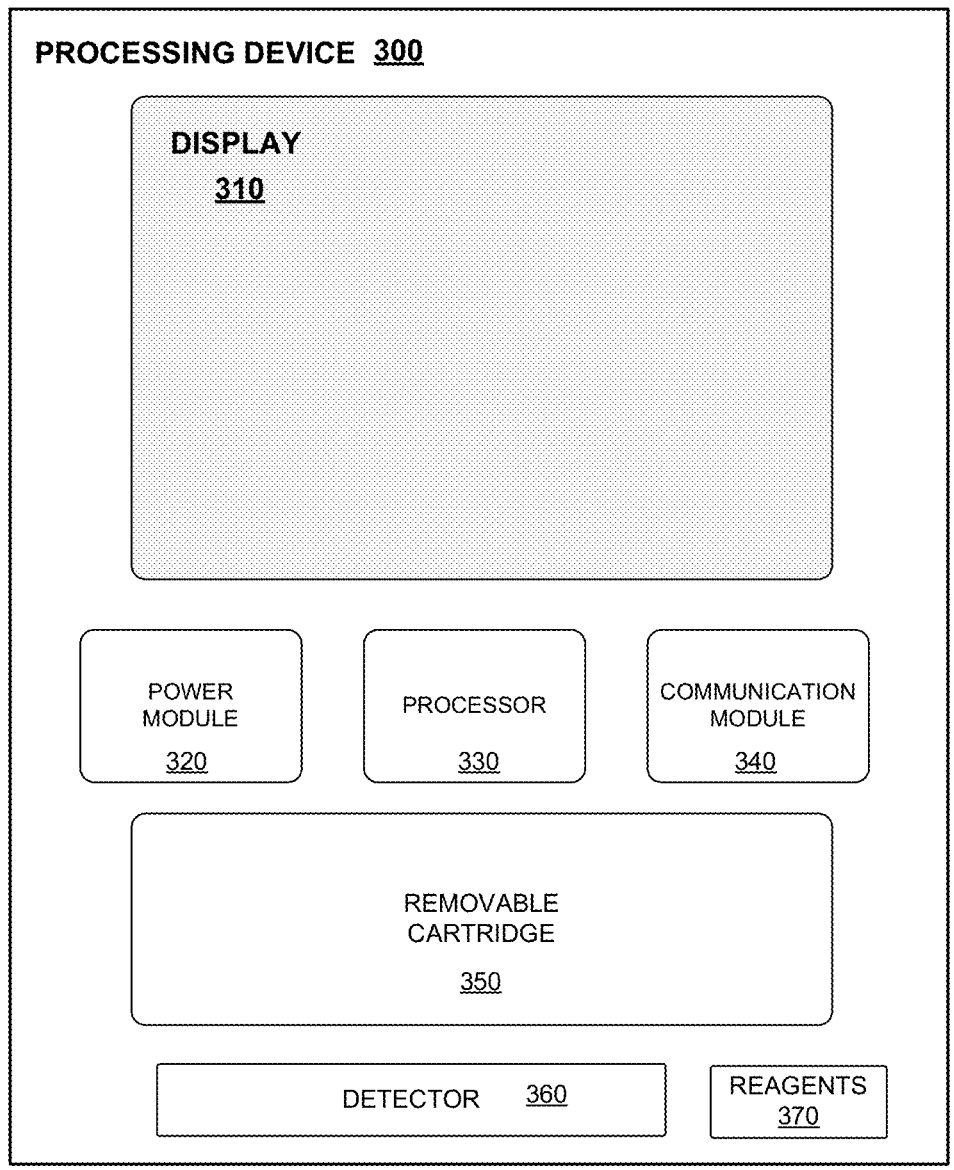
FIG. 3A illustrates various exemplary components of a processing device.

FIG. 3A illustrates a high level example of a sample processing device 300. A sample processing device may be provided at any location, including a sample collection site. The sample processing device may be in or on a subject, or may be carried by the subject. The sample processing device may be easily mobile or transportable. The sample processing device may travel with the subject. The sample processing device may be a benchtop device or a handheld device. The sample processing device may be located remote to a laboratory. Any number of sample processing devices may be distributed geographically in any manner. For example, one or more sample collection sites may have one or more devices.

Figure 3B:
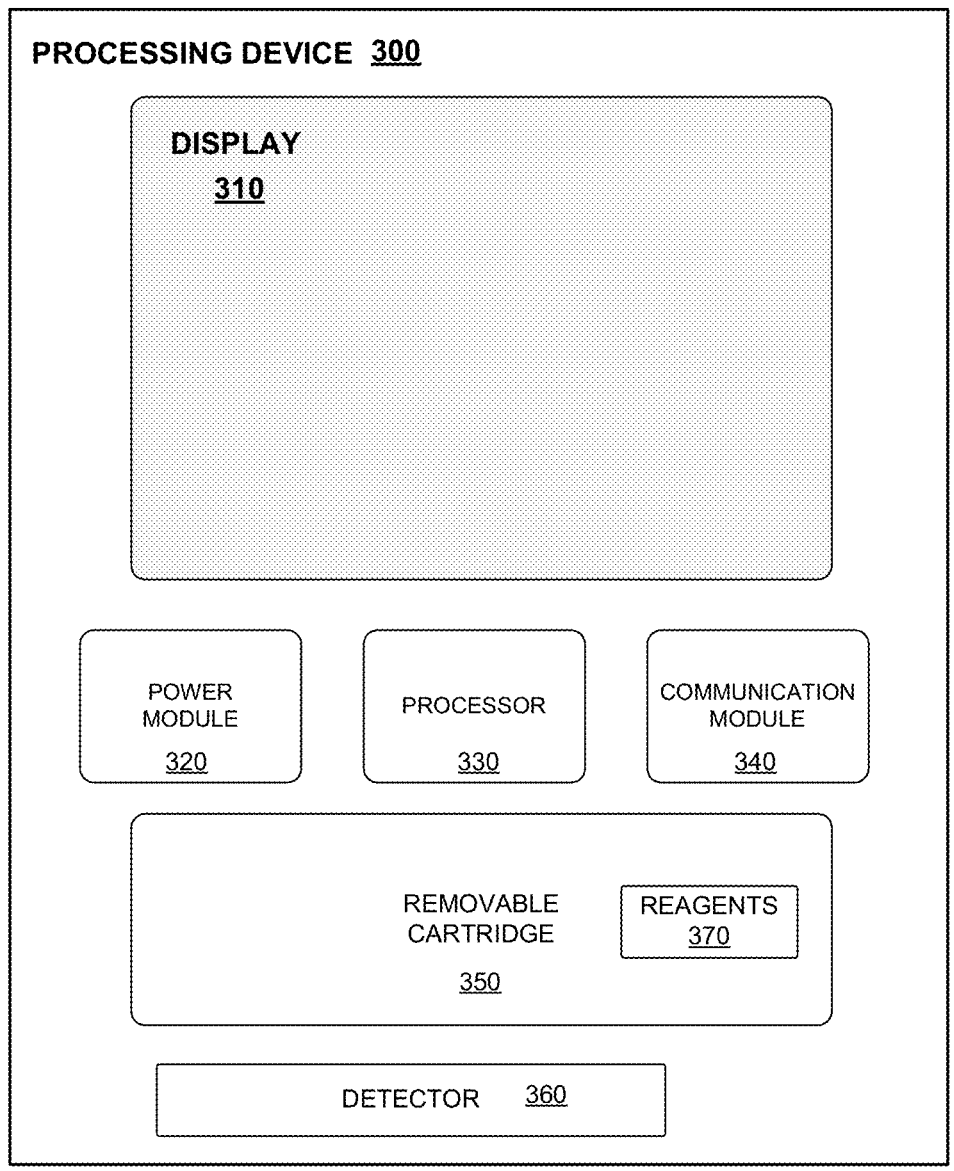
FIG. 3B illustrates another example of a device.

The sample processing device 300 may be configured to accept a removable cartridge 350. The removable cartridge and/or device may have any other characteristics or components as described elsewhere herein. The removable cartridge may be configured to accept a sample and/or deliver the sample to the device. The removable cartridge may have one or more reagents provided thereon. For example FIG. 3B provides an illustration of one or more reagents provided on the removable cartridge. Alternatively, one or more reagents 370 may be provided on board the device, such as shown in FIG. 3A. The device may comprise one or more reagent units that may contain and/or confine one or more reagents. The reagents may originally be provided on the device, the reagents may be provided to the reagent units from or on the cartridge, or both on-board the device and within the cartridge.

In other embodiments, the sample processing device need not have a removable cartridge. One or more functions as described for the cartridge may be provided by the device itself.

The sample processing device and/or a cartridge may comprise all reagents, liquid- and solid-phase reagents, required to perform one or more of the chemical reactions and/or other processing steps, including physical processing, as described elsewhere herein. For example, for a luminogenic ELISA assay the reagents within the device may include a sample diluent, a detector conjugate (for example, three enzyme-labeled antibodies), a surface labeled with antibodies binders, a wash solution, and an enzyme substrate.

Enzyme-linked ImmunoSorbent assays ("ELISA") are assays using antibodies to bind a target analyte in a solution or on a substrate. One useful immunoassay that can be run on a device disclosed herein is ELISA. For example, tips having adherent antibodies or target antigens may be used in ELISAs performed by devices and according to methods disclosed herein.

Performing an ELISA generally involves at least one antibody capable of binding an antigen of interest (i.e., an analyte that is indicative of influenza viral infection). A sample containing or suspected to contain the antigen of interest is immobilized on a support (e.g., a tip or other support having a surface for immobilization) either non-specifically (e.g., via adsorption to the surface) or specifically (e.g., via capture by another antibody specific to the same antigen, in a "sandwich" ELISA). After the antigen is immobilized the detection antibody is added, forming a complex with the antigen. The detection antibody can be conjugated to an enzyme, or can itself be detected by a secondary antibody which is in turn conjugated to an enzyme. Upon addition of a substrate for the conjugated enzyme, a detectable signal is generated which indicates the presence and/or quantity of the antigen in the sample. The choice of substrates will depend on the enzyme conjugated. Suitable substrates include fluorogenic and chromogenic substrates. Those of skill in the art would be understand and be able to determine which parameters of such assays that can be modified to increase the signal detected as well as other variations of ELISAs known in the art.

In some ELISAs, a solid phase capture surface can include an attached first antibody to which a sample (e.g., diluted blood, plasma, or biological specimen) can be added. If present, an analyte in the sample can bind to the first antibody and become immobilized. An enzyme reagent can be added that includes, for example, an antibody coupled or conjugated to an enzyme (e.g., alkaline phosphatase or horseradish peroxidase) that produces a detectable product, or can be otherwise detected. If the antibody portion of the enzyme reagent can bind the analyte, then the enzyme reagent also becomes immobilized at the capture surface. Addition of a substrate for the enzyme can result in a product producing an effect, for example, light that can be measured and plotted as shown. In this manner the amount of analyte present in a sample can be measured.

Thus, for example, an exemplary ELISA which may be performed using a device, system, or method as disclosed herein includes a solid phase capture surface (e.g., a tip) on which a first antibody is immobilized. The first antibody is specific for a test antigen (e.g., antibody specific for a target blood analyte, such as cholesterol, or for e.g., neuraminidase on the coat of a virus of interest, or other antigen). If the test antigen is present in a test sample (e.g., whole blood, plasma, or serum) that is exposed to the antibody immobilized on the surface, then the test antigen can become immobilized (captured) at the capture surface. Addition of a second, labeled antibody that binds to the first antibody (e.g., where the first antibody has a biotin label, and the second antibody has an avidin label and a detectable label; or where the first antibody is a sheep antibody including an Fc portion, the second antibody may be an antibody targeting sheep Fc and labeled with alkaline phosphatase (AP) which can be detected following addition of AP substrate) allows the detection and quantification of the amount of antigen in the sample. The first antibody, which is bound to the substrate, is not washed out by the addition of the second antibody. Such detection and quantification may be accomplished by providing substrate for alkaline phosphatase, leading to the production of colored, fluorescent, luminescent (e.g., chemiluminescent), or otherwise detectable compounds which may be detected and measured.

Alternatively, after the blood sample is placed in contact with the surface having the immobilized first antibody (labeled with an enzyme which catalyzes a reaction that produces a first detectable compound) that targets a first antigen, a second antibody, targeting a second antigen and labeled with a second enzyme which can produce a second detectable compound may be added. The first antibody, which is bound to the substrate, is not washed out by the addition of the second antibody, and may be detected by providing the substrate and proper reaction conditions for the production of a first detectable product by enzyme linked to the first antibody. Binding and subsequent detection of the second, labeled antibody at the capture surface indicates the presence of both the first and the second test antigens in the test sample. Both the first and second detectable compounds produced by the enzymes linked to the antibodies may be detected by any means desired, including by detection of fluorescence, luminescence, chemiluminescence, absorbance, or other means for detecting the products of the enzymatic reactions due to the attached enzymes.

For example, photomultipliers tubes, charge-coupled devices, photodiodes, cameras, spectrophotometers, and other components and devices may be used to measure light emitted or affected during the performance of an ELISA. For example, the amount of light detected (e.g., in relative light units, or other measurements of luminosity) during the performance of an ELISA on a sample may be compared to a standard curve (e.g., a calibration curve prepared for a particular assay, device, cartridge, or reagent) to calculate the concentration of the target analyte in the sample. Analytes that have been detected and their levels measured in blood samples using ELISAs performed on devices and systems as disclosed herein include: vitamin B-12, folic acid, thyroxine, testosterone, estradiol, cotinine, vancomycin, hemoglobin A1c, prostate specific antigen, human chorionic gonadotropin, luteinizing hormone, parathyroid hormone, alpha-fetoprotein, prealbumin, cardiac troponin T, C-reactive protein, hepatitis B surface antigen (HbsAg), immunoglobulin E (IgE), immunoglobulin G (IgG), Dengue virus IgG, rheumatoid factor IgM, West Nile Virus IgM, anti-HIV 1 antibodies, anti-HIV 2 antibodies, anti-nuclear antibodies, influenza A, influenza B, and *streptococcus*.

ELISAs are also used, for example, in competitive binding experiments, in which the concentration of an analyte in a solution may be measured by adding a known amount of labeled analyte, and measuring the binding of the analyte. Increased concentrations of the sample analyte (which does not include the label) interfere ("compete") with the binding of the labeled analyte, allowing calculation of the amount of analyte in the sample.

Additional reagents can be provided as needed. In some embodiments, reagents can be incorporated into a device to provide for sample pretreatment. Examples of pretreatment reagents include, without limitation, white cell lysis reagents, reagents for liberating analytes from binding factors in the sample, enzymes, and detergents. The pretreatment reagents can also be added to a diluent contained within the device.

Reagents according to the present invention include without limitation wash buffers, enzyme substrates, dilution buffers, conjugates, enzyme-labeled conjugates, DNA amplifiers, sample diluents, wash solutions, sample pretreatment reagents including additives such as detergents, polymers, chelating agents, albumin-binding reagents, enzyme inhibitors, enzymes, anticoagulants, red-cell agglutinating agents, antibodies, or other materials necessary to run an assay on a device. An enzyme-labeled conjugate can be either a polyclonal antibody or monoclonal antibody labeled with an enzyme that can yield a detectable signal upon reaction with an appropriate substrate. Non-limiting examples of such enzymes are alkaline phosphatase and horseradish peroxidase. In some embodiments, the reagents comprise immunoassay reagents. Reagents defining assay specificity may be provided, which may optionally include, for example, monoclonal antibodies, polyclonal antibodies, proteins, nucleic acid probes or other polymers such as affinity matrices, carbohydrates or lipids. In general, reagents, especially those that are relatively unstable when mixed with liquid, are confined separately in a defined region (for example, a reagent unit) within the device and/or cartridge.

In some embodiments, a reagent unit may contain a small volume of reagent. For example, a reagent unit may contain approximately about 5 microliters or less to about 1 milliliter of liquid. In some embodiments, the unit may contain about 20-200 microliters of liquid. In a further embodiment, the reagent unit contains 100 microliters of fluid. In an embodiment, a reagent unit contains about 40 microliters of fluid. A reagent unit may include any volume described elsewhere herein, which may include volumes of sample. The volume of liquid in a reagent unit may vary depending on the type of assay being run or the sample of bodily fluid provided. In an embodiment, the volumes of the reagents do not have to be predetermined, but must be more than a known minimum. In some embodiments, the reagents are initially stored dry and dissolved upon initiation of the assay being run on the device.

The sample processing device may comprise a display 310. The display may be a video display or other type of user interface. The display may function as a user interface. The display may permit a user to operate the sample processing device. The display may be configured to accept an input from the user relating to a subject identity, other information about the subject, information about the sample, information about one or more clinical test, information about sample preparation steps, information about a laboratory, and/or information about a medical care provider.

The display may output information to an operator of the device. The display may prompt the operator to perform one or more steps in the operation of the device. The display may display information about the sample collected, the subject, and/or data relating to one or more preparation step performed or chemical reaction run. The display may output information about one or more automated process that may be implemented by the device. The display may provide one or more alert for an error detected, or when one or more parameters are met (e.g., certain detected signals exceed a predetermined threshold). A display may display results on the device.

The sample processing device 300 may comprise one or more components useful for collecting the sample, preparing the sample for a clinical test, and/or running a chemical reaction, or other test or analysis. The sample processing device may also comprise one or more components useful for detecting one or more signal relating to the sample or components of the device. For example, the sample processing device may include, but is not limited to, a sample collection unit, centrifuge, magnetic separator, filter, pipette or other fluid handling system, vessels, containers, assay units, reagent units, heater, thermal block, cytometer, spectrophotometer, imaging systems, microscopy station, light source, optical detector, photometer, temperature sensor, motion sensor, or sensor for electrical properties. Fluid may be transferred from one component to another via a fluid handling system, such as a pipette, channels, or pumps.

In some embodiments, the fluid handling system may be a pipettor. The pipettor may be a multi-head pipettor. In some instances, each of the pipette heads may be of the same type or may be of different types. For example, the pipette heads may be air displacement pipettes and/or positive displacement pipettes. In some instances, the fluid handling system may be capable of picking up and/or removing one or more pipette tip. The pipette tips may be individually added or removed from the pipette head. The pipette head may transfer the pipette tip from a first location to a second location. A pipette tip may be capable of connecting to and forming a fluid-tight seal with a pipette head or screwing into it or attaching in other ways. A sample or other fluid may be aspirated and/or dispensed by the pipette tip.

The pipette tip may have an interior surface and an exterior surface. The pipette tip may have a first end and an opposing second end. In some embodiments, both the first and second ends may be open. In some embodiments, the first end may have a diameter that is greater than the diameter of the second end. The pipette tip may or may not be coated with reagents and/or capturing binders such as antibodies. In some instances, an interior surface of the pipette tip may be coated with a reagent and/or capturing binders. A chemical reaction may take place within the pipette tip. The chemical reaction may take place within the pipette tip while the tip is attached to a pipette head, or when the tip is separated from the pipette head. Alternatively, chemical reactions may take place within one or more vessel. The pipette may deliver a sample or other fluid to, or aspirate a sample or other fluid from, a vessel. The pipette tip may be capable of being at least partially inserted into a vessel.

The pipettor may be utilized to transfer a sample or other fluid within the device. The pipettor may assist with the preparation of a sample. The pipettor may assist with the running of a chemical reaction.

The sample processing device may be capable of performing at least one sample preparation step and/or running one or more, two or more, three or more, four or more, five or more, six or more, seven or more, eight or more, nine or more, ten or more, twenty or more, thirty or more, or fifty or more chemical reactions. The device may be capable of performing one or more, two or more, three or more, four or more, five or more, six or more, seven or more, eight or more, nine or more, ten or more, twenty or more, thirty or more, or fifty or more different types of assays. These may occur simultaneously and/or in sequence. The sample preparation and/or chemical reactions that may occur may be governed by protocols that may be individualized to a subject's needs and/or sent back and forth from a server and/or stored or inputted locally. The subject's needs may be based on a prescription or instructions that the subject has received from a health care professional. The device may be configured to accommodate a wide range of sample preparation and/or chemical reactions.

The sample processing device 300 may include one or more detector 360 which may be capable of detecting one or more signal relating to the sample. The detector may be able to detect all emissions from the electromagnetic spectrum. Alternatively the detector may be able to detect a selected range of emission from the electromagnetic spectrum. For example, an optical detector may detect an optical signal relating to a chemical reaction that had taken place on the device. An electrical property sensor or other sensor may detect the voltage, current, impedance, resistance, or any other electrical property of a sample. A temperature sensor may determine the temperature of a thermal block, upon which a sample may rest. A sensor may determine the speed of a centrifuge. A sensor may determine the position, velocity, and/or acceleration of a pipette and/or the successful execution of a protocol.

One or more detectable signal may be detected by a detector 360. The detectable signal can be a luminescent signal, including but not limited to photoluminescence, electroluminescence, chemiluminescence, fluorescence, phosphorescence or any emission from the electromagnetic spectrum. In some embodiments, one or more label may be employed during a chemical reaction. The label may permit the generation of a detectable signal. Methods of detecting labels are well known to those of skill in the art. Thus, for example, where the label is a radioactive label, means for detection may include a scintillation counter or photographic film as in autoradiography. Where the label is a fluorescent label, it may be detected by exciting the fluorochrome with the appropriate wavelength of light and detecting the resulting fluorescence by, for example, microscopy, visual inspection, via photographic film, by the use of electronic detectors such as digital cameras, charge coupled devices (CCDs) or photomultipliers and phototubes, or other detection device. In some instances, cameras may utilize CCDs, CMOS, may be lensless cameras (e.g., Frankencamera), open-source cameras, or may utilize or any other visual detection technology known or later developed in the art. In some embodiments, imaging devices may employ 2-d imaging, 3-d imaging, and/or 4-d imaging (incorporating changes over time). Similarly, enzymatic labels are detected by providing appropriate substrates for the enzyme and detecting the resulting reaction product. Finally, simple colorimetric labels are often detected simply by observing the color associated with the label. For example, conjugated gold often appears pink, while various conjugated beads appear the color of the bead.

In some embodiments, an imaging unit may be provided. Examples of imaging units may include any of the detectors and/or optical detection devices as described elsewhere herein. For example, imaging units may be cameras which may utilize CCDs, CMOS, may be lensless cameras (e.g., Frankencamera), open-source cameras, or may utilize or any other visual detection technology known or later developed in the art. An imaging unit may capture static images and/or may capture moving images. For example, the imaging unit may capture a series of digital images. An imaging unit may capture video images. An imaging device may be a camera or a sensor that detects and/or records electromagnetic radiation and associated spatial and/or temporal dimensions.

In one example, the imaging unit may capture one or more digital image of a sample. For example, the imaging unit may capture an image of a tissue sample. The picture of the tissue sample may be transmitted to a pathologist or other health care professional. Analysis and/or oversight may occur for the image of the tissue sample. Analysis and/or oversight may occur on-board or remotely, by a health care professional or a software program. In other examples, the imaging unit may capture images of a sample, and/or any form of preparation of the sample such as chemical reactions or physical processing steps occurring with the sample. For example, a video may be taken of a chemical reaction. Any description herein of data may also apply to data representative of images, and vice versa.

Imaging may be used to, e.g., detect, examine, identify, characterize, and quantify cells in a sample, such as in, e.g., a blood sample, a urine sample, biopsy tissue, or other sample. Such use of imaging and other techniques may be termed "cytometry." Cytometry includes observations and measurements of cells, such as red blood cells, platelets, white blood cells, including qualitative and quantitative observations and measurements of cell numbers, cell types, cell surface markers, internal cellular markers, and other characteristics of cells of interest. Where a biological sample includes or is a blood sample, the sample may be divided into portions, and may be diluted (e.g., to provide greater volume for ease of handling, to alter the density or concentration of cellular components in the sample to provide a desired diluted density, concentration, or cell number or range of these, etc.). The sample may be treated with agents which affect coagulation, or may be treated or handled so as to concentrate or precipitate sample components (e.g., ethylene diamine tetraacetic acid (EDTA) or heparin may be added to the sample, or the sample may be centrifuged or cells allowed to settle). A sample may be treated by adding dyes or other reagents which may react with and mark particular cells or particular cellular components. For example, dyes which mark cell nuclei (e.g., hematoxylin dyes, cyanine dyes, drag dyes such as Draq5, and others); dyes which mark cell cytoplasm (e.g., eosin dyes, including fluorescein dyes, and others) may be used separately or together to aid in visualization, identification, and quantification of cells. More specific markers, including antibodies and antibody fragments specific for cellular targets, such as cell surface proteins, intracellular proteins and compartments, and other targets, are also useful in cytometry.

Biological samples may be measured and analyzed by cytometry using optical means, including, for example, photodiode detectors, photomultipliers, charge-coupled devices, laser diodes, spectrophotometers, cameras, microscopes, or other devices which measure light intensity (of a single wavelength, of multiple wavelengths, or of a range, or ranges, of wavelengths of light), form an image, or both. A field of view including a sample may be imaged, or may be scanned, or both, using such detectors. A biological sample may be measured and analyzed by cytometry prior to processing, dilution, separation, centrifugation, coagulation, or other alteration. A biological sample may be measured and analyzed by cytometry during or following processing, dilution, separation, centrifugation, coagulation, or other alteration of the sample. For example, a biological sample may be measured and analyzed by cytometry directly following receipt of the sample. In other examples, a biological sample may be measured and analyzed by cytometry during or after processing, dilution, separation, centrifugation, coagulation, or other alteration of the sample.

For example, a blood sample may be prepared for cytometry by sedimentation or centrifugation. A sedimented or pellet portion of such a sample may be resuspended in a buffer of choice prior to cytometric analysis (e.g., by aspiration, stirring, sonication, or other processing). A biological sample may be diluted or resuspended with water, or with a saline solution, such as a buffered saline solution prior to cytometric analysis. A solution used for such dilution or resuspension may or may not include a fixative (e.g., formaldehyde, paraformaldehyde, or other agent which cross-links proteins). A solution used for such dilution or resuspension may provide an osmotic gradient between the surrounding solution and the interior, or an interior compartment, of cells in the sample, effective that the cell volume of some or all cells in the sample is altered. For example, where the resulting solution concentration following dilution is less than the effective concentration of the interior of a cell, or of an interior cell compartment, the volume of such a cell will increase (i.e., the cell will swell). A biological sample may be diluted with a solution which may or may not include an osmoticant (such as, for example, glucose, sucrose, or other sugar; salts such as sodium, potassium, ammonium, or other salt; or other osmotically active compound or ingredient). In embodiments, an osmoticant may be effective to maintain the integrity of cells in the sample, by, for example, stabilizing or reducing possible osmotic gradients between the surrounding solution and the interior, or an interior compartment, of such cells. In embodiments, an osmoticant may be effective to provide or to increase osmotic gradients between the surrounding solution and the interior, or an interior compartment, of such cells, effective that the cells at least partially collapse (where the cellular interior or an interior compartment is less concentrated than the surrounding solution), or effective that the cells swell (where the cellular interior or an interior compartment is more concentrated than the surrounding solution).

For example, a biological sample may be measured or analyzed following dilution of the sample with a solution including dyes. For example, a biological sample may be measured or analyzed following dilution of a portion of the sample with a solution including antibodies or antibody fragments. For example, a biological sample may be measured or analyzed following dilution of the sample with a solution including particles. Particles added to a biological sample may serve as standards (e.g., may serve as size standards, where the size or size distribution of the particles is known, or as concentration standards, where the number, amount, or concentration of the particles is known), or may serve as markers (e.g., where the particles bind or adhere to particular cells or types of cells, to particular cell markers or cellular compartments, or where the particles bind to all cells in a sample).

For example, a biological sample may be measured or analyzed following processing which may separate one or more types of cells from another cell type or types. Such separation may be accomplished by gravity (e.g., sedimentation); centrifugation; filtration; contact with a substrate (e.g., a surface, such as a wall or a bead, containing antibodies, lectins, or other components which may bind or adhere to one cell type in preference to another cell type); or other means. Separation may be aided or accomplished by alteration of a cell type or types. For example, a solution may be added to a biological sample, such as a blood sample, which causes some or all cells in the sample to swell. Where one type of cell swells faster than another type or types of cell, cell types may be differentiated by observing or measuring the sample following addition of the solution. Such observations and measurements may be made at a time, or at multiple times, selected so as to accentuate the differences in response (e.g., size, volume, internal concentration, or other property affected by such swelling) and so to increase the sensitivity and accuracy of the observations and measurements. In some instances, a type or types of cells may burst in response to such swelling, allowing for improved observations and measurements of the remaining cell type or types in the sample.

Observation, measurement and analysis of a biological sample by cytometry may include photometric measurements, for example, using a photodiode, a photomultiplier, a laser diode, a spectrophotometer, a charge-coupled device, a camera, a microscope, or other means or device. Cytometry may include preparing and analyzing images of cells in a biological sample (e.g., two-dimensional images), where the cells are labeled (e.g., with fluorescent, chemiluminescent, enzymatic, or other labels) and plated (e.g., allowed to settle on a substrate) and imaged by a camera. The camera may include a lens, and may be attached to or used in conjunction with a microscope. Cells may be identified in the two-dimensional images by their attached labels (e.g., from light emitted by the labels).

An image of cells prepared and analyzed by a cytometer as disclosed herein may include no cells, one cell, or multiple cells. A cell or cell in an image of a cytometer, as disclosed herein, may be labeled, as disclosed above. A cell or cell in an image of a cytometer, as disclosed herein, may be labeled, as disclosed above, effective to identify the image, and the subject from whom the sample was taken.

Cytometric measurements of cells from samples of blood have been made using devices, systems, and methods embodying features disclosed herein. Cytometric images have been used, for example, to count the numbers of cells (e.g., providing the number of cells per volume of blood), to determine the sizes and size distribution of cells in the sample (including mean, standard deviation, and other size measures), and to identify cell types based on cell surface markers. Typically, the total concentration of red blood cells and platelets is in the range of about $1-3\times10^6$ cells per microliter (e.g., about $2\times10^6$ cells per microliter). Cells were allowed to settle on the floor of a channel within the cuvette, allowing an image to be taken of a single focal plane that was sufficient to detect all the cells in the volume within the image area; thus a count of the cells in a single image provided a count of the cells in the volume of blood represented by that image. Since the dimensions of the channel were known, the volume of blood above the area shown in the image allowed accurate calculation of the density of cells within that volume. Volume is also measured by inclusion of known concentrations of beads (the images of which are distinguishable from blood cell images) as indicators; since the concentration of the beads was known, counting the numbers of beads in a field allowed a precise calculation of the volume of sample from which an image was taken.

Optical images included fluorescence images for detecting red, blue and green wavelengths (useful, for example, for detecting and measuring fluorescence from dyes attached to specific cell-surface markers), and darkfield images (useful for detecting cell shape and outlines, and for measuring cell size and volume). Fluorescence images may be used, for example, to identify and quantitate different cell types in the sample. Darkfield images are based on light scattered from the objects in the cuvette, and they provide information regarding the size, shape, and number of objects in the cuvette. Forward scatter measurements were used to quantify cell size. Side scatter measurements were used to determine, identify, and categorize cell morphology.

Data from the images was processed by a controller associated with the sample processing device. The following measurements may be calculated: 1) number of red blood cells in the cuvette; 2) average volume of red blood cells in the cuvette; 3) red blood cell distribution width (RDW) of red blood cells in the cuvette; 4) number of platelets in the cuvette; 5) average volume of platelets in the cuvette; and 6) platelet distribution width of platelets in the cuvette.

Microscopy methods that may be used with devices and systems disclosed herein include but are not limited to bright field, oblique illumination, dark field, dispersion staining, phase contrast, differential interference contrast (DIC), polarized light, epifluorescence, interference reflection, fluorescence, confocal (including CLASS), confocal laser scanning microscopy (CLSM), structured illumination, stimulated emission depletion, electron, scanning probe, infrared, laser, widefield, light field microscopy, lensless on-chip holographic microscopy, digital and conventional holographic microscopy, extended depth-of-field microscopy, optical scatter imaging microscopy, deconvolution microscopy, defocusing microscopy, quantitative phase microscopy, diffraction phase microscopy, confocal Raman microscopy, scanning acoustic microscopy and X-ray microscopy. Magnification levels used by microscopy may include, as nonlimiting examples, up to 2×, 5×, 10×, 20×, 40×, 60×, 100×, 100×, 1000×, or higher magnifications. Feasible magnification levels will vary with the type of microscopy used. For example, images produced by some forms of electron microscopy may involve magnification of up to hundreds of thousands of times. Multiple microscopy images may be recorded for the same sample to generate time-resolved data, including videos. Individual or multiple cells may be imaged simultaneously, by parallel imaging or by recording one image that encompasses multiple cells. A microscopic objective may be immersed in media to change its optical properties, such as through oil immersion. A microscopic objective may be moved relative to the sample by means of a rotating CAM to change the focus. Cytometry data may be processed automatically or manually, and may further include analyses of cell or tissue morphology, such as by a pathologist for diagnostic purposes.

The microscopic objective can be finely positioned to focus the image via an actuator, such as by a cam connected to a motor. The objective may be focused on one or more planes of the sample. Focusing may be automated by image analysis procedures by computing the image sharpness of digital images among other methods.

Cell counting can be performed using cytometry, e.g., imaging with or without microscopy. In situations where the subjects may be bright-field illuminated, the preferred embodiment is to illuminate the subjects from the front with a white light and to sense the cells with an imaging sensor. Subsequent digital processing will count the cells. Where the cells are infrequent or are small, the preferred embodiment is to attach a specific or non-specific fluorescent marker, and then illuminate the subject field with a laser or other suitable light source. Confocal scanning imaging may be used. In embodiments, up to 500 or 1000 cells of any given type may be counted. In other embodiments, various numbers of cells of any given type may be counted, including but not limited to more than or equal to about 1 cell, 5 cells, 10 cells, 30 cells, 50 cells, 100 cells, 150 cells, 200 cells, 300 cells, 500 cells, 700 cells, 1000 cells, 1500 cells, 2000 cells, 3000 cells, 5000 cells. Cells may be counted using available counting algorithms. Cells can be recognized by their characteristic fluorescence, size and shape.

In some microscopy embodiments, brightfield illumination may be achieved by the use of a white light source along with a stage-condenser to create Koehler illumination. Brightfield images of cells, which may detect properties similar to that of forward scattering in flow cytometry, can reveal cell size, phase-dense material within the cells and colored features in the cell if the cells have been previously stained. In one example embodiment, the Wright-Giemsa staining method can be used to stain human whole blood smear. Brightfield imaging shows characteristic patterns of staining of human leukocytes. The characteristically shaped red cells can also be identified in these images.

In some microscopy embodiments, darkfield imaging may be achieved by the use of a ringlight based illumination scheme, or other epi- or trans-darkfield illumination schemes available. Darkfield imaging may, for example, be used to determine light scattering properties of cells, equivalent to side scatter in flow cytometry, such as when imaging human leukocytes. The internal and external features of the cell which scatter more light appear brighter and the features which scatter lesser amounts of light appear darker in a darkfield image. Cells such as granulocytes have internal granules of size range (100-500 nm) which can scatter significant amount of light and generally appear brighter in darkfield images. Furthermore, the outer boundary of any cell may scatter light and may appear as a ring of bright light. The diameter of this ring may directly give the size of the cell. Microscopy methods may additionally be used to measure cell volume. For example, red blood cell volume may be measured. To increase accuracy, red blood cells may be transformed into spheres through the use of anionic or zwitterionic surfactants, and dark field imaging used to measure the size of each sphere, from which cell volumes may be calculated.

In some microscopy embodiments, small cells or formed elements which may be below the diffraction-limited resolution limit of the microscope, may be labeled with fluorescent markers; the sample may be excited with light of appropriate wavelength and an image may be captured. The diffraction pattern of the fluorescent light emitted by the labeled cell may be quantified using computer analysis and correlated with the size of the cell. The computer programs used for these embodiments is described elsewhere herein. To improve the accuracy of this method, the cells may be transformed into spheres by the use of anionic and zwitterionic surfactants.

Cell imaging may be used to extract one or more of the following kinds of information for each cell (but is not limited to the following): Cell size; Quantitative measure of cell granularity or light scattering (also popularly called side scatter, based on flow cytometry parlance); Quantitative measure of fluorescence in each spectral channel of imaging, after compensating for cross-talk between spectral channels, or intracellular distribution pattern of fluorescent or other staining; Shape of the cell, as quantified by standard and custom shape attributes such as aspect ratio, Feret diameters, Kurtosis, moment of inertia, circularity, solidity etc.; Color, color distribution and shape of the cell, in cases where the cells have been stained with dyes (not attached to antibodies or other types of receptor); Intracellular patterns of staining or scattering, color or fluorescence that are defined as quantitative metrics of a biological feature such as morphology, for example density of granules within cells in a darkfield image, or the number and size of nucleolar lobes in a Giemsa-Wright stained image of polymorphonuclear neutrophils etc.; Co-localization of features of the cell revealed in images acquired in different channels; Spatial location of individual cells, cellular structures, populations of cells, intracellular proteins, ions, carbohydrates and lipids or secretions (such as to determine the source of secreted proteins).

A wide range of cell-based assays can be designed to use the information gathered by cytometry. For example, an assay for performing a 5-part leukocyte differential may be provided. The reportables in this case may, for example, be number of cells per microliter of blood for the following types of leukocytes: monocytes, lymphocytes, neutrophils, basophils and eosinophils. Reportables may also be used to classify leukocyte differentiation, or identify T and B-cell populations.

Fluorescence microscopy generally involves labeling of cells or other samples with fluorescent labels, described in more detail below. Microscopic imaging of fluorescently labeled samples may gather information regarding the presence, amounts, and locations of the target that is labeled at a given moment in time or over a period of time. Fluorescence may also be used to enhance sensitivity for detecting cells, cellular structures, or cellular function. In fluorescence microscopy, a beam of light is used to excite the fluorescent molecules, which then emit light of a different wavelength for detection. Sources of light for exciting fluorophores are well known in the art, including but not limited to xenon lamps, lasers, LEDs, and photodiodes. Detectors include but are not limited to PMTs, CCDs, and cameras.

Spectroscopy includes any and all assays that produce luminescence or change light (e.g., color chemistry). These may include one or more of the following: spectrophotometry, fluorimetry, luminometry, turbidimetry, nephelometry, refractometry, polarimetry, and measurement of agglutination.

Spectrophotometry refers to measuring a subject's reflection or transmission of electromagnetic waves, including visible, UV, and infrared light. Spectrophotometry may, for example, be used to determine nucleic acid concentrations in a sample, such as by measuring absorbance at a wavelength of about 260 nm, to determine protein concentration by measuring absorbance at a wavelength of about 280 nm, and/or to determine salt concentration by measuring absorbance at a wavelength of about 230 nm.

Other examples of spectrophotometry may include infrared (IR) spectroscopy. Examples of infrared spectroscopy include near-infrared spectroscopy, far-infrared spectroscopy laser-Raman spectroscopy, Raman confocal laser spectroscopy, Fourier Transform infrared spectroscopy, and any other infrared spectroscopy technique. Frequencies of less than about 650 cm-1 are typically used for far-infrared spectroscopy, frequencies greater than about 4000 cm-1 are typically used for near-infrared spectroscopy, while frequencies between about biomedical applications, including in screening and diagnosis of cancer, arthritis, and other diseases, determining chemical compositions of biological fluids, determining septic state, and others. IR spectroscopy may be used on solid samples, such as tissue biopsies, cell cultures, or Pap smears; or on liquid samples, such as blood, urine, synovial fluid, mucus, and others. IR spectroscopy may be used to differentiate between normal and cancerous cells as described in U.S. Pat. No. 5,186,162, herein incorporated by reference. IR spectroscopy may also be used on blood samples to detect markers for cancers of various solid organs. IR spectroscopy may also be used to determine cellular immunity in patients, such as to diagnose immunodeficiencies, autoimmune disorders, infectious diseases, allergies, hypersensitivity, and tissue transplant compatibility.

IR spectroscopy may be used to determine glucose levels in blood, which is of use for diabetic patients, such as for monitoring insulin response. IR spectroscopy may further be used to measure other substances in blood samples, such as alcohol levels, fatty acid content, cholesterol levels, hemoglobin concentration. IR spectroscopy can also distinguish between synovial fluid from healthy and arthritic patients.

Fluorimetry refers to measuring the light emitted by a fluorescent molecule coupled to a subject upon exciting the fluorescent molecule with incident light. Fluorimetry may use any of the fluorescent molecules, labels, and targets as described for cytometric assays above. In some embodiments, fluorimetry uses substrate molecules that change in fluorescence based on an enzymatic activity, such as converting NAD+ to NADH or vice versa or producing beta-galactosidase from a precursor molecule. Fluorimetry may be used with a polarized excitation source to measure fluorescence polarization or anisotropy of a subject, which may provide information about the size and/or binding state.

Colorimetry refers to measuring the transmissive color absorption of a subject, preferably by backlighting the subject with white light with the result sensed by an imaging sensor. Examples include some assays that use oxidases or peroxidases combined with a dye that becomes colored in the presence of hydrogen peroxide. One method that measures peroxidase activity in whole cell suspensions of human white blood cells is disclosed in Menegazzi, et al., J. Leukocyte Biol 52: 619-624 (1992), which is herein incorporated by reference in its entirety. Such assays may be used to detect analytes that include but are not limited to alcohols, cholesterols, lactate, uric acid, glycerol, triglycerides, glutamate, glucose, choline, NADH. Some of the enzymes that may be used include horseradish peroxidase, lactoperoxidase, microperoxidase, alcohol oxidase, cholesterol oxidase, NADH oxidase. Other nonlimiting examples of colorimetric assays include dye-based assays to determine protein concentration, such as Bradford, Lowry, biureat, and Nano-orange methods. The pH of a sample may also be determined by colorimetric assays with indicator dyes, including but not limited to phenolphtalein, thymolphtalein, alizarin Yellow R, indigo carmine, m-cresol purple, cresol red, thymol blue, xylenol blue, 2,2',2'',4,4'-pentamethoxytriphenyl carbinol, benzopurpurin 4B, metanil yellow, 4-phenylazodiphenylamine, malachite green, quinaldine red, orange IV, thymol blue, xylenol blue, and combinations thereof.

Luminometry uses no illumination method as the subject emits its own photons. The emitted light can be weak and can be detecting using an extremely sensitive sensor such as a photomultiplier tube (PMT). Luminometry includes assays that produce chemiluminescence, such as those using luciferases or some assays using peroxidases.

For turbidimetry, the preferred embodiment for sensing is backlighting the subject with white light with the result sensed by an imaging sensor. For turbidimetry, the reduction of the intensity of the transmitted light is measured. Turbidimetry may be used, for example, to determine a concentration of cells in solution. In some embodiments, turbidimetry is measured by nephelometry.

Nephelometry measures the light that is transmitted or scattered after passing through a subject in a suspension, typically a substrate bound to an immunoglobin such as IgM, IgG, and IgA.

Polarimetry measures the polarization of, typically, electromagnetic waves by a subject. Polarimetry assays include circular dichroism, which may provide structural information and light scattering assays, which may provide information about the size and/or shape of the subject. One nonlimiting example of light scattering assays uses dynamic light scattering (DLS). Subjects for these assays do not require labeling.

The sample processing device 300 may have a processor 330 that may provide instructions to one or more components of the device. The processor may act as a controller that may instruct one or more component of the device. For example, the processor may provide an instruction to a pipette to aspirate or dispense a fluid. The processor may provide an instruction that controls the temperature of a heater (which may optionally heat and/or cool the device). The processor may provide an instruction to an optical detector to detect one or more signal. The processor may also receive instructions and/or collected data. For example, a processor may act in accordance with one or more protocol. The protocol may be provided on board the device or may be provided from a source external to the device. The processor may also receive data regarding signals detected by the device. The processor may or may not analyze signals that have been detected by the device. The processor may or may not compare one or more detected signal with a threshold value.

A communication module 340 may be provided on the device 300. A communication unit may be part of a laboratory or set-up which includes the device. The communication module may permit the device to communicate with an external machine. For example, the communication module may receive one or more protocol or set of instructions from an external source. In some embodiments, the external source may be a laboratory. The communication module may also permit the device to transmit data to an external machine. Data may be transmitted via a transmission unit. For example, the device may transmit data to a laboratory or to a health care professional. The device may transmit data to a cloud computing infrastructure, which may be accessed by a laboratory, health care professional, or other entity. The communication module may permit wireless and/or wired communication.

The sample processing device 300 may also comprise a power module 320. The power module may connect the device to an external power source, or may be provided as an internal local power source. For example, the power module may connect the device to a grid or utility. The device may include a plug that may be connected to an electric socket. The device may be connected to any other external power source, which may include an electricity generation device, such as a generator, or any renewable energy source (e.g., solar, wind, water, geothermal), or energy storage source (e.g., battery, ultracapacitor). The power module may be a local power source. For example, the power module may be an energy storage device, such as a battery or ultracapacitor. Any battery chemistry known or later developed in the art may be used. Alternatively, a local power source may include a local energy generation device, such as a device that utilizes renewable energy. The power module may provide electricity to run the rest of the sample processing device.

One or more component of the device may be contained within a housing. The housing may partially or completely surround components of the device. A display may be provided on the housing so that the display may be visible.

The device may be a benchtop device. The device may be portable or worn. A plurality of devices may fit within a room. The device may have a total volume of less than, greater than, or equal to about 4 $m^3$, 3 $m^3$, 2.5 $m^3$, 2 $m^3$, 1.5 $m^3$, 1 $m^3$, 0.75 $m^3$, 0.5 $m^3$, 0.3 $m^3$, 0.2 $m^3$, 0.1 $m^3$, 0.08 $m^3$, 0.05 $m^3$, 0.03 $m^3$, 0.01 $m^3$, 0.005 $m^3$, 0.001 $m^3$, 500 $cm^3$, 100 $cm^3$, 50 $cm^3$, 10 $cm^3$, 5 $cm^3$, 1 $cm^3$, 0.5 $cm^3$, 0.1 $cm^3$, 0.05 $cm^3$, or 0.01 $cm^3$. The device may have a footprint covering a lateral area of the device. In some embodiments, the device footprint may be less than, greater than, or equal to about 4 $m^2$, 3 $m^2$, 2.5 $m^2$, 2 $m^2$, 1.5 $m^2$, 1 $m^2$, 0.75 $m^2$, 0.5 $m^2$, 0.3 $m^2$, 0.2 $m^2$, 0.1 $m^2$, 0.08 $m^2$, 0.05 $m^2$, 0.03 $m^2$, 100 $cm^2$, 80 $cm^2$, 70 $cm^2$, 60 $cm^2$, 50 $cm^2$, 40 $cm^2$, 30 $cm^2$, 20 $cm^2$, 15 $cm^2$, 10 $cm^2$, 7 $cm^2$, 5 $cm^2$, 1 $cm^2$, 0.5 $cm^2$, 0.1 $cm^2$, 0.05 $cm^2$, or 0.01 $cm^2$. The device may have a lateral dimension (e.g., width, length, or diameter) or a height less than, greater than, or equal to about 4 m, 3 m, 2.5 m, 2 m, 1.5 m, 1.2 m, 1 m, 80 cm, 70 cm, 60 cm, 50 cm, 40 cm, 30 cm, 25 cm, 20 cm, 15 cm, 12 cm, 10 cm, 8 cm, 5 cm, 3 cm, 1 cm, 0.5 cm, 0.1 cm, 0.05 cm, or 0.01 cm. The lateral dimensions and/or height may vary from one another. Alternatively, they may be the same. In some instances, the device may be a tall and thin device, or may be a short and squat device. The height to lateral dimension ratio may be greater than or equal to 100:1, 50:1, 30:1, 20:1, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10, 1:20, 1:30, 1:50, or 1:100.

The device may have any weight. The device may be capable of being lifted manually by a human. The device may be capable of being on or in a human. The device may be molted or mounted to a ground, wall, ceiling, and/or wall. The device may be sized and/or shaped to be ingestible by a human. Examples of device weights may include but are not limited to less than, greater than, or equal to about 20 kg, 15 kg, 10 kg, 8 kg, 6 kg, 5 kg, 4 kg, 3 kg, 2 kg, 1 kg, 0.7 kg, 0.5 kg, 0.3 kg, 0.1 kg, 0.05 kg, 0.01 kg, 5 g, 1 g, 0.5 g, 0.1 g, 0.05 g, or 0.01 g.

In some embodiments, methods above, alone or in combination, are implemented with the aid or one or more systems and devices provided in Patent Cooperation Treaty Application No. PCT/US2011/53188; Patent Cooperation Treaty Application No. PCT/US2012/57155; U.S. patent application Ser. No. 13/244,947; U.S. patent application Ser. No. 13/244,949; U.S. patent application Ser. No. 13/244,950; U.S. patent application Ser. No. 13/244,951; U.S. patent application Ser. No. 13/244,952; U.S. patent application Ser. No. 13/244,953; U.S. patent application Ser. No. 13/244,954; U.S. patent application Ser. No. 13/244,956; and U.S. patent application Ser. No. 13/769,820, entitled "Systems and Methods for Multi-Analysis," filed Feb. 18, 2013 (which also claims priority to PCT/US2011/53188), the contents of all of which applications are hereby incorporated by reference herein in their entireties.

Figure 4:
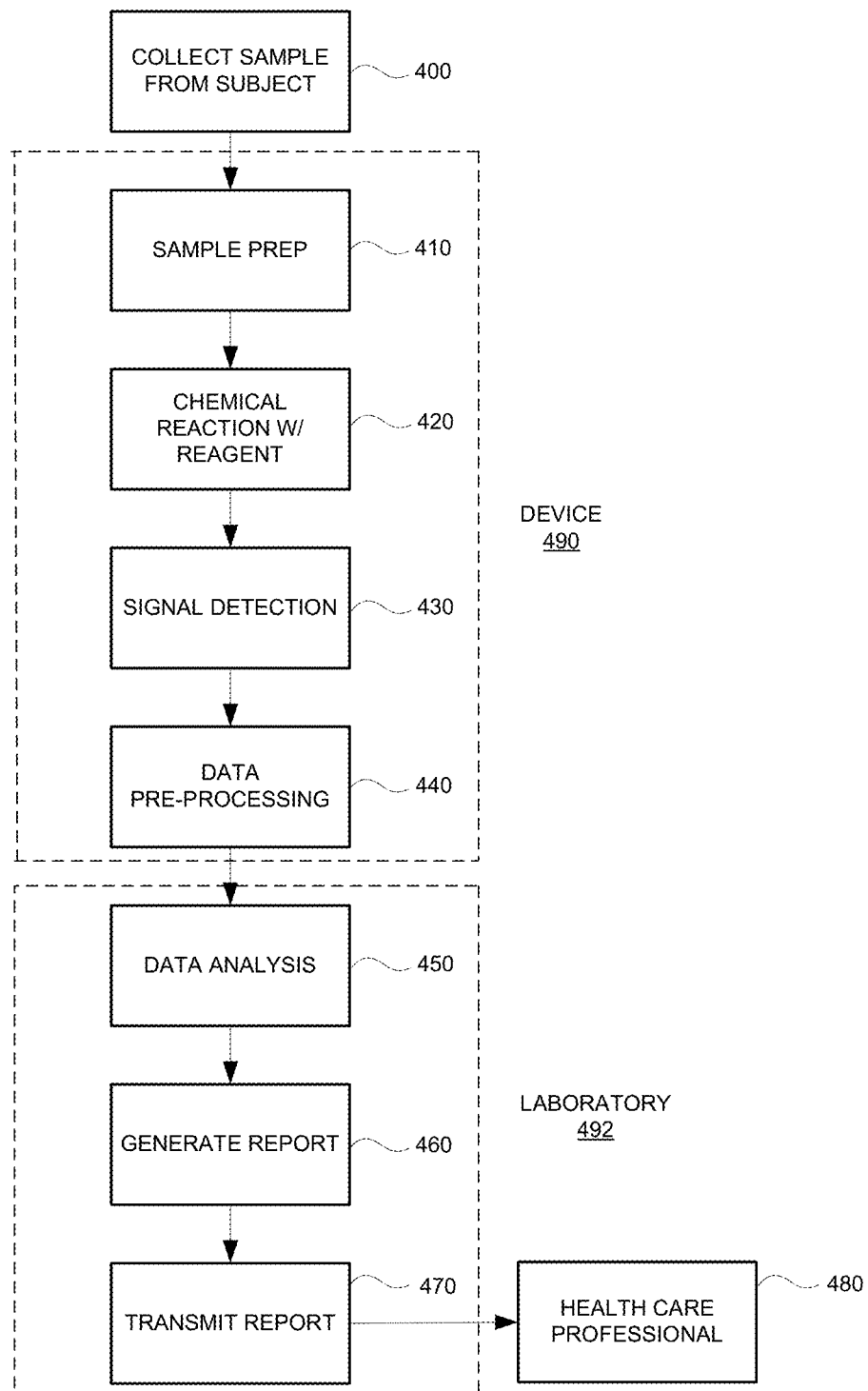
FIG. 4 shows an example of a sample collection, processing, and analysis method.

FIG. 4 shows an example of a sample collection, processing, and analysis method. One or more of the following steps may occur in such a method. The order of the steps may be modified, or one or more step may be optional or may be substituted by another step. Steps illustrated in FIG. 4 by boxes numbered from 400 to 440 represent steps which may be considered pre-analytic steps. Pre-analytic steps include sample collection, verification, preparation, including oversight, calibration, running of controls, acquisition of raw data, and other steps as shown in the figure and as disclosed herein. In embodiments, oversight of pre-analytic steps may be performed at one or more times before, during, and after sample collection and testing, or may be continuous throughout a period or periods before, during, and after sample collection and testing. Steps illustrated in FIG. 4 by boxes numbered from 450 to 460 represent steps which may be considered analytic steps. Analytic steps include analysis of data received from a device at a sample collection site, as indicated in the figure and as disclosed herein. In embodiments, oversight of analytic steps may be performed at one or more times before, during, and after analysis, or may be continuous throughout a period or periods before, during, and after analysis. Steps illustrated in FIG. 4 by boxes numbered from 470 to 480 represent steps which may be considered post-analytic steps. Post-analytic steps include review of the analysis of data, comparison with controls, calibrations, device and sample identification and information, review of report generation and of the report generated for a particular test, and other steps as indicated in the figure and as disclosed herein. In embodiments, oversight of post-analytic steps may be performed at one or more times before, during, and after post-analysis, or may be continuous throughout a period or periods before, during, and after post-analysis. Methods disclosed herein, and devices and systems useful in the practice of such methods, may be, or may be used with, or may be part of, a laboratory automation system (LAS), or a laboratory information system (LIS), or an electronic medical record system (EMR). In embodiments of the methods, systems, and devices disclosed herein, a method, system or device as disclosed herein may be integrated with a LAS, a LIS, or an EMR. In embodiments, an EMR may be integrated with an LAS, a LIS, and methods, systems, or devices as disclosed herein.

The method may include collecting a sample from a subject 400, preparing the sample for running a chemical reaction 410, permitting a chemical reaction with one or more reagent 420, detecting a signal relating to the sample, chemical reaction, and/or component of the device 430, pre-processing the detected signals without performing analysis, analyzing the data 450, generating a report based on the data 460, transmitting a report 470, providing the report to a health care professional 480, and/or displaying a report on the device and/or screen or other display device.

One or more of these steps may be provided by any device or entity. The demarcations illustrated in the figures are provided by way of example only, and are in no way limiting. For example, a sample may be collected 400 external to a device 490. Alternatively, the sample may be collected directly at the device, or may be collected by the device. This may occur at a sample collection site. The sample prep 410, chemical reaction 420, or signal detection steps 430, may be performed by the device 490.

In some embodiments, a sample may be prepared for a subsequent qualitative and/or quantitative evaluation. Such a sample preparation for evaluation step may include one or more of the sample prep 410, chemical reaction 420, and/or signal detection 430 steps. In some embodiments, a sample may be processed by receiving the sample 400, and/or preparing the sample for a subsequent qualitative and/or quantitative evaluation, to yield data necessary for the subsequent qualitative and/or quantitative evaluation. Sample processing may also include transmitting the data from the device. In some instances, the data may be transmitted to a health care professional of an authorized analytical facility.

One, two or all these of these steps may take place, and one, two, or all of the steps that take place may occur at the device at a sample collection site. Alternatively, they may take place at another entity, such as a laboratory. The point of service site near or on the body (such as the home) of the subject may be a laboratory or sample collection site.

Data collected by the device may be in a raw state. This may include signals detected at the device. The data may optionally undergo pre-processing 440. Data pre-processing does not perform actual data analysis or comparison with any threshold values. Data pre-processing may involve modifying the format of data. In some instances, data pre-processing may occur at a device 490 at a sample collection site. Then the pre-processed data may be transmitted to a laboratory. Alternatively, data pre-processing 440 may occur at a laboratory 492. Raw data may be sent from a device to the laboratory where pre-processing may occur. Alternatively, no pre-processing occurs within the method.

Examples of raw data include, but are not limited to, the following: light data, including light intensity, wavelength, polarization, and other data regarding light, e.g., output from optical detectors such as photomultiplier tubes, photodiodes, charge-coupled devices, luminometers, spectrophotometers, cameras, and other light sensing components and devices, including absorbance data, transmittance data, turbidity data, luminosity data, wavelength data (including intensity at one, two, or more wavelengths or across a range of wavelengths), reflectance data, refractance data, birefringence data, polarization, and other light data. Light data may provide information about the presence, number, or other characteristic of an analyte, cell, particle, or other subject of interest in a sample, tissue, container, or field of view. Light data may provide information about the presence, progress, or completion of a chemical reaction or physical process.

Raw data includes image data, e.g., data from digital or analog cameras, including images of tissues, including tissue slices and biopsy samples; images of cells, particles, crystals, or other elements which may be present in a sample; images may include two-dimensional images of cells particles, or crystals, such as fluorescently labeled or chemiluminescent cells; two-dimensional images of light scattered by cells, particles, or crystals; two-dimensional images of cells, particles or crystals taken using phase contrast, bright-field, dark-field, interference contrast, or other technique; two-dimensional images of cells in a tissue slice or other histological specimen, where the cells may, or may not be stained. Images may include three-dimensional images of cells particles, or crystals, such as fluorescently labeled or chemiluminescent cells; three-dimensional images of light scattered by cells, particles, or crystals; three-dimensional images of cells, particles or crystals taken using phase contrast, bright-field, dark-field, interference contrast, or other technique; three-dimensional images of cells in a tissue slice or other histological specimen, where the cells may, or may not be stained. Raw data includes cell counts, cell shape, numbers of stained or labeled cells, and intensity of staining or labeling.

Raw data includes temperature measurements, duration measurements, pH measurements, ion and other analyte measurements, particle counts, hematocrit measurements, and other measurements of chemical and physical characteristics of a sample, or of sample constituents. Raw data includes data measuring or indicating the progress of a chemical reaction or physical change, including color changes due to enzymatic action on the product of a chemical reaction. Such raw data provides data from chemical assays, including measurements of light emitted or absorbed during or following chemical reactions, binding reactions, competition reactions, and other reactions and assays. Such raw data may provide a direct measure of the chemical reaction or assay, or further processing or analysis based on the raw data may be required to provide a desired measurement.

Raw data may be pre-processed by a device prior to transmission to a laboratory location. In embodiments, raw data is transmitted from a sample collection location to a laboratory location without pre-processing.

Data analysis may occur 450 in accordance with an embodiment of the invention. Data analysis may include a subsequent qualitative and/or quantitative evaluation of a sample. The quantitative and/or qualitative analysis may involve a determination of clinical relevance of the biological sample or lack thereof. Data analysis may include one or more comparison of the data with a threshold value. Said comparison may be used to determine the presence or concentration of one or more analyte, or may be useful for analytical methods and/or pathological analysis described elsewhere herein. Data analysis may occur at a laboratory 492. In some embodiments, the laboratory may be a certified laboratory. The data that may be analyzed may be raw data or pre-processed data. A device may process a sample without analyzing the sample. Data analysis does not occur on the device in this scenario. In some embodiments, processing the sample on the device does not yield a determination of the presence or concentration level of one or more analytes, two or more analytes, three or more analytes, four or more analytes, five or more analytes, six or more analytes, seven or more analytes, eight or more analytes, nine or more analytes, ten or more analytes, twelve or more analytes, fifteen or more analytes, or twenty or more analytes. In some instances, processing the sample on the device does not yield a determination of the presence or concentration of one or more, or any number of analytes (including those described elsewhere herein), belonging to the categories of cardiac marker, blood gas, electrolyte, lactate, hemoglobin, or coagulation factors. In some embodiments, processing the sample on the device does not yield a determination of the presence or concentration of one or more, two or more, three or more, or any number of analytes (including those described elsewhere herein), belonging to the following: sodium, potassium, chloride, $TCO_2$, anion Gap, ionized calcium, glucose, urea nitrogen, creatinine, lactate, hematocrit, hemoglobin, pH, $PCO_2$, $PO_2$, $HCO_3$, base excess, $sO_2$, ACT Kaolin, ACT Celite, PT/INR, cTnI, CK-MB, and BNP. In some instances, processing the sample does not include a display of the presence or concentration of one or more, or any number of analytes (including those described elsewhere herein), belonging to the categories of cardiac marker, blood gas, electrolyte, lactate, hemoglobin, or coagulation factors. Similarly, in some instances, processing the sample does not include a display of the presence or concentration of one or more, or any number of analytes (including those described elsewhere herein), belonging to the following: sodium, potassium, chloride, $TCO_2$, anion Gap, ionized calcium, glucose, urea nitrogen, creatinine, lactate, hematocrit, hemoglobin, pH, $PCO_2$, $PO_2$, $HCO_3$, base excess, $sO_2$, ACT Kaolin, ACT Celite, PT/INR, cTnI, CK-MB, and BNP.

Data analysis may include a qualitative and/or quantitative evaluation of the sample. Said qualitative and/or quantitative evaluation of the sample may yield a determination of the presence or concentration of one or more, two or more, three or more, four or more, five or more, six or more, ten or more, fifteen or more, or twenty or more analytes. In some examples, analytes may belong to categories involved in one or more of the following types of research and/or analyses: immunoassay, nucleic acid assay, receptor-based assay, cytometric assay, colorimetric assay, enzymatic assay, electrophoretic assay, electrochemical assay, spectroscopic assay, chromatographic assay, microscopic assay, topographic assay, calorimetric assay, turbidmetric assay, agglutination assay, radioisotope assay, viscometric assay, coagulation assay, clotting time assay, protein synthesis assay, histological assay, culture assay, osmolarity assay, and/or other types of assays or combinations thereof. Analytes being tested may be involved in one or more types of reactions selected from the following: Chemistry—Routine Chemistry, Hematology (includes cell-based assays, coagulation and andrology), Microbiology—Bacteriology (includes "Molecular Biology"), Chemistry—Endocrinology, Microbiology—Virology, Diagnostic Immunology—General Immunology, Chemistry—Urinalysis, Immunohematology—ABO Group & Rh type, Diagnostic Immunology—Syphilis Serology, Chemistry—Toxicology, Immunohematology—Antibody Detection (transfusion), Immunohematology—Antibody Detection (non-transfusion), Histocompatibility, Microbiology—Mycobacteriology, Microbiology—Mycology, Microbiology—Parasitology, Immunohematology—Antibody Identification, Immunohematology—Compatibility Testing, Pathology—Histopathology, Pathology—Oral Pathology, Pathology—Cytology, Radiobioassay, and/or Clinical Cytogenetics. One or more measurement may include: proteins, nucleic acids (DNA, RNA, hybrids thereof, microRNA, RNAi, EGS, Antisense), metabolites, gasses, ions, particles (including crystals), small molecules and metabolites thereof, elements, toxins, enzymes, lipids, carbohydrates, prion, formed elements (e.g., cellular entities (e.g., whole cell, cell debris, cell surface markers)). In some embodiments, one or more analytes belonging to categories of cardiac marker, blood gas, electrolyte, lactate, hemoglobin, or coagulation factors. In some embodiments, one or more analytes may include sodium, potassium, chloride, $TCO_2$, anion Gap, ionized calcium, glucose, urea nitrogen, creatinine, lactate, hematocrit, hemoglobin, pH, $PCO_2$, $PO_2$, $HCO_3$, base excess, $sO_2$, ACT Kaolin, ACT Celite, PT/INR, cTnI, CK-MB, and/or BNP.

The data that may be analyzed may be provided from a device 490 or may be modified at the laboratory 492 or other entity prior to being analyzed. In another embodiment of the invention, the data analysis 450 may occur on the device without occurring at a laboratory. Alternatively, data analysis may occur on both the device and at the laboratory or the device may be the laboratory. The analysis may occur at a point of service location, such as a home, office, doctor's office/hospital, retailer site, or other point of service location. Any description herein of a laboratory location or other location, may apply to any other point of service location described elsewhere herein.

A report may be generated 460 based on the data. A report may be based on analyzed data 450 or may be based on data in its raw or pre-processed form. The report may be generated based on a qualitative and/or quantitative evaluation of the sample. The report may be generated at a laboratory 492, such as an authorized analytical facility. Alternatively, the report can be generated at the device, or by any other entity. The report may be transmitted 470. The report may be transmitted by the same entity that generated the report. Alternatively, a different entity can transmit the report. The report may be transmitted by a laboratory 492, such as an authorized analytical facility, a device 490, cartridge, or any other entity.

The report may be received by a health care professional 480. The health care professional may be provided at a location separate from the device 490 and/or the laboratory 492. The health care professional may be capable of relying on the report in order to diagnose, treat, and/or provide disease prevention for the subject.

Thus, as previously described, any one or more of these steps may be optional. Any one or more of these steps may be performed at a sample collection site or in or on a subject by a device 490 or may be performed at a laboratory 492, or at any other entity. In some embodiments, the location where a data analysis 450 step may be performed may be certified, or may undergo review or oversight.

A device may be configured to process a sample. Sample processing may include receiving a sample 400 and/or preparing a sample for subsequent qualitative and/or quantitative evaluation, to yield necessary for the subsequent qualitative and/or quantitative evaluation. Preparing the sample for subsequent qualitative and/or quantitative evaluation may include one or more sample preparation step 410, chemical reaction step or physical processing step 420, and/or detection step 430. Processing the sample may include adding one or more reagent or fixatives. Sample processing may optionally also include transmitting data electronically. The data may be transmitted to a health care professional of an authorized analytical facility and/or displayed on the screen. The data may be transmitted and/or displayed simultaneously.

The sample may be collected from a subject 400 in any manner described elsewhere herein. For example, a fingerstick may collect the sample from the subject. In other examples, feces, urine, or tissue may be collected in an operating and/or emergency room, or any other sample collection mechanism described elsewhere herein may be utilized. The collected sample may be provided to a device 490. The sample collection may occur at a sample collection site, or elsewhere. The sample may be provided to the device at a sample collection site.

Optionally, the sample may be prepared for a chemical reaction and/or physical processing step 410. The sample preparation step may include one or more of the following: centrifugation, separation, filtration, dilution, enriching, purification, precipitation, incubation, pipetting, transport, chromatography, cell lysis, cytometry, pulverization, grinding, activation, ultrasonication, micro column processing, processing with magnetic beads or nanoparticles, or other sample preparation steps. The sample may be transferred within a device. Sample preparation may include one or more step to separate blood into serum and/or particulate fractions, or to separate any other sample into various components. Sample preparation may include one or more step to dilute and/or concentrate blood, or other biological samples. Sample preparation may include adding an anticoagulant or other ingredients to a sample. Sample preparation may also include purification of a sample. Sample preparation may involve altering the density of a sample, and/or creating a density profile of a sample. In some instances, denser portions of a sample may be separated from less dense portions of a sample. Sample preparation may include separating solid components of a sample from aqueous components of a sample. In some examples, sample preparation may involve centrifugation, incubation and/or cell lysis. Sample preparation may include causing the sample to flow, such as a laminar flow. Sample preparation may include transporting a sample from one portion of a device to another. Sample preparation may include incubating a sample. The sample preparation may include a process to render a biological sample applicable prior to undergoing a chemical reaction and/or running an assay. The sample preparation step may render a biological sample ready for running one or more clinical test, which may include adding a series of reagents, running a protocol and/or running an assay.

Optionally, the sample may undergo a chemical reaction with a reagent 420. The chemical reaction may occur following a sample preparation step. Alternatively, the chemical reaction need not follow a sample preparation step. Sample preparation steps may occur prior to, concurrently with, and/or after a chemical reaction. In some embodiments, preparing a sample for qualitative and/or quantitative evaluation may include permitting a chemical reaction. One or more type of assay, as described elsewhere herein may occur. For example, a sample preparation step (or e.g., a chemical reaction that may occur while preparing a sample for qualitative and/or quantitative evaluation) may include one or more of the types of chemical reactions selected from immunoassay, nucleic acid assay, receptor-based assay, cytometric assay, colorimetric assay, enzymatic assay, electrophoretic assay, electrochemical assay, spectroscopic assay, chromatographic assay, microscopic assay, topographic assay, calorimetric assay, turbidmetric assay, agglutination assay, radioisotope assay, viscometric assay, coagulation assay, clotting time assay, protein synthesis assay, histological assay, culture assay, osmolarity assay, and/or other types of assays or combinations thereof. In some embodiments, a heater and/or thermal block may be employed. The chemical reaction may include providing the sample at a desired temperature. The chemical reaction may also include maintaining and/or varying the temperature of the sample before, during, and/or after the chemical reaction. Any description herein of chemical reaction may include any type of reaction that may occur in the device. For instance, chemical reactions may include physical interactions, chemical interactions, and/or other physical interactions or transformations. In some embodiments, a display (such as a screen) or sensors in a device may conduct imaging externally. For example, the device may be capable of conducting MRI, ultrasound, or other scans.

The sample preparation and/or chemical reaction may occur in response to one or more instructions. The instructions may be stored locally on the device or may be provided from an external source. In some embodiments, the external source is a laboratory. In some embodiments, the sample preparation and/or chemical reaction procedures may be self-educated. For example, they may be capable of picking up different ways of preparing a sample and/or making it ready for analysis. In some embodiments, the sample preparation procedures may be able to self adjust to utilize various sample preparation techniques given a set of parameters. The sample preparation adjustment or maintenance may or may not rely on signals detected relating to a sample, and/or to parameters and/or instructions provided by an operator. The sample preparation procedures may be self-learning.

One or more controller that may provide instructions to conduct a sample preparation and/or chemical reaction may be capable of self-learning.

The adjustments may be made in response to new instructions that may be generated locally on the device or that may be provided from the external source. For example, new instructions may be updated and/or pushed down from the external source. There may be a dynamic process in which the sample preparation and/or chemical reaction and/or physical processing steps are performed in accordance with changeable instructions. Any description herein relating to a sample preparation and/or chemical reaction may also include any physical processing steps.

One or more signal may be detected 430 from the device. The signal may be detected after a sample preparation step has been done and/or after a chemical reaction and/or physical processing step has taken place. In some embodiments, one or more signal may be detected even if no sample preparation and/or chemical reaction has taken place on the sample. The signals may be based on a reading of a sample that may or may not have undergone an assay. The signals may be based on a measurement relating to the device.

In some instances, one or more additional sample preparation steps may occur. For instance, an additional sample preparation for qualitative and/or quantitative evaluation may occur. Such preparation may be made based on at least one of: prior preparation of the biological sample and/or analysis of the data by the health care professional. Reflex testing may occur based on earlier results. The reflex testing may occur in an automatic and dynamic manner before, during, or after the test/analyses. Earlier evaluation may yield further testing, which may be automated.

Optionally, data may undergo pre-processing 440. Raw data of detected signals may or may not undergo pre-processing. Pre-processing may affect the format of the raw data. For example, the pre-processing may normalize a format of the data. The pre-processing may put the data into a desired form. Pre-processing may occur without performing any analysis of the data. In some embodiments, the pre-processing may alter the form of the data without altering the content of the data. In some instances, pre-processing does not compare the data with any threshold values or perform any valuation judgments.

The data may be analyzed 450, as described elsewhere herein. Data analysis may include a subsequent qualitative and/or quantitative evaluation of a sample. Optionally, a report may be generated based on the raw data, pre-processed data, or the analyzed data. The report and/or the data may be transmitted to a health care professional. A software system may perform chemical analysis and/or pathological analysis, or these could be distributed amongst combinations of lab, clinical, and referenced/contracted specialty personnel (e.g., lab and John's Hopkins laboratory for specialty experts of some diseases or to engage them as part of/in a certified laboratory).

In some embodiments, the report may be reviewed before being transmitted to the health care professional. In some instances, the data may be reviewed before or after the report is generated. The review may occur by one or more pathologist or other qualified person. The pathologist may be associated with a laboratory 492. The pathologist may or may not be physically located at the laboratory facility. The pathologist may be employed by the laboratory. For an authorized analytical facility, oversight may be provided via a regulatory body. In some embodiments, the laboratory may be a CLIA certified laboratory. A board certified entity (which may include board-certified personnel) may review the data/reports and provide a measure of quality control and verification. In some embodiments, the board certified entity may include one or more pathologist.

In some embodiments, a device may be a certified device. The device may be under the oversight of a regulatory body. A board certified entity may review the data/reports of the device and provide a measure of quality control, performance of calibrators, of a test, and verification. A health care professional may review and/or provide oversight of the data/reports from the device. Alternatively, a software program may be provided that may review data generated by the device. The software program may be created by or under the review of a health care professional. The software program may be maintained by an authorized person, such as a health care professional.

Figure 8:
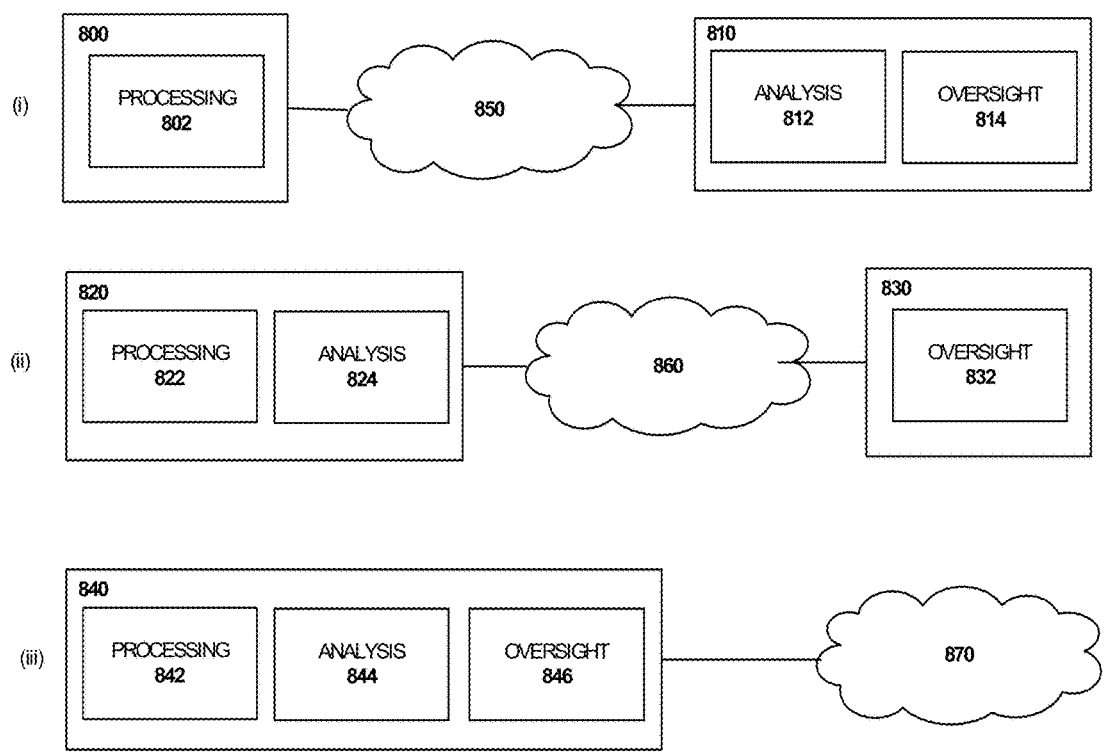
FIG. 8 shows examples of a system providing sample processing, analysis, and oversight.

FIG. 8 shows examples of a system providing sample processing, analysis, and oversight.

FIG. 8(*i*) shows an example of a device 800 which may be capable of performing a sample processing 802 step. The device may be capable of communicating with a laboratory 810. The laboratory may be capable of performing a subsequent analysis 812 step and may provide oversight 814. Oversight and/or analysis may be provided by a health care professional and/or software program. The device may communicate with the laboratory across a network 850, including any of those described elsewhere herein. A cloud computing infrastructure may be provided. The device may be provided in or on a subject, or at a sample collection site. The laboratory may be an authorized analytical facility, such as a CLIA certified facility which could be the device or cartridge.

FIG. 8(*ii*) shows an example of a device 820 which may be capable of performing a sample processing 822 step and an analysis step 824. The device may be capable of communicating with a laboratory 830. The laboratory may be capable of providing oversight 832. Oversight may be provided by a health care professional and/or a software program. The device may communicate with the laboratory across a network 860, including any of those described elsewhere herein. A cloud computing infrastructure may be provided. The cloud computing infrastructure may be part of the system/infrastructure/device. The device may be provided in or on a subject, or at a sample collection site. The laboratory may be an authorized analytical facility, such as a CLIA certified facility.

FIG. 8(*iii*) shows an example of a device 840 which may be capable of performing a sample processing 842 step, analysis step 844, and providing oversight 846. In some embodiments, the oversight may be provided by an oversight software program on the device. The device may communicate with a network 870, including any of those described elsewhere herein. A cloud computing infrastructure may be provided. The device may be provided in or on a subject, or at a sample collection site. In some embodiments, the device may be certified by a regulatory body. In some instances, the device may be CLIA certified.

In embodiments of the devices, systems, and methods disclosed herein, the handling of a sample may comprise one of three stages: a first stage which may be termed a "pre-analysis" stage; a second stage which may be termed an "analysis" stage; and a third stage which may be termed a "post-analysis" stage. In embodiments, a pre-analysis stage may include such actions and steps as, e.g., sample collection, sample preparation, sample testing, detection of a signal from a sample or observation or imaging of a sample; data pre-processing (if any), and other actions and steps prior to analysis of data obtained regarding a sample. For example, a pre-analytic action may include initiation of a test, and may include contacting a sample with a reagent, detection of the amount of light emitted from, or the amount of light absorbed by, a sample following contact with a reagent, or other such action or step. In embodiments, an analysis stage may include such actions and steps as, e.g., analysis of data obtained regarding a sample, generation of a report regarding the sample and its analysis, and other actions and steps regarding the analysis of data obtained regarding a sample. For example, an analytic action or step may include correcting raw data based on device environmental data and/or calibrations specific for the device or reagents used to examine the sample; calculation of a value, e.g., a concentration value, a hematocrit value, a volume of a cell, or other value; determination of a type or types of cells, particles, or other subject in a sample; or other step or action. In embodiments, a post-analysis stage may include such actions and steps as, e.g., transmission of a report regarding a sample, contacting or receiving communications from a health care professional or other provider regarding such a report, and other actions and steps subsequent to the analysis of data obtained regarding a sample. For example, a post-analytic action or step may comprise a determination of whether or not a test is accurate, e.g., by comparing outliers, controls, and replicates to the results of an analysis. For example, a post-analytic action or step may comprise highlighting values or results that are outliers or may be a cause for concern (e.g., above or below a normal or acceptable range, or indicative of an abnormal condition), or combinations of results which, together, may indicate the presence of an abnormal condition. Such post-analytic action, communicated to a physician or other health-care provider may better insure that the physician or other health-care provider is made aware of, and cognizant of, possible concerns and may thus be more likely to take appropriate action.

In embodiments of devices, systems and methods disclosed herein, a test of a sample may be performed within a device.

In embodiments of devices, systems and methods disclosed herein, a test of a sample may be initiated within a device, and raw data derived from the sample may be transmitted to a different location, e.g., a laboratory location. Transmission of raw data may be via the cloud or other network. In embodiments where a test of a sample may be initiated within a device, and raw data is transmitted to another location, the test may be completed at a location other than within the device; for example, a test may be completed at a laboratory location using raw data transmitted to the laboratory location via the cloud, or via another network. In such embodiments, the test of the sample is started at the sample collection site (within the device) and is completed at the laboratory location. In embodiments, a test of the sample may be started and completed within the device at the sample collection site. In embodiments, testing of a sample may be started and completed within a device, and raw data derived from the sample may be transmitted to a different location, e.g., a laboratory location.

In embodiments of the devices, systems, and methods disclosed herein, the device may be placed at a sample collection site that is physically distant from the laboratory, and processes a sample without physical transport of the sample from the device to the laboratory. In embodiments of the devices, systems, and methods disclosed herein, the device, although placed at a sample collection site that is physically distant from the laboratory, operates under the control of the laboratory, and operates under the oversight of the laboratory. In embodiments of the devices, systems, and methods disclosed herein, control and oversight of the device at a sample collection site may be effected by a processor at the laboratory location or by an individual affiliated with the laboratory. The laboratory may be an authorized analytical facility, and may be a CLIA-compliant laboratory, CLIA-certified laboratory, or CLIA-waived laboratory.

A device as disclosed herein may be, or comprise, a sample processing device. A device as disclosed herein may be, or comprise, a sample processing unit.

In embodiments, a device for performing a sample processing step as disclosed herein may be a CLIA-certified device; may be a device operated in a CLIA-certified laboratory or location; may be a CLIA-compliant device; may be a device operated in a CLIA-compliant laboratory or location; may be a device operated by a CLIA-certified operator; may be a device operated by a CLIA-compliant operator; may be a device operated in a CLIA-compliant manner; may be a CLIA-waived device; may be a device cleared for use by a regulatory body empowered to do so; may be a device cleared for use by the U.S. Food and Drug Administration; may be a device classified as exempt by the U.S. Food and Drug Administration; may be a device cleared for use, e.g., under section 510(k) of the U.S. Food, Drug and Cosmetic Act; may be a device with no substantial equivalent under section 510(k) of the U.S. Food, Drug and Cosmetic Act; or the device may have no governmental certification.

In embodiments, a device as disclosed herein may be or comprise a CLIA-waived device, and may perform a CLIA-compliant or CLIA-certified test on or with a sample. In embodiments, a device as disclosed herein may be or comprise a CLIA-waived device, and may perform a CLIA-waived test on or with a sample. In embodiments, a device as disclosed herein may be or comprise a CLIA-compliant or CLIA-certified device, and may perform a CLIA-compliant or CLIA-certified test on or with a sample. In embodiments, a device as disclosed herein may be or comprise a CLIA-compliant or CLIA-certified device, and may perform a CLIA-waived test on or with a sample. In embodiments, a device as disclosed herein may be in or at a CLIA-compliant or CLIA-certified laboratory or location, and may perform a CLIA-compliant or CLIA-certified test on or with a sample. In embodiments, a device as disclosed herein may be in or at a CLIA-compliant or CLIA-certified laboratory or location, and may perform a CLIA-waived test on or with a sample.

In embodiments, a device as disclosed herein may operate under the oversight or control of a laboratory. For example, a device as disclosed herein may process a sample at a sample collection site under the oversight of a laboratory, where the laboratory is placed at a laboratory location that is physically distant from the sample collection site. Thus, in embodiments, the device, while physically distant from the laboratory, operates as part of the laboratory due to its operation being controlled by the laboratory. In embodiments, the device, while physically distant from the laboratory, operates as part of the laboratory due to its operation being under the oversight of the laboratory. In embodiments, testing may be performed on a device located at a sample collection site, and raw data and/or results may be transmitted to a laboratory at a laboratory location. Such raw data and/or results may be analyzed at a laboratory at a laboratory location. The laboratory may be an authorized analytical facility, and may be a CLIA certified laboratory. Thus, laboratory certified results may be obtained from testing performed at a sample collection site.

In embodiments, testing may be initiated on a device located at a sample collection site, and may be continued and may be completed in a laboratory at a laboratory location (e.g., using raw data transmitted from the device). In embodiments, testing may thus be completed at a laboratory location, and analysis may be performed at a laboratory location from results obtained from testing initiated at a sample collection site and completed in a laboratory at a laboratory location. The laboratory may be an authorized analytical facility, and may be a CLIA certified laboratory. Thus, laboratory certified results may be obtained from testing initiated at a sample collection site and completed in a laboratory at a laboratory location.

In embodiments, oversight of the operation of a device may be on-going, e.g., may comprise oversight at multiple times during the operation of a device, and may comprise continuous oversight of the operation of a device during the operation of the device. For example, oversight may comprise oversight of the operation of the device at multiple times during the testing of a sample, and may comprise continuous oversight of the operation of the device during the testing of a sample. Oversight of a protocol for the operation of a device during the testing of a sample may include updating the protocol with new process steps, corrected process steps, or new commands regarding process steps. Oversight may be provided or performed using a processor. Oversight may be provided or performed using a processor at a sample collection site (e.g., on a device), using a processor at a laboratory location, using a processor that is part of the cloud, or of a network (which cloud or network may or may not include a processor on a device or at a laboratory location). Oversight may be performed or provided by an individual (e.g., an individual affiliated with an authorized analytical facility). Oversight may include using any one or more of such processors in conjunction with an individual (e.g., an individual affiliated with an authorized analytical facility).

Protocols may receive and utilize identifying data and information identifying the device in use, the cartridge, the sample, the patient, and other information and data. Identifying information and data may identify a particular device, its past history, present status, present condition, environmental information regarding the device and its environs, and other data and information. For example, in embodiments, patient identification may be retained with each sample from beginning to end of sample collection, testing, analysis, and reporting of results. In embodiments, patient identification may be retained with each sample from beginning to end of sample collection, testing, analysis, reporting of results, and billing. Identifying information and data may identify a particular cartridge, its contents (including reagents, disposables, and sample information), its past history, present status, present condition, environmental information regarding the cartridge and its environs, and other data and information. Identifying information and data may identify a particular patient, including a patient's identity, age, sex, medications, medical history, test history, present status, present condition, and other data and information. Identifying information and data may identify a particular sample, its mode of collection, patient derived from, condition (sample volume, whether contacted with heparin, EDTA, filtered, coagulated, whether or not there is an air bubble present, whether a blood sample may have undergone hemolysis, or is lipemic), and other data and information. Identifying information and data may specify an analysis to be performed, or that has been performed, on data from a sample. Identifying information and data may specify post-analytic actions to be performed, such as regarding a report, comparison with other test data or analysis, or other action or step.

Protocols may be updated and may be tailored to specific devices, or environmental conditions within or around the device, e.g., taking into account the specific properties and characteristics of sensors, motors, physical dimensions, and other properties and characteristics of an individual device; taking into account the temperature, humidity, air pressure, position and movement of internal modules or components within the device; condition and status of motors, sensors, or other components; taking into account calibrations of motors, sensors, and other components; and other properties and characteristics. Protocols may be updated and may be tailored to specific reagents and disposables, e.g., taking into account control reagents, calibrations of reagents, the specific properties and characteristics of reagents in a cartridge, of tips in a cartridge, of the temperature of a cartridge, or other characteristic or property. Oversight may comprise oversight during or following analysis of data, and may provide for further testing, or re-testing of a sample or of additional samples from a patient.

Use of protocols that include device-specific information, cartridge-specific information, or other information and data specific for sensors, devices, reagents, and other components and elements of testing of a sample, including calibration and control information, provides for correction and scaling of raw data to insure that values and observations obtained from such raw data is correct, consistent, and reproducible. Such values and observations obtained are reproducible across devices, and over time (e.g., from subsequent samples) allowing for comparison of patient results with group and historical values for better screening, diagnosis and treatment based on test results and analysis. Oversight as disclosed herein provides oversight of the integrity of performance of tests, and of results of tests, including oversight of each sample, oversight of the testing of each sample, oversight of the scaling and calibration of raw data obtained during testing, oversight of test integrity, oversight of use and analysis of data in view of controls, calibrators, replicates, and outliers, oversight of the analysis of data in view of device and reagent environmental and calibration information, oversight of the analysis of test results, oversight of the reporting of test results and analysis, and oversight of post-analytic activity and communications. Device and cartridge information may be retained in the cloud or other network; may be retained on or with each device or cartridge; or may be retained, partially or completely, in both locations.

Devices, systems, methods, and protocols as disclosed herein provide multifunctional capabilities, allowing a single device at a sample collection site to perform multiple tests, including multiple types of tests, on a sample; such test may be run rapidly, requiring only small amounts of sample (e.g., requiring only the amount of blood available from a finger-stick), and may be run reliably and accurately, allowing for reproducibility and reliable comparison across devices and samples. Thus, the devices disclosed herein are multifunctional; the assays they perform are multifunctional; the controls are multifunctional; and the oversight is multifunctional. Multifunctional includes the ability to perform multiple types of assays, including nucleic acid assays, general chemistry assays, cytometry (e.g., cell imaging, flow cytometry) assays, ELISA assays, and others (e.g., as disclosed in U.S. patent application Ser. No. 13/244,947), on a single device and from a single sample.

Devices, systems, methods, and protocols as disclosed herein provide rapid results from testing a small volume sample; such testing and results can be automated, and the rapid provision of such results, e.g. by a laboratory to a health care provider, provides rapid and reliable information for better patient care. Laboratories, such as CLIA-compliant and CLIA-certified laboratories, may have pathologists in place, or readily available, for review and interpretation of results, for further analysis, and for possible recommendations regarding further testing and/or treatment. As disclosed herein, embodiments of devices, systems, methods, including protocols and oversight as disclosed herein may include some or all of the features, elements, and capabilities disclosed, and may include these features, elements, and capabilities in any combination of some or all of such features, elements, and capabilities.

In embodiments, oversight may include at least the following processes: 1) sample collection; 2) receipt of data (e.g., test data, raw data, device data, cartridge data, sample data, patient data, etc.); 3) recognition of a status or problem related to the data); analysis of the status or problem in view of the sample, the test being performed, the device, reagents, etc. performing the test, etc.; and 4) sending instructions to the device, operator, or physician (e.g., general practitioner, pathologist, or other healthcare provider) based on the data and analysis, for further action or modification or cessation of present actions. Such oversight may be intermittent (e.g., occur once or at a few times before, during, or after testing), or may be continuous (on-going during testing, or on-going from a time before testing, and may continue through or beyond the period of testing). In embodiments, oversight may be dynamic oversight, allowing updating of protocols as events occur or data is obtained, to insure proper procedures, proper quality, proper integrity, and proper results from such testing. Such oversight and testing may be "patient-aware", i.e. may take into account the identity, characteristics (e.g., age, sex, medical history, medication, condition, physician, insurance coverage, or other factor related to the patient for whom the test is being conducted. In this way, the sample and sample analysis may always be linked to the patient throughout the testing process—at the pre-analytical stage, at the analytical stage, and at the post-analytical stage. As disclosed herein, all these tests and analysis may be provided without physically transporting a sample to a laboratory location. Sample collection and processing by the device at a sample collection site, followed by transmission of raw data to the laboratory location allows testing, analysis, and reporting of result to be performed without physically transporting a sample to a laboratory location. The transmission of raw data to the laboratory location provides "digital" transport of a sample or effectively a "virtual sample" obviating a need for physically transporting a sample to a laboratory location. Oversight and control of the operation of the device at the sample collection site by a protocol, provided by the cloud or other network, or directly from a laboratory location, allows for the control and operation of the device by the laboratory. Such control and operation may be by a CLIA-compliant laboratory, which may be a CLIA-certified laboratory.

For example, protocols used by the device in processing the sample may be provided by the laboratory, may be updated by the laboratory, and their proper application may be overseen by the laboratory. Protocols may include instructions and procedures directing the forms of processing and testing to apply to a sample; the order of performing such processing and testing of a sample; the timing of such processing and testing of a sample; the pre-processing, if any, of data obtained by the processing and testing of a sample; the compilation of data, including raw data (and pre-processed data, if any), obtained by the processing and testing of a sample; the transmission of data, including raw data (and pre-processed data, if any), obtained by the processing and testing of a sample, to a laboratory; the receipt of further instructions from a laboratory in response to the data transmitted from the device to the laboratory; further processing or testing of a sample pursuant to any further instructions from a laboratory in response to the data transmitted from the device to the laboratory; and the disposal of sample and other wastes following such processing and testing of a sample.

In embodiments, oversight by the laboratory may include oversight of the operation of the device; oversight of sensing operations within the device; oversight of the analysis of data transmitted by the device to the laboratory; oversight of a report generated pursuant to the analysis of such data; oversight of billing for services provided; and other oversight. In embodiments, oversight by a laboratory may include oversight of the collection of a sample at the sample collection site, of the placement of the sample in a cartridge at the sample collection site, of the placement of a cartridge in a device at a sample collection site, or other oversight. Such oversight may include confirmation that proper instructions for such procedures had been provided, and that proper procedures had been followed. In embodiments, oversight may include oversight of the confirmation of insurance coverage of a subject prior to, concurrent with, or subsequent to the processing a sample. Control or oversight of the device may be implemented, for example, via electronic communication such as via a cloud computing infrastructure, other telephonic communication (which may include microwave or radio components, e.g., via cell-phone links), radio communication, infrared linkages, and communication utilizing other forms of electromagnetic radiation. Electronic communication between a device at a sample collection site and a laboratory at a laboratory location may include downloading of protocols; transfer or updating of protocols; communication of device information (e.g., device identification; device status; temperature or other environmental information; date, time or sequence information; supply status (e.g., supply of reagents, supply of cartridges, or other materials); and other device information); communication of patient or subject information; communication of sample information (e.g., identification information related to a sample; data obtained from a sample; information regarding processing applied to a sample; information regarding equipment and procedures used to obtain data from the sample; and other data regarding or derived from a sample); communication of insurance information; communication of payment information; and communication of other information. Such oversight may be provided or performed using a processor, e.g., a processor at a sample collection site, at a laboratory location, that is part of the cloud, or of a network; may be provided or performed by an individual (e.g., an individual affiliated with an authorized analytical facility); and may include using a processor in conjunction with an individual (e.g., an individual affiliated with an authorized analytical facility).

In embodiments, oversight by the laboratory may include oversight of the operation of the device. In embodiments, oversight of operation of the device may include checking the status of the device. In embodiments, oversight of operation of the device may include performing calibration of the device. In embodiments, oversight of operation of the device may include oversight of the identification of a subject prior to processing a sample. Oversight of operation of the device may include oversight of the identification of an operator (e.g., regarding proper certification, eligibility, etc.) prior to processing a sample. In embodiments, oversight of operation of the device may include oversight of the identification of a cartridge for use in processing and testing a sample. In embodiments, oversight of operation of the device may include providing a protocol, oversight of receipt of a protocol, or updating of a protocol for use in processing and testing a sample. In embodiments, oversight of operation of the device may include oversight of the processing and testing of a sample by the device, including oversight of selection and use of reagents, transport of reagents and sample within the device, performance of sample processing and testing within the device, collection of data from the sample, collection of data from control or calibration reagents and tests; and related sample processing and testing operations. In embodiments, oversight of operation of the device may include oversight of any pre-processing of data obtained by testing of a sample. In embodiments, oversight of the operation of the device may include instructions to re-test a sample, or to test controls, replicates, or other materials. Oversight of the operation of the device may include collection of device information, including device identification, device status, temperature, and other information. In embodiments, oversight of the operation of the device may include collection of images transmitted by the device, e.g., from a camera within the device. In embodiments, oversight of the operation of the device may include analysis of device information or of images transmitted by the device. In embodiments, oversight of the operation of the device may include transmission, receipt, or analysis of quality control information, device status or condition information, assay information, control information or data, calibration information or data, or other information. Such oversight of operations may be provided or performed using a processor, e.g., a processor at a sample collection site, at a laboratory location, that is part of the cloud, or of a network; may be provided or performed by an individual (e.g., an individual affiliated with an authorized analytical facility); and may include using a processor in conjunction with an individual (e.g., an individual affiliated with an authorized analytical facility).

In embodiments, oversight of the operation of the device may include transmission of instructions to the device. Instructions may include protocols, instructions to begin operations according to a protocol, instructions to interrupt or pause operations according to a protocol, instructions to stop or end operations according to a protocol, instructions to dynamically adjust or modify operation or a protocol, and other instructions. In embodiments, oversight of the operation of the device may include transmission of instructions from the laboratory location to the device at the sample collection site. In embodiments, oversight of the operation of the device may include transmission of instructions from the laboratory location to the device at the sample collection site accordance with procedures and requirements of a regulatory body, an authorized analytical facility, or a CLIA-certified laboratory. In embodiments, oversight may include oversight by personnel of a laboratory, such as CLIA-compliant laboratory or a CLIA-certified laboratory. In embodiments, oversight may include remote oversight by personnel of a laboratory, such as CLIA-compliant laboratory or a CLIA-certified laboratory. In embodiments, oversight by personnel of a laboratory may include oversight to insure that appropriate sample collection, sample processing, and other steps are taken. In embodiments, oversight of the operation of the device may include transmission of instructions to the device prior to processing a sample. In embodiments, oversight of the operation of the device may include transmission of instructions to the device prior to testing a sample. In embodiments, oversight of the operation of the device may include transmission of instructions to the device for collecting data from a sample. In embodiments, oversight of operation of the device may include oversight of transmission of the data, including raw data and pre-processed data (if any) to a laboratory. In embodiments, oversight of the operation of the device may include instructions to collect data from controls, replicates, device information, or other information. In embodiments, oversight of operation of the device may include oversight of receipt of instructions from the laboratory pursuant to the transmission of data following processing and testing of a sample. In embodiments, oversight of operation of the device may include transmission of instructions from the laboratory to the device effecting retesting of a sample pursuant to data or information transmitted from the device to the laboratory. In embodiments, oversight of operation of the device may include oversight of the disposal of sample and any waste following processing and testing of the sample. In embodiments, oversight of operation of the device may include other device operations. Such oversight may be provided or performed using a processor, e.g., a processor at a sample collection site, at a laboratory location, that is part of the cloud, or of a network; may be provided or performed by an individual (e.g., an individual affiliated with an authorized analytical facility); and may include using a processor in conjunction with an individual (e.g., an individual affiliated with an authorized analytical facility).

Analysis of the sample may be performed at a location physically distant from the sample collection site at the laboratory (which may be an authorized analytical facility, and may be a CLIA certified laboratory). Analysis of the sample may be performed at a location physically distant from the sample collection site according to the requirements of a regulatory body. A regulatory body may be a CLIA regulatory body, may be the U.S. Food and Drug Administration, or other regulatory body. A regulatory body may be a U.S. regulatory body, may be an international regulatory body, or may be a regulatory body of a nation other than the United States.

In embodiments, oversight by the laboratory may include oversight of the analysis of data transmitted by the device to the laboratory. In embodiments, oversight of analysis of data transmitted by the device may include pre-analytic oversight, analytic oversight, and post-analytic oversight. In embodiments, oversight of analysis of data transmitted by the device may include oversight of the transmission of raw data to the laboratory. In embodiments, oversight of analysis of data transmitted by the device may include oversight of the transmission of pre-processed data to the laboratory. In embodiments, oversight of analysis of data transmitted by the device may include oversight of the analysis of data, including raw data, pre-processed data, and other data, that is performed at the laboratory. In embodiments, oversight of data transmission may include oversight of encryption of data, oversight of mode of transmission of data, oversight of timing or sequence of transmission of data, and confirmation of complete transmission or receipt of data. In embodiments, oversight of analysis of data transmitted by the device may include oversight of the analysis of data, including raw data, pre-processed data, and other data, by a processor at the laboratory. In embodiments, oversight of analysis of data transmitted by the device may include oversight of the analysis of data, including raw data, pre-processed data, and other data, that is performed in conjunction with an individual at the laboratory, or affiliated with the laboratory. In embodiments, oversight of analysis of data transmitted by the device may include oversight of the analysis of data, including raw data, pre-processed data, in accordance with procedures and requirements of a regulatory body. In embodiments, oversight of analysis of data transmitted by the device may include oversight of the analysis of data, including raw data, pre-processed data, in accordance with procedures and requirements of an authorized analytical facility. In embodiments, oversight of analysis of data transmitted by the device may include oversight of the analysis of data, including raw data, pre-processed data, in accordance with procedures and requirements of a CLIA-certified laboratory. Such oversight of analysis may be provided or performed using a processor, e.g., a processor at a sample collection site, at a laboratory location, that is part of the cloud, or of a network; may be provided or performed by an individual (e.g., an individual affiliated with an authorized analytical facility); and may include using a processor in conjunction with an individual (e.g., an individual affiliated with an authorized analytical facility).

In embodiments, oversight of analysis of data transmitted by the device may include performance of the analysis at the laboratory location. In embodiments, oversight of analysis of data may be performed by a processor, and may include software oversight, oversight by or in conjunction with an individual (e.g., an individual affiliated with an authorized analytical facility), oversight by or in conjunction with a laboratory automation system (LAS), oversight by or in conjunction with a laboratory information system (LIS), or oversight by or in conjunction with an electronic medical records system (EMR). In embodiments, oversight of analysis of data transmitted by the device may include transmission of instructions from the laboratory location to the device at the sample collection site; such transmission of instructions from the laboratory location to the device at the sample collection site may be in accordance with procedures and requirements of a regulatory body, an authorized analytical facility, or a CLIA-certified laboratory. In embodiments, oversight of analysis of data transmitted by the device may include receipt at the laboratory of device information, cartridge information, patient identification information, calibration information, and other information from the device. Such oversight may be provided or performed using a processor; may be provided or performed by an individual (e.g., an individual affiliated with an authorized analytical facility); and may include using a processor in conjunction with an individual (e.g., an individual affiliated with an authorized analytical facility).

In embodiments, oversight of a report generated pursuant to the analysis of data transmitted by a device to a laboratory may include compilation of data and analysis to be reported; oversight including review and oversight of the integrity of the process, the operation, and of the assay that generated the data to be reported, including review and oversight of data integrity, testing integrity, and analysis integrity; preparation of a report; review of the report for accuracy and completeness; review of the report via a processor at the laboratory location; review of the report by an individual affiliated with the laboratory; oversight of the transmission of the report to recipients, including oversight of the transmission of the report to recipients, including confirmation of proper confidentiality and confirmation of its receipt; and other oversight. In embodiments, oversight of a report generated pursuant to the analysis of data transmitted by a device to a laboratory may be performed in accordance with procedures and requirements of a regulatory body, an authorized analytical facility, or a CLIA-certified laboratory. Such oversight of report generation may utilize automation of technical and operational steps and so be effective to minimize possible human error. Such reporting oversight may be provided or performed using a processor; may be provided or performed by an individual (e.g., an individual affiliated with an authorized analytical facility); and may include using a processor in conjunction with an individual (e.g., an individual affiliated with an authorized analytical facility).

In embodiments, oversight of billing for services provided may be performed using a processor at the laboratory location. In embodiments, oversight of billing for services provided may be performed by an individual affiliated with the laboratory. In embodiments, oversight of billing for services provided may be performed in accordance with procedures and requirements of a regulatory body, an authorized analytical facility, or a CLIA-certified laboratory. Such billing oversight may be provided or performed using a processor; may be provided or performed by an individual (e.g., an individual affiliated with an authorized analytical facility); and may include using a processor in conjunction with an individual (e.g., an individual affiliated with an authorized analytical facility).

For example, in embodiments of the devices, systems, and methods disclosed herein, e.g., as illustrated in FIG. 8, a device at a sample collection site may receive a protocol from a laboratory at a laboratory location. In embodiments, the protocol may be updated by further instructions from the laboratory. A protocol may include instructions regarding a cartridge, or cartridges, which may be used in accordance with the protocol. A subject may wish to provide a sample for testing. In embodiments of the devices, systems, and methods disclosed herein, the subject may provide identification information, or testing information (e.g., an order from a physician or other health provider regarding a test or tests to be performed; identification information regarding an operator, etc.) to the device or to an operator of the device at the sample collection site. The device may provide such identification or testing information to the laboratory. The laboratory may use such identification or testing information to determine the eligibility or appropriateness of the test or of the subject for the test (e.g., by determination of insurance status and coverage, billing information, sex, age, or health status of the subject, or other means). In view of the identification or testing information, the laboratory may provide instructions to the subject or operator (e.g., via a device user interface, a device audio link, telephone, or other means) regarding collection of a sample, the proper cartridge to be used, or other information. Collection of the sample may require no processing of the sample by the subject or by an operator. For example, sample collection may be automated, sample processing may be automated, and other functions may be automated, providing better control and integrity of sample collection, processing and analysis; such control may aid in compliance with CLIA or other regulatory standards, e.g., by reducing the possibility of operator variance or error. In view of the identification or testing information, the laboratory may provide instructions, including but not limited to, a protocol, to the device. Such instructions may cause the device (e.g., via a user interface, audio output, or other means) to request confirmation or further information from the subject or operator at the sample collection site. A sample may be obtained from the subject at the sample collection site. The sample may be placed in the device, or the sample may be placed in a cartridge and the cartridge with the sample may be placed in the device. The device may transmit status, test, or identification information to the laboratory. In view of the cartridge, status, test, or identification information, the laboratory may transmit instructions, including but not limited to a protocol, to the device. For example, the laboratory may transmit instructions to the device effecting the rejection of the sample, or of the cartridge with the sample, if the sample, cartridge, protocol, identification information, or other information do not match or are otherwise incompatible with proper operation, processing, or testing of the sample by the device, or if the subject lacks insurance coverage or if the test is otherwise inappropriate for the subject, the cartridge, or the device. In view of the cartridge, status, test, or identification information, the laboratory may transmit a protocol, or update a protocol, to the device. The laboratory may transmit instructions to the device effecting the processing and testing of the sample. The transmission of instructions from the laboratory to the device may be via the cloud, telephone, radio, network, LAN, other electronic or electromagnetic means, or any other communications link Instructions effecting the processing and testing of a sample may include instructions effecting transport of the sample, of reagents, or of device components within or to the device; may include instructions effecting mixing of the sample and reagents; may include instructions effecting processing and/or testing of the sample; may include instructions effecting observation or measurement of the sample, including instructions effecting acquisition of data from the sample; may include instructions effecting the transmission of data (which may include raw data and pre-processed data) from the device to the laboratory; and may include instructions effecting the disposal of the sample and waste resulting from the processing and testing of the sample. These instructions enable the device to process a sample without physical transport of the sample from the device to the laboratory. The laboratory may analyze the data received from the device. Laboratory analysis of data received from the device may be dynamic analysis (e.g., analysis may be confirmed, altered or updated in view of information or data provided with or about the sample or test). The laboratory may provide further instructions to the device pursuant to the analysis of the data received from the device. Such further instructions may effect further processing or testing of the sample in the device at the sample collection site. The laboratory may prepare a report based on the data from the sample and its analysis. The laboratory may notify a subject, a health provider, an insurance company, or a payer regarding the processing and testing of the sample. The laboratory may send a report to a subject, a health provider, an insurance company, or a payer regarding the processing and testing of the sample. The laboratory may prepare bill information, or may prepare a bill, regarding the processing and testing of the sample. The laboratory may send a bill regarding the processing and testing of the sample to the subject, an insurance company, or a payer. Thus, control and oversight of the device at a sample collection site may be effected by a processor at the laboratory location, by an individual affiliated with the laboratory, or both. The laboratory may be an authorized analytical facility, and may be a CLIA certified or CLIA-compliant laboratory.

In embodiments, oversight of the operation of a device, oversight of the analysis of data from a sample, or other oversight may comprise oversight by software. Such oversight software may be software cleared under section 510(k) of the U.S. Food, Drug and Cosmetic Act, or cleared or approved under other statutes or by another regulatory body, and such software may be run by, or running in a CLIA-compliant or CLIA-certified laboratory or location. Such oversight software may be software cleared under section 510(k) of the U.S. Food and Cosmetic Act, or cleared or approved under other statutes or by another regulatory body, and such software may be run by, or running in a location other than a CLIA-compliant or CLIA-certified laboratory or location. Such oversight software may be software cleared under section 510(k) of the U.S. Food, Drug and Cosmetic Act, or cleared or approved under other statutes or by another regulatory body, and such software may be run by, or running in the cloud or other network; such software running in the cloud or other network may be run by, or running under the oversight of a CLIA-compliant or CLIA-certified laboratory or location, or may not be run by, or running under the oversight of a CLIA-compliant or CLIA-certified laboratory or location.

In some embodiments, a method for evaluating a biological sample may be provided. The method may include receiving and/or preparing a sample on board a device. The method may include performing analysis on-board the device. Alternatively, the method may include performing analysis external and/or remote to the device. For example, the analysis may occur at a laboratory or by an affiliate of the laboratory. In some embodiments, the analysis may occur both on-board the device and external to the device.

The analysis may be performed by a health care professional of a laboratory, or any other affiliate of the laboratory. The analysis may be performed by a software program. A processor may perform one or more steps of the software program, thereby effecting such analysis. In some embodiments, one, two or more types of analysis may be provided by the analysis software program. In some embodiments, the analysis may be performed by both the health care professional and the software program. In some examples, the analysis may be performed by a software program on-board the device, by a health care professional external to the device, and/or by a software program external to the device.

The method may further include providing oversight of the analysis. The method may include performing oversight on-board the device. Alternatively, the method may include performing oversight external and/or remote to the device. For example, the oversight may occur at a laboratory or by an affiliate of the laboratory. The laboratory may be an authorized analytical facility, and may be CLIA-certified laboratory. In some embodiments, the oversight may occur both on-board the device and external to the device.

In some embodiments, analysis may be conducted by a health care professional and oversight may be conducted by a health care professional, analysis may be conducted by a health care professional and oversight may be conducted by a software program, analysis may be conducted by a software program and oversight may be conducted by a health care professional, or analysis may be conducted by a software program and oversight may be conducted by a software program. The same health care professional or different health care professionals may be used for analysis and/or oversight. The same software program or different software programs may be used for analysis and/or oversight. Any description of laboratories, health care professionals, software, and/or infrastructure that may perform oversight may also apply to analysis, or vice versa.

The oversight may be performed by a health care professional of a laboratory, or any other affiliate of the laboratory. The oversight may be performed by a software program. A processor may perform one or more steps of the software program, thereby effecting such oversight. In some embodiments, the oversight may be performed by both the health care professional and the software program. In some examples, the oversight may be performed by a software program on-board the device, by a health care professional external to the device, and/or by a software program external to the device. Any combination of analysis and oversight may be provided.

Oversight may include pre-analytical oversight, may include analytical oversight, and may include post-analytical oversight. Pre-analytical oversight may include oversight of the acquisition and processing of a sample by a device at a sample collection site. Such oversight may be performed at a laboratory location by a processor or by an individual affiliated with a laboratory. The laboratory may be a sample collection site, and sample collection may be manual or may be automated. The laboratory may be an authorized analytical facility, and may be a CLIA-certified laboratory.

Analytical oversight may include oversight of the acquisition of data from a sample by the device. Such oversight may be performed at a laboratory location by a processor or by an individual affiliated with a laboratory, which may be may be an authorized analytical facility, and may be a CLIA-certified laboratory. Analytical oversight may include oversight of the transmission of data from the device to the laboratory. Oversight of data transmission may include oversight of encryption of data, oversight of mode of transmission of data, oversight of timing or sequence of transmission of data, and confirmation of complete transmission or receipt of data. Such oversight may be performed at a laboratory location by a processor or by an individual affiliated with a laboratory, which may be may be an authorized analytical facility, and may be a CLIA-certified laboratory. Analytical oversight may include oversight of the analysis of data transmitted from the device to the laboratory. Oversight of the analysis of data transmitted from the device to the laboratory may include instructions to collect data from controls, replicates, device information, or other information. Oversight of the analysis of data transmitted from the device to the laboratory may include use of controls for multiple assay methodologies available or in use on the same device, available or in use at the same time, or at substantially the same time, for analysis, calibration, or control. Oversight of the analysis of data transmitted from the device to the laboratory may include comparisons with, or use of, data from controls, replicates, device information, or other information. Such oversight, including oversight of multiple assay methodologies, may be performed at the same time, or at substantially the same time. Such oversight may be performed at a laboratory location by a processor or by an individual affiliated with a laboratory, which may be may be an authorized analytical facility, and may be a CLIA-certified laboratory.

Post-analytical oversight may include preparation of a report regarding the data and the analysis of data obtained from a sample. Post-analytical oversight may include identification of outliers or other data or information requiring further review. Post-analytical oversight may include use of a processor to provide further analysis regarding clinically abnormal values or other data or information requiring further review. Post-analytical oversight may include notification of an individual affiliated with the laboratory regarding outliers or other data or information requiring further review. Post-analytical oversight may include providing an individual affiliated with the laboratory with data, analysis, or information regarding outliers or other data or information requiring further review. Post-analytical oversight may be performed at a laboratory location by a processor or by an individual affiliated with a laboratory, which may be may be an authorized analytical facility, and may be a CLIA-certified laboratory.

Figure 5:
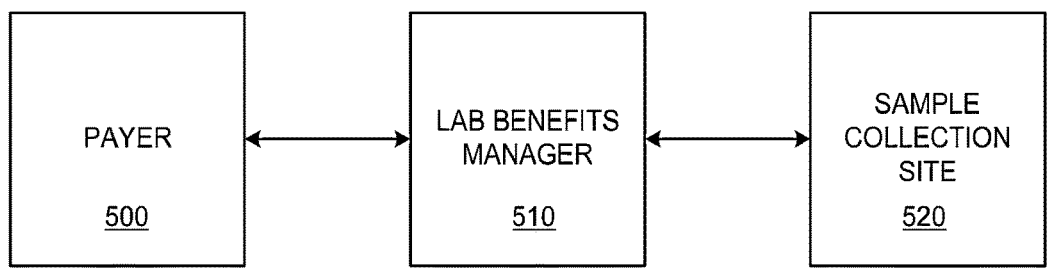
FIG. 5 shows a laboratory benefit manager in communication with a payer and a sample collection site.

FIG. 5 shows a laboratory benefit management (LBM) entity 510 in communication with a payer 500 and sample collection site 520. The LBM may be in communication with a payer at a payer location and the sample collection site at a point of service location. The LBM may be provided at a facility at the LBM location. The LBM may be at a different location than the payer and the sample collection site. In some embodiments, the sample collection site may be a retailer, insurance company, entity, or any sample collection site as described elsewhere herein. For example, the payer, LBM, and point of service may be provided in different facilities.

The LBM 510 may be an entity. For example, the LBM may be a company, corporation, organization, partnership, business, or one or more individuals that form an entity. The LBM may be configured to communicate with one or more other entity regarding financial transactions and services. The LBM may provide instructions regarding financial transactions and services and manage financial processes.

The payer 500 may be an entity that may pay or partially pay for one or more health or medical related services for a subject. The payer may have a contract or agreement with the subject or a sponsor of the subject to provide some form of medical coverage. The payer may be a public payer or private payer. In some instances, the payer may be a government payer or a health insurance company. Examples of government payers may include, but are not limited to Medicare, Medicaid, Federal Employees Health Benefits Program, Veterans Health Administration, State Children's Health Insurance Program, Military Health System/TRICARE, Indian Health Service, or other publicly funded health insurance programs. Examples of types of private payers may include, but are not limited to, health maintenance organizations (HMO), preferred provider organization (PPO), independent practice association (IPA), point of service (POS) plans, or managed care or indemnity insurance plans. Examples of health insurance companies may include but are not limited to Aetna, Blue Cross Blue Shield Association, CIGNA, Kaiser Permanente, Humana, Health Net, UnitedHealth Group, or Wellpoint.

The sample collection site 520 may be a point of service location. A sample collection site may be provided at a point of service location. Any discussion of a point of service may also apply to a sample collection site at a point of service location. A point of service location may be a location remote to the LBM where a sample may be collected from a subject or provided by a subject. In some embodiments, a sample collection site may be a retailer. Examples of point of service locations and retailers are provided in further detail elsewhere herein. In some embodiments, the sample collection site may comprise a device, as described in further detail elsewhere herein.

The LBM may receive information from a sample collection site, and/or may receive information from a payer. The LBM may provide information to a sample collection site, and/or may provide information to a payer. The LBM may communicate with the payer and sample collection site in any manner known or later developed in the art, including, but not limited to using a sample processing device, network device, mobile device, telephone, postage, courier, delivery, or any other communication techniques described elsewhere herein. The communication may occur over a network, including any form of network as described elsewhere herein. One-way or two-way communication may be provided between the LBM and the payer, and between the LBM and the sample collection site. The LBM, payer, and sample collection site may have one or more communication unit. The communication unit may be configured to provide communication between the LBM, payer, and sample collection site. The communication unit may be configured to provide wireless or wired communication.

The LBM may also perform financial transactions with the payer and with the sample collection site. In some instances, the financial transactions may be two-way financial transactions, or may be one-way financial transactions. In one example, the payer may pay the LBM. The LBM may pay the sample collection site. The payment the LBM provides the sample collection site may be derived from the payment the LBM receives from the payer.

The LBM, payer, and sample collection site may have a processor and memory that may keep track of the communications and/or payments. The LBM, payer, and/or sample collection site may interact with one or more third party that may keep track of the communications and/or payments. The one or more third parties may be financial institutions. A processor may have access to one or more memory that may contain information about payments received or disbursed. For example, an LBM may have a processor that accesses one or more memory or data storage unit containing information about a payment received from the payer and a payment provided to a sample collection site.

The payments may be provided based on use of a device provided at the sample collection site. The LBM may request a payment from the payer based on use of the device. The LBM may provide a payment to the sample collection site based on use of the device. Alternatively, the LBM may request a payment from the sample collection site based on use of the device.

The LBM may comprise one or more data storage unit comprising information of the subject, or may have the ability to access information of the subject, said informing comprising insurance status of said subject, copayment status of prior and pending clinical test(s), medical records relating to the subject, payment information relating to the subject, identification information of the subject, or other information associate with the subject or financial transactions associated with the subject.

In some alternate embodiments, a payer may receive an electronic bill from a sample collections site and/or an LBM. In some instances, a health care professional may receive an electronic payment from the sample collection site and/or the LBM.

Figure 6:
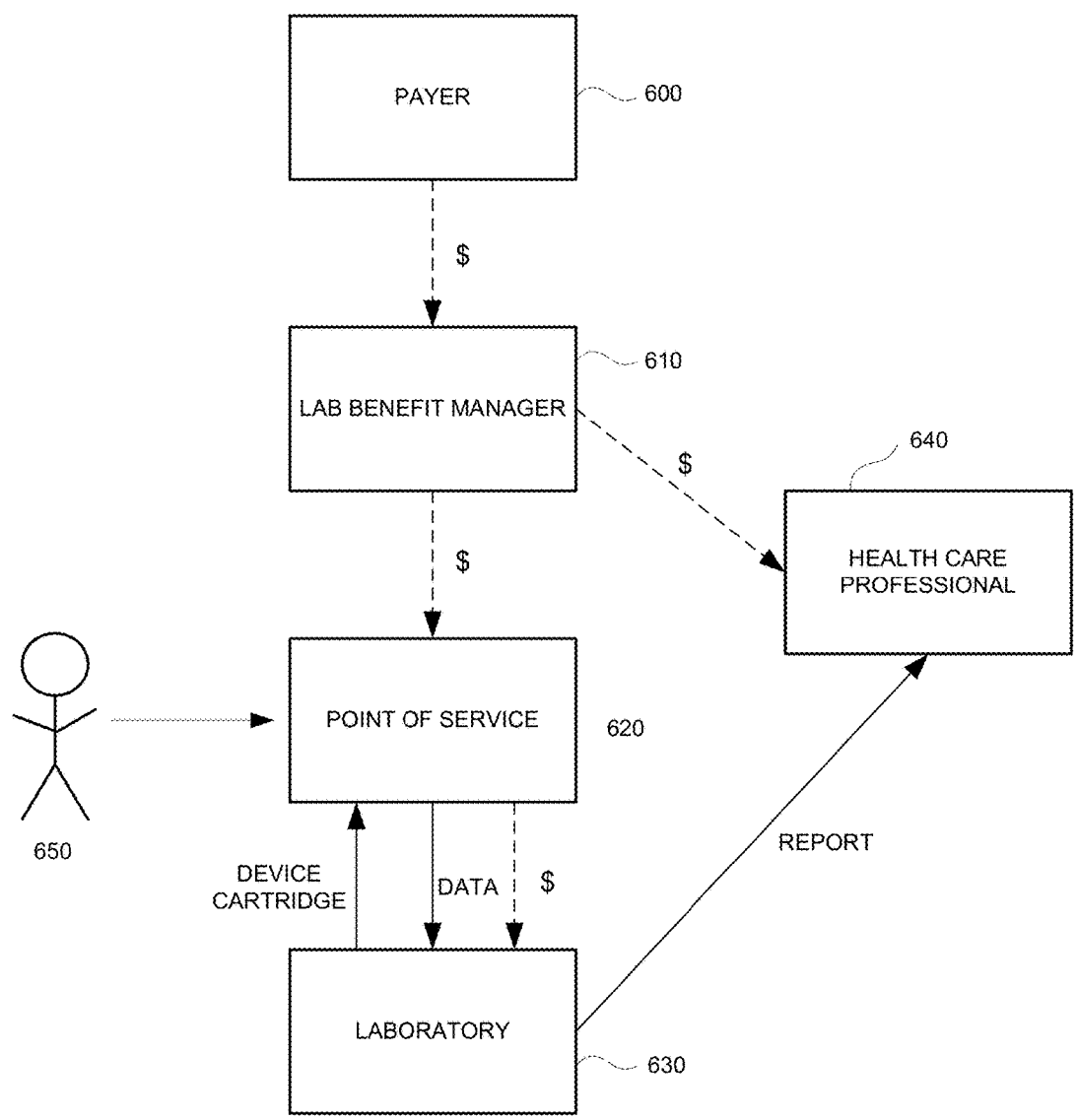
FIG. 6 shows a laboratory benefit system provided in accordance with an embodiment of the invention.

FIG. 6 shows a laboratory benefit system provided in accordance with an embodiment of the invention. A point of service 620 may be in communication with a laboratory 630. The point of service may be a sample collection site and any description herein of a point of service may also apply to a sample collection site and vice versa. The point of service may also be in communication with an LBM 610 who may also be in communication with a payer 600. The LBM and the laboratory may be in communication with a health care professional 640. A subject 650 may provide a sample to a point of service.

A point of service 620 may be a sample collection center that may have a device that may be configured to facilitate collection of a biological sample from a subject 650. As previously described, the sample may be collected from the subject at the point of service, or may be provided to the device at the point of service.

The sample collection center may be capable of communicating with a laboratory 630. The laboratory may be a certified laboratory. The sample collection center may communicate with the laboratory via a sample processing device located at the sample collection center. The sample collection center may communicate with the laboratory in additional ways. Data collected by the device may be transmitted from the point of service 620 to the laboratory. Such data may be related to the sample collected from the subject. Any type of data described previously herein, including raw data, pre-processed data, or analyzed data may be provided to the laboratory.

The laboratory may provide the device to the point of service location. In one example, the laboratory may either sell or lease/rent the device to the sample collection center. The laboratory may request a payment from the sample collection center for the sales and/or leasing of the device to the sample collection center. The sample collection center may provide a payment to the laboratory for the ownership or use of the device. The device may be operated by a device operator. The operator may be affiliated with the point of service location. The operator may be an employee or otherwise affiliated with the sample collection center. The operator may or may not be trained in the use of the device. The sample collection center may be another entity separate from the laboratory. The sample collection center may be affiliated with the point of service location or may be operated by a separate entity. The sample collection center may be any of the point of service locations described elsewhere herein, including but not limited to retailers (e.g., Blue Cross, Blue Shield, Health Net, Aetna, Cigna), hospitals, medical facilities, and any other point of service. In one example, the device may be operated by a technician or other individual associated with a retailer or other point of service. The laboratory may be functioning as a wholesaler of the device. Alternatively, one or more intermediary entities may be provided that may purchase devices from the laboratory, and in turn provide/sell devices to point of service locations.

In an alternate example, the laboratory may pay the point of service location for providing the device at the sample collection center, which may be located at the point of service location. The laboratory may pay the point of service location for permitting use of the device at the point of service location and for permitting the setup of the sample collection center at the point of service. For example, the laboratory may be permitted to rent out space at a retailer, where the laboratory may setup a sample collection center having one or more devices. The device may be operated by personnel who is or is not trained in the use of the device. The device operator may be affiliated with the laboratory. The device operator may or may not be an employee of the laboratory. The device and device operator may be using the point of service location as a sample collection site that is remote to the laboratory.

The laboratory may provide a cartridge to a point of service location. The cartridge may be configured to be inserted into, or otherwise interface with the device. The cartridge may or may not be disposable. The laboratory may or may not provide disposables to the service location for use with the device. Any description herein of cartridges may also apply to the disposables and vice versa. In one example, the laboratory may either sell the cartridge to the sample collection center. The sample collection center may be affiliated with the point of service location and/or with a separate entity. The sample collection center may be run by the point of service location and/or a separate entity. The laboratory may request a payment from the sample collection center for the sales of the cartridge to the sample collection center. The sample collection center may provide a payment to the laboratory for the cartridges. The operator of the device may be affiliated with the point of service location. The laboratory may be functioning as a wholesaler of the cartridge. Alternatively, one or more intermediary entities may be provided that may purchase cartridges from the laboratory, and in turn provide/sell cartridges to point of service locations.

In an alternate example, the laboratory need not request payment from for providing the cartridge at the sample collection center. The device may be operated by personnel who is or is not trained in the use of the device. The device operator may be affiliated with the laboratory. The device operator may or may not be an employee of the laboratory. The device and device operator may be using the point of service location as a sample collection site that is remote to the laboratory. The cartridge may be used as part of the sample collection service at the point of service location, for a device that may be operated by a laboratory-affiliated individual.

The laboratory 630 may be capable of communicating with a health care professional 640. The health care professional may be at a location separate from the laboratory and the point of service. The health care professional may or may not have an existing relationship with the subject 650. The health care professional may have issued a prescription for the subject to go to the point of service location and perform one or more test. The health care professional may or may not have a relationship with point of service or with the laboratory. In some embodiments, the laboratory may send a report to the health care professional. The medical report may be based on data collected from a device at the point of service. The medical report may be based on an analysis of the data collected from the device. In some embodiments, analysis of data may include the comparison of collected data with one or more threshold value to determine the presence or concentration of at least one analyte. In some embodiments, the laboratory may have a processor that may be configured to access a data storage unit that may have information relating to the one or more threshold value. The analysis may occur at the laboratory 630 and the report may be generated at the laboratory. Alternatively, the analysis may occur at the device and the report may be generated by the device or at the laboratory.

In some embodiments, a report may be provided to a subject 650. The report transmitted to the subject may or may not be the same as the report provided to the health care professional 640. The reports may be sent simultaneously, or the health care professional may receive the report first, or vice versa.

An LBM 610 may be provided that may communicate with a payer 600 and a point of service 620. The LBM may or may not communicate with a health care professional 640 and/or a laboratory 630.

The laboratory 630 and LBM 610 may be separate entities. The laboratory and LBM may be separate corporations, companies, organizations, institutions, partnerships, one or more individuals, or any other type of entity as described elsewhere herein. The laboratory and LBM may be incorporated as separate legal entities. The LBM may be a laboratory benefits manager, and the laboratory may be a wholesaler. The laboratory and LBM may be housed in separate facilities. Alternatively, they may share facilities.

The LBM 610 may charge a payer 600 based on use of the device at the point of service 620. For example, per use of the device, the LBM may charge the payer a fee. The size of the fee may depend on one or more factors, such as the type of use of the device (e.g., number of analytes whose presence or concentration were detected, the number of chemical reactions, the amount of sample preparation, the types of reactions that take place, the number of device components that are used), the analysis conducted in relationship to the data collected from the device (e.g., more complex analysis may result in a different fee from more straightforward analysis), the payer relationship with the subject, the payer relationship with the point of service if any. The LBM and payer may have an agreement in place that may determine the payment plan between the payer and the LBM.

The LBM 610 may provide a payment to a point of service 620 based on use of the device at the point of service. For example, per use of the device, the LBM may provide a payment to the point of service. In another example, for the amount of time that the device is located at the point of service, the LBM may provide a payment to the point of service. The size of the fee may depend on one or more factors, such as the type of use of the device (e.g., number of analytes whose presence or concentration were detected, the number of chemical reactions, the amount of sample preparation, the types of reactions that take place, the number of device components that are used), the analysis conducted in relationship to the data collected from the device (e.g., more complex analysis may result in a different fee from more straightforward analysis). The LBM and point of service may have an agreement in place that may determine the payment plan between the point of service and the LBM and the LBM. In alternate embodiments, the LBM may provide a payment to a laboratory 630. Any description herein of providing payment to a point of service may also apply to a laboratory. The LBM may provide a payment to the laboratory instead of providing a payment to the point of service, or in addition to providing a payment to the point of service.

In some embodiments, the LBM 610 may divide a payment received from the payer 600 into a technical fee and a professional fee. In one example, the LBM may provide a payment to a health care professional 640 based on the professional fee. The LBM may provide a payment to the sample collection center 620 based on the technical fee. In some embodiments, the sample collection center may be operated by a point of service, such as a retailer, hospital, or any other point of service. In some embodiments, the sample collection center may be operated by a laboratory. The payment may be provided to the entity for the point of service location, or to a laboratory who may be operating a sample collection center at a point of service location.

The LBM may make the determination of how to divide the payment from the payer. The technical fee and/or professional fees may be based on agreements that the LBM may have with the health care professional, point of service, and/or laboratory. The professional fee may also or alternatively be based on agreements that the health care professional may have with the payer and/or laboratory.

The LBM may further divide the payment from the payer into a transaction fee. The transaction fee may be an amount that goes to the LBM. The LBM may be able to keep a fraction of the payment made by the payer.

Figure 7:
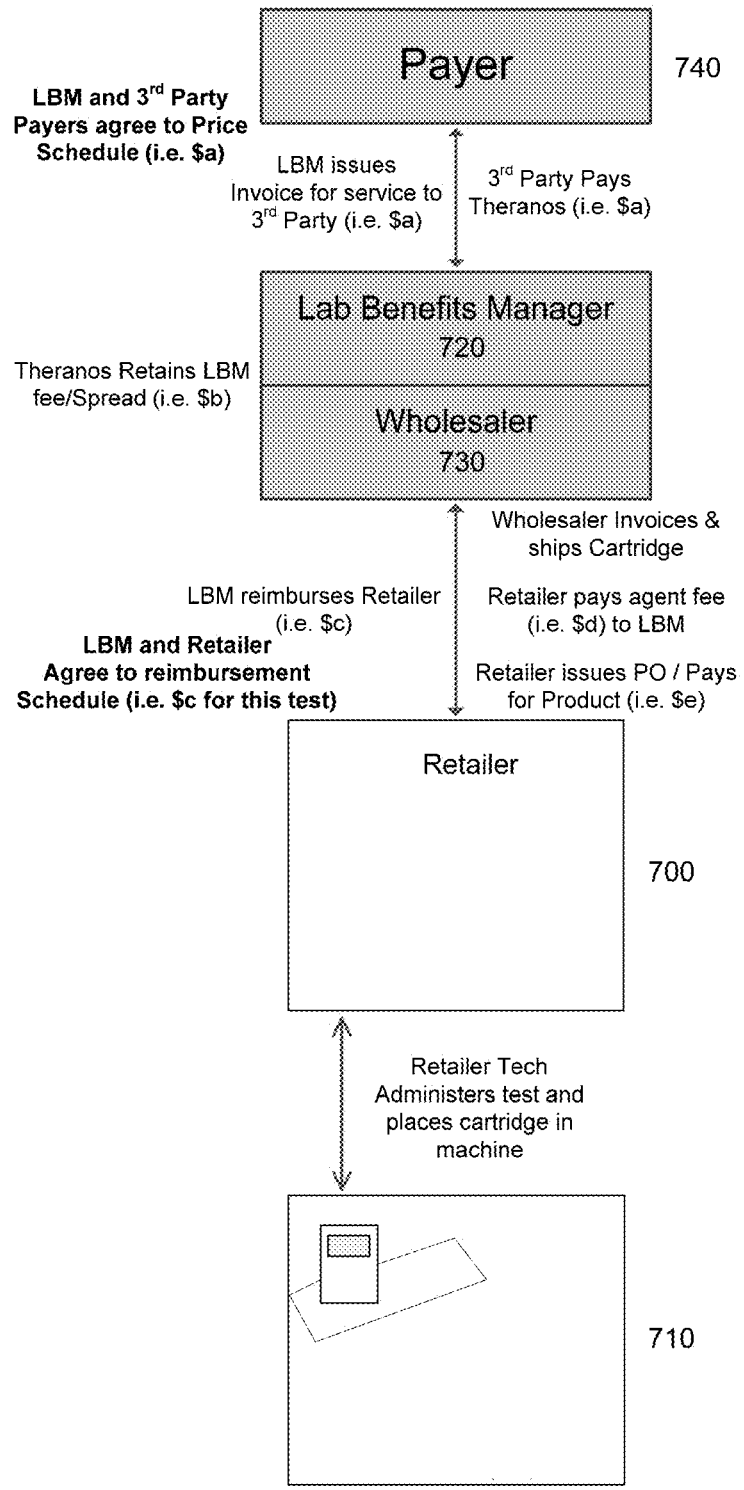
FIG. 7 shows an example of a laboratory benefit manager/wholesaler model in accordance with an embodiment of the invention.

FIG. 7 shows an example of a lab benefits manager/wholesaler model in accordance with an embodiment of the invention. A retailer 700 (or other point of service), such as a pharmacy, may have one or more sample processing device located at the retailer site. A retailer technician may operate the sample processing device, and may place a cartridge into the device 710. The cartridge may or may not contain a sample from a subject collected at the retailer site.

A laboratory benefit manager 720 may be an LBM as described elsewhere herein. The laboratory benefit manager may be an entity.

A laboratory benefit manager 720 and a wholesaler 730 may be provided within the model. The laboratory benefit manager and the wholesaler may be separate entities. The laboratory benefit manager and the wholesaler may be separate legal entities, corporate entities, corporations, partnerships, organizations, and/or groups of one or more individuals. The laboratory benefit manager and the wholesaler may be housed in different facilities or in the same facility.

A laboratory benefit manager 720 may be in communication with one or more payers 740. The laboratory benefit manager may issue an invoice for a service to the payers. The payer may pay the laboratory benefit manager. For example, the laboratory benefit manager may request a $a (e.g., $28 to provide a numerical example) fee from the payer, who pays the laboratory benefit manager, the $a. The laboratory benefit manager may retain a LBM fee. For example, a $b (e.g., $1 to provide a numerical example) fee may be retained by the laboratory benefit manager.

The laboratory benefit manager 720 may reimburse the retailer 700 for the balance of the amount. For example, the laboratory benefit manager may pay the retailer the remaining $c, (e.g., $27). $c may equal $a minus $b.

The retailer may also have fees associated with the laboratory benefit manager and/or the wholesaler. For example, the retailer may have an agent fee that the retailer may pay the laboratory benefit manager. In one example, the agent fee is $d (e.g., $8 to provide a numerical example). The retailer may also issue a purchase order or pay for a product. For example, the retailer may pay for the purchase or use of the device at the retailer site and/or cartridges. The retailer may pay the laboratory benefit manager. Alternatively, the retailer may pay the wholesaler for the purchase or use of the device and/or cartridges. In one example, the payment for the product may be $e (e.g., $9 to provide a numerical example).

From a laboratory benefit manager perspective, there may be a financial benefit to following the model. For example, the laboratory benefit manager may receive an LBM fee based on the device use. For example, the LBM fee may be $b per transaction. The laboratory benefit manager may also receive an agent fee from the retailer. For example, the laboratory benefit manager may receive an $d admin fee. In some instances, the laboratory benefit manager may also receive a product fee from the retailer. For example, the laboratory benefit manager may receive a $e product fee.

From a retailer perspective, there may be financial benefit to following the model. For example, the retailer may receive a service income of $c. The service income may be provided through the laboratory benefit manager. The laboratory benefit manager may provide the service income based on a payment received from a payer. The laboratory benefit manager may subtract an LBM fee from the amount received from the payer, and may pass the rest on to the retailer as a service income. In additional embodiments, the laboratory benefit manager may also subtract a professional fee, which may be provided to a health care professional or other entity, with the remainder of the balance going to the retailer as a service income. Thus, as shown in FIG. 7, the total revenue may be provided from a $c service income. Costs to the retailer may include an administration fee (e.g., the $d fee shown), and/or a product fee (e.g., the $e fee shown). The costs may be about $f (e.g., $17 to provide a numerical example). $f may equal $d plus $e. The costs to the retailer may be lower than the service income. For example, a $g (e.g., $10 to provide a numerical example) gross margin is illustrated for the retailer. In some instances, $g=$c minus $f.

The table below illustrates examples of the model.

| P&L Impacts | Retailer |
| --- | --- |
| Service Income | $c |
| Total Revenue | $c |
| COGS | $f ($d admin fee + $e product cost) |
| Gross Margin | $g |

Any of the dollar amounts are provided by way of example only and shall not be construed as limiting. Any numerical value may be inserted for the various dollar values.

In some embodiments, a subject may be associated with a payer. For example, a payer, such as a health insurance company, government payer, or any other payer as described herein, may provide coverage for the subject. A payer may pay some or all of the subject's medical bills. In some embodiments, when a subject arrives at a point of service, the identification of the subject may be verified. The identification of the subject may be verified using the device, and/or verified by personnel at the point of service. For example, the personnel at the point of service may view the subject's identification and/or insurance card. The device may or may not capture an image of the subject and/or collect one or more biometric parameter from the subject. Verification may occur on-board the device. Alternatively, the identification of the subject may be collected at the point of service and may be further verified at another entity or location. For example, a laboratory, health care professional, or payer may verify the subject identity. The device, laboratory, health care professional, and/or payer may be capable of accessing subject information, such as electronic health records. Verification may occur rapidly and/or in real-time. For example, verification may occur within 10 minutes or less, 5 minutes or less, 3 minutes or less, 1 minute or less, 45 seconds or less, 30 seconds or less, 20 seconds or less, 15 seconds or less, 10 seconds or less, 5 seconds or less, 3 seconds or less, 1 second or less, 0.5 seconds or less, or 0.1 seconds or less. The verification may be automated without requiring any human intervention.

The system may verify the identity of the subject for the system's records, insurance coverage, to prevent fraud, or any other purpose. The verification may be performed by the device. The verification may occur at any time. In one example, the subject's identity may be verified prior to preparing the subject's sample for the test. The subject's identity may be verified prior to providing a sample to the device and/or cartridge. The verification of the subject's identity may be provided prior to, currently with, or after verifying the subject's insurance coverage. The verification of the subject's identity may be provided prior to, currently with, or after verifying the subject has received a prescription to undergo said qualitative and/or quantitative evaluation. The verification may take place through communications with the medical care provider, laboratory, payer, laboratory benefits manager, or any other entity. Verification may occur by accessing one or more data storage units. The data storage units may include an electronic medical records database and/or a payer database. Verification may occur rapidly and/or in real-time. For example, verification may occur within 10 minutes or less, 5 minutes or less, 3 minutes or less, 1 minute or less, 45 seconds or less, 30 seconds or less, 20 seconds or less, 15 seconds or less, 10 seconds or less, 5 seconds or less, 3 seconds or less, 1 second or less, 0.5 seconds or less, or 0.1 seconds or less. The verification may be automated without requiring any human intervention.

The verification may include information provided by the subject. For example, the verification may include scanning an identification card and/or insurance card of the subject. The verification may include taking a picture of the subject and/or the subject's face. For example, the verification may include taking a two-dimensional or three-dimensional snapshot of the subject. Cameras may be used which may provide a two-dimensional digital image of the subject and/or that may be capable of formulating a three-dimensional or four-dimensional image of the subject. A four-dimensional image of the subject may incorporate changes over time. The verification may include taking a picture of the subject's face for identification. The verification may include taking a picture of another portion of the subject's face for identification, including but not limited to the patient's whole body, arm, hand, leg, torso, foot, or any other portion of the body. The verification may employ a video camera and/or a microphone that may capture additional visual and/or audio information. The verification may include comparing the subject's movements (e.g., gait), or voice.

The verification may include entering personal information related to the subject, such as the subject's name, insurance policy number, answers to key questions, and/or any other information. The verification may include collecting one or more biometric read-out of the subject. For example, the verification may include a fingerprint, handprint, footprint, retinal scan, temperature readout, weight, height, audio information, electrical readouts, or any other information. The biometric information may be collected by the device. For example, the device may have a touchscreen upon which the subject may put the subject's palm to be read by the device. The touchscreen may be capable of scanning one or more body part of the subject, and/or receiving a temperature, electrical, and/or pressure readout from the subject. Alternatively, the device may receive the biometric information from other devices. For example, the device may receive the subject's weight from a scale that may be separate from the device. The information may be sent directly from the other devices (e.g., over wired or wireless connection) or may be entered manually.

The verification may also include information based on a sample collected from the subject. For example, the verification may include a genetic signature of the subject. When the sample is provided to the device, the device may use at least part of the sample to determine the genetic signature of the subject. For example, the device may perform one or more nucleic acid amplification step and may determine key genetic markers for the subject. This may form the subject's genetic signature. The subject's genetic signature may be obtained prior to, concurrently with, or after processing the sample on the device. The subject's genetic signature may be stored on one or more data storage unit. For example, the subject's genetic signature may be stored in the subject's electronic medical records. The subject's collected genetic signature may be compared with the subject's genetic signature already stored in the records, if it exists. Any other unique identifying characteristic of the subject may be used to verify the subject's identity.

Methods for the amplification of nucleic acids, including DNA and/or RNA, are known in the art. Amplification methods may involve changes in temperature, such as a heat denaturation step, or may be isothermal processes that do not require heat denaturation. The polymerase chain reaction (PCR) uses multiple cycles of denaturation, annealing of primer pairs to opposite strands, and primer extension to exponentially increase copy numbers of the target sequence. Denaturation of annealed nucleic acid strands may be achieved by the application of heat, increasing local metal ion concentrations (e.g. U.S. Pat. No. 6,277,605), ultrasound radiation (e.g. WO/2000/049176), application of voltage (e.g. U.S. Pat. No. 5,527,670, U.S. Pat. No. 6,033,850, U.S. Pat. No. 5,939,291, and U.S. Pat. No. 6,333,157), and application of an electromagnetic field in combination with primers bound to a magnetically-responsive material (e.g. U.S. Pat. No. 5,545,540), which are hereby incorporated by reference in their entirety. In a variation called RT-PCR, reverse transcriptase (RT) is used to make a complementary DNA (cDNA) from RNA, and the cDNA is then amplified by PCR to produce multiple copies of DNA (e.g. U.S. Pat. No. 5,322,770 and U.S. Pat. No. 5,310,652, which are hereby incorporated by reference in their entirety).

One example of an isothermal amplification method is strand displacement amplification, commonly referred to as SDA, which uses cycles of annealing pairs of primer sequences to opposite strands of a target sequence, primer extension in the presence of a dNTP to produce a duplex hemiphosphorothioated primer extension product, endonuclease-mediated nicking of a hemimodified restriction endonuclease recognition site, and polymerase-mediated primer extension from the 3' end of the nick to displace an existing strand and produce a strand for the next round of primer annealing, nicking and strand displacement, resulting in geometric amplification of product (e.g. U.S. Pat. No. 5,270,184 and U.S. Pat. No. 5,455,166, which are hereby incorporated by reference in their entirety). Thermophilic SDA (tSDA) uses thermophilic endonucleases and polymerases at higher temperatures in essentially the same method (European Pat. No. 0 684 315, which is hereby incorporated by reference in its entirety).

Other amplification methods include rolling circle amplification (RCA) (e.g., Lizardi, "Rolling Circle Replication Reporter Systems," U.S. Pat. No. 5,854,033); helicase dependent amplification (HDA) (e.g., Kong et al., "Helicase Dependent Amplification Nucleic Acids," U.S. Pat. Appln. Pub. No. US 2004-0058378 A1); and loop-mediated isothermal amplification (LAMP) (e.g., Notomi et al., "Process for Synthesizing Nucleic Acid," U.S. Pat. No. 6,410,278), which are hereby incorporated by reference in their entirety. In some cases, isothermal amplification utilizes transcription by an RNA polymerase from a promoter sequence, such as may be incorporated into an oligonucleotide primer. Transcription-based amplification methods commonly used in the art include nucleic acid sequence based amplification, also referred to as NASBA (e.g. U.S. Pat. No. 5,130,238); methods which rely on the use of an RNA replicase to amplify the probe molecule itself, commonly referred to as Qβ replicase (e.g., Lizardi, P. et al. (1988) *BioTechnol.* 6, 1197-1202); self-sustained sequence replication (e.g., Guatelli, J. et al. (1990) *Proc. Natl. Acad. Sci. USA* 87, 1874-1878; Landgren (1993) *Trends in Genetics* 9, 199-202; and HELEN H. LEE et al., NUCLEIC ACID AMPLIFICATION TECHNOLOGIES (1997)); and methods for generating additional transcription templates (e.g. U.S. Pat. No. 5,480,784 and U.S. Pat. No. 5,399,491), which are hereby incorporated by reference in their entirety. Further methods of isothermal nucleic acid amplification include the use of primers containing non-canonical nucleotides (e.g. uracil or RNA nucleotides) in combination with an enzyme that cleaves nucleic acids at the non-canonical nucleotides (e.g. DNA glycosylase or RNaseH) to expose binding sites for additional primers (e.g. U.S. Pat. No. 6,251,639, U.S. Pat. No. 6,946,251, and U.S. Pat. No. 7,824,890), which are hereby incorporated by reference in their entirety. Isothermal amplification processes can be linear or exponential.

Nucleic acid amplification for subject identification may comprise sequential, parallel, or simultaneous amplification of a plurality of nucleic acid sequences, such as about, less than about, or more than about 10, 11, 12, 13, 14, 15, 20, 25, 30, 35, 40, 50, 100, or more target sequences. In some embodiments, a subjects entire genome or entire transcriptome is non-specifically amplified, the products of which are probed for one or more identifying sequence characteristics. An identifying sequence characteristic includes any feature of a nucleic acid sequence that can serve as a basis of differentiation between individuals. In some embodiments, an individual is uniquely identified to a selected statistical significance using about, less than about, or more than about 10, 11, 12, 13, 14, 15, 20, 25, 30, 35, 40, 50, 100, or more identifying sequences. In some embodiments, the statistical significance is about, or smaller than about $10^{-2}$, $10^{-3}$, $10^{-4}$, $10^{-5}$, $10^{-6}$, $10^{-7}$, $10^{-8}$, $10^{-9}$, $10^{-10}$, $10^{-11}$, $10^{-12}$, $10^{-13}$, $10^{-14}$, $10^{-15}$, or smaller. Examples of identifying sequences include Restriction Fragment Length Polymorphisms (RFLP; Botstein, et al., Am. J. Hum. Genet. 32: 314-331, 1980; WO 90/13668), Single Nucleotide Polymorphisms (SNPs; Kwok, et al., Genomics 31: 123-126, 1996), Randomly Amplified Polymorphic DNA (RAPD; Williams, et al., Nucl. Acids Res. 18: 6531-6535, 1990), Simple Sequence Repeats (SSRs; Zhao & Kochert, Plant Mol. Biol. 21: 607-614, 1993; Zietkiewicz, et al. Genomics 20: 176-183, 1989), Amplified Fragment Length Polymorphisms (AFLP; Vos, et al., Nucl. Acids Res. 21: 4407-4414, 1995), Short Tandem Repeats (STRs), Variable Number of Tandem Repeats (VNTR), microsatellites (Tautz, Nucl. Acids. Res. 17: 6463-6471, 1989; Weber and May, Am. J. Hum. Genet. 44: 388-396, 1989), Inter-Retrotransposon Amplified Polymorphism (IRAP), Long Interspersed Elements (LINE), Long Tandem Repeats (LTR), Mobile Elements (ME), Retrotransposon Microsatellite Amplified Polymorphisms (REMAP), Retrotransposon-Based Insertion Polymorphisms (RBIP), Short Interspersed Elements (SINE), and Sequence Specific Amplified Polymorphism (SSAP). Additional examples of identifying sequences are known in the art, for example in US20030170705, which is incorporated herein by reference. A genetic signature may consist of multiple identifying sequences of a single type (e.g. SNPs), or may comprise a combination of two or more different types of identifying sequences in any number or combination.

Genetic signatures can be used in any process requiring the identification of one or more subjects, such as in paternity or maternity testing, in immigration and inheritance disputes, in breeding tests in animals, in zygosity testing in twins, in tests for inbreeding in humans and animals; in evaluation of transplant suitability such as with bone marrow transplants; in identification of human and animal remains; in quality control of cultured cells; in forensic testing such as forensic analysis of semen samples, blood stains, and other biological materials; in characterization of the genetic makeup of a tumor by testing for loss of heterozygosity; and in determining the allelic frequency of a particular identifying sequence. Samples useful in the generation of a genetics signature include evidence from a crime scene, blood, blood stains, semen, semen stains, bone, teeth, hair, saliva, urine, feces, fingernails, muscle or other soft tissue, cigarettes, stamps, envelopes, dandruff, fingerprints, items containing any of these, and combinations thereof. In some embodiments, two or more genetic signatures are generated and compared. In some embodiments, one or more genetics signatures are compared to one or more known genetic signatures, such as genetic signatures contained in a database.

A system may also verify whether the subject has received instruction to undergo a clinical test from a health care professional. The system may thus verify whether a subject has received an order from a health care professional to undertake a qualitative and/or quantitative evaluation of a biological sample. For example, the system may verify whether the subject has received a prescription from the health care professional to take the test. The system may verify whether the subject has received instructions from the health care professional to provide a sample to the device. The system may also verify whether the subject was authorized to go to a particular point of service to undergo the test. The verification may occur with aid of the device. The verification may occur at any time. In one example, the subject's authorization to take the test may be verified prior to preparing the subject's sample for the test. The subject's authorization to take the test may be verified prior to providing a sample to the device and/or cartridge. The verification of the subject's authorization may be provided after verifying the subject's identification. The verification of the subject's authorization may be provided before or after verifying the subject has insurance coverage for the clinical test. The system may verify whether the subject is covered by health insurance for a qualitative and/or quantitative evaluation of a sample, within the verifying step is performed prior to, concurrently with, or after processing a biological sample with the aid of a device, or transmitting the data from the device. The verification may take place through communications with the medical care provider, laboratory, payer, laboratory benefits manager, or any other entity. Verification may occur rapidly and/or in real-time. For example, verification may occur within 10 minutes or less, 5 minutes or less, 3 minutes or less, 1 minute or less, 45 seconds or less, 30 seconds or less, 20 seconds or less, 15 seconds or less, 10 seconds or less, 5 seconds or less, 3 seconds or less, 1 second or less, 0.5 seconds or less, or 0.1 seconds or less. The verification may be automated without requiring any human intervention.

The system may also verify whether the subject has insurance coverage for the clinical test. The system may verify whether the subject has insurance coverage to provide a sample to the device. The system may also verify whether the subject has insurance coverage for going to the point of service and undergoing the test. The verification may occur at any time. In one example, the subject's insurance coverage may be verified prior to preparing the subject's sample for the test. The subject's insurance coverage may be verified prior to providing a sample to the device and/or cartridge. The verification of the subject's insurance coverage may be provided after verifying the subject's identification. The verification of the subject's insurance coverage may be provided before or after verifying the subject has received a prescription to take the clinical test. The verification may take place through communications with the medical care provider, laboratory, payer, laboratory benefits manager, or any other entity. The verification may occur with the aid of the device. Verification may occur rapidly and/or in real-time. For example, verification may occur within 10 minutes or less, 5 minutes or less, 3 minutes or less, 1 minute or less, 45 seconds or less, 30 seconds or less, 20 seconds or less, 15 seconds or less, 10 seconds or less, 5 seconds or less, 3 seconds or less, 1 second or less, 0.5 seconds or less, or 0.1 seconds or less. The verification may be automated without requiring any human intervention.

The system may also verify whether the clinical test is appropriate for the subject. The system may verify whether an order for a qualitative and/or quantitative evaluation is within a set of policy restrictions. Such policy restrictions may form guidelines. Such policy restrictions may be policy restriction of a payer, prescribing physician or other ordering health care professional, laboratory, governmental or regulatory body, or any other entity. Such verification may depend on one or more known characteristic of the subject including but not limited to gender, age, or past medical history. A clinical decision support system may be provided. The system may be capable of accessing one or more medical records, or information associated with the subject. The system may be able to access records relating to the identity of the subject, insurance coverage of the subject, past and present medical treatments of the subject, biological features of the subject, and/or prescriptions provided to the subject. The system may be able to access electronic health records and/or pull up patient records and history. The system may also be able to pull up payer records, such as insurance and financial information relating to the subject. The verification may occur with the aid of the device.

In some embodiments, prior to providing a qualitative and/or quantitative evaluation, the system may be capable of accessing one or more records database and/or payer database. In some instances, the system may be capable of determining which records database and/or payer database to access prior to providing said qualitative and/or quantitative evaluation, and/or prior to accessing said databases. The system may make such determination based on the subject's identity, the subject's payer information, information collected about the sample, the proposed qualitative and/or quantitative evaluation, and/or any other information.

In one example, an inappropriate test may be a pregnancy test for a male subject or a PSA level (prostrate-specific antigen) for a female subject. Such tests may fall outside the policy restrictions of a payer or prescribing physician. Such ordering errors may be detectable by reviewing the test ordered and information associated with the subject. Such information associated with the subject may include medical records for the subject or identifying information about the subject. In one example, the appropriateness of the test is verified prior to preparing the subject's sample for the test. The subject's test appropriateness may be verified prior to, concurrently with, or subsequent to providing a sample to the device and/or cartridge. The verification of the subject's test appropriateness may be provided after or prior to verifying the subject's identification and/or insurance coverage. The verification may take place through communications with the medical care provider, laboratory, payer, laboratory benefits manager, or any other entity. A clinical decision support system may operate rapidly and/or in real-time. For example, verification may occur within 10 minutes or less, 5 minutes or less, 3 minutes or less, 1 minute or less, 45 seconds or less, 30 seconds or less, 20 seconds or less, 15 seconds or less, 10 seconds or less, 5 seconds or less, 3 seconds or less, 1 second or less, 0.5 seconds or less, or 0.1 seconds or less. The clinical decision support system may be automated without requiring any human intervention.

In some embodiments, qualified personnel may assist with collecting the subject's identity and/or providing a sample from the subject to the device. The qualified personnel may be an authorized technician that has been trained to use the device. The qualified personnel may be a designated operator of the device. The qualified personnel may or may not be a health care professional. In some embodiments, the identity of the qualified personnel may be verified. The qualified personnel's identity may be verified prior to, currently with, or after receiving the biological sample, transmitting the data from the device electronically and/or analyzing the transmitted data. The qualified personnel's identity may be verified prior to, currently with, or after verifying the identity of the subject. The qualified person's identity may be verified using one or more of the techniques described elsewhere herein.

Figure 9:
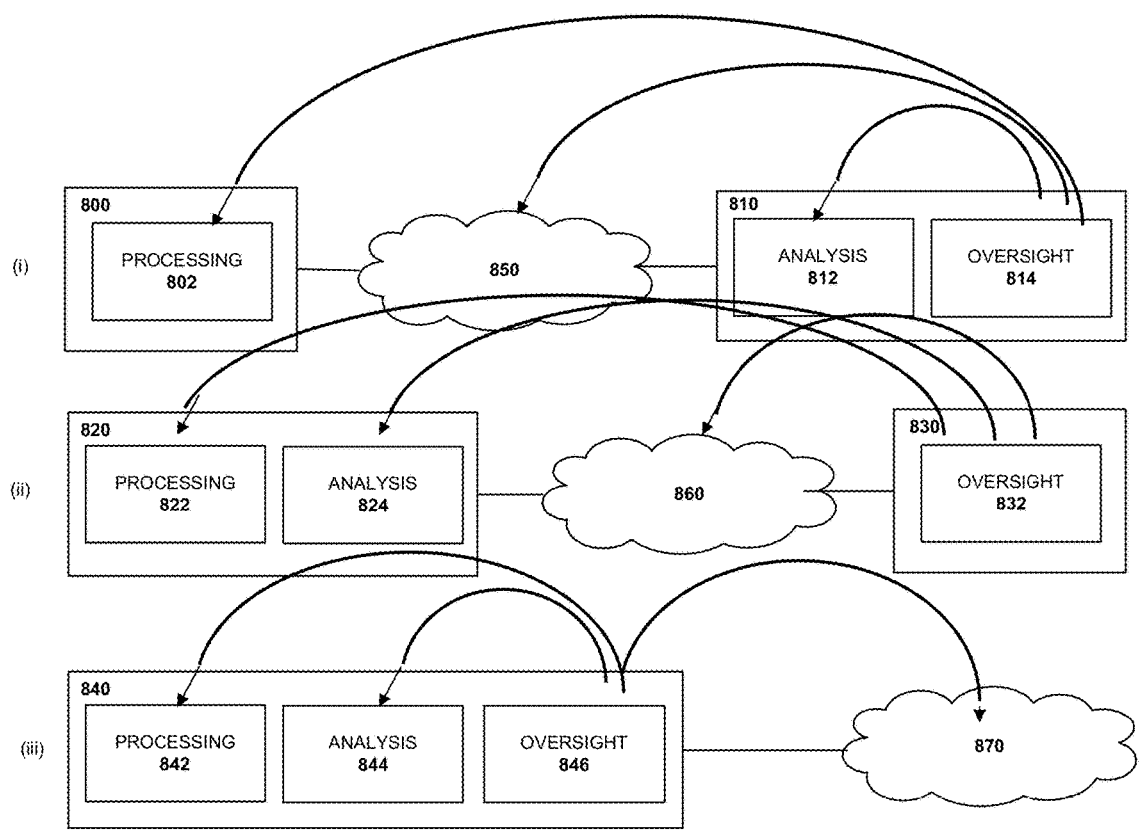
FIG. 9 shows further examples of a system providing sample processing, analysis, and oversight.

FIG. 9 shows further examples of a system providing sample processing, analysis, and oversight. The numbers in the boxes in FIG. 9 have the same meanings as the corresponding numbers in FIG. 8. As shown in FIG. 9, arrows from the oversight box indicate that oversight may be oversight of analysis, oversight of communication over a network (such as the cloud, as exemplified by the cloud cartoon in the figure), and oversight of processing, e.g., oversight of the operation of a device processing a sample. As discussed above, oversight of operation of a device may be continuous oversight, e.g., during processing of a sample, and may include oversight in view of device information (including device identification, device status, device condition, and other device information), cartridge information, sample information, patient information, environmental information regarding a device, cartridge, sample, or other environmental information, and other information and data about or transmitted from a device. Such oversight may be oversight of oversight of analysis, oversight of communication, and oversight of processing, for each example in which oversight may be located at a laboratory location, or at a sample collection site. In embodiments, oversight may be located in the cloud or other network. In further embodiments, oversight includes oversight of post-analytic actions or steps.

Figure 10A:
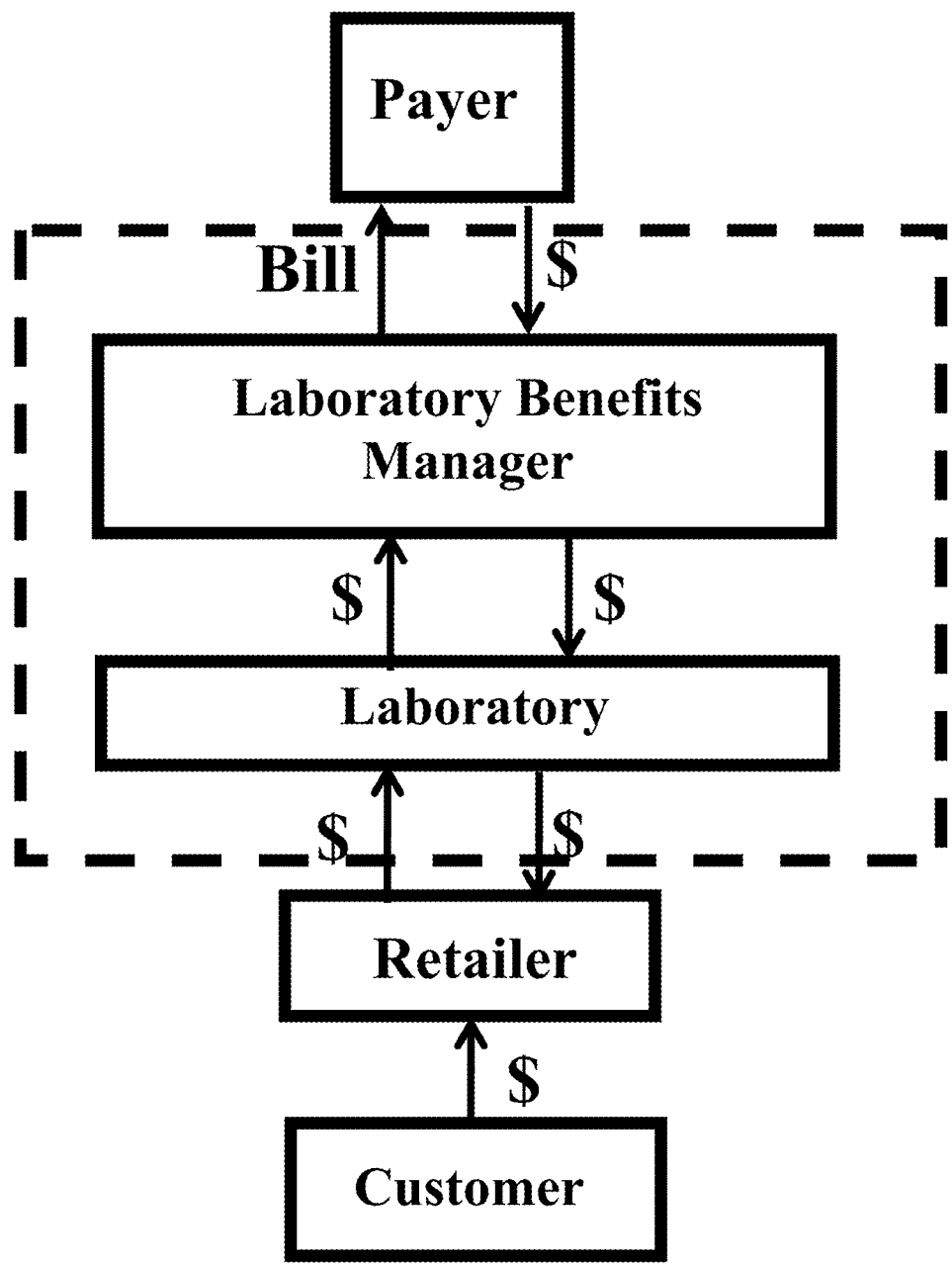
FIG. 10A shows an example of a laboratory benefit system provided in accordance with an embodiment of the invention.
Figure 10B:
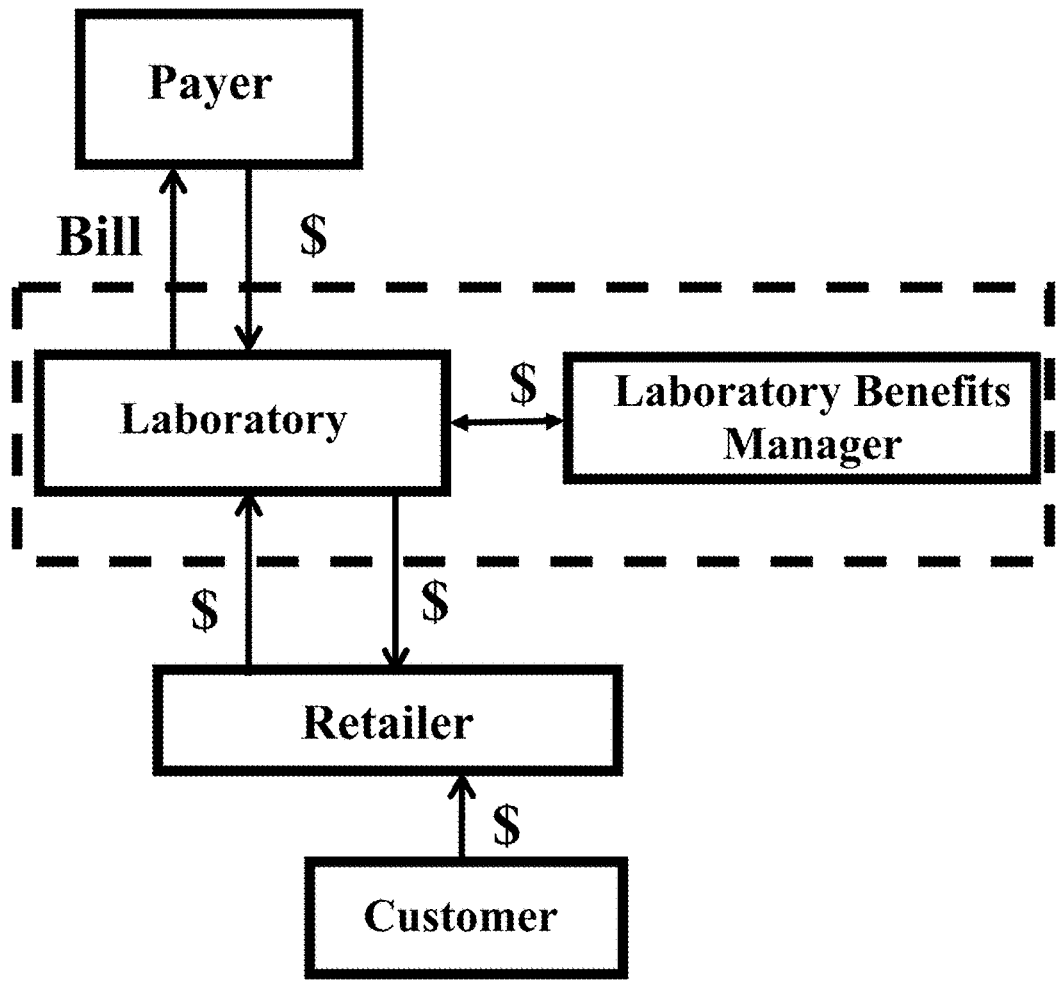
FIG. 10B shows an example of a laboratory benefit system provided in accordance with an embodiment of the invention.
Figure 10C:
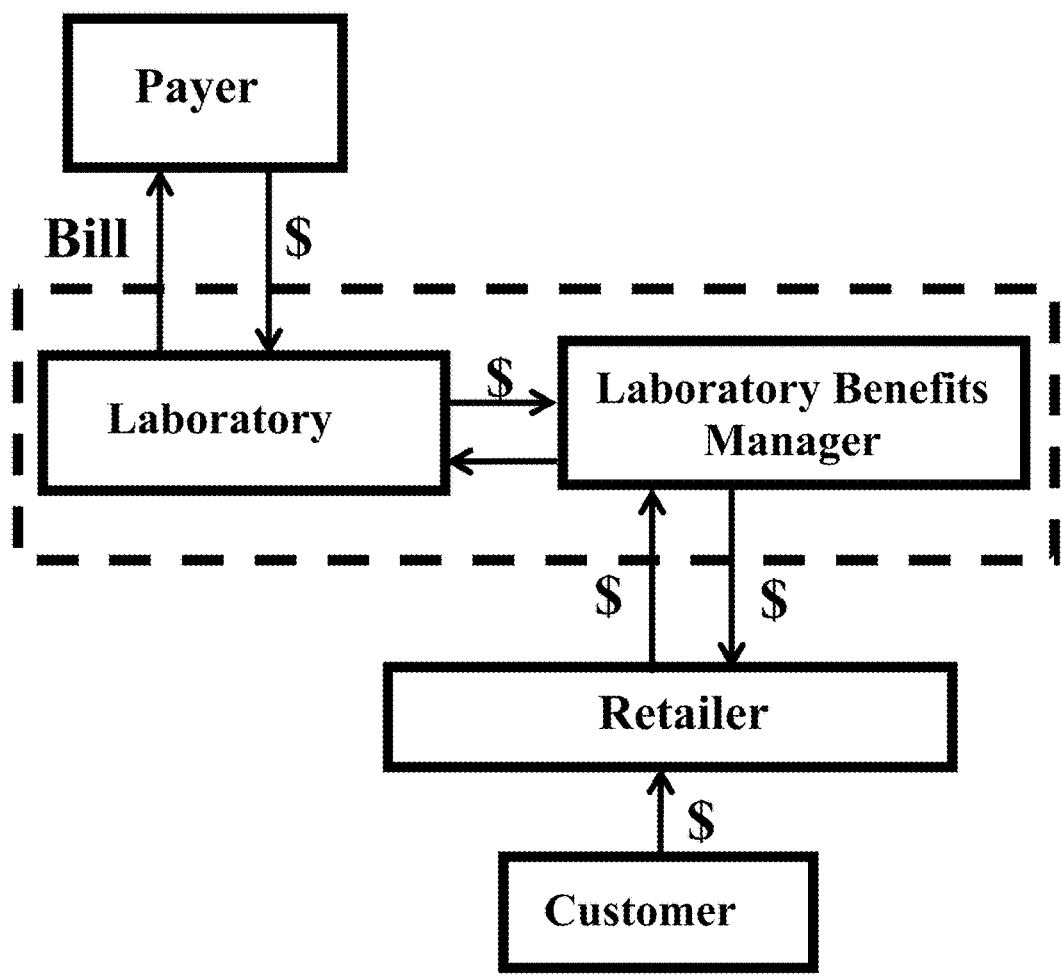
FIG. 10C shows an example of a laboratory benefit system provided in accordance with an embodiment of the invention.
Figure 10D:
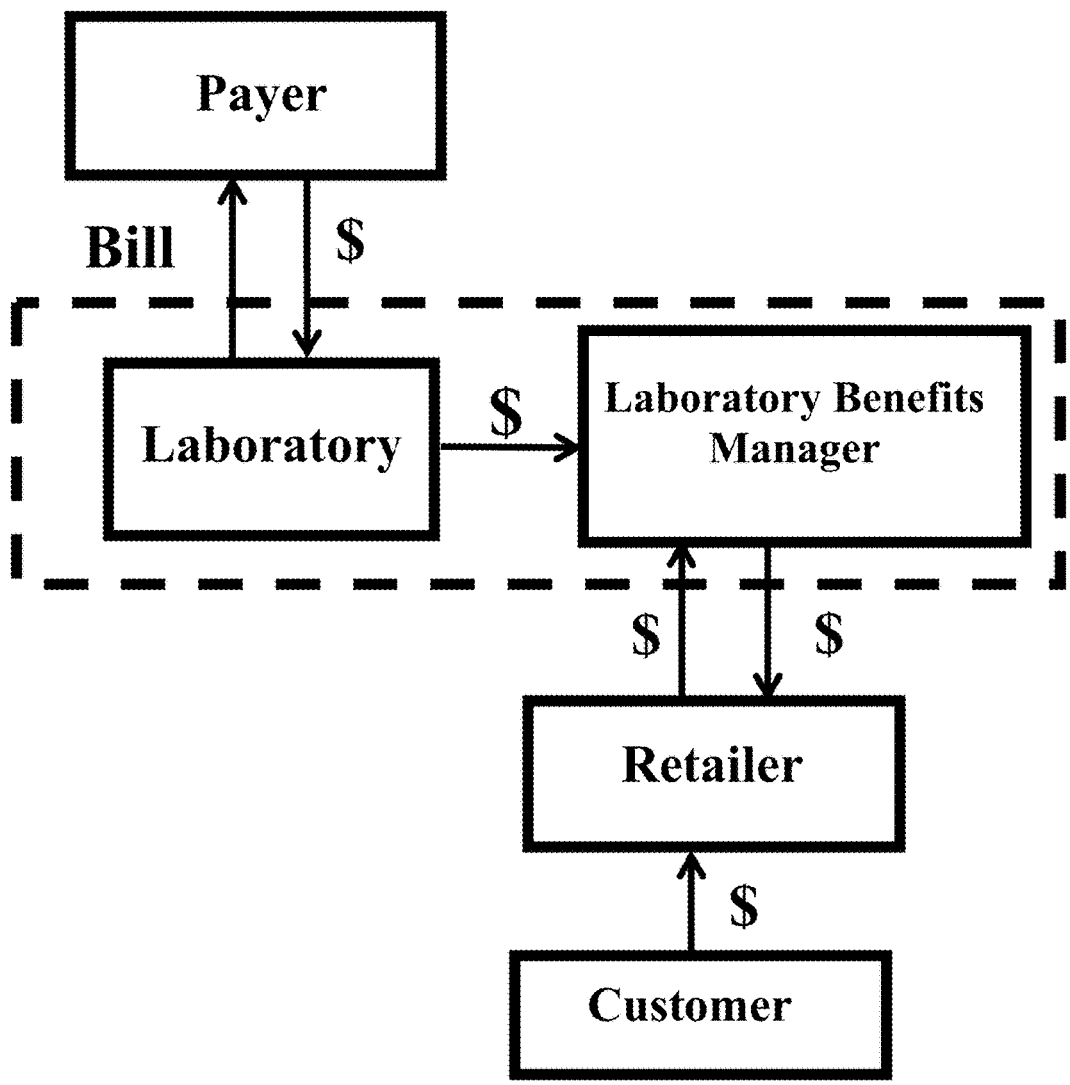
FIG. 10D shows an example of a laboratory benefit system provided in accordance with an embodiment of the invention.

FIG. 10A, 10B, 10C, and FIG. 10D show examples of a laboratory benefit management system provided in accordance with an embodiment of the invention. Advantages of scenarios as illustrated in FIGS. 10A, 10B, 10C, and 10D, and as discussed herein, include providing a retailer with the ability to recognize revenue, e.g., upon receipt of payment. Such payment may be received from a customer, as shown in FIGS. 10A, 10B, 10C, and 10D; may be received from a laboratory, as shown in FIGS. 10A and 10B; or from a LBM, as shown in FIGS. 10C and 10D. As illustrated in the figure, a laboratory benefits manager (LBM) may communicate with, or be part of, a laboratory. (The dashed box around the boxes representing Laboratory and LBM, respectively, indicate that a laboratory and a LBM may be the same entity, or may be separate entities.) A test may be offered at a sample collection site, such as a retail site. The boxes labeled "Retailer" represent a sample collection site, which may be, for example, a store, another commercial location, a pharmacy, a health care facility, or other sample collection site. A customer, indicated by the boxes labeled "Customer", may desire a service, such as a blood test, a urine test, or other test; the customer may pay a retailer for such a test; alternatively, a customer may pay only a portion of the amount owed for such a test (e.g., a copay). In embodiments, a customer does not pay the retailer, and the retailer receives payment from another party (e.g., a laboratory, a LBM, an insurance company, a health plan, a governmental agency, or other payer). A laboratory may provide services (e.g., may perform tests of a biological sample), may provide equipment, may provide disposables, and may do other acts for which payment may be expected. A laboratory or a LBM may send an invoice (e.g., a bill) to a payer requesting payment, as indicated by the arrow marked "Bill" in the figures. Dollar signs indicate payments. The head of the arrows indicates the directionality of the indicated action; for example, the upward-pointing arrow in FIG. 10A, labeled "Bill", indicates that an LBM may bill a payer; and the downward-pointing arrow near the arrow labeled "Bill" indicates that a payer may provide a payment to the LBM. As shown, a laboratory may receive payments from a payer. A laboratory may provide payment or other moneys to a LBM. A laboratory may share payments or other moneys with a LBM. A LBM may receive payments from a payer. A LBM may provide payment or other moneys to a laboratory. A laboratory may share payments or other moneys with a LBM. In embodiments, a laboratory may provide information along with, separate from, or in addition to the payment or moneys, e.g., identification information, test information, insurance information, or other information. A LBM may manage payer relationships and contacts. A LBM may pay a retailer. For example, a LBM may reimburse a retailer an amount of money, e.g., according to a test that was performed. In embodiments, a laboratory may reimburse a retailer. A retailer may pay a fee or provide other payment to a LBM (e.g., may pay a service fee, an agent fee, or other fee). In embodiments, a laboratory or LBM may retain a fee from moneys paid by a retailer. In embodiments, a laboratory or LBM may retain a fee from moneys paid by a payer; in embodiments, a LBM may pay a fee to a laboratory. A laboratory may be an authorized laboratory, and may be a CLIA-compliant or CLIA-certified laboratory.

As indicated by the dashed boxes, a laboratory and a LBM may be the same entity, or may be separate entities. In addition, a laboratory may be a wholesaler, i.e., may provide equipment, supplies, etc. (e.g., devices, cartridges, and other materials useful for the practice of the methods disclosed herein, and for obtaining the devices and systems as disclosed herein). In embodiments, such items may be provided by third parties that need not be a laboratory.

As indicated in FIG. 10A, a customer may deal directly with a retailer, and may provide payment to a retailer. A retailer may deal with a laboratory, and pay, or pass payment to a laboratory (e.g., for services, equipment, materials, or other payments); the laboratory may pay a retailer (e.g., a fee). A laboratory may deal with a LBM, and payments (including fees, reimbursements, or other payments) may pass in either or both directions between a LBM and a laboratory. A LBM may deal with a payer (e.g., a health plan, insurance company, governmental agency, or other payer) by, for example, billing the payer for services (e.g., for the service provided to the customer) or for other costs or billable actions. A payer may pay a LBM per such a bill. In embodiments, a LBM and a laboratory may be the same entity, in which case the payer and the retailer deal with that entity.

As indicated in FIG. 10B, a customer may deal directly with a retailer, and may provide payment to a retailer. A retailer may deal with a laboratory, and pay, or pass payment to a laboratory (e.g., for services, equipment, materials, or other payments); the laboratory may pay a retailer (e.g., a fee). A laboratory may deal with a LBM, and payments (including fees, reimbursements, or other payments) may pass in either or both directions between a LBM and a laboratory. A laboratory may deal with a payer (e.g., a health plan, insurance company, governmental agency, or other payer) by, for example, billing the payer for services (e.g., for the service provided to the customer) or for other costs or billable actions. A payer may pay a laboratory per such a bill. In the scenario illustrated in FIG. 10B, the LBM does not deal directly with the payer, and the retailer does not deal directly with the LBM. In embodiments, a LBM and a laboratory may be the same entity, in which case the payer and the retailer deal with that entity.

As indicated in FIG. 10C, a customer may deal directly with a retailer, and may provide payment to a retailer. A retailer may deal with a LBM, and pay, or pass payment to a LBM (e.g., for services, equipment, materials, or other payments); the LBM may pay a retailer (e.g., a fee). A laboratory may deal with a LBM, and payments (including fees, reimbursements, or other payments) may pass in either or both directions between a LBM and a laboratory. A laboratory may deal with a payer (e.g., a health plan, insurance company, governmental agency, or other payer) by, for example, billing the payer for services (e.g., for the service provided to the customer) or for other costs or billable actions. A payer may pay a laboratory per such a bill. In the scenario illustrated in FIG. 10C, the retailer deals with the LBM, and does not deal directly with the laboratory; and the payer deals with the laboratory, and does not deal directly with the LBM. In embodiments, a LBM and a laboratory may be the same entity, in which case the payer and the retailer deal with that entity.

As indicated in FIG. 10D, a customer may deal directly with a retailer, and may provide payment to a retailer. A retailer may deal with a LBM, and pay, or pass payment to a LBM (e.g., for services, equipment, materials, or other payments); the LBM may pay a retailer (e.g., a fee). A laboratory may deal with a LBM, and payments (including fees, reimbursements, or other payments) may pass from the laboratory to the LBM. In the scenario illustrated in FIG. 10D, the laboratory pays the LBM, but the LBM does not pay the laboratory (the laboratory receives payment from the payer. A laboratory may deal with a payer (e.g., a health plan, insurance company, governmental agency, or other payer) by, for example, billing the payer for services (e.g., for the service provided to the customer) or for other costs or billable actions. A payer may pay a laboratory per such a bill. In the scenario illustrated in FIG. 10D, the LBM does not deal directly with the payer; and the laboratory does not deal directly with the retailer. In embodiments, a LBM and a laboratory may be the same entity, in which case the payer and the retailer deal with that entity.

The publications discussed or cited herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed. All publications mentioned herein are incorporated herein by reference to disclose and describe the structures and/or methods in connection with which the publications are cited. The following applications are also incorporated herein by reference for all purposes: U.S. application Ser. Nos. 61/766,076 and 13/769,779.

It should be understood from the foregoing that, while particular implementations have been illustrated and described, various modifications can be made thereto and are contemplated herein. It is also not intended that the invention be limited by the specific examples provided within the specification. While the invention has been described with reference to the aforementioned specification, the descriptions and illustrations of the preferable embodiments herein are not meant to be construed in a limiting sense. Furthermore, it shall be understood that all aspects of the invention are not limited to the specific depictions, configurations or relative proportions set forth herein which depend upon a variety of conditions and variables. Various modifications in form and detail of the embodiments of the invention will be apparent to a person skilled in the art. It is therefore contemplated that the invention shall also cover any such modifications, variations and equivalents.

What is claimed is:

1. A method of evaluating a biological sample collected from a subject, said method comprising:
   (a) receiving at a laboratory location data transmitted from a device having a housing, said device placed at a designated sample collection site, said data comprising raw data obtained from said biological sample, wherein the device is configured to process the biological sample within said housing by:
   (i) receiving the biological sample, wherein the biological sample is provided in a cartridge, wherein said cartridge also contains a reagent and a disposable component for use in analyzing the biological sample;
   (ii) preparing the biological sample using said reagent and said disposable component, and yielding raw data within said housing for a subsequent qualitative and/or quantitative evaluation of the biological sample, wherein yielding raw data comprises a process or reaction performed with the biological sample or a portion thereof within said housing, said raw data comprising (1) numerical values representative of a physical process or chemical reaction regarding the biological sample or a portion thereof, said process or reaction performed by the device within a disposable component, and (2) electronic data representative of an image of the biological sample or a portion thereof; and
   (iii) transmitting electronically the raw data from said sample collection site to an authorized analytical facility and/or an affiliate thereof for performance of said subsequent evaluation at said laboratory location;
   (b) analyzing the raw data transmitted from the device at the authorized analytical facility and/or the affiliate thereof, to provide said evaluation of said biological sample, wherein said analyzing comprises applying cartridge-specific and device-specific calibration information to the raw data in the performance of automated analyses performed using a processor; and
   (c) providing automated oversight of integrity of said analysis and operation of said device, said oversight comprising monitoring of the device environment, automated evaluation of an image of the sample within the device, and automated review of the data comprising scaling and calibration of raw data, wherein the automated oversight is performed at said laboratory location using a processor effective to determine whether or not said data requires further review; wherein, if no further review is required, said oversight is effective to verify the validity of the data to insure that values and observations obtained from said raw data are correct, consistent, and reproducible, and to verify the validity of the results obtained from the analysis of said data, such that results generated from said analysis can be utilized by a health care professional for screening, diagnosis or treatment of said subject.

2. The method of claim 1, wherein the biological sample comprises a cell, and said raw data comprises electronic data representative of an image of a cell.

3. The method of claim 2, wherein said electronic data representative of an image of a cell in said biological sample comprises electronic data derived from an optical assessment of histology of said cell, morphology of said cell, hematology, or cell count.

4. The method of claim 1, wherein preparing the biological sample and yielding raw data within said housing comprises transporting a reagent or a biological sample with a pipette within said housing.

5. The method of claim 1, wherein preparing the biological sample and yielding raw data within said housing comprises centrifuging a biological sample within said housing.

6. The method of claim 1, wherein the device performs a Clinical Laboratory Improvement Amendments (CLIA)-waived test.

7. The method of claim 1, wherein the device is a Clinical Laboratory Improvement Amendments (CLIA)-compliant device, is operated in compliance with CLIA, is operated by a CLIA-compliant laboratory, or is operated in a CLIA-compliant location.

8. The method of claim 1, wherein the device is a Clinical Laboratory Improvement Amendments (CLIA)-certified device, is operated by a CLIA-certified laboratory, is operated in a CLIA-certified location, is operated under the oversight of a CLIA-compliant laboratory, or is operated under the oversight of a CLIA-certified laboratory.

9. The method of claim 1, wherein the device is a device that has been cleared for use by the U.S. Food and Drug Administration.

10. The method of claim 1, wherein the device has been classified as exempt by the U.S. Food and Drug Administration.

11. The method of claim 1, wherein the device is a device that has not been cleared or approved by any regulatory body.

12. The method of claim 1, wherein the authorized analytical facility and/or affiliate thereof is a Clinical Laboratory Improvement Amendments (CLIA)-compliant laboratory or a CLIA-certified laboratory.

13. The method of claim 1, wherein the device is operated under the control or oversight of a Clinical Laboratory Improvement Amendments (CLIA)-compliant or CLIA-certified laboratory.

14. The method of claim 1, wherein the device is a Clinical Laboratory Improvement Amendments (CLIA)-waived device operated under the control of a CLIA-compliant or CLIA-certified laboratory.

15. The method of claim 1, wherein the device is operated under the oversight or control of a CLIA-compliant laboratory, and wherein the device is a Clinical Laboratory Improvement Amendments (CLIA)-compliant device; or CLIA-certified device; or a device that has been cleared for use by the U.S. Food and Drug Administration; or a device which has been classified as exempt by the U.S. Food and Drug Administration; or a device that has not been cleared or approved by any regulatory body.

16. The method of claim 1, wherein the device is a sample processing device or a sample processing unit.

17. The method of claim 1, wherein the device has been classified by a regulatory body as a sample processing device or a sample processing unit.

18. The method of claim 1, wherein said designated sample collection site is a site selected from the group consisting of a retailer site, the subject's home, a health assessment location, and a health treatment location.

19. The method of claim 1, wherein receiving data comprises receiving data from an image of a physical process or chemical reaction performed by the device with said biological sample.

20. The method of claim 1, wherein preparing the biological sample and yielding raw data within said housing comprises yielding raw data within said housing from at least two assays selected from an immunoassay, a nucleic acid assay, a receptor-based assay, and an enzymatic assay.

\* \* \* \* \*